US011919959B2

(12) United States Patent
Bicknell et al.

(10) Patent No.: US 11,919,959 B2
(45) Date of Patent: *Mar. 5, 2024

(54) INHIBITORS OF THE INTERACTION BETWEEN CLEC14A AND MULTIMERIN-2 FOR INHIBITION OF ANGIOGENESIS

(71) Applicant: Cancer Research Technology Limited, London (GB)

(72) Inventors: Roy Bicknell, Birmingham (GB); Peter Noy, Nottingham (GB); Kabir Ali Khan, Toronto (CA)

(73) Assignee: Cancer Research Technology Limited, London (GB)

( * ) Notice: Subject to any disclaimer, the term of this patent is extended or adjusted under 35 U.S.C. 154(b) by 417 days.

This patent is subject to a terminal disclaimer.

(21) Appl. No.: 16/992,497

(22) Filed: Aug. 13, 2020

(65) Prior Publication Data

US 2021/0070867 A1 Mar. 11, 2021

Related U.S. Application Data

(63) Continuation of application No. 15/544,323, filed as application No. PCT/GB2016/050134 on Jan. 21, 2016, now Pat. No. 10,808,031.

(30) Foreign Application Priority Data

Jan. 21, 2015 (GB) .................................... 1501004

(51) Int. Cl.
| | |
|---|---|
| C07K 16/28 | (2006.01) |
| C07K 16/30 | (2006.01) |
| A61P 35/00 | (2006.01) |
| G01N 33/50 | (2006.01) |
| A61K 39/00 | (2006.01) |

(52) U.S. Cl.
CPC ...... *C07K 16/2851* (2013.01); *A01K 67/0278* (2013.01); *A61P 35/00* (2018.01); *C07K 16/30* (2013.01); *G01N 33/5008* (2013.01); *A01K 2217/075* (2013.01); *A01K 2227/105* (2013.01); *A01K 2267/0375* (2013.01); *A61K 2039/505* (2013.01); *C07K 2317/34* (2013.01); *C07K 2317/56* (2013.01); *C07K 2317/565* (2013.01); *C07K 2317/70* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,348,376 A | 9/1982 | Goldenberg |
| 4,946,778 A | 8/1990 | Ladner et al. |
| 5,350,674 A | 9/1994 | Boenisch et al. |
| 5,399,346 A | 3/1995 | Anderson et al. |
| 5,585,089 A | 12/1996 | Queen |
| 5,585,362 A | 12/1996 | Wilson et al. |
| 5,693,762 A | 12/1997 | Queen |
| 5,739,116 A | 4/1998 | Hamann et al. |
| 5,767,285 A | 6/1998 | Hamann et al. |
| 5,773,001 A | 6/1998 | Hamann et al. |
| 5,800,988 A | 9/1998 | Casterman et al. |
| 5,840,526 A | 11/1998 | Casterman et al. |
| 5,874,541 A | 2/1999 | Casterman et al. |
| 6,005,079 A | 12/1999 | Casterman et al. |
| 6,015,695 A | 1/2000 | Casterman et al. |
| 6,225,118 B1 | 5/2001 | Grant et al. |
| 6,326,193 B1 | 12/2001 | Liu et al. |
| 6,765,087 B1 | 7/2004 | Casterman et al. |
| 7,659,241 B2 | 2/2010 | Senter et al. |
| 10,808,031 B2 * | 10/2020 | Bicknell ............ G01N 33/5008 |
| 2006/0088522 A1 | 4/2006 | Boghaert et al. |
| 2011/0008840 A1 | 1/2011 | Hoffee et al. |

FOREIGN PATENT DOCUMENTS

| | | |
|---|---|---|
| EP | 1589107 A1 | 10/2005 |
| WO | 9532425 A1 | 11/1995 |
| WO | 9606641 A1 | 3/1996 |
| WO | 9634103 A1 | 10/1996 |
| WO | 9734103 A1 | 9/1997 |
| WO | 9749805 A2 | 12/1997 |
| WO | 9832845 A1 | 7/1998 |
| WO | 0129058 A1 | 4/2001 |
| WO | 0196584 A2 | 12/2001 |
| WO | 0236771 A1 | 5/2002 |
| WO | 2004046191 A2 | 6/2004 |
| WO | 2011027132 A1 | 3/2011 |
| WO | 2013187556 A1 | 12/2013 |
| WO | 2013187724 A1 | 12/2013 |
| WO | 2014153270 A1 | 9/2014 |

OTHER PUBLICATIONS

Tame (J. Comput. Aided Mol. Des. Mar. 1999; 13 (2): 99-108.*
Dixon (Proteins. 1997; Suppl 1: 198-204).*
Lensink et al. (Proteins. 2007; 69: 704-718).*
Robinson et al (JP, 6:308-319, 2020).*
Rudikoff et al., "Single amino acid substitution altering antigen-binding specificity," Proc. Natl. Acad. Sci. USA 79(6):1979-83 (1982).
Suchting et al. Soluble Robo4 receptor inhibits in vivo angiogenesis and endothelial cell migration. FASEB J. Jan. 2005;19(1):121-3.

(Continued)

*Primary Examiner* — Brad Duffy

(74) *Attorney, Agent, or Firm* — McNeill Baur PLLC

(57) ABSTRACT

The invention provides a method of inhibiting angiogenesis in an individual, the method comprising administering to the individual an agent that inhibits the interaction between CLEC14A and MMRN2. The inhibitor may be an antibody, a polypeptide, a peptide, a polynucleotide, a peptidomimetic, a natural product, a carbohydrate, an aptamer or a small molecule.

4 Claims, 25 Drawing Sheets

Figure 1:
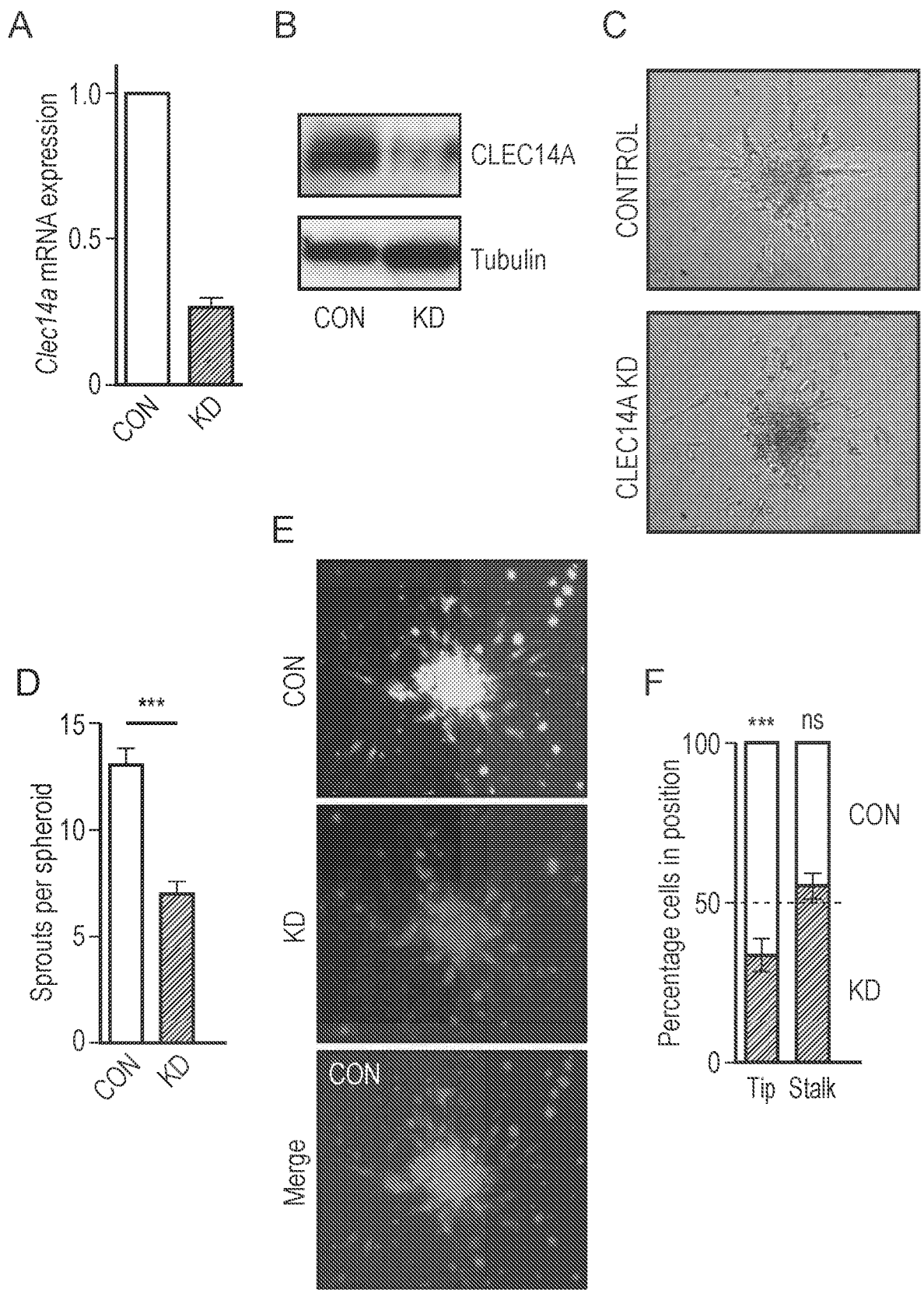

Specification includes a Sequence Listing.

(56) References Cited

OTHER PUBLICATIONS

Ten Berge et al. Selective expansion of a peripheral blood CD8+ memory T cell subset expressing both granzyme B and L-selectin during primary viral infection in renal allograft recipients. Transplant Proc. Dec. 1998;30(8):3975-7.
Terskikh et al. "Peptabody": a new type of high avidity binding protein. Proc Natl Acad Sci U S A. Mar. 4, 1997;94(5):1663-8.
Thijssen et al. Galectin-1 is essential in tumor angiogenesis and is a target for antiangiogenesis therapy. Proc Natl Acad Sci U S A. Oct. 24, 2006;103(43):15975-80.
Thompson et al. CLUSTAL1 W: improving the sensitivity of progressive multiple sequence alignment through sequence weighting, position-specific gap penalties and weight matrix choice. Nucleic Acids Res. Nov. 11, 1994;22(22):4673-80.
Tsai et al. Growth suppression of human colorectal carcinoma in nude mice by monoclonal antibody C27-abrin A chain conjugate. Dis Colon Rectum. Oct. 1995;38(10):1067-74.
Ui-Tei et al. Sensitive assay of RNA interference in Drosophila and Chinese hamster cultured cells using firefly luciferase gene as target. FEBS Lett. Aug. 18, 2000;479(3):79-82.
Vaughan & Sollazzo. Of minibody, camel and bacteriophage. Comb Chem High Throughput Screen. Aug. 2001;4(5):417-30.
Vaughan et al. Human antibodies by design. Nat Biotechnol. Jun. 1998;16(6):535-9.
Verhoeyen et al. Reshaping human antibodies: grafting an antilysozyme activity. Science. Mar. 25, 1988;239(4847):1534-6.
Welch-Reardon et al. Angiogenic sprouting is regulated by endothelial cell expression of Slug. J Cell Sci. May 1, 2014;127(Pt 9):2017-28.
Welti et al. Recent molecular discoveries in angiogenesis and antiangiogenic therapies in cancer. J Clin Invest. Aug. 2013;123(8):3190-200.
Wilman. Prodrugs in cancer chemotherapy. Biochem Soc Trans. Apr. 1986;14(2):375-82.
Winkler et al., J. Imm. 265:4505-4515 (2000).
Winter et al. Making antibodies by phage display technology. Annu Rev Immunol. 1994;12:433-55.
Wrighton et al. Increased potency of an erythropoietin peptide mimetic through covalent dimerization. Nat Biotechnol. Nov. 1997;15(12):1261-5.
Zanivan et al. SILAC-based proteomics of human primary endothelial cell morphogenesis unveils tumor angiogenic markers. Mol Cell Proteomics. Dec. 2013;12(12):3599-611.
Zelensky & Gready. The C-type lectin-like domain superfamily. FEBS J. Dec. 2005;272(24):6179-217.
Zhuang et al. Shear stress, tip cells and regulators of endothelial migration. Biochem Soc Trans. Dec. 2011;39(6):1571-5.
Ziyad & Iruela-Arispe. Molecular mechanisms of tumor angiogenesis. Genes Cancer. Dec. 2011;2(12):1085-96.
Zola. Monoclonal Antibodies: A manual of techniques. 1st ed. Jul. 31, 1987. CRC Press, Boca Raton, Florida.
Melkko et al. Encoded self-assembling chemical libraries. Nat Biotechnol. May 2004;22(5):568-74.
Milone et al. Chimeric receptors containing CD137 signal transduction domains mediate enhanced survival of T cells and increased antileukemic efficacy in vivo. Mol Ther. Aug. 2009;17(8):1453-64.
Mitchell et al. Radiobiology and clinical application of halogenated pyrimidine radiosensitizers. Int J Radiat Biol. Nov. 1989;56(5):827-36.
Monnet et al. Synthetic peptides derived from the variable regions of an anti-CD4 monoclonal antibody bind to CD4 and inhibit HIV-1 promoter activation in virus-infected cells. J Biol Chem. Feb. 5, 1999;274(6):3789-96.
Moran et al. Radio Frequency Tag Encoded Combinatorial Library Method for the Discovery of Tripeptide-Substituted Cinnamic Acid Inhibitors of the Protein Tyrosine Phosphatase PTP1B. J Am Chem Soc. Nov. 1995;117(43):10787-8.
Muckenschnabel et al. SpeedScreen: label-free liquid chromatography-mass spectrometry-based high-throughput screening for the discovery of orphan protein ligands. Anal Biochem. Jan. 15, 2004;324(2):241-9.
Mumtaz et al. Design of liposomes for circumventing the reticuloendothelial cells. Glycobiology. Nov. 1991;1(5):505-10.
Mura et al. Identification and angiogenic role of the novel tumor endothelial marker CLEC14A. Oncogene. Jan. 19, 2012;31(3):293-305.
Nanda & St Croix. Tumor endothelial markers: new targets for cancer therapy. Curr Opin Oncol. Jan. 2004;16(1):44-9.
Nanda et al. Tumor endothelial marker 1 (Tem1) functions in the growth and progression of abdominal tumors. Proc Natl Acad Sci U S A. Feb. 28, 2006;103(9):3351-6.
National Cancer Institute. Bevacizumab Combined With Chemotherapy Improves Progression-Free Survival for Patients With Advanced Breast Cancer. Press Release Apr. 14, 2005, updated Jun. 16, 2005. https://www.cancer.gov/newscenter/pressreleases/AvastinBreast. Wayback machine version Jan. 7, 2006.
National Cancer Institute. DTP—Anti-cancer Agent Mechanism Database. http://dtp.nci.nih.gov/docs/cancer/searches/standard_mechanism.html. Wayback machine version Oct. 3, 2014.
Neri & Bicknell. Tumour vascular targeting. Nat Rev Cancer. Jun. 2005;5(6):436-46.
Nicaise et al. Affinity transfer by CDR grafting on a nonimmunoglobulin scaffold. Protein Sci. Jul. 2004;13(7):1882-91.
Nicolaou et al. Radiofrequency Encoded Combinatorial Chemistry. Angew Chem Int Ed Engl. Nov. 3, 1995;34(20):2289-91.
Nishikawa & Huang. Nonviral vectors in the new millennium: delivery barriers in gene transfer. Hum Gene Ther. May 20, 2001;12(8):861-70.
Noy et al. Blocking CLEC14A-MMRN2 binding inhibits sprouting angiogenesis and tumour growth. Oncogene. Nov. 19, 2015;34(47):5821-31.
Noy PJ, "Blocking CLEC14A-MMRN2 binding inhibits sprouting angiogenesis and tumour growth," Oncogene, Nov. 19, 2015, 34(47):5821-5831.
O'Shannessy. Determination of kinetic rate and equilibrium binding constants for macromolecular interactions: a critique of the surface plasmon resonance literature. Curr Opin Biotechnol. Feb. 1994;5(1):65-71.
Ohlmeyer et al. Complex synthetic chemical libraries indexed with molecular tags. Proc Natl Acad Sci U S A. Dec. 1, 1993;90(23):10922-6.
Pasqualini et al. Alpha v integrins as receptors for tumor targeting by circulating ligands. Nat Biotechnol. Jun. 1997;15(6):542-6.
Pessi et al. A designed metal-binding protein with a novel fold. Nature. Mar. 25, 1993;362(6418):367-9.
Pfaffl. A new mathematical model for relative quantification in real-time RT-PCR. Nucleic Acids Res. May 1, 2001;29(9):e45.
Pinilla et al. Advances in the use of synthetic combinatorial chemistry: mixture-based libraries. Nat Med. Jan. 2003;9(1):118-22.
Pircher et al. Favorable prognosis of operable non-small cell lung cancer (NSCLC) patients harboring an increased expression of tumor endothelial markers (TEMs). Lung Cancer. Aug. 2013;81(2):252-8.
Plant et al. Phospholipid/alkanethiol bilayers for cell-surface receptor studies by surface plasmon resonance. Anal Biochem. Apr. 10, 1995;226(2):342-8.
Primus et al. Bispecific antibody mediated targeting of nidocarboranes to human colon carcinoma cells. Bioconjug Chem. Sep.-Oct. 1996;7(5):532-5.
Qiu et al. Small antibody mimetics comprising two complementarity-determining regions and a framework region for tumor targeting. Nat Biotechnol. Aug. 2007;25(8):921-9.
Quiocho. Protein engineering. Making of the minibody. Nature. Mar. 25, 1993;362(6418):293-4.
Ramström & Lehn. Drug discovery by dynamic combinatorial libraries. Nat Rev Drug Discov. Jan. 2002;1(1):26-36.
Ran et al. Infarction of solid Hodgkin's tumors in mice by antibody-directed targeting of tissue factor to tumor vasculature. Cancer Res. Oct. 15, 1998;58(20):4646-53.

(56) References Cited

OTHER PUBLICATIONS

Rho et al. Clec14a is specifically expressed in endothelial cells and mediates cell to cell adhesion. Biochem Biophys Res Commun. Jan. 7, 2011;404(1):103-8.

Rippmann et al. Fusion of the tissue factor extracellular domain to a tumour stroma specific single-chain fragment variable antibody results in an antigen-specific coagulation-promoting molecule. Biochem J. Aug. 1, 2000;349 Pt 3:805-12.

Sadelain et al. The basic principles of chimeric antigen receptor design. Cancer Discov. Apr. 2013;3(4):388-98.

Sambrook & Russell. Molecular Cloning: A Laboratory Manual. 3rd ed. 2001. Cold Spring Harbor Laboratory Press, New York.

Sanz-Moncasi et al. Identification of a high molecular weight endothelial cell surface glycoprotein, endoGlyx-1, in normal and tumor blood vessels. Lab Invest. Sep. 1994;71(3):366-73.

Saunders. Reporter molecules in genetically engineered mice. Methods Mol Biol. 2003;209:125-43.

Schaffitzel et al. Ribosome display: an in vitro method for selection and evolution of antibodies from libraries. J Immunol Methods. Dec. 10, 1999;231(1-2):119-35.

Scott & Smith. Searching for peptide ligands with an epitope library. Science. Jul. 27, 1990;249(4967):386-90.

Sebestyén et al. Efficiency and limitations of the 'portioning-mixing' peptide synthesis. Peptides 1992. Proceedings of the 22nd European Peptide Symposium, Sep. 13-19, 1992 Interlaken, Switzerland. pp. 63-64.

Senter et al. Anti-tumor effects of antibody-alkaline phosphatase conjugates in combination with etoposide phosphate. Proc Natl Acad Sci U S A. Jul. 1988;85(13):4842-6.

Shenoy & Singh. Chemical radiosensitizers in cancer therapy. Cancer Invest. 1992;10(6):533-51.

Shewach & Lawrence. Gemcitabine and radiosensitization in human tumor cells. Invest New Drugs. 1996;14(3):257-63.

Shi et al. Chimeric antigen receptor for adoptive immunotherapy of cancer: latest research and future prospects. Mol Cancer. Sep. 21, 2014;13:219.

Shuker et al. Discovering high-affinity ligands for proteins: SAR by NMR. Science. Nov. 29, 1996;274(5292):1531-4.

Soderlind et al. Recombining germline-derived CDR sequences for creating diverse single-framework antibody libraries. Nat Biotechnol. Aug. 2000;18(8):852-6.

Soderlind et al. The immune diversity in a test tube—non-immunised antibody libraries and functional variability in defined protein scaffolds. Comb Chem High Throughput Screen. Aug. 2001;4(5):409-16.

Song et al. CD27 costimulation augments the survival and antitumor activity of redirected human T cells in vivo. Blood. Jan. 19, 2012;119(3):696-706.

Stapor et al. The Distribution of Fluid Shear Stresses in Capillary Sprouts. Cardiovasc Eng Technol. Jun. 2011;2(2):124-36.

Stella & Himmelstein. Prodrugs: A Chemical Approach to Targeted Drug Delivery. In: Borchardt et al (eds) Directed Drug Delivery—A Multidisciplinary Problem. Humana Press, Clifton, NJ. 1985; pp. 247-267.

Genbank Accession No. NM_175060, version of Sep. 6, 2014.
Genbank Accession No. NP_778230, version of Sep. 6, 2014.
Genbank Accession No. XP_006718033, version of Sep. 6, 2014.

Giovannoni et al. Isolation of anti-angiogenesis antibodies from a large combinatorial repertoire by colony filter screening. Nucleic Acids Res. Mar. 1, 2001;29(5):E27.

Green & Sambrook. Molecular Cloning: A Laboratory Manual. 4th ed. 2012. Cold Spring Harbor Laboratory Press, New York.

Griffiths et al. Isolation of high affinity human antibodies directly from large synthetic repertoires. EMBO J. Jul. 15, 1994;13(14):3245-60.

Gussow et al., Methods in Enzymology 203:99-121 (1991).

Haanen et al. Selective expansion of cross-reactive CD8(+) memory T cells by viral variants. J Exp Med. Nov. 1, 1999;190(9):1319-28.

Han et al. Chimeric antigen receptor-engineered T cells for cancer immunotherapy: progress and challenges. J Hematol Oncol. Jul. 8, 2013;6:47.

Harlow & Lane. Antibodies: A Laboratory Manual. 1988. Cold Spring Harbor Laboratory, Cold Spring Harbor, NY.

Harlow & Lane. Using Antibodies: A Laboratory Manual. 1999. Cold Spring Harbor Laboratory Press, Cold Spring Harbor, NY.

Hartley et al. DNA interstrand cross-linking and in vivo antitumor activity of the extended pyrrolo[2,1-c][1,4] benzodiazepine dimer SG2057. Invest New Drugs. Jun. 2012;30(3):950-8.

Heap et al. Analysis of a 17-amino acid residue, virus-neutralizing microantibody. J Gen Virol. Jun. 2005;86(Pt 6):1791-800.

Helmling et al. Inhibition of ghrelin action in vitro and in vivo by an RNA-Spiegelmer. Proc Natl Acad Sci U S A. Sep. 7, 2004;101(36):13174-9.

Hoogenboom & Winter. By-passing immunisation. Human antibodies from synthetic repertoires of germline VH gene segments rearranged in vitro. J Mol Biol. Sep. 20, 1992;227(2):381-8.

Horsman. Nicotinamide and other benzamide analogs as agents for overcoming hypoxic cell radiation resistance in tumours. A review. Acta Oncol. 1995;34(5):571-87.

Huang et al. Tumor infarction in mice by antibody-directed targeting of tissue factor to tumor vasculature. Science. Jan. 24, 1997;275(5299):547-50.

Hughes. Antibody-drug conjugates for cancer: poised to deliver? Nat Rev Drug Discov. Sep. 2010;9(9):665-7.

Hurrell. Monoclonal Hybridoma Antibodies: Techniques and applications. Jul. 1, 1982. CRC Press, Boca Raton, FL.

Iliakis & Kurtzman. Keynote address: application of non-hypoxic cell sensitizers in radiobiology and radiotherapy: rationale and future prospects. Int J Radiat Oncol Biol Phys. May 1989;16(5):1235-41.

ImMunoGeneTics Information system. www.IMGT.org. Wayback machine version Jan. 15, 2016.

International Search Report and Written Opinion issued in PCT/GB2016/050134, dated Jul. 20, 2016, 17 pages.

International Search Report issued in corresponding PCT Application No. PCT/GB2016/050134, dated Jul. 20, 2016, 7 pages.

Jeffrey et al. Dipeptide-based highly potent doxorubicin antibody conjugates. Bioorg Med Chem Lett. Jan. 15, 2006;16(2):358-62.

Jin et al. A PKA-Csk-pp60Src signaling pathway regulates the switch between endothelial cell invasion and cell-cell adhesion during vascular sprouting. Blood. Dec. 16, 2010;116(25):5773-83.

Kerr et al. Encoded combinatorial peptide libraries containing non-natural amino acids. J Am Chem Soc. Mar. 1993;115(6):2529-31.

Kettleborough et al. Humanization of a mouse monoclonal antibody by CDR-grafting: the importance of framework residues on loop conformation. Protein Eng. Oct. 1991;4(7):773-83.

Khan & Bicknell. Anti-angiogenic alternatives to VEGF blockade. Clin Exp Metastasis. Feb. 2016;33(2):197-210.

Khan et al. CLEC14A—multimerin-2 interaction: a potential target for anti-angiogenic therapy. Conference Abstract P047, "Angiogenesis and Vascular Remodelling: New Perspectives", Biochemical Society, Jul. 14-16, 2014, University of Chester, UK. www.biochemistry.org/Portals/0/Conferences/Abstracts/SA163/SA163P047.pdf[retrieved on Apr. 26, 2016] and www.biochemistry.org/Events/tabid/379/View/Posters/MeetingNo/SA163/Default.aspx [retrieved on Apr. 26, 2016].

Khan et al., "Anti-angiogenic alternatives to VEGF blockage," Clin. Exp. Mestastasis, vol. 33, No. 2, Nov. 30, 2015, 197-210.

Khan et al., "CLEC14A—multimerin-2 interaction: a potential target for anti-angiogenic therapy," Jul. 16, 2014, https://www.biochemistry.com/Portals/0/Conferences/Abstracts/SA163SA163P047.pdf, Abstract, 1 page.

Ki et al. Human antibodies targeting the C-type lectin-like domain of the tumor endothelial cell marker clec14a regulate angiogenic properties in vitro. Oncogene. Nov. 28, 2013;32(48):5449-57.

Ki et al., "Human antibodies targeting the C-type lectin-like domain of the tumor endothelial cell marker clec14a regulate angiogenic properties in vitro," Oncogene, vol. 32, No. 48, May 6, 2013, pp. 5449-5457.

(56) References Cited

OTHER PUBLICATIONS

Kohler & Milstein. Continuous cultures of fused cells secreting antibody of predefined specificity. Nature. Aug. 7, 1975;256(5517):495-7.
Korff et al. Three-dimensional spheroidal culture of cytotrophoblast cells mimics the phenotype and differentiation of cytotrophoblasts from normal and preeclamptic pregnancies. Exp Cell Res. Jul. 15, 2004;297(2):415-23.
Ladner. Antibodies cut down to size. Nat Biotechnol. Aug. 2007;25(8):875-7.
Lash. Making the case for antibody-drug conjugates. In vivo: The Business & Medicine Report. Dec. 2010;32-8.
Laune et al. Systematic exploration of the antigen binding activity of synthetic peptides isolated from the variable regions of immunoglobulins. J Biol Chem. Dec. 5, 1997;272(49):30937-44.
Ledley. Nonviral gene therapy: the promise of genes as pharmaceutical products. Hum Gene Ther. Sep. 1995;6(9):1129-44.
Lefranc et al. IMGT, the international ImMunoGeneTics information system. Nucleic Acids Res. Jan. 2009;37(Database issue):D1006-12.
Lefranc. IMGT databases, web resources and tools for immunoglobulin and T cell receptor sequence analysis, http://imgt.cines.fr. Leukemia. Jan. 2003;17(1):260-6.
Lloyd et al., Protein Engineering, Design & Selection 22:159-168 (2009).
Lorenzon et al. MULTIMERIN2 impairs tumor angiogenesis and growth by interfering with VEGF-A/VEGFR2 pathway. Oncogene. Jun. 28, 2012;31(26):3136-47.
Maciag et al. An endothelial cell growth factor from bovine hypothalamus: identification and partial characterization. Proc Natl Acad Sci U S A. Nov. 1979;76(11):5674-8.
Maclean et al. Encoded combinatorial chemistry: synthesis and screening of a library of highly functionalized pyrrolidines. Proc Natl Acad Sci U S A. Apr. 1, 1997;94(7):2805-10.
Mahato et al. Prodrugs for improving tumor targetability and efficiency. Adv Drug Deliv Rev. Jul. 18, 2011;63(8):659-70.
Malmqvist. BIACORE: an affinity biosensor system for characterization of biomolecular interactions. Biochem Soc Trans. Feb. 1999;27(2):335-40.
Masiero et al. A core human primary tumor angiogenesis signature identifies the endothelial orphan receptor ELTD1 as a key regulator of angiogenesis. Cancer Cell. Aug. 12, 2013;24(2):229-41.
McCafferty et al. Phage antibodies: filamentous phage displaying antibody variable domains. Nature. Dec. 6, 1990;348(6301):552-4.
McGinn et al. Radiosensitizing nucleosides. J Natl Cancer Inst. Sep. 4, 1996;88(17):1193-203.
Abysis. http://www.bioinf.org.uk/abysis/sequence_input/key_annotation/key_annotation.html.
Adams et al. Initial assessment of human gene diversity and expression patterns based upon 83 million nucleotides of cDNA sequence. Nature. Sep. 28, 1995;377(6547 Suppl):3-174.
Adis R&D Profile. Brentuximab vedotin. Drugs R D. 2011;11(1):85-95.
Aiello et al. Suppression of retinal neovascularization in vivo by inhibition of vascular endothelial growth factor (VEGF) using soluble VEGF-receptor chimeric proteins. Proc Natl Acad Sci U S A. Nov. 7, 1995;92(23):10457-61.
Altinoglu et al. Near-infrared emitting fluorophore-doped calcium phosphate nanoparticles for in vivo imaging of human breast cancer. ACS Nano. Oct. 28, 2008;2(10):2075-84.
Andersson-Engels et al. In vivo fluorescence imaging for tissue diagnostics. Phys Med Biol. May 1997;42(5):815-24.
Aricescu et al. A time-and cost-efficient system for high-level protein production in mammalian cells. Acta Crystallogr D Biol Crystallogr. Oct. 2006;62(Pt 10):1243-50.
Arkin & Wells. Small-molecule inhibitors of protein-protein interactions: progressing towards the dream. Nat Rev Drug Discov. Apr. 2004;3(4):301-17.
Bagshawe et al. A cytotoxic agent can be generated selectively at cancer sites. Br J Cancer. Dec. 1988;58(6):700-3.

Bagshawe. Antibody directed enzymes revive anti-cancer prodrugs concept. Br J Cancer. Nov. 1987;56(5):531-2.
Bagshawe. Antibody-directed enzyme prodrug therapy: a review. Drug Develop Res. Feb. 1995;34(2):220-30.
Baker et al. Use of the mouse aortic ring assay to study angiogenesis. Nat Protoc. Dec. 22, 2011;7(1):89-104.
Barrett et al. Treatment of advanced leukemia in mice with mRNA engineered T cells. Hum Gene Ther. Dec. 2011;22(12):1575-86.
Bauminger & Wilchek. The use of carbodiimides in the preparation of immunizing conjugates. Methods Enzymol. 1980;70(A):151-9.
Beck-Sickinger & Weber. Combinatorial Strategies in Biology and Chemistry. Dec. 2001. John Wiley & Sons, Ltd, Chichester, UK.
Bergers & Hanahan. Modes of resistance to anti-angiogenic therapy. Nat Rev Cancer. Aug. 2008;8(8):592-603.
Bianchi et al. High level expression and rational mutagenesis of a designed protein, the minibody. From an insoluble to a soluble molecule. J Mol Biol. Feb. 18, 1994;236(2):649-59.
Bignon et al. Lysyl oxidase-like protein-2 regulates sprouting angiogenesis and type IV collagen assembly in the endothelial basement membrane. Blood. Oct. 6, 2011;118(14):3979-89.
Brenner & Lerner. Encoded combinatorial chemistry. Proc Natl Acad Sci U S A. Jun. 15, 1992;89(12):5381-3.
Brown. Keynote address: hypoxic cell radiosensitizers: where next? Int J Radiat Oncol Biol Phys. Apr. 1989;16(4):987-93.
Brown. Sensitizers and protectors in radiotherapy. Cancer. May 1, 1985;55(9 Suppl):2222-8.
Burrows & Thorpe. Eradication of large solid tumors in mice with an immunotoxin directed against tumor vasculature. Proc Natl Acad Sci U S A. Oct. 1, 1993;90(19):8996-9000.
Cancer Research Technology. Presentation: Chimeric Antigen Receptors (CARs) targeting CLEC14A on the tumour vasculature. Jun. 2014.
Carpentier et al. Angiogenesis Analyzer for ImageJ. 4th ImageJ User and Developer Conference proceedings. 2012. Mondorf-les-Bains, Luxembourg. 198-201. http://image.bio.methods.free.fr/ImageJ/?Angiogenesis-Analyzer-for-ImageJ. [webpage accessed Aug. 21, 2017].
Carpentier et al. Angiogenesis Analyzer for ImageJ. 4th ImageJ User and Developer Conference proceedings. 2012. Mondorf-les-Bains, Luxembourg. 198-201. http://imagej.nih.gov/ij/macros/toolsets/Angiogenesis%20Analyzer.txt. [webpage accessed Aug. 21, 2017].
Carter & Senter. Antibody-drug conjugates for cancer therapy. Cancer J. May-Jun. 2008;14(3):154-69.
Chari et al. Antibody-Drug Conjugates: An Emerging Concept in Cancer Therapy. Angew Chem Int Ed. Apr. 7, 2014;53(15):3796-827.
Chatal, Monoclonal Antibodies in Immunoscintigraphy. Oct. 31, 1989. CRC Press, Boca Raton, Florida.
Chaudhary et al. TEM8/ANTXR1 blockade inhibits pathological angiogenesis and potentiates tumoricidal responses against multiple cancer types. Cancer Cell. Feb. 14, 2012;21(2):212-26.
Chin et al. In-vivo optical detection of cancer using chlorin e6—polyvinylpyrrolidone induced fluorescence imaging and spectroscopy. BMC Med Imaging. Jan. 8, 2009;9:1.
Collins et al. Cosmix-plexing: a novel recombinatorial approach for evolutionary selection from combinatorial libraries. J Biotechnol. Jun. 2001;74(4):317-38.
Colombatti et al. The EMILIN/Multimerin family. Front Immunol. Jan. 6, 2012;2:93.
Cotten et al. High-efficiency receptor-mediated delivery of small and large (48 kilobase gene constructs using the endosome-disruption activity of defective or chemically inactivated adenovirus particles. Proc Natl Acad Sci U S A. Jul. 1, 1992;89(13):6094-8.
Cullen et al. Host-derived tumor endothelial marker 8 promotes the growth of melanoma. Cancer Res. Aug. 1, 2009;69(15):6021-6.
Daniels et al. A tenascin-C aptamer identified by tumor cell SELEX: systematic evolution of ligands by exponential enrichment. Proc Natl Acad Sci U S A. Dec. 23, 2003;100(26):15416-21.
De Bock et al. Role of PFKFB3-driven glycolysis in vessel sprouting. Cell. Aug. 1, 2013;154(3):651-63.
Desjobert et al. The PRH/Hex repressor protein causes nuclear retention of Groucho/TLE co-repressors. Biochem J. Jan. 1, 2009;417(1):121-32.

(56) References Cited

OTHER PUBLICATIONS

Dougherty et al. Photodynamic therapy. J Natl Cancer Inst. Jun. 17, 1998;90(12):889-905.
Dübel. Handbook of Therapeutic Antibodies. 1st ed. 2007. Wiley-VCH, Weinheim, Germany.
Duwel et al. Reduced tumor growth and angiogenesis in endoglin-haploinsufficient mice. Tumour Biol. 2007;28(1):1-8.
Edwards et al., J. Mol. Bio. 14;334(1):103-118 (2003).
Ellington & Szostak. Selection in vitro of single-stranded DNA molecules that fold into specific ligand-binding structures. Nature. Feb. 27, 1992;355(6363):850-2.
Felici et al. Peptide and protein display on the surface of filamentous bacteriophage. Biotechnol Annu Rev. 1995;1:149-83.
Fivash et al. BIAcore for macromolecular interaction. Curr Opin Biotechnol. Feb. 1998;9(1):97-101.
Fraker & Speck. Protein and cell membrane iodinations with a sparingly soluble chloroamide, 1,3,4,6-tetrachloro-3a,6a-diphrenylglycoluril. Biochem Biophys Res Commun. Feb. 28, 1978;80(4):849-57.
Frank. The SPOT-synthesis technique. Synthetic peptide arrays on membrane supports—principles and applications. J Immunol Methods. Sep. 1, 2002;267(1):13-26.
Gao et al. Molecular cloning of a proteolytic antibody light chain. J Biol Chem. Dec. 23, 1994;269(51):32389-93.
Garland et al. The use of Teflon cell culture bags to expand functionally active CD8+ cytotoxic T lymphocytes. J Immunol Methods. Jul. 30, 1999;227(1-2):53-63.
Gartner et al. DNA-templated organic synthesis and selection of a library of macrocycles. Science. Sep. 10, 2004;305(5690):1601-5.
Genbank Accession No. NM_024756.2, version of Sep. 6, 2014.

\* cited by examiner

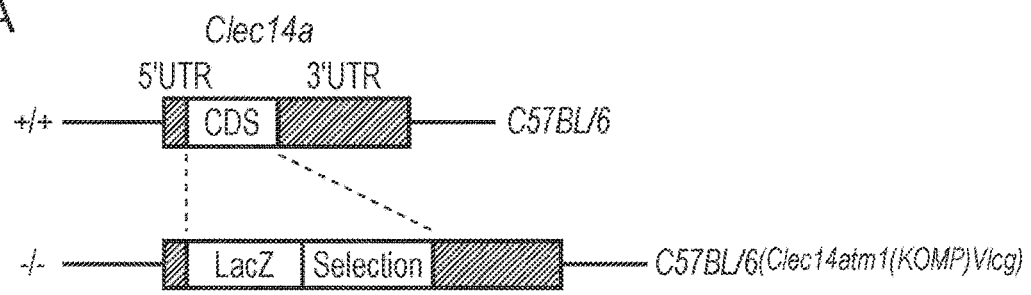
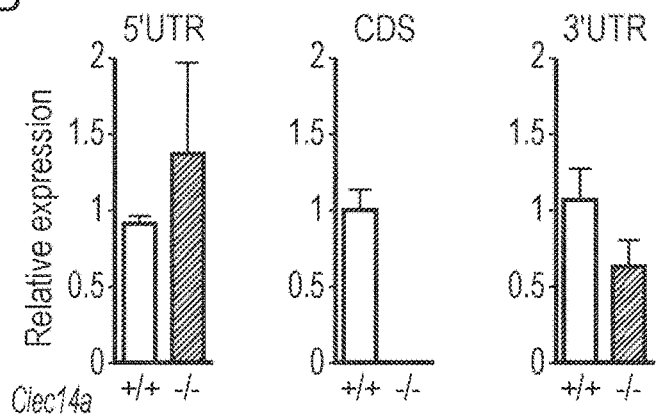
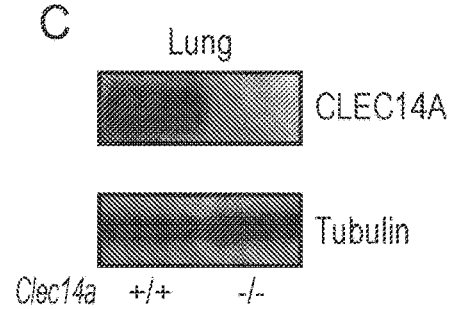
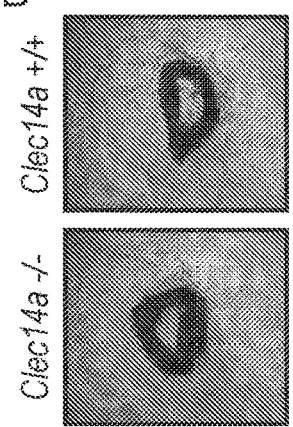
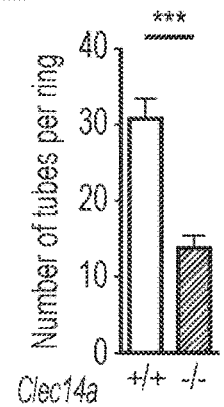
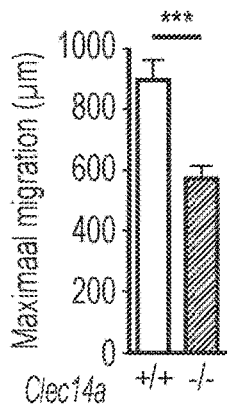
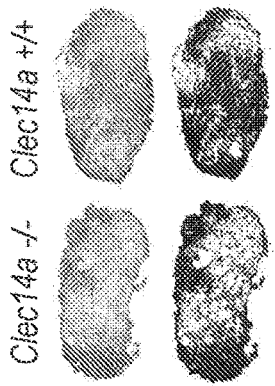
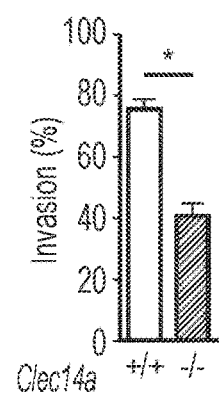
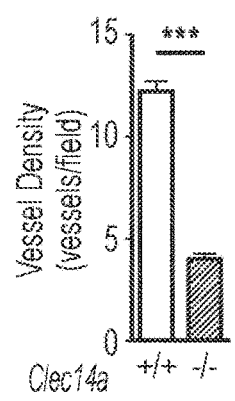
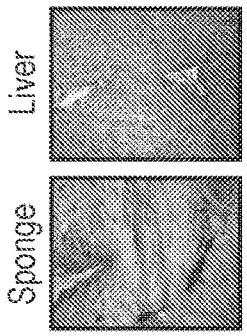
FIG. 2

A: CLEC14A POLYPEPTIDE SEQUENCE (SEQ ID NO: 17)

```
  1  MRPAFALCLL WQALWPGPGG GEHPTADRAG CSASGACYSL HHATMKRQAA EEACILRGGA
 61  LSTVRAGAEL RAVLALLRAG PGPGGGSKDL LFWVALERRR SHCTLENEPL RGFSWLSSDP
121  GGLESDTLQW VEEPQRSCTA RRCAVLQATG GVEPAGWKEM RCHLRANGYL CKYQFEVLCP
181  APRPGAASNL SYRAPFQLHS AALDFSPPGT EVSALCRGQL PISVTCIADE IGARWDKLSG
241  DVLCPCPGRY LRAGKCAELP NCLDDLGGFA CECATGFELG KDGRSCVTSG EGQPTLGGTG
301  VPTRRPPATA TSPVPQRTWP IRVDEKLGET PLVPEQDNSV TSIPEIPRWG SQSTMSTLQM
361  SLQAESKATI TPSGSVISKF NSTTSSATPQ AFDSSSAVVF IFVSTAVVVL VILTMTVLGL
421  VKLCFHESPS SQPRKESMGP PGLESDPEPA ALGSSSAHCT NNGVKVGDCD LRDRAEGALL
481  AESPLGSSDA
```

B: CLEC14A cDNA SEQUENCE (SEQ ID NO: 18)

```
   1  CTCCTCTTGC TCTAAGCAGG GTGTTTGACC TTCTAGTCGA CTGCGTCCCC TGTACCCGGC
  61  GCCAGCTGTG TTCCTGACCC CAGAATAACT CAGGGCTGCA CCGGGCCTGG CAGCGCTCCG
 121  CACACATTTC CTGTCGCGGC CTAAGGGAAA CTGTTGGCCG CTGGGCCCGC GGGGGGATTC
 181  TTGGCAGTTG GGGGGTCCGT CGGGAGCGAG GGCGGAGGGG AAGGGAGGGG GAACCGGGTT
 241  GGGGAAGCCA GCTGTAGAGG GCGGTGACCG CGCTCCAGAC ACAGCTCTGC GTCCTCGAGC
 301  GGGACAGATC CAAGTTGGGA GCAGCTCTGC GTGCGGGGCC TCAGAGAATG AGGCCGGCGT
 361  TCGCCCTGTG CCTCCTCTGG CAGGCGCTCT GGCCCGGGCC GGGCGGCGGC GAACACCCCA
 421  CTGCCGACCG TGCTGGCTGC TCGGCCTCGG GGCCTGCTA CAGCCTGCAC CACGCTACCA
 481  TGAAGCGGCA GGCGGCCGAG GAGGCCTGCA TCCTGCGAGG TGGGGCGCTC AGCACCGTGC
 541  GTGCGGGCGC CGAGCTGCGC GCTGTGCTCG CGCTCCTGCG GGCAGGCCCA GGGCCCGGAG
 601  GGGGCTCCAA AGACCTGCTG TTCTGGGTCG CACTGGAGCG CAGGCGTTCC CACTGCACCC
 661  TGGAGAACGA GCCTTTGCGG GGTTTCTCCT GGCTGTCCTC CGACCCCGGC GGTCTCGAAA
 721  GCGACACGCT GCAGTGGGTG GAGGAGCCCC AACGCTCCTG CACCGCGCGG AGATGCGCGG
 781  TACTCCAGGC CACCGGTGGG GTCGAGCCCG CAGGCTGGAA GGAGATGCGA TGCCACCTGC
 841  GCGCCAACGG CTACCTGTGC AAGTACCAGT TTGAGGTCTT GTGTCCTGCG CCGCGCCCCG
 901  GGGCCGCCTC TAACTTGAGC TATCGCGCGC CCTTCCAGCT GCACAGCGCC GCTCTGGACT
 961  TCAGTCCACC TGGGACCGAG GTGAGTGCGC TCTGCCGGGG ACAGCTCCCG ATCTCAGTTA
1021  CTTGCATCGC GGACGAAATC GGCGCTCGCT GGGACAAACT CTCGGGCGAT GTGTTGTGTC
1081  CCTGCCCCGG GAGGTACCTC CGTGCTGGCA AATGCGCAGA GCTCCCTAAC TGCCTAGACG
1141  ACTTGGGAGG CTTTGCCTGC GAATGTGCTA CGGGCTTCGA GCTGGGGAAG GACGGCCGCT
1201  CTTGTGTGAC CAGTGGGGAA GGACAGCCGA CCCTTGGGGG GACCGGGGTG CCCACCAGGC
1261  GCCCGCCGGC CACTGCAACC AGCCCCGTGC CGCAGAGAAC ATGGCCAATC AGGGTCGACG
1321  AGAAGCTGGG AGAGACACCA CTTGTCCCTG AACAAGACAA TTCAGTAACA TCTATTCCTG
1381  AGATTCCTCG ATGGGGATCA CAGAGCACGA TGTCTACCCT TCAAATGTCC CTTCAAGCCG
1441  AGTCAAAGGC CACTATCACC CCATCAGGGA GCGTGATTTC CAAGTTTAAT TCTACGACTT
1501  CCTCTGCCAC TCCTCAGGCT TTCGACTCCT CCTCTGCCGT GGTCTTCATA TTTGTGAGCA
1561  CAGCAGTAGT AGTGTTGGTG ATCTTGACCA TGACAGTACT GGGGCTTGTC AAGCTCTGCT
```

FIG. 9

1621 TTCACGAAAG CCCCTCTTCC CAGCCAAGGA AGGAGTCTAT GGGCCCGCCG GGCCTGGAGA
1681 GTGATCCTGA GCCCGCTGCT TTGGGCTCCA GTTCTGCACA TTGCACAAAC AATGGGGTGA
1741 AAGTCGGGGA CTGTGATCTG CGGGACAGAG CAGAGGGTGC CTTGCTGGCG GAGTCCCCTC
1801 TTGGCTCTAG TGATGCATAG GGAAACAGGG GACATGGGCA CTCCTGTGAA CAGTTTTTCA
1861 CTTTTGATGA AACGGGGAAC CAAGAGGAAC TTACTTGTGT AACTGACAAT TTCTGCAGAA
1921 ATCCCCCTTC CTCTAAATTC CCTTTACTCC ACTGAGGAGC TAAATCAGAA CTGCACACTC
1981 CTTCCCTGAT GATAGAGGAA GTGGAAGTGC CTTTAGGATG GTGATACTGG GGACCGGGT
2041 AGTGCTGGGG AGAGATATTT TCTTATGTTT ATTCGGAGAA TTTGGAGAAG TGATTGAACT
2101 TTTCAAGACA TTGGAAACAA ATAGAACACA ATATAATTTA CATTAAAAAA TAATTTCTAC
2161 CAAAATGGAA AGGAAATGTT CTATGTTGTT CAGGCTAGGA GTATATTGGT TCGAAATCCC
2221 AGGGAAAAAA ATAAAAATAA AAAATTAAAG GATTGT

C: CLEC14A CODING SEQUENCE (SEQ ID NO: 19)

ATGAGGCCGG CGTTCGCCCT GTGCCTCCTC TGGCAGGCGC TCTGGCCCGG GCCGGGCGGC 60
GGCGAACACC CCACTGCCGA CCGTGCTGGC TGCTCGGCCT CGGGGGCCTG CTACAGCCTG 120
CACCACGCTA CCATGAAGCG GCAGGCGGCC GAGGAGGCCT GCATCCTGCG AGGTGGGGCG 180
CTCAGCACCG TGCGTGCGGG CGCCGAGCTG CGCGCTGTGC TCGCGCTCCT GCGGGCAGGC 240
CCAGGGCCCG GAGGGGCTC CAAAGACCTG CTGTTCTGGG TCGCACTGGA GCGCAGGCGT 300
TCCCACTGCA CCCTGGAGAA CGAGCCTTTG CGGGTTTCT CCTGGCTGTC CTCCGACCCC 360
GGCGGTCTCG AAAGCGACAC GCTGCAGTGG GTGGAGGAGC CCAACGCTC CTGCACCGCG 420
CGGAGATGCG CGGTACTCCA GGCCACCGGT GGGGTCGAGC CCGCAGGCTG GAAGGAGATG 480
CGATGCCACC TGCGCGCCAA CGGCTACCTG TGCAAGTACC AGTTTGAGGT CTTGTGTCCT 540
GCGCCGCGCC CCGGGGCCGC CTCTAACTTG AGCTATCGCG CGCCCTTCCA GCTGCACAGC 600
GCCGCTCTGG ACTTCAGTCC ACCTGGGACC GAGGTGAGTG CGCTCTGCCG GGACAGCTC 660
CCGATCTCAG TTACTTGCAT CGCGGACGAA ATCGGCGCTC GCTGGGACAA ACTCTCGGGC 720
GATGTGTTGT GTCCCTGCCC CGGGAGGTAC CTCCGTGCTG GCAAATGCGC AGAGCTCCCT 780
AACTGCCTAG ACGACTTGGG AGGCTTTGCC TGCGAATGTG CTACGGGCTT CGAGCTGGGG 840
AAGGACGGCC GCTCTTGTGT GACCAGTGGG GAAGGACAGC CGACCCTTGG GGGGACCGGG 900
GTGCCCACCA GGCGCCCGCC GGCCACTGCA ACCAGCCCG TGCCGCAGAG AACATGGCCA 960
ATCAGGGTCG ACGAGAAGCT GGGAGAGACA CCACTTGTCC CTGAACAAGA CAATTCAGTA 1020
ACATCTATTC CTGAGATTCC TCGATGGGA TCACAGAGCA CGATGTCTAC CCTTCAAATG 1080
TCCCTTCAAG CCGAGTCAAA GGCCACTATC ACCCCATCAG GAGCGTGAT TTCCAAGTTT 1140
AATTCTACGA CTTCCTCTGC CACTCCTCAG GCTTCGACT CCTCCTCTGC CGTGGTCTTC 1200
ATATTTGTGA GCACAGCAGT AGTAGTGTTG GTGATCTTGA CCATGACAGT ACTGGGGCTT 1260
GTCAAGCTCT GCTTTCACGA AAGCCCCTCT TCCCAGCCAA GGAAGGAGTC TATGGGCCCG 1320
CCGGGCCTGG AGAGTGATCC TGAGCCCGCT GCTTTGGGCT CCAGTTCTGC ACATTGCACA 1380
AACAATGGGG TGAAAGTCGG GGACTGTGAT CTGCGGGACA GAGCAGAGGG TGCCTTGCTG 1440
GCGGAGTCCC CTCTTGGCTC TAGTGATGCA TAG

FIG. 9 (Continued)

MMRN2 polypeptide sequence (SEQ ID NO: 20) and coding sequence (SEQ ID NO: 21)

```
atgatcctgagcttgctgttcagccttgggggcccctgggctggggctgctgggggca
 M  I  L  S  L  L  F  S  L  G  G  P  L  G  W  G  L  L  G  A
tgggcccaggcttccagtactagcctctctgatctgcagagctccaggacacctggggtc
 W  A  Q  A  S  S  T  S  L  S  D  L  Q  S  S  R  T  P  G  V
tggaaggcagaggctgaggacaccggcaaggacccgttggacgtaactggtgccctac
 W  K  A  E  A  E  D  T  G  K  D  P  V  G  R  N  W  C  P  Y
ccaatgtccaagctggtcaccttactagctctttgcaaaacagagaaattcctcatccac
 P  M  S  K  L  V  T  L  L  A  L  C  K  T  E  K  F  L  I  H
tcgcagcagccgtgtccgcagggagctccagactgccagaaagtcaaagtcatgtaccgc
 S  Q  Q  P  C  P  Q  G  A  P  D  C  Q  K  V  K  V  M  Y  R
atggcccacaagccagtgtaccaggtcaagcagaaggtgctgacctctttggctggagg
 M  A  H  K  P  V  Y  Q  V  K  Q  K  V  L  T  S  L  A  W  R
Tgctgccctggctacacgggccccaactgcgagcaccac gattccatggcaatccctgag
 C  C  P  G  Y  T  G  P  N  C  E  H  H  D  S  M  A  I  P  E
cctgcagatcctggtgacagccaccaggaacctcaggatggaccagtcagcttcaaacct
 P  A  D  P  G  D  S  H  Q  E  P  Q  D  G  P  V  S  F  K  P
ggccaccttgctgcagtgatcaatgaggttgaggtgcaacaggaacagcaggaacatctg
 G  H  L  A  A  V  I  N  E  V  E  V  Q  Q  E  Q  Q  E  H  L
ctgggagatctccagaatgatgtgcaccgggtggcagacagcctgccaggcctgtggaaa
 L  G  D  L  Q  N  D  V  H  R  V  A  D  S  L  P  G  L  W  K
gcctgcctggtaacctcacagctgcagtgatggaagcaaatcaaacagggcacgagttc
 A  L  P  G  N  L  T  A  A  V  M  E  A  N  Q  T  G  H  E  F
cctgatagatccttggagcaggtgctgctaccccacgtggacaccttcctacaagtgcat
 P  D  R  S  L  E  Q  V  L  L  P  H  V  D  T  F  L  Q  V  H
ttcagccccatctggaggagctttaaccaaagcctgcacagccttacccaggccataaga
 F  S  P  I  W  R  S  F  N  Q  S  L  H  S  L  T  Q  A  I  R
aacctgtctcttgacgtggaggccaaccgccaggccatctccagagtccaggacagtgcc
 N  L  S  L  D  V  E  A  N  R  Q  A  I  S  R  V  Q  D  S  A
gtggccagggctgacttccaggagcttggtgccaaatttgaggccaaggtccaggagaac
 V  A  R  A  D  F  Q  E  L  G  A  K  F  E  A  K  V  Q  E  N
actcagagagtgggtcagctgcgacaggacgtggaggaccgcctgcacgccagcactttt
 T  Q  R  V  G  Q  L  R  Q  D  V  E  D  R  L  H  A  Q  H  F
accctgcaccgctcgatctcagagctccaagccgatgtggacaccaaattgaagaggctg
 T  L  H  R  S  I  S  E  L  Q  A  D  V  D  T  K  L  K  R  L
```

FIG. 10

```
cacaaggctcaggaggccccagggaccaatggcagtctggtgttggcaacgcctggggct
  H  K  A  Q  E  A  P  G  T  N  G  S  L  V  L  A  T  P  G  A
ggggcaaggcctgagccggacagcctgcaggccaggctgggccagctgcagaggaacctc
  G  A  R  P  E  P  D  S  L  Q  A  R  L  G  Q  L  Q  R  N  L
tcagagctgcacatgaccacggcccgcagggaggaggagttgcagtacaccctggaggac
  S  E  L  H  M  T  T  A  R  R  E  E  E  L  Q  Y  T  L  E  D
atgagggccaccctgacccggcacgtggatgagatcaaggaactgtactccgaatcggac
  M  R  A  T  L  T  R  H  V  D  E  I  K  E  L  Y  S  E  S  D
gagactttcgatcagattagcaaggtggagcggcaggtggaggagctgcaggtgaaccac
  E  T  F  D  Q  I  S  K  V  E  R  Q  V  E  E  L  Q  V  N  H
acggcgctccgtgagctgcgcgtgatcctgatggagaagtctctgatcatggaggagaac
  T  A  L  R  E  L  R  V  I  L  M  E  K  S  L  I  M  E  E  N
aaggaggaggtggagcggcagctcctggagctcaacctcacgctgcagcacctgcaggt
  K  E  E  V  E  R  Q  L  L  E  L  N  L  T  L  Q  H  L  Q  G
ggccatgccgacctcatcaagtacgtgaaggactgcaattgccagaagctctatttagac
  G  H  A  D  L  I  K  Y  V  K  D  C  N  C  Q  K  L  Y  L  D
Ctggacgtcatccgggagggccagagggacgccacgcgtgccctggag gagacccaggtg
  L  D  V  I  R  E  G  Q  R  D  A  T  R  A  L  E  E  T  Q  V
Agcctggacgagcggcggcagctggacggctcctccctgcaggccctgcagaacgccgtg
  S  L  D  E  R  R  Q  L  D  G  S  S  L  Q  A  L  Q  N  A  V
gacgccgtgtcgctggccgtggacgcgcacaaagcggagggcgagcgggcgcgggcggcc
  D  A  V  S  L  A  V  D  A  H  K  A  E  G  E  R  A  R  A  A
acgtcgcggctccggagccaagtgcaggcgctggatgacgaggtgggcgcgctgaaggcg
  T  S  R  L  R  S  Q  V  Q  A  L  D  D  E  V  G  A  L  K  A
gccgcggccgaggcccgccacgaggtgcgccagctgcacagcgccttcgccgccctgctg
  A  A  A  E  A  R  H  E  V  R  Q  L  H  S  A  F  A  A  L  L
gaggacgcgctgcggcacgaggcggtgctggccgcgctcttcggggaggaggtgctggag
  E  D  A  L  R  H  E  A  V  L  A  A  L  F  G  E  E  V  L  E
gagatgtctgagcagacgccgggaccgctgcccctgagctacgagcagatccgcgtggcc
  E  M  S  E  Q  T  P  G  P  L  P  L  S  Y  E  Q  I  R  V  A
ctgcaggacgccgctagcgggctgcaggagcaggcgctcggctgggacgagctggccgcc
  L  Q  D  A  A  S  G  L  Q  E  Q  A  L  G  W  D  E  L  A  A
Cgagtgacggccctggagcaggcctcggagccccgcggccg gcagagcacctggagccc
  R  V  T  A  L  E  Q  A  S  E  P  P  R  P  A  E  H  L  E  P
```

FIG. 10 (Continued)

```
agccacgacgcgggccgcgaggaggccgccaccaccgccctggccgggctggcgcgggag
 S  H  D  A  G  R  E  E  A  A  T  T  A  L  A  G  L  A  R  E
ctccagagcctgagcaacgacgtcaagaatgtcgggcggtgctgcgaggctgaggccggg
 L  Q  S  L  S  N  D  V  K  N  V  G  R  C  C  E  A  E  A  G
gccggggccgcctccctcAACgcctcccttgacggcctccacaacgcactcttcgccact
 A  G  A  A  S  L  N  A  S  L  D  G  L  H  N  A  L  F  A  T
cagcgcagcttggagcagcaccagcggctcttccacagcctctttgggaacttccaaggg
 Q  R  S  L  E  Q  H  Q  R  L  F  H  S  L  F  G  N  F  Q  G
ctcatggaagccAACgtcagcctggacctggggaagctgcagaccatgctgagcaggaaa
 L  M  E  A  N  V  S  L  D  L  G  K  L  Q  T  M  L  S  R  K
gggaagaagcagcagaaagacctggaagctccccggaagagggacaagaaggaagcggag
 G  K  K  Q  Q  K  D  L  E  A  P  R  K  R  D  K  K  E  A  E
cctttggtggacatacgggtcacagggcctgtgccaggtgccttgggcgcggcgctctgg
 P  L  V  D  I  R  V  T  G  P  V  P  G  A  L  G  A  A  L  W
gaggcaggatcccctgtggccttctatgccagcttttcagaagggacggctgccctgcag
 E  A  G  S  P  V  A  F  Y  A  S  F  S  E  G  T  A  A  L  Q
acagtgaagttcaacaccacatacatcaacattggcagcagctacttccctgaacatggc
 T  V  K  F  N  T  T  Y  I  N  I  G  S  S  Y  F  P  E  H  G
tacttccgagcccctgagcgtggtgtctacctgtttgcagtgagcgttgaatttggccca
 Y  F  R  A  P  E  R  G  V  Y  L  F  A  V  S  V  E  F  G  P
gggccaggcaccgggcagctggtgtttggaggtcaccatcggactccagtctgtaccact
 G  P  G  T  G  Q  L  V  F  G  G  H  H  R  T  P  V  C  T  T
gggcaggggagtggaagcacagcaacggtctttgccatggctgagctgcagaagggtgag
 G  Q  G  S  G  S  T  A  T  V  F  A  M  A  E  L  Q  K  G  E
cgagtatggtttgagttaacccagggatcaataacaaagagaagcctgtcgggcactgca
 R  V  W  F  E  L  T  Q  G  S  I  T  K  R  S  L  S  G  T  A
tttgggggcttcctgatgtttaagacctga
 F  G  G  F  L  M  F  K  T  -
```

FIG. 10 (Continued)

CRT4 Variable heavy chain (SEQ ID NO: 7):

MAQVQLQQSGAELMKPGASVKISCKATGYTFSSYWIEWVNRRPGHGLEWIGEILPGSGSTNYNEKFKGKA
TFTADTSSNTAYMQLSSLTSEDSAVYYCARGGDYDEEYYLMDYWGQGTTLTVSS

CRT4 Variable light chain (SEQ ID NO: 8):

QIVLTQSPAIMSASPGEKVTMTCSASSSVSYMYWYQQKPGSSPRLLIYDTSNLASGVPVRFSGSGS
GTSYSLTISRMEAEDAATYYCQQWSSYPLTFGAGTKLEIKRAA

CRT4 Variable heavy chain (SEQ ID NO: 15):

ATGGCCCAGGTTCAGCTGCAGCAGTCTGGAGCTGAGCTGATGAAGCCTGGGGCCTCAGTGAAGATATCCTGC
AAGGCTACTGGCTACACATTCAGTAGCTACTGGATAGAGTGGGTAAACCGGAGGCCTGGACATGGCCTTGA
G
TGGATTGGAGAGATTTTACCTGGAAGTGGTAGTACTAATTACAATGAGAAGTTCAAGGGCAAGGCCACATTC
ACTGCAGATACATCCTCCAATACAGCCTACATGCAACTCAGCAGCCTCACATCTGAGGACTCTGCCGTCTAT
TACTGTGCGAGAGGGGGGGATTACGACGAAGAATACTATCTCATGGACTACTGGGGTCAAGGCACCACTCT
C
ACAGTCTCCTCA

CRT4 Variable light chain (SEQ ID NO: 16):

CAAATTGTTCTCACCCAGTCTCCAGCAATCATGTCTGCATCTCCAGGGGAGAAGGTCACCATGACCTGCAGTG
CCAGCTCAAGTGTAAGTTACATGTACTGGTACCAGCAGAAGCCAGGATCCTCCCCCAGA**CTCCTGATTTATGA
CACATCCAACCTGGCT**TCTGGAGTCCCTGTTCGCTTCAGTGGCAGTGGGTCTGGGACCTCTTACTCTCTCACAA
TCAGCCGAATGGAGGCTGAAGATGCTGCCACTTATTACTGCCAGCAGTGGAGTAGTTACCCGCTCACGTTCG
GTGCTGGGACCAAGCTGGAAATCAAACGTGCGGCCGC

FIG. 11

A) Chimera 5 – CLEC14A with CTLD of CD141
Amino acid sequence of CD141 CTLD

MLGVLVLGALALAGLGFPAPAEPQPGGSQCVEHDCFALYPGPATFLNASQICDGLRGHLMTVRSSVAA
DVISLLLNGDGGVGRRRLWIGLQLPPGCGDPKRLGPLRGFQWVTGDNNTSYSRWARLDLNGAPLCGPL
CVAVSAAEATVPSEPIWEEQQCEVKADGFLCEF

Amino acid sequence of whole Chimera 5 fused to GFP tag

MLGVLVLGALALAGLGFPAPAEPQPGGSQCVEHDCFALYPGPATFLNASQICDGLRGHLMTVRSSVAA
DVISLLLNGDGGVGRRRLWIGLQLPPGCGDPKRLGPLRGFQWVTGDNNTSYSRWARLDLNGAPLCGPL
CVAVSAAEATVPSEPIWEEQQCEVKADGFLCEF<u>QFEVLCPAPRPGAASNLSYRAPFQLHSAALDFSPP</u>
<u>GTEVSALCRGQLPISVTCIADEIGARWDKLSGDVLCPCPGRYLRAGKCAELPNCLDDLGGFACECATG</u>
<u>FELGKDGRSCVTSGEGQPTLGGTGVPTRRPPATATSPVPQRTWPIRVDEKLGETPLVPEQDNSVTSIP</u>
<u>EIPRWGSQSTMSTLQMSLQAESKATITPSGSVISKFNSTTSSATPQAFDSSSAVVFIFVSTAVVVLVI</u>
<u>LTMTVLGLVKLCFHESPSSQPRKESMGPPGLESDPEPAALGSSSAHCTNNGVKVGDCDLRDRAEGALL</u>
<u>AESPLGSSDALQSTVPRARDPPVATMVSKGEELFTGVVPILVELDGDVNGHKFSVSGEGEGDATYGKL</u>
*TLKFICTTGKLPVPWPTLVTTLTYGVQCFSRYPDHMKQHDFFKSAMPEGYVQERTIFFKDDGNYKTRA*
*EVKFEGDTLVNRIELKGIDFKEDGNILGHKLEYNYNSHNVYIMADKQKNGIKVNFKIRHNIEDGSVQL*
*ADHYQQNTPIGDGPVLLPDNHYLSTQSALSKDPNEKRDHMVLLEFVTAAGITLGMDELYK-*

CD141 CTLD in bold
CLEC14A rest of molecule <u>underlined</u>
*GFP tag in italics*

B) Chimera 6 – CLEC14A with SUSHI of CD141
Amino acid sequence of whole Chimera 6 fused to GFP tag MRPAFALCLLWQALWPGPGGEHPTADRAGCSASGACYSLHHATMKRQAAEEACILRGGALSTVRAGA
ELRAVLALLRAGPGPGGGSKDLLFWVALERRRSHCTLENEPLRGFSWLSSDPGGLESDTLQWVEEPQR
SCTARRCAVLQATGGVEPAGWKEMRCHLRANGYLCKY<u>HFPATCRPLAVEPGAAAAAVSITYGTPFAAR</u>
<u>GADFQALPVGSSAAVAPLGLQLMCTAPPGAVQGHWAREAPGACPGRYLRAGKCAELPNCLDDLGGFAC</u>
ECATGFELGKDGRSCVTSGEGQPTLGGTGVPTRRPPATATSPVPQRTWPIRVDEKLGETPLVPEQDNS
VTSIPEIPRWGSQSTMSTLQMSLQAESKATITPSGSVISKFNSTTSSATPQAFDSSSAVVFIFVSTAV
VVLVILTMTVLGLVKLCFHESPSSQPRKESMGPPGLESDPEPAALGSSSAHCTNNGVKVGDCDLRDRA
EGALLAESPLGSSDALQSTVPRARDPPVATMVSKGEELFTGVVPILVELDGDVNGHKFSVSGEGEGDA
*TYGKLTLKFICTTGKLPVPWPTLVTTLTYGVQCFSRYPDHMKQHDFFKSAMPEGYVQERTIFFKDDGN*
*YKTRAEVKFEGDTLVNRIELKGIDFKEDGNILGHKLEYNYNSHNVYIMADKQKNGIKVNFKIRHNIED*
*GSVQLADHYQQNTPIGDGPVLLPDNHYLSTQSALSKDPNEKRDHMVLLEFVTAAGITLGMDELYK-*

CLEC14A CTLD in bold
CD141 sushi in <u>underline</u>
CLEC14A rest of molecule in standard text
*GFP tag in italics*

FIG. 14

```
CLEC14A  MRPAFALCLLWQALWPGPGGGEHPTADRAGCSASGACYSLHHATMKRQAAEEACILRGGA   60
CD141    MLGVLVLGALALAGLGFPAPAEPQPGGSQ--CVEHDCFEALYPGPATFLNASQICDGLRGH   58
                  *     :  ..    *   *   .*..  *: :*    **:. *:* :*.

CLEC14A  LSTVRAGAELRAVLALLRAGPPGGGSKDLLFWVALERRSHCTLENE-PLRGFSWLSSD    119
CD141    LMTVRSSVAADVISLLLNGDGGVGRRR----LWIGLQLPPGCGDPKRLGPLRGFQWVTGD   114
          *.***:..*:  :: **:.* . . :.:    *   .* *. * :: * ****:*::.*

CLEC14A  PGGLESDTLQWVEEPQRSCTARRCAVLQATGGVEPAG--WKEMRCHLRANGYLCKY      173
CD141    -NNTSYSRWARLDLNGAPLCGPLCVAVSAAEATVPSEPIWEEQQCEVKADGFLCEF      169
          .. *  .  :: : .    .   *** :.   *..   *:*::*.::.*:**:
```

FIG. 16

Amino acid alignment of CLEC14A CTLD and CD141 CTLD

SEQUENCE LISTING

<160> NUMBER OF SEQ ID NOS: 87

<210> SEQ ID NO 1

```
<211> LENGTH: 6
<212> TYPE: PRT
<213> ORGANISM: Mus <mouse, genus>

<400> SEQUENCE: 1

Ser Ser Tyr Trp Ile Glu
1               5

<210> SEQ ID NO 2
<211> LENGTH: 12
<212> TYPE: PRT
<213> ORGANISM: Mus <mouse, genus>

<400> SEQUENCE: 2

Trp Ile Gly Glu Ile Leu Pro Gly Ser Gly Ser Thr
1               5                  10

<210> SEQ ID NO 3
<211> LENGTH: 14
<212> TYPE: PRT
<213> ORGANISM: Mus <mouse, genus>

<400> SEQUENCE: 3

Ala Arg Gly Gly Asp Tyr Asp Glu Glu Tyr Tyr Leu Met Asp
1               5                  10

<210> SEQ ID NO 4
<211> LENGTH: 6
<212> TYPE: PRT
<213> ORGANISM: Mus <mouse, genus>

<400> SEQUENCE: 4

Ser Tyr Met Tyr Trp Tyr
1               5

<210> SEQ ID NO 5
<211> LENGTH: 10
<212> TYPE: PRT
<213> ORGANISM: Mus <mouse, genus>

<400> SEQUENCE: 5

Leu Leu Ile Tyr Asp Thr Ser Asn Leu Ala
1               5                  10

<210> SEQ ID NO 6
<211> LENGTH: 8
<212> TYPE: PRT
<213> ORGANISM: Mus <mouse, genus>

<400> SEQUENCE: 6

Gln Gln Trp Ser Ser Tyr Pro Leu
1               5

<210> SEQ ID NO 7
<211> LENGTH: 124
<212> TYPE: PRT
<213> ORGANISM: Mus <mouse, genus>

<400> SEQUENCE: 7

Met Ala Gln Val Gln Leu Gln Gln Ser Gly Ala Glu Leu Met Lys Pro
1               5                  10                  15

Gly Ala Ser Val Lys Ile Ser Cys Lys Ala Thr Gly Tyr Thr Phe Ser
            20                  25                  30

Ser Tyr Trp Ile Glu Trp Val Asn Arg Arg Pro Gly His Gly Leu Glu
```

35                  40                  45

Trp Ile Gly Glu Ile Leu Pro Gly Ser Gly Ser Thr Asn Tyr Asn Glu
        50                  55                  60

Lys Phe Lys Gly Lys Ala Thr Phe Thr Ala Asp Thr Ser Ser Asn Thr
65                  70                  75                  80

Ala Tyr Met Gln Leu Ser Ser Leu Thr Ser Glu Asp Ser Ala Val Tyr
                85                  90                  95

Tyr Cys Ala Arg Gly Gly Asp Tyr Asp Glu Gly Tyr Tyr Leu Met Asp
            100                 105                 110

Tyr Trp Gly Gln Gly Thr Thr Leu Thr Val Ser Ser
        115                 120

<210> SEQ ID NO 8
<211> LENGTH: 109
<212> TYPE: PRT
<213> ORGANISM: Mus <mouse, genus>

<400> SEQUENCE: 8

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
                20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Ile Lys Arg Ala Ala
            100                 105

<210> SEQ ID NO 9
<211> LENGTH: 18
<212> TYPE: DNA
<213> ORGANISM: Mus <mouse, genus>
<220> FEATURE:
<221> NAME/KEY: source
<222> LOCATION: 1..18
<223> OTHER INFORMATION: /mol_type="unassigned DNA"
      /organism="Mus <mouse, genus>"

<400> SEQUENCE: 9
agtagctact ggatagag                                                    18

<210> SEQ ID NO 10
<211> LENGTH: 39
<212> TYPE: DNA
<213> ORGANISM: Mus <mouse, genus>
<220> FEATURE:
<221> NAME/KEY: source
<222> LOCATION: 1..39
<223> OTHER INFORMATION: /mol_type="unassigned DNA"
      /organism="Mus <mouse, genus>"

<400> SEQUENCE: 10
tggattggag agattttacc tggaagtggt agtactaat                             39

<210> SEQ ID NO 11
<211> LENGTH: 42

```
<212> TYPE: DNA
<213> ORGANISM: Mus <mouse, genus>
<220> FEATURE:
<221> NAME/KEY: source
<222> LOCATION: 1..42
<223> OTHER INFORMATION: /mol_type="unassigned DNA"
      /organism="Mus <mouse, genus>"

<400> SEQUENCE: 11
gcgagagggg gggattacga cgaagaatac tatctcatgg ac                    42

<210> SEQ ID NO 12
<211> LENGTH: 18
<212> TYPE: DNA
<213> ORGANISM: Mus <mouse, genus>
<220> FEATURE:
<221> NAME/KEY: source
<222> LOCATION: 1..18
<223> OTHER INFORMATION: /mol_type="unassigned DNA"
      /organism="Mus <mouse, genus>"

<400> SEQUENCE: 12
agttacatgt actggtac                                               18

<210> SEQ ID NO 13
<211> LENGTH: 30
<212> TYPE: DNA
<213> ORGANISM: Mus <mouse, genus>
<220> FEATURE:
<221> NAME/KEY: source
<222> LOCATION: 1..30
<223> OTHER INFORMATION: /mol_type="unassigned DNA"
      /organism="Mus <mouse, genus>"

<400> SEQUENCE: 13
ctcctgattt atgacacatc caacctggct                                  30

<210> SEQ ID NO 14
<211> LENGTH: 24
<212> TYPE: DNA
<213> ORGANISM: Mus <mouse, genus>
<220> FEATURE:
<221> NAME/KEY: source
<222> LOCATION: 1..24
<223> OTHER INFORMATION: /mol_type="unassigned DNA"
      /organism="Mus <mouse, genus>"

<400> SEQUENCE: 14
cagcagtgga gtagttaccc gctc                                        24

<210> SEQ ID NO 15
<211> LENGTH: 372
<212> TYPE: DNA
<213> ORGANISM: Mus <mouse, genus>
<220> FEATURE:
<221> NAME/KEY: source
<222> LOCATION: 1..372
<223> OTHER INFORMATION: /mol_type="unassigned DNA"
      /organism="Mus <mouse, genus>"

<400> SEQUENCE: 15
atggcccagg ttcagctgca gcagtctgga gctgagctga tgaagcctgg ggcctcagtg    60
aagatatcct gcaaggctac tggctacaca ttcagtagct actggataga gtgggtaaac   120
cggaggcctg acatggcct tgagtggatt ggagagattt acctggaag tggtagtact    180 aattacaatg agaagttcaa gggcaaggcc acattcactg cagatacatc ctccaataca   240
gcctacatgc aactcagcag cctcacatct gaggactctg ccgtctatta ctgtgcgaga   300
```

-continued

```
gggggggatt acgacgaaga atactatctc atggactact ggggtcaagg caccactctc    360
acagtctcct ca                                                        372

<210> SEQ ID NO 16
<211> LENGTH: 329
<212> TYPE: DNA
<213> ORGANISM: Mus <mouse, genus>
<220> FEATURE:
<221> NAME/KEY: source
<222> LOCATION: 1..329
<223> OTHER INFORMATION: /mol_type="unassigned DNA"
      /organism="Mus <mouse, genus>"

<400> SEQUENCE: 16
caaattgttc tcacccagtc tccagcaatc atgtctgcat ctccagggga gaaggtcacc     60
atgacctgca gtgccagctc aagtgtaagt tacatgtact ggtaccagca gaagccagga   120
tcctccccca gactcctgat ttatgacaca tccaacctgg cttctggagt ccctgttcgc   180
ttcagtggca gtgggtctgg gacctcttac tctctcacaa tcagccgaat ggaggctgaa   240
gatgctgcca cttattactg ccagcagtgg agtagttacc cgctcacgtt cggtgctggg   300
accaagctgg aaatcaaacg tgcggccgc                                     329

<210> SEQ ID NO 17
<211> LENGTH: 490
<212> TYPE: PRT
<213> ORGANISM: Homo sapiens

<400> SEQUENCE: 17
```

Met Arg Pro Ala Phe Ala Leu Cys Leu Leu Trp Gln Ala Leu Trp Pro
1               5                   10                  15

Gly Pro Gly Gly Gly Glu His Pro Thr Ala Asp Arg Ala Gly Cys Ser
            20                  25                  30

Ala Ser Gly Ala Cys Tyr Ser Leu His His Ala Thr Met Lys Arg Gln
        35                  40                  45

Ala Ala Glu Glu Ala Cys Ile Leu Arg Gly Gly Ala Leu Ser Thr Val
    50                  55                  60

Arg Ala Gly Ala Glu Leu Arg Ala Val Leu Ala Leu Leu Arg Ala Gly
65                  70                  75                  80

Pro Gly Pro Gly Gly Gly Ser Lys Asp Leu Leu Phe Trp Val Ala Leu
                85                  90                  95

Glu Arg Arg Arg Ser His Cys Thr Leu Glu Asn Glu Pro Leu Arg Gly
            100                 105                 110

Phe Ser Trp Leu Ser Ser Asp Pro Gly Gly Leu Glu Ser Asp Thr Leu
        115                 120                 125

Gln Trp Val Glu Glu Pro Gln Arg Ser Cys Thr Ala Arg Arg Cys Ala
    130                 135                 140

Val Leu Gln Ala Thr Gly Gly Val Glu Pro Ala Gly Trp Lys Glu Met
145                 150                 155                 160

Arg Cys His Leu Arg Ala Asn Gly Tyr Leu Cys Lys Tyr Gln Phe Glu
                165                 170                 175

Val Leu Cys Pro Ala Pro Arg Pro Gly Ala Ala Ser Asn Leu Ser Tyr
            180                 185                 190

Arg Ala Pro Phe Gln Leu His Ser Ala Ala Leu Asp Phe Ser Pro Pro
        195                 200                 205

Gly Thr Glu Val Ser Ala Leu Cys Arg Gly Gln Leu Pro Ile Ser Val
    210                 215                 220

Thr Cys Ile Ala Asp Glu Ile Gly Ala Arg Trp Asp Lys Leu Ser Gly
225                 230                 235                 240

Asp Val Leu Cys Pro Cys Pro Gly Arg Tyr Leu Arg Ala Gly Lys Cys
            245                 250                 255

Ala Glu Leu Pro Asn Cys Leu Asp Asp Leu Gly Gly Phe Ala Cys Glu
        260                 265                 270

Cys Ala Thr Gly Phe Glu Leu Gly Lys Asp Gly Arg Ser Cys Val Thr
    275                 280                 285

Ser Gly Glu Gly Gln Pro Thr Leu Gly Gly Thr Gly Val Pro Thr Arg
290                 295                 300

Arg Pro Pro Ala Thr Ala Thr Ser Pro Val Pro Gln Arg Thr Trp Pro
305                 310                 315                 320

Ile Arg Val Asp Glu Lys Leu Gly Glu Thr Pro Leu Val Pro Glu Gln
                325                 330                 335

Asp Asn Ser Val Thr Ser Ile Pro Glu Ile Pro Arg Trp Gly Ser Gln
            340                 345                 350

Ser Thr Met Ser Thr Leu Gln Met Ser Leu Gln Ala Glu Ser Lys Ala
        355                 360                 365

Thr Ile Thr Pro Ser Gly Ser Val Ile Ser Lys Phe Asn Ser Thr Thr
370                 375                 380

Ser Ser Ala Thr Pro Gln Ala Phe Asp Ser Ser Ser Ala Val Val Phe
385                 390                 395                 400

Ile Phe Val Ser Thr Ala Val Val Val Leu Val Ile Leu Thr Met Thr
                405                 410                 415

Val Leu Gly Leu Val Lys Leu Cys Phe His Glu Ser Pro Ser Ser Gln
            420                 425                 430

Pro Arg Lys Glu Ser Met Gly Pro Pro Gly Leu Glu Ser Asp Pro Glu
        435                 440                 445

Pro Ala Ala Leu Gly Ser Ser Ser Ala His Cys Thr Asn Asn Gly Val
450                 455                 460

Lys Val Gly Asp Cys Asp Leu Arg Asp Arg Ala Glu Gly Ala Leu Leu
465                 470                 475                 480

Ala Glu Ser Pro Leu Gly Ser Ser Asp Ala
                485                 490

<210> SEQ ID NO 18
<211> LENGTH: 2256
<212> TYPE: DNA
<213> ORGANISM: Homo sapiens
<220> FEATURE:
<221> NAME/KEY: source
<222> LOCATION: 1..2256
<223> OTHER INFORMATION: /mol_type="unassigned DNA"
      /organism="Homo sapiens"

<400> SEQUENCE: 18
ctcctcttgc tctaagcagg gtgtttgacc ttctagtcga ctgcgtcccc tgtacccggc    60
gccagctgtg ttcctgaccc cagaataact cagggctgca ccgggcctgg cagcgctccg   120
cacacatttc ctgtcgcggc ctaagggaaa ctgttggccg ctgggcccgc gggggattc    180 ttggcagttg gggggtccgt cgggagcgag ggcggagggg aagggagggg gaaccgggtt   240
ggggaagcca gctgtagagg gcggtgaccg cgctccagac acagctctgc gtcctcgagc   300
gggacagatc caagttggga gcagctctgc gtgcggggcc tcagagaatg aggcggcgt    360 tcgccctgtg cctcctctgg caggcgctct ggcccgggcc gggcggcggc gaacacccca   420

| | |
|---|---|
| ctgccgaccg tgctggctgc tcggcctcgg gggcctgcta cagcctgcac cacgctacca | 480 |
| tgaagcggca ggcggccgag gaggcctgca tcctgcgagg tggggcgctc agcaccgtgc | 540 |
| gtgcgggcgc cgagctgcgc gctgtgctcg cgctcctgcg ggcaggccca gggcccggag | 600 |
| ggggctccaa agacctgctg ttctgggtcg cactggagcg caggcgttcc cactgcaccc | 660 |
| tggagaacga gcctttgcgg ggtttctcct ggctgtcctc cgaccccggc ggtctcgaaa | 720 |
| gcgacacgct gcagtgggtg gaggagcccc aacgctcctg caccgcgcgg agatgcgcgg | 780 |
| tactccaggc caccggtggg gtcgagcccg caggctggaa ggagatgcga tgccacctgc | 840 |
| gcgccaacgg ctacctgtgc aagtaccagt ttgaggtctt gtgtcctgcg ccgcgccccg | 900 |
| gggccgcctc taacttgagc tatcgcgcgc ccttccagct gcacagcgcc gctctggact | 960 |
| tcagtccacc tgggaccgag gtgagtgcgc tctgccgggg acagctcccg atctcagtta | 1020 |
| cttgcatcgc ggacgaaatc ggcgctcgct gggacaaact ctcgggcgat gtgttgtgtc | 1080 |
| cctgccccgg gaggtacctc cgtgctggca aatgcgcaga gctccctaac tgcctagacg | 1140 |
| acttgggagg ctttgcctgc gaatgtgcta cgggcttcga gctggggaag gacggccgct | 1200 |
| cttgtgtgac cagtggggaa ggacagccga cccttggggg gaccggggtg cccaccaggc | 1260 |
| gcccgccggc cactgcaacc agcccgtgc cgcagagaac atggccaatc agggtcgacg | 1320 |
| agaagctggg agagacacca cttgtccctg aacaagacaa ttcagtaaca tctattcctg | 1380 |
| agattcctcg atggggatca cagagcacga tgtctaccct tcaaatgtcc cttcaagccg | 1440 |
| agtcaaaggc cactatcacc ccatcaggga gcgtgatttc caagtttaat tctacgactt | 1500 |
| cctctgccac tcctcaggct ttcgactcct cctctgccgt ggtcttcata tttgtgagca | 1560 |
| cagcagtagt agtgttggtg atcttgacca tgacagtact ggggcttgtc aagctctgct | 1620 |
| ttcacgaaag cccctcttcc cagccaagga aggagtctat gggcccgccg ggcctggaga | 1680 |
| gtgatcctga gcccgctgct ttgggctcca gttctgcaca ttgcacaaac aatggggtga | 1740 |
| aagtcgggga ctgtgatctg cgggacagag cagagggtgc cttgctggcg gagtcccctc | 1800 |
| ttggctctag tgatgcatag ggaaacaggg gacatgggca ctcctgtgaa cagttttca | 1860 |
| cttttgatga acggggaac caagaggaac ttacttgtgt aactgacaat ttctgcagaa | 1920 |
| atcccccttc ctctaaattc cctttactcc actgaggagc taaatcagaa ctgcacactc | 1980 |
| cttccctgat gatagaggaa gtggaagtgc ctttaggatg gtgatactgg gggaccgggt | 2040 |
| agtgctgggg agagatattt tcttatgttt attcggagaa tttggagaag tgattgaact | 2100 |
| tttcaagaca ttggaaacaa atagaacaca atataattta cattaaaaaa taatttctac | 2160 |
| caaaatggaa aggaaatgtt ctatgttgtt caggctagga gtatattggt tcgaaatccc | 2220 |
| agggaaaaaa ataaaaataa aaaattaaag gattgt | 2256 |

<210> SEQ ID NO 19
<211> LENGTH: 1473
<212> TYPE: DNA
<213> ORGANISM: Homo sapiens
<220> FEATURE:
<221> NAME/KEY: source
<222> LOCATION: 1..1473
<223> OTHER INFORMATION: /mol_type="unassigned DNA"
      /organism="Homo sapiens"

<400> SEQUENCE: 19

| | |
|---|---|
| atgaggccgg cgttcgccct gtgcctcctc tggcaggcgc tctggcccgg gccgggcggc | 60 |
| ggcgaacacc ccactgccga ccgtgctggc tgctcggcct cggggggcctg ctacagcctg | 120 |

| | |
|---|---|
| caccacgcta ccatgaagcg gcaggcggcc gaggaggcct gcatcctgcg aggtggggcg | 180 |
| ctcagcaccg tgcgtgcggg cgccgagctg cgcgctgtgc tcgcgctcct gcgggcaggc | 240 |
| ccagggcccg gaggggctc caaagacctg ctgttctggg tcgcactgga gcgcaggcgt | 300 |
| tcccactgca ccctggagaa cgagcctttg cggggtttct cctggctgtc ctccgacccc | 360 |
| ggcggtctcg aaagcgacac gctgcagtgg gtggaggagc cccaacgctc ctgcaccgcg | 420 |
| cggagatgcg cggtactcca ggccaccggt ggggtcgagc ccgcaggctg gaaggagatg | 480 |
| cgatgccacc tgcgcgccaa cggctacctg tgcaagtacc agtttgaggt cttgtgtcct | 540 |
| gcgccgcgcc ccggggccgc ctctaacttg agctatcgcg cgcccttcca gctgcacagc | 600 |
| gccgctctgg acttcagtcc acctgggacc gaggtgagtg cgctctgccg ggacagctc | 660 |
| ccgatctcag ttacttgcat cgcggacgaa atcggcgctc gctgggacaa actctcgggc | 720 |
| gatgtgttgt gtccctgccc cggaggtac ctccgtgctg gcaaatgcgc agagctccct | 780 |
| aactgcctag acgacttggg aggctttgcc tgcgaatgtg ctacgggctt cgagctgggg | 840 |
| aaggacggcc gctcttgtgt gaccagtggg gaaggacagc cgacccttgg ggggaccggg | 900 |
| gtgcccacca ggcgcccgcc ggccactgca accagccccg tgccgcagag aacatggcca | 960 |
| atcagggtcg acgagaagct gggagagaca ccacttgtcc ctgaacaaga caattcagta | 1020 |
| acatctattc ctgagattcc tcgatgggga tcacagagca cgatgtctac ccttcaaatg | 1080 |
| tcccttcaag ccgagtcaaa ggccactatc accccatcag ggagcgtgat ttccaagttt | 1140 |
| aattctacga cttcctctgc cactcctcag gctttcgact cctcctctgc cgtggtcttc | 1200 |
| atatttgtga gcacagcagt agtagtgttg gtgatcttga ccatgacagt actggggctt | 1260 |
| gtcaagctct gctttcacga aagcccctct tcccagccaa ggaaggagtc tatgggcccg | 1320 |
| ccgggcctgg agagtgatcc tgagcccgct gctttgggct ccagttctgc acattgcaca | 1380 |
| aacaatgggg tgaaagtcgg ggactgtgat ctgcgggaca gagcagaggg tgccttgctg | 1440 |
| gcggagtccc ctcttggctc tagtgatgca tag | 1473 |

<210> SEQ ID NO 20
<211> LENGTH: 949
<212> TYPE: PRT
<213> ORGANISM: Homo sapiens

<400> SEQUENCE: 20

Met Ile Leu Ser Leu Leu Phe Ser Leu Gly Gly Pro Leu Gly Trp Gly
1               5                   10                  15

Leu Leu Gly Ala Trp Ala Gln Ala Ser Ser Thr Ser Leu Ser Asp Leu
            20                  25                  30

Gln Ser Ser Arg Thr Pro Gly Val Trp Lys Ala Glu Ala Glu Asp Thr
        35                  40                  45

Gly Lys Asp Pro Val Gly Arg Asn Trp Cys Pro Tyr Pro Met Ser Lys
    50                  55                  60

Leu Val Thr Leu Leu Ala Leu Cys Lys Thr Glu Lys Phe Leu Ile His
65                  70                  75                  80

Ser Gln Gln Pro Cys Pro Gln Gly Ala Pro Asp Cys Gln Lys Val Lys
                85                  90                  95

Val Met Tyr Arg Met Ala His Lys Pro Val Tyr Gln Val Lys Gln Lys
            100                 105                 110

Val Leu Thr Ser Leu Ala Trp Arg Cys Cys Pro Gly Tyr Thr Gly Pro
        115                 120                 125

Asn Cys Glu His His Asp Ser Met Ala Ile Pro Glu Pro Ala Asp Pro

```
                130             135             140
Gly Asp Ser His Gln Glu Pro Gln Asp Gly Pro Val Ser Phe Lys Pro
145                 150                 155                 160

Gly His Leu Ala Ala Val Ile Asn Glu Val Glu Val Gln Gln Glu Gln
                165                 170                 175

Gln Glu His Leu Leu Gly Asp Leu Gln Asn Asp Val His Arg Val Ala
                180                 185                 190

Asp Ser Leu Pro Gly Leu Trp Lys Ala Leu Pro Gly Asn Leu Thr Ala
                195                 200                 205

Ala Val Met Glu Ala Asn Gln Thr Gly His Glu Phe Pro Asp Arg Ser
210                 215                 220

Leu Glu Gln Val Leu Leu Pro His Val Asp Thr Phe Leu Gln Val His
225                 230                 235                 240

Phe Ser Pro Ile Trp Arg Ser Phe Asn Gln Ser Leu His Ser Leu Thr
                245                 250                 255

Gln Ala Ile Arg Asn Leu Ser Leu Asp Val Glu Ala Asn Arg Gln Ala
                260                 265                 270

Ile Ser Arg Val Gln Asp Ser Ala Val Ala Arg Ala Asp Phe Gln Glu
                275                 280                 285

Leu Gly Ala Lys Phe Glu Ala Lys Val Gln Glu Asn Thr Gln Arg Val
290                 295                 300

Gly Gln Leu Arg Gln Asp Val Glu Asp Arg Leu His Ala Gln His Phe
305                 310                 315                 320

Thr Leu His Arg Ser Ile Ser Glu Leu Gln Ala Asp Val Asp Thr Lys
                325                 330                 335

Leu Lys Arg Leu His Lys Ala Gln Glu Ala Pro Gly Thr Asn Gly Ser
                340                 345                 350

Leu Val Leu Ala Thr Pro Gly Ala Gly Ala Arg Pro Glu Pro Asp Ser
                355                 360                 365

Leu Gln Ala Arg Leu Gly Gln Leu Gln Arg Asn Leu Ser Glu Leu His
                370                 375                 380

Met Thr Thr Ala Arg Arg Glu Glu Glu Leu Gln Tyr Thr Leu Glu Asp
385                 390                 395                 400

Met Arg Ala Thr Leu Thr Arg His Val Asp Glu Ile Lys Glu Leu Tyr
                405                 410                 415

Ser Glu Ser Asp Glu Thr Phe Asp Gln Ile Ser Lys Val Glu Arg Gln
                420                 425                 430

Val Glu Glu Leu Gln Val Asn His Thr Ala Leu Arg Glu Leu Arg Val
                435                 440                 445

Ile Leu Met Glu Lys Ser Leu Ile Met Glu Glu Asn Lys Glu Glu Val
                450                 455                 460

Glu Arg Gln Leu Leu Glu Leu Asn Leu Thr Gln His Leu Gln Leu Gly
465                 470                 475                 480

Gly His Ala Asp Leu Ile Lys Tyr Val Lys Asp Cys Asn Cys Gln Lys
                485                 490                 495

Leu Tyr Leu Asp Leu Asp Val Ile Arg Glu Gly Gln Arg Asp Ala Thr
                500                 505                 510

Arg Ala Leu Glu Glu Thr Gln Val Ser Leu Asp Glu Arg Arg Gln Leu
                515                 520                 525

Asp Gly Ser Ser Leu Gln Ala Leu Gln Asn Ala Val Asp Ala Val Ser
                530                 535                 540

Leu Ala Val Asp Ala His Lys Ala Glu Gly Glu Arg Ala Arg Ala Ala
545                 550                 555                 560
```

```
Thr Ser Arg Leu Arg Ser Gln Val Gln Ala Leu Asp Asp Glu Val Gly
            565                 570                 575

Ala Leu Lys Ala Ala Ala Glu Ala Arg His Glu Val Arg Gln Leu
        580                 585                 590

His Ser Ala Phe Ala Ala Leu Leu Glu Asp Ala Leu Arg His Glu Ala
            595                 600                 605

Val Leu Ala Ala Leu Phe Gly Glu Val Leu Glu Glu Met Ser Glu
610                 615                 620

Gln Thr Pro Gly Pro Leu Pro Leu Ser Tyr Glu Gln Ile Arg Val Ala
625                 630                 635                 640

Leu Gln Asp Ala Ala Ser Gly Leu Gln Glu Gln Ala Leu Gly Trp Asp
            645                 650                 655

Glu Leu Ala Ala Arg Val Thr Ala Leu Glu Gln Ala Ser Glu Pro Pro
            660                 665                 670

Arg Pro Ala Glu His Leu Glu Pro Ser His Asp Ala Gly Arg Glu Glu
            675                 680                 685

Ala Ala Thr Thr Ala Leu Ala Gly Leu Ala Arg Glu Leu Gln Ser Leu
            690                 695                 700

Ser Asn Asp Val Lys Asn Val Gly Arg Cys Cys Glu Ala Glu Ala Gly
705                 710                 715                 720

Ala Gly Ala Ala Ser Leu Asn Ala Ser Leu Asp Gly Leu His Asn Ala
            725                 730                 735

Leu Phe Ala Thr Gln Arg Ser Leu Glu Gln His Gln Arg Leu Phe His
            740                 745                 750

Ser Leu Phe Gly Asn Phe Gln Gly Leu Met Glu Ala Asn Val Ser Leu
            755                 760                 765

Asp Leu Gly Lys Leu Gln Thr Met Leu Ser Arg Lys Gly Lys Lys Gln
            770                 775                 780

Gln Lys Asp Leu Glu Ala Pro Arg Lys Arg Asp Lys Lys Glu Ala Glu
785                 790                 795                 800

Pro Leu Val Asp Ile Arg Val Thr Gly Pro Val Pro Gly Ala Leu Gly
            805                 810                 815

Ala Ala Leu Trp Glu Ala Gly Ser Pro Val Ala Phe Tyr Ala Ser Phe
            820                 825                 830

Ser Glu Gly Thr Ala Ala Leu Gln Thr Val Lys Phe Asn Thr Thr Tyr
            835                 840                 845

Ile Asn Ile Gly Ser Ser Tyr Phe Pro Glu His Gly Tyr Phe Arg Ala
850                 855                 860

Pro Glu Arg Gly Val Tyr Leu Phe Ala Val Ser Val Glu Phe Gly Pro
865                 870                 875                 880

Gly Pro Gly Thr Gly Gln Leu Val Phe Gly Gly His His Arg Thr Pro
            885                 890                 895

Val Cys Thr Thr Gly Gln Gly Ser Gly Ser Thr Ala Thr Val Phe Ala
            900                 905                 910

Met Ala Glu Leu Gln Lys Gly Glu Arg Val Trp Phe Glu Leu Thr Gln
            915                 920                 925

Gly Ser Ile Thr Lys Arg Ser Leu Ser Gly Thr Ala Phe Gly Gly Phe
            930                 935                 940

Leu Met Phe Lys Thr
945

<210> SEQ ID NO 21
<211> LENGTH: 2850
```

<212> TYPE: DNA
<213> ORGANISM: Homo sapiens
<220> FEATURE:
<221> NAME/KEY: source
<222> LOCATION: 1..2850
<223> OTHER INFORMATION: /mol_type="unassigned DNA"
      /organism="Homo sapiens"

<400> SEQUENCE: 21

```
atgatcctga gcttgctgtt cagccttggg ggccccctgg gctgggggct gctgggggca      60
tgggcccagg cttccagtac tagcctctct gatctgcaga gctccaggac acctggggtc     120
tggaaggcag aggctgagga caccggcaag gaccccgttg gacgtaactg gtgccctac      180
ccaatgtcca agctggtcac cttactagct ctttgcaaaa cagagaaatt cctcatccac     240
tcgcagcagc cgtgtccgca gggagctcca gactgccaga aagtcaaagt catgtaccgc     300
atggcccaca agccagtgta ccaggtcaag cagaaggtgc tgacctcttt ggcctggagg     360
tgctgccctg gctacacggg ccccaactgc gagcaccacg attccatggc aatccctgag     420
cctgcagatc ctggtgacag ccaccaggaa cctcaggatg accagtcag cttcaaacct      480
ggccaccttg ctgcagtgat caatgaggtt gaggtgcaac aggaacagca ggaacatctg     540
ctgggagatc tccagaatga tgtgcaccgg gtggcagaca gctgccagg cctgtggaaa      600
gccctgcctg gtaacctcac agctgcagtg atggaagcaa atcaaacagg gcacgagttc     660
cctgatagat ccttggagca ggtgctgcta ccccacgtgg acaccttcct acaagtgcat     720
ttcagcccca tctggaggag cttttaaccaa agcctgcaca gccttaccca ggccataaga     780
aacctgtctc ttgacgtgga ggccaaccgc caggccatct ccagagtcca ggacagtgcc     840
gtggccaggg ctgacttcca ggagcttggt gccaaatttg aggccaaggt ccaggagaac     900
actcagagag tgggtcagct cgacaggac gtggaggacc gcctgcacgc ccagcacttt      960
accctgcacc gctcgatctc agagctccaa gccgatgtgg acaccaaatt gaagaggctg    1020
cacaaggctc aggaggcccc aggaccaat ggcagtctgg tgttggcaac gcctgggct      1080
ggggcaaggc ctgagccgga cagcctgcag gccaggctgg gccagctgca gaggaacctc    1140
tcagagctgc acatgaccac ggcccgcagg gaggaggagt tgcagtacac cctggaggac    1200
atgagggcca ccctgacccg gcacgtggat gagatcaagg aactgtactc cgaatcggac    1260
gagactttcg atcagattag caaggtggag cggcaggtgg aggagctgca ggtgaaccac    1320
acggcgctcc gtgagctgcg cgtgatcctg atggagaagt ctctgatcat ggaggagaac    1380
aaggaggagg tggagcggca gctcctggag ctcaacctca gctgcagca cctgcagggt    1440
ggccatgccg acctcatcaa gtacgtgaag gactgcaatt gccagaagct ctatttagac    1500
ctggacgtca tccgggaggg ccagagggac gccacgcgtg ccctggagga gacccaggtg    1560
agcctggacg agcggcggca gctggacggc tcctccctgc aggccctgca gaacgccgtg    1620
gacgccgtgt cgctggccgt ggacgcgcac aaagcggagg gcgagcgggc gcgggcggcc    1680
acgtcgcggc tccggagcca agtgcaggcg ctggatgacg aggtgggcgc gctgaaggcg    1740
gccgcggccg aggcccgcca cgaggtgcgc cagctgcaca gcgccttcgc cgccctgctg    1800
gaggacgcgc tgcggcacga ggcggtgctg ccgcgctct cggggagga ggtgctggag     1860
gagatgtctg agcagacgcc gggaccgctg ccctgagct acgagcagat ccgcgtggcc    1920
ctgcaggacg ccgctagcgg gctgcaggag caggcgctcg gctggacga gctgccgcc     1980
cgagtgacgg ccctggagca ggcctcggag ccccgcggc cggcagagca cctggagccc    2040
agccacgacg cgggccgcga ggaggccgcc accaccgccc tggccgggct ggcgcgggag    2100
```

```
ctccagagcc tgagcaacga cgtcaagaat gtcgggcggt gctgcgaggc tgaggccggg    2160
gccggggccg cctccctcaa cgcctcoctt gacggcctcc acaacgcact cttcgccact    2220
cagcgcagct tggagcagca ccagcggctc ttccacagcc tctttgggaa cttccaaggg    2280
ctcatggaag ccaacgtcag cctggacctg gggaagctgc agaccatgct gagcaggaaa    2340
gggaagaagc agcagaaaga cctggaagct ccccggaaga gggacaagaa ggaagcggag    2400
cctttggtgg acatacgggt cacagggcct gtgccaggtg ccttgggcgc ggcgctctgg    2460
gaggcaggat cccctgtggc cttctatgcc agcttttcag aagggacggc tgccctgcag    2520
acagtgaagt tcaacaccac atacatcaac attggcagca gctacttccc tgaacatggc    2580
tacttccgag ccctgagcg tggtgtctac ctgtttgcag tgagcgttga atttggccca    2640
gggccaggca ccgggcagct ggtgtttgga ggtcaccatc ggactccagt ctgtaccact    2700
gggcagggga gtggaagcac agcaacggtc tttgccatgg ctgagctgca aagggtgag    2760 cgagtatggt ttgagttaac ccagggatca ataacaaaga gaagcctgtc gggcactgca    2820
tttgggggct tcctgatgtt taagacctga                                    2850

<210> SEQ ID NO 22
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="unassigned DNA"
      /note="CLEC14A primer"
      /organism="Artificial Sequence"

<400> SEQUENCE: 22
tagtaggaat tcgagagaat gaggccggcg ttcgccctg                           39

<210> SEQ ID NO 23
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="unassigned DNA"
      /note="CLEC14A primer"
      /organism="Artificial Sequence"

<400> SEQUENCE: 23
agaaccgcgg ccgctggagg agtcgaaagc ctgaggagt                           39

<210> SEQ ID NO 24
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="unassigned DNA"
      /note="CLEC14A primer"
      /organism="Artificial Sequence"

<400> SEQUENCE: 24
tagtaggaat tcgagagaat gaggccagcg cttgccctg                           39

<210> SEQ ID NO 25
<211> LENGTH: 36
<212> TYPE: DNA
```

```
<213> ORGANISM: Artificial Sequence
<220> FEATURE:
<221> NAME/KEY: source
<222> LOCATION: 1..36
<223> OTHER INFORMATION: /mol_type="unassigned DNA"
      /note="CLEC14A primer"
      /organism="Artificial Sequence"

<400> SEQUENCE: 25
ctactagcgg ccgctcgtgg aagaggtgtc gaaagt                              36

<210> SEQ ID NO 26
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="CLEC14A primer"
      /organism="Artificial Sequence"

<400> SEQUENCE: 26
tagtagttaa ttaagagaga atgaggccgg cgttc                               35

<210> SEQ ID NO 27
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="CLEC14A primer"
      /organism="Artificial Sequence"

<400> SEQUENCE: 27
tagtagttaa ttaagagaga atgaggccag cgctt                               35

<210> SEQ ID NO 28
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="Fc primer"
      /organism="Artificial Sequence"

<400> SEQUENCE: 28
ctactagttt aaactcattt acccggagac aggga                               35

<210> SEQ ID NO 29
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="MMRN2 primer"
      /organism="Artificial Sequence"

<400> SEQUENCE: 29
ccggaccggt caggcttcca gtactagcc                                      29

<210> SEQ ID NO 30
<211> LENGTH: 29
```

```
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="MMRN2 primer"
      /organism="Artificial Sequence"

<400> SEQUENCE: 30
cggggtaccg gtcttaaaca tcaggaagc                               29

<210> SEQ ID NO 31
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="5'UTR primer"
      /organism="Artificial Sequence"

<400> SEQUENCE: 31
ttccttttcc agggtttgtg                                         20

<210> SEQ ID NO 32
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="5' UTR primer"
      /organism="Artificial Sequence"

<400> SEQUENCE: 32
gcctacaagg tggcttgaat                                         20

<210> SEQ ID NO 33
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="CDS primer"
      /organism="Artificial Sequence"

<400> SEQUENCE: 33
aagctgtgct cctgctcttg                                         20

<210> SEQ ID NO 34
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="CDS primer"
      /organism="Artificial Sequence"

<400> SEQUENCE: 34
tcctgagtgc actgtgagat g                                       21

<210> SEQ ID NO 35
```

```
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="3' UTR primer"
      /organism="Artificial Sequence"

<400> SEQUENCE: 35
ctgtagaggg cggtgacttt                                                20

<210> SEQ ID NO 36
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="3' UTR primer"
      /organism="Artificial Sequence"

<400> SEQUENCE: 36
agctgctccc aagtcctct                                                 19

<210> SEQ ID NO 37
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="mACTB primer"
      /organism="Artificial Sequence"

<400> SEQUENCE: 37
ctaaggccaa ccgtgaaaag                                                20

<210> SEQ ID NO 38
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="mACTB primer"
      /organism="Artificial Sequence"

<400> SEQUENCE: 38
accagaggca tacagggaca                                                20

<210> SEQ ID NO 39
<211> LENGTH: 12
<212> TYPE: PRT
<213> ORGANISM: Homo sapiens

<400> SEQUENCE: 39

Glu Arg Arg Arg Ser Cys His Thr Leu Glu Asn Glu
1               5                   10

<210> SEQ ID NO 40
<211> LENGTH: 8
<212> TYPE: PRT
<213> ORGANISM: Mus <mouse, genus>
```

```
<400> SEQUENCE: 40

Gly Tyr Thr Phe Ser Ser Tyr Trp
1               5

<210> SEQ ID NO 41
<211> LENGTH: 8
<212> TYPE: PRT
<213> ORGANISM: Mus <mouse, genus>

<400> SEQUENCE: 41

Ile Leu Pro Gly Ser Gly Ser Thr
1               5

<210> SEQ ID NO 42
<211> LENGTH: 15
<212> TYPE: PRT
<213> ORGANISM: Mus <mouse, genus>

<400> SEQUENCE: 42

Ala Arg Gly Gly Asp Tyr Asp Glu Glu Tyr Tyr Leu Met Asp Tyr
1               5                   10                  15

<210> SEQ ID NO 43
<211> LENGTH: 5
<212> TYPE: PRT
<213> ORGANISM: Mus <mouse, genus>

<400> SEQUENCE: 43

Ser Ser Val Ser Tyr
1               5

<210> SEQ ID NO 44
<211> LENGTH: 9
<212> TYPE: PRT
<213> ORGANISM: Mus <mouse, genus>

<400> SEQUENCE: 44

Gln Gln Trp Ser Ser Tyr Pro Leu Thr
1               5

<210> SEQ ID NO 45
<211> LENGTH: 15
<212> TYPE: PRT
<213> ORGANISM: Mus <mouse, genus>

<400> SEQUENCE: 45

Ala Arg Gly Gly Asp Tyr Asp Glu Glu Tyr Tyr Val Met Asp Tyr
1               5                   10                  15

<210> SEQ ID NO 46
<211> LENGTH: 14
<212> TYPE: PRT
<213> ORGANISM: Mus <mouse, genus>

<400> SEQUENCE: 46

Ala Arg Gly Gly Asp Tyr Asp Glu Glu Tyr Tyr Ala Met Asp
1               5                   10

<210> SEQ ID NO 47
<211> LENGTH: 15
<212> TYPE: PRT
<213> ORGANISM: Mus <mouse, genus>

<400> SEQUENCE: 47
```

```
Ala Arg Gly Gly Asp Tyr Asp Glu Glu Tyr Tyr Ala Met Asp Tyr
1               5                   10                  15
```

<210> SEQ ID NO 48
<211> LENGTH: 10
<212> TYPE: PRT
<213> ORGANISM: Mus <mouse, genus>

<400> SEQUENCE: 48

```
Gln Gln Trp Ser Ser Tyr Pro Leu Thr Phe
1               5                   10
```

<210> SEQ ID NO 49
<211> LENGTH: 122
<212> TYPE: PRT
<213> ORGANISM: Mus <mouse, genus>

<400> SEQUENCE: 49

```
Met Ala Gln Val Gln Leu Gln Gln Ser Gly Ala Glu Leu Met Lys Pro
1               5                   10                  15

Gly Ala Ser Val Lys Ile Ser Cys Lys Ala Thr Gly Tyr Thr Phe Ser
                20                  25                  30

Ser Tyr Trp Ile Glu Trp Val Asn Arg Arg Pro Gly His Gly Leu Glu
            35                  40                  45

Trp Ile Gly Glu Ile Leu Pro Gly Ser Gly Ser Thr Asn Tyr Asn Glu
        50                  55                  60

Lys Phe Lys Gly Lys Ala Thr Phe Thr Ala Asp Thr Ser Ser Asn Thr
65                  70                  75                  80

Ala Tyr Met Gln Leu Ser Ser Leu Thr Ser Glu Asp Ser Ala Val Tyr
                85                  90                  95

Tyr Cys Ala Arg Gly Gly Asp Tyr Asp Glu Glu Tyr Tyr Leu Met Asp
            100                 105                 110

Tyr Trp Gly Gln Gly Thr Thr Leu Thr Val
        115                 120
```

<210> SEQ ID NO 50
<211> LENGTH: 110
<212> TYPE: PRT
<213> ORGANISM: Mus <mouse, genus>

<400> SEQUENCE: 50

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Ile Lys Arg Ala Ala Ala
            100                 105                 110
```

<210> SEQ ID NO 51
<211> LENGTH: 60
<212> TYPE: PRT

<213> ORGANISM: Mus <mouse, genus>

<400> SEQUENCE: 51

Met Ala Glu Val Gln Leu Gln Gln Ser Gly Ala Glu Leu Met Lys Pro
1               5                   10                  15

Gly Ala Ser Val Lys Ile Ser Cys Lys Ala Thr Gly Tyr Thr Phe Ser
            20                  25                  30

Ser Tyr Trp Ile Glu Trp Val Lys Gln Arg Pro Gly His Gly Leu Glu
        35                  40                  45

Trp Ile Gly Glu Ile Leu Pro Gly Ser Gly Ser Thr
50                  55                  60

<210> SEQ ID NO 52
<211> LENGTH: 58
<212> TYPE: PRT
<213> ORGANISM: Mus <mouse, genus>

<400> SEQUENCE: 52

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro
50                  55

<210> SEQ ID NO 53
<211> LENGTH: 60
<212> TYPE: PRT
<213> ORGANISM: Mus <mouse, genus>

<400> SEQUENCE: 53

Met Ala Glu Val Gln Leu Gln Gln Ser Gly Ala Glu Leu Met Lys Pro
1               5                   10                  15

Gly Ala Ser Val Lys Ile Ser Cys Lys Ala Thr Gly Tyr Thr Phe Ser
            20                  25                  30

Ser Tyr Trp Ile Glu Trp Val Asn Gln Arg Pro Gly His Gly Leu Glu
        35                  40                  45

Trp Ile Gly Glu Ile Leu Pro Gly Ser Gly Ser Thr
50                  55                  60

<210> SEQ ID NO 54
<211> LENGTH: 107
<212> TYPE: PRT
<213> ORGANISM: Mus <mouse, genus>

<400> SEQUENCE: 54

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
50                  55                  60

Gly Ser Gly Thr Ser Tyr Ser Leu Thr Ile Ser Arg Met Glu Ala Glu
65                  70                  75                  80

-continued

Asp Gly Ala Thr Tyr Tyr Cys Gln Gln Trp Ser Ser Tyr Pro Leu Thr
                85                  90                  95

Phe Gly Ala Gly Thr Lys Leu Glu Leu Lys Arg
            100                 105

<210> SEQ ID NO 55
<211> LENGTH: 249
<212> TYPE: PRT
<213> ORGANISM: Mus <mouse, genus>

<400> SEQUENCE: 55

Met Ala Gln Val Gln Leu Gln Gln Ser Gly Ala Glu Leu Met Lys Pro
1               5                   10                  15

Gly Ala Ser Val Lys Ile Ser Cys Lys Ala Thr Gly Tyr Thr Phe Ser
            20                  25                  30

Ser Tyr Trp Ile Glu Trp Val Asn Arg Arg Pro Gly His Gly Leu Glu
        35                  40                  45

Trp Ile Gly Glu Ile Leu Pro Gly Ser Gly Ser Thr Asn Tyr Asn Glu
50                  55                  60

Lys Phe Lys Gly Lys Ala Thr Phe Thr Ala Asp Thr Ser Ser Asn Thr
65                  70                  75                  80

Ala Tyr Met Gln Leu Ser Ser Leu Thr Ser Glu Asp Ser Val Val Tyr
                85                  90                  95

Tyr Cys Ala Arg Gly Gly Asp Tyr Asp Glu Tyr Tyr Leu Met Asp
            100                 105                 110

Tyr Trp Gly Gln Gly Thr Thr Leu Thr Val Ser Ser Gly Gly Gly Gly
        115                 120                 125

Ser Gly Gly Gly Gly Ser Gly Gly Gly Gly Ser Gln Ile Val Leu Thr
    130                 135                 140

Gln Ser Pro Ala Ile Met Ser Ala Ser Pro Gly Glu Lys Val Thr Met
145                 150                 155                 160

Thr Cys Ser Ala Ser Ser Ser Val Ser Tyr Met Tyr Trp Tyr Gln Gln
                165                 170                 175

Lys Pro Gly Ser Ser Pro Arg Leu Leu Ile Tyr Asp Thr Ser Asn Leu
            180                 185                 190

Ala Ser Gly Val Pro Val Arg Phe Ser Gly Ser Gly Ser Gly Thr Ser
        195                 200                 205

Tyr Ser Leu Thr Ile Ser Arg Met Glu Ala Glu Asp Ala Ala Thr Tyr
    210                 215                 220

Tyr Cys Gln Gln Trp Ser Ser Tyr Pro Leu Thr Phe Gly Ala Gly Thr
225                 230                 235                 240

Lys Leu Glu Ile Lys Arg Ala Ala Ala
                245

<210> SEQ ID NO 56
<211> LENGTH: 246
<212> TYPE: PRT
<213> ORGANISM: Mus <mouse, genus>

<400> SEQUENCE: 56

Met Ala Glu Val Gln Leu Gln Gln Ser Gly Ala Glu Leu Met Lys Pro
1               5                   10                  15

Gly Ala Ser Val Lys Ile Ser Cys Lys Ala Thr Gly Tyr Thr Phe Ser
            20                  25                  30

Ser Tyr Trp Ile Glu Trp Val Lys Gln Arg Pro Gly His Gly Leu Glu
        35                  40                  45

```
Trp Ile Gly Glu Ile Leu Pro Gly Ser Gly Ser Thr Asn Tyr Asn Glu
         50                  55                  60

Lys Phe Lys Gly Lys Ala Thr Phe Thr Ala Asp Thr Ser Ser Asn Thr
 65                  70                  75                  80

Ala Tyr Met Gln Leu Ser Ser Leu Thr Ser Glu Asp Ser Ala Val Tyr
                 85                  90                  95

Tyr Cys Ala Arg Gly Gly Asp Tyr Asp Glu Tyr Tyr Val Met Asp
                100                 105                 110

Tyr Trp Gly Gln Gly Thr Ser Val Thr Val Ser Ser Gly Gly Gly
                115                 120                 125

Ser Gly Gly Gly Ser Gly Gly Gly Ser Gln Ile Val Leu Thr
        130                 135                 140

Gln Ser Pro Ala Ile Met Ser Ala Ser Pro Gly Glu Lys Val Thr Met
145                 150                 155                 160

Thr Cys Ser Ala Ser Ser Val Ser Tyr Met Tyr Trp Tyr Gln Gln
                165                 170                 175

Lys Pro Gly Ser Ser Pro Arg Leu Leu Ile Tyr Asp Thr Ser Asn Leu
                180                 185                 190

Ala Ser Gly Val Pro Val Arg Phe Ser Gly Ser Gly Ser Gly Thr Ser
                195                 200                 205

Tyr Ser Leu Thr Ile Ser Arg Met Glu Ala Glu Asp Ala Ala Thr Tyr
        210                 215                 220

Tyr Cys Gln Gln Trp Ser Ser Tyr Pro Leu Thr Phe Gly Ala Gly Thr
225                 230                 235                 240

Lys Leu Glu Leu Lys Arg
                245

<210> SEQ ID NO 57
<211> LENGTH: 246
<212> TYPE: PRT
<213> ORGANISM: Mus <mouse, genus>

<400> SEQUENCE: 57

Met Ala Glu Val Gln Leu Gln Gln Ser Gly Ala Glu Leu Met Lys Pro
  1               5                  10                  15

Gly Ala Ser Val Lys Ile Ser Cys Lys Ala Thr Gly Tyr Thr Phe Ser
                 20                  25                  30

Ser Tyr Trp Ile Glu Trp Val Asn Gln Arg Pro Gly His Gly Leu Glu
                 35                  40                  45

Trp Ile Gly Glu Ile Leu Pro Gly Ser Gly Ser Thr Asn Tyr Asn Glu
         50                  55                  60

Lys Phe Lys Gly Lys Ala Thr Phe Thr Ala Asp Thr Ser Ser Asn Thr
 65                  70                  75                  80

Ala Tyr Met Gln Leu Ser Ser Leu Thr Ser Glu Asp Ser Ala Val Tyr
                 85                  90                  95

Tyr Cys Ala Arg Gly Gly Asp Tyr Asp Glu Tyr Tyr Ala Met Asp
                100                 105                 110

Tyr Trp Gly Gln Gly Thr Ser Val Thr Leu Ser Ser Gly Gly Gly
                115                 120                 125

Ser Gly Gly Gly Ser Gly Gly Gly Ser Gln Ile Val Leu Thr
        130                 135                 140

Gln Ser Pro Ala Ile Met Ser Ala Ser Pro Gly Glu Lys Val Thr Met
145                 150                 155                 160

Thr Cys Ser Ala Ser Ser Val Ser Tyr Met Tyr Trp Tyr Gln Gln
                165                 170                 175
```

```
Lys Pro Gly Ser Ser Pro Arg Leu Leu Ile Tyr Asp Thr Ser Asn Leu
            180                 185                 190

Ala Ser Gly Val Pro Val Arg Phe Ser Gly Ser Gly Ser Gly Thr Ser
        195                 200                 205

Tyr Ser Leu Thr Ile Ser Arg Met Glu Ala Glu Asp Ala Ala Thr Tyr
    210                 215                 220

Tyr Cys Gln Gln Trp Ser Ser Tyr Pro Leu Thr Phe Gly Ala Gly Thr
225                 230                 235                 240

Lys Leu Glu Leu Lys Arg
                245

<210> SEQ ID NO 58
<211> LENGTH: 42
<212> TYPE: DNA
<213> ORGANISM: Mus <mouse, genus>
<220> FEATURE:
<221> NAME/KEY: source
<222> LOCATION: 1..42
<223> OTHER INFORMATION: /mol_type="unassigned DNA"
      /organism="Mus <mouse, genus>"

<400> SEQUENCE: 58
gcaagagggg gggattacga cgaagaatac tatgtcatgg ac                          42

<210> SEQ ID NO 59
<211> LENGTH: 42
<212> TYPE: DNA
<213> ORGANISM: Mus <mouse, genus>
<220> FEATURE:
<221> NAME/KEY: source
<222> LOCATION: 1..42
<223> OTHER INFORMATION: /mol_type="unassigned DNA"
      /organism="Mus <mouse, genus>"

<400> SEQUENCE: 59
gcaagagggg gggattacga cgaagaatac tatgctatgg ac                          42

<210> SEQ ID NO 60
<211> LENGTH: 24
<212> TYPE: DNA
<213> ORGANISM: Mus <mouse, genus>
<220> FEATURE:
<221> NAME/KEY: source
<222> LOCATION: 1..24
<223> OTHER INFORMATION: /mol_type="unassigned DNA"
      /organism="Mus <mouse, genus>"

<400> SEQUENCE: 60
ggctacacat tcagtagcta ctgg                                              24

<210> SEQ ID NO 61
<211> LENGTH: 23
<212> TYPE: DNA
<213> ORGANISM: Mus <mouse, genus>
<220> FEATURE:
<221> NAME/KEY: source
<222> LOCATION: 1..23
<223> OTHER INFORMATION: /mol_type="unassigned DNA"
      /organism="Mus <mouse, genus>"

<400> SEQUENCE: 61
attttacctg gagtggtagt act                                               23

<210> SEQ ID NO 62
<211> LENGTH: 45
```

```
<212> TYPE: DNA
<213> ORGANISM: Mus <mouse, genus>
<220> FEATURE:
<221> NAME/KEY: source
<222> LOCATION: 1..45
<223> OTHER INFORMATION: /mol_type="unassigned DNA"
      /organism="Mus <mouse, genus>"

<400> SEQUENCE: 62
gcgagagggg gggattacga cgaagaatac tatctcatgg actac            45

<210> SEQ ID NO 63
<211> LENGTH: 15
<212> TYPE: DNA
<213> ORGANISM: Mus <mouse, genus>
<220> FEATURE:
<221> NAME/KEY: source
<222> LOCATION: 1..15
<223> OTHER INFORMATION: /mol_type="unassigned DNA"
      /organism="Mus <mouse, genus>"

<400> SEQUENCE: 63
tcaagtgtaa gttac                                             15

<210> SEQ ID NO 64
<211> LENGTH: 27
<212> TYPE: DNA
<213> ORGANISM: Mus <mouse, genus>
<220> FEATURE:
<221> NAME/KEY: source
<222> LOCATION: 1..27
<223> OTHER INFORMATION: /mol_type="unassigned DNA"
      /organism="Mus <mouse, genus>"

<400> SEQUENCE: 64
cagcagtgga gtagttaccc gctcacg                                27

<210> SEQ ID NO 65
<211> LENGTH: 45
<212> TYPE: DNA
<213> ORGANISM: Mus <mouse, genus>
<220> FEATURE:
<221> NAME/KEY: source
<222> LOCATION: 1..45
<223> OTHER INFORMATION: /mol_type="unassigned DNA"
      /organism="Mus <mouse, genus>"

<400> SEQUENCE: 65
gcaagagggg gggattacga cgaagaatac tatgtcatgg actac            45

<210> SEQ ID NO 66
<211> LENGTH: 24
<212> TYPE: DNA
<213> ORGANISM: Mus <mouse, genus>
<220> FEATURE:
<221> NAME/KEY: source
<222> LOCATION: 1..24
<223> OTHER INFORMATION: /mol_type="unassigned DNA"
      /organism="Mus <mouse, genus>"

<400> SEQUENCE: 66
attttacctg gaagtggtag tact                                   24

<210> SEQ ID NO 67
<211> LENGTH: 45
<212> TYPE: DNA
<213> ORGANISM: Mus <mouse, genus>
<220> FEATURE:
<221> NAME/KEY: source
```

```
<222> LOCATION: 1..45
<223> OTHER INFORMATION: /mol_type="unassigned DNA"
      /organism="Mus <mouse, genus>"

<400> SEQUENCE: 67
gcaagagggg gggattacga cgaagaatac tatgctatgg actac           45

<210> SEQ ID NO 68
<211> LENGTH: 366
<212> TYPE: DNA
<213> ORGANISM: Mus <mouse, genus>
<220> FEATURE:
<221> NAME/KEY: source
<222> LOCATION: 1..366
<223> OTHER INFORMATION: /mol_type="unassigned DNA"
      /organism="Mus <mouse, genus>"

<400> SEQUENCE: 68
atggcccagg ttcagctgca gcagtctgga gctgagctga tgaagcctgg ggcctcagtg   60
aagatatcct gcaaggctac tggctacaca ttcagtagct actggataga gtgggtaaac  120
cggaggcctg acatggcct tgagtggatt ggagagattt acctggaag tggtagtact  180 aattacaatg agaagttcaa gggcaaggcc acattcactg cagatacatc ctccaataca  240
gcctacatgc aactcagcag cctcacatct gaggactctg tcgtctatta ctgtgcgaga  300
gggggggatt acgacgaaga atactatctc atggactact ggggtcaagg caccactctc  360
acagtc                                                             366

<210> SEQ ID NO 69
<211> LENGTH: 321
<212> TYPE: DNA
<213> ORGANISM: Mus <mouse, genus>
<220> FEATURE:
<221> NAME/KEY: source
<222> LOCATION: 1..321
<223> OTHER INFORMATION: /mol_type="unassigned DNA"
      /organism="Mus <mouse, genus>"

<400> SEQUENCE: 69
caaattgttc tcacccagtc tccagcaatc atgtctgcat ctccagggga gaaggtcacc   60
atgacctgca gtgccagctc aagtgtaagt tacatgtact ggtaccagca gaagccagga  120
tcctccccca gactcctgat ttatgacaca tccaacctgg cttctggagt ccctgttcgc  180
ttcagtggca gtgggtctgg gacctcttac tctctcacaa tcagccgaat ggaggctgaa  240
gatgctgcca ttattactg ccagcagtgg agtagttacc cgctcacgtt cggtgctggg  300
accaagctgg aaatcaaacg t                                            321

<210> SEQ ID NO 70
<211> LENGTH: 366
<212> TYPE: DNA
<213> ORGANISM: Mus <mouse, genus>
<220> FEATURE:
<221> NAME/KEY: source
<222> LOCATION: 1..366
<223> OTHER INFORMATION: /mol_type="unassigned DNA"
      /organism="Mus <mouse, genus>"

<400> SEQUENCE: 70
atggccgagg ttcagcttca gcagtctgga gctgagctga tgaagcctgg ggcctcagtg   60
aagatatcct gcaaggctac tggctacaca ttcagtagct actggataga gtgggtaaag  120
cagaggcctg acatggcct tgagtggatt ggagagattt acctggaag tggtagtact  180
```

```
aattacaatg agaagttcaa gggcaaggcc acattcactg cagatacatc ctccaacaca    240
gcctacatgc aactcagcag cctgacatct gaggactctg ccgtctatta ctgtgcaaga    300 ggggggatt acgacgaaga atactatgtc atggactact ggggtcaagg aacctcagtc     360
actgtc                                                              366

<210> SEQ ID NO 71
<211> LENGTH: 321
<212> TYPE: DNA
<213> ORGANISM: Mus <mouse, genus>
<220> FEATURE:
<221> NAME/KEY: source
<222> LOCATION: 1..321
<223> OTHER INFORMATION: /mol_type="unassigned DNA"
      /organism="Mus <mouse, genus>"

<400> SEQUENCE: 71
caaattgttc tcacccagtc tccagcaatc atgtctgcat ctccagggga gaaggtcacc    60
atgacctgca gtgccagctc aagtgtaagt tacatgtact ggtaccagca gaagccagga   120
tcctccccca gactcctgat ttatgacaca tccaacctgg cttctggagt ccctgttcgc   180
ttcagtggca gtgggtctgg gacctcttac tctctcacaa tcagccgaat ggaggctgaa   240
gatgctgcca cttattactg ccagcagtgg agtagttacc cgctcacgtt cggtgctggg   300
accaagctgg agctgaaacg t                                             321

<210> SEQ ID NO 72
<211> LENGTH: 366
<212> TYPE: DNA
<213> ORGANISM: Mus <mouse, genus>
<220> FEATURE:
<221> NAME/KEY: source
<222> LOCATION: 1..366
<223> OTHER INFORMATION: /mol_type="unassigned DNA"
      /organism="Mus <mouse, genus>"

<400> SEQUENCE: 72
atggccgagg ttcagcttca gcagtctgga gctgagctga tgaagcctgg ggcctcagtg    60
aagatatcct gcaaggctac tggctacaca ttcagtagct actggataga gtgggtaaat   120
cagaggcctg gacatggcct tgagtggatt ggagagattt acctggaagt ggtagtact   180 aattacaatg agaagttcaa gggcaaggcc acattcactg cagatacatc ctccaacaca   240
gcctacatgc aactcagcag cctgacatct gaggactctg ccgtctatta ctgtgcaaga   300 ggggggatt acgacgaaga atactatgct atggactact ggggtcaagg aacctcagtc    360
accctc                                                              366

<210> SEQ ID NO 73
<211> LENGTH: 321
<212> TYPE: DNA
<213> ORGANISM: Mus <mouse, genus>
<220> FEATURE:
<221> NAME/KEY: source
<222> LOCATION: 1..321
<223> OTHER INFORMATION: /mol_type="unassigned DNA"
      /organism="Mus <mouse, genus>"

<400> SEQUENCE: 73
caaattgttc tcacccagtc tccagcaatc atgtctgcat ctccagggga gaaggtcacc    60
atgacctgca gtgccagctc aagtgtaagt tacatgtact ggtaccagca gaagccagga   120
tcctccccca gactcctgat ttatgacaca tccaacctgg cttctggagt ccctgttcgc   180
```

```
ttcagtggca gtgggtctgg gacctcttac tctctcacaa tcagccgaat ggaggctgaa    240
gatgctgcca cttattactg ccagcagtgg agtagttacc cgctcacgtt cggtgctggg    300
accaagctgg agctgaaacg t                                              321
```

```
<210> SEQ ID NO 74
<211> LENGTH: 747
<212> TYPE: DNA
<213> ORGANISM: Mus <mouse, genus>
<220> FEATURE:
<221> NAME/KEY: source
<222> LOCATION: 1..747
<223> OTHER INFORMATION: /mol_type="unassigned DNA"
      /organism="Mus <mouse, genus>"

<400> SEQUENCE: 74
atggcccagg ttcagctgca gcagtctgga gctgagctga tgaagcctgg ggcctcagtg     60
aagatatcct gcaaggctac tggctacaca ttcagtagct actggataga gtgggtaaac    120
cggaggcctg gacatggcct tgagtggatt ggagagattt acctggaag tggtagtact     180 aattacaatg agaagttcaa gggcaaggcc acattcactg cagatacatc ctccaataca    240
gcctacatgc aactcagcag cctcacatct gaggactctg tcgtctatta ctgtgcgaga    300
gggggggatt acgacgaaga atactatctc atggactact ggggtcaagg caccactctc    360
acagtctcct caggtggagg cggttcaggc ggaggtggc ctggcggtgg cggatcgcaa     420
attgttctca cccagtctcc agcaatcatg tctgcatctc caggggagaa ggtcaccatg    480
acctgcagtg ccagctcaag tgtaagttac atgtactggt accagcagaa gccaggatcc    540
tcccccagac tcctgattta tgacacatcc aacctggctt ctggagtccc tgttcgcttc    600
agtggcagtg gtctgggac ctcttactct ctcacaatca gccgaatgga ggctgaagat     660
gctgccactt attactgcca gcagtggagt agttacccgc tcacgttcgg tgctgggacc    720
aagctggaaa tcaaacgtgc ggccgca                                        747
```

```
<210> SEQ ID NO 75
<211> LENGTH: 738
<212> TYPE: DNA
<213> ORGANISM: Mus <mouse, genus>
<220> FEATURE:
<221> NAME/KEY: source
<222> LOCATION: 1..738
<223> OTHER INFORMATION: /mol_type="unassigned DNA"
      /organism="Mus <mouse, genus>"

<400> SEQUENCE: 75
atggccgagg ttcagcttca gcagtctgga gctgagctga tgaagcctgg ggcctcagtg     60
aagatatcct gcaaggctac tggctacaca ttcagtagct actggataga gtgggtaaag    120
cagaggcctg gacatggcct tgagtggatt ggagagattt acctggaag tggtagtact     180 aattacaatg agaagttcaa gggcaaggcc acattcactg cagatacatc ctccaacaca    240
gcctacatgc aactcagcag cctgacatct gaggactctg ccgtctatta ctgtgcaaga    300
gggggggatt acgacgaaga atactatgtc atggactact ggggtcaagg aacctcagtc    360
actgtctcct caggtggagg cggttcaggc ggaggtggc ctggcggtgg cggatcgcaa     420
attgttctca cccagtctcc agcaatcatg tctgcatctc caggggagaa ggtcaccatg    480
acctgcagtg ccagctcaag tgtaagttac atgtactggt accagcagaa gccaggatcc    540
tcccccagac tcctgattta tgacacatcc aacctggctt ctggagtccc tgttcgcttc    600
agtggcagtg gtctgggac ctcttactct ctcacaatca gccgaatgga ggctgaagat     660
```

```
gctgccactt attactgcca gcagtggagt agttacccgc tcacgttcgg tgctgggacc    720
aagctggagc tgaaacgt                                                  738

<210> SEQ ID NO 76
<211> LENGTH: 738
<212> TYPE: DNA
<213> ORGANISM: Mus <mouse, genus>
<220> FEATURE:
<221> NAME/KEY: source
<222> LOCATION: 1..738
<223> OTHER INFORMATION: /mol_type="unassigned DNA"
      /organism="Mus <mouse, genus>"

<400> SEQUENCE: 76
atggccgagg ttcagcttca gcagtctgga gctgagctga tgaagcctgg ggcctcagtg     60
aagatatcct gcaaggctac tggctacaca ttcagtagct actggataga gtgggtaaat    120
cagaggcctg acatggcct tgagtggatt ggagagattt acctggaag tggtagtact      180 aattacaatg agaagttcaa gggcaaggcc acattcactg cagatacatc ctccaacaca    240
gcctacatgc aactcagcag cctgacatct gaggactctg ccgtctatta ctgtgcaaga    300 ggggggatt acgacgaaga atactatgct atggactact gggtcaagg aacctcagtc     360 accctctcct caggtggagg cggttcaggc ggaggtggct ctggcggtgg cggatcgcaa    420
attgttctca cccagtctcc agcaatcatg tctgcatctc caggggagaa ggtcaccatg    480
acctgcagtg ccagctcaag tgtaagttac atgtactggt accagcagaa gccaggatcc    540
tcccccagac tcctgattta tgacacatcc aacctggctt ctggagtccc tgttcgcttc    600
agtggcagtg ggtctgggac ctcttactct ctcacaatca gccgaatgga ggctgaagat    660
gctgccactt attactgcca gcagtggagt agttacccgc tcacgttcgg tgctgggacc    720
aagctggagc tgaaacgt                                                  738

<210> SEQ ID NO 77
<211> LENGTH: 14
<212> TYPE: PRT
<213> ORGANISM: Mus <mouse, genus>

<400> SEQUENCE: 77

Ala Arg Gly Gly Asp Tyr Asp Glu Glu Tyr Tyr Val Met Asp
1               5                   10

<210> SEQ ID NO 78
<211> LENGTH: 13
<212> TYPE: PRT
<213> ORGANISM: Mus <mouse, genus>

<400> SEQUENCE: 78

Trp Ile Gly Glu Ile Leu Pro Gly Ser Gly Ser Thr Asn
1               5                   10

<210> SEQ ID NO 79
<211> LENGTH: 36
<212> TYPE: DNA
<213> ORGANISM: Mus <mouse, genus>
<220> FEATURE:
<221> NAME/KEY: source
<222> LOCATION: 1..36
<223> OTHER INFORMATION: /mol_type="unassigned DNA"
      /organism="Mus <mouse, genus>"

<400> SEQUENCE: 79
```
tggattggag agattttacc tggaagtggt agtact 36

```
<210> SEQ ID NO 80
<211> LENGTH: 39
<212> TYPE: PRT
<213> ORGANISM: Homo sapiens

<400> SEQUENCE: 80
```

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr
        35

```
<210> SEQ ID NO 81
<211> LENGTH: 12
<212> TYPE: PRT
<213> ORGANISM: Homo sapiens

<400> SEQUENCE: 81
```

Gln Leu Pro Pro Gly Cys Gly Asp Pro Lys Arg Leu
1               5                   10

```
<210> SEQ ID NO 82
<211> LENGTH: 20
<212> TYPE: PRT
<213> ORGANISM: Homo sapiens

<400> SEQUENCE: 82
```

Thr Ser Tyr Ser Arg Trp Ala Arg Leu Asp Leu Asn Gly Ala Pro Leu
1               5                   10                  15

Cys Gly Pro Leu
            20

```
<210> SEQ ID NO 83
<211> LENGTH: 169
<212> TYPE: PRT
<213> ORGANISM: Homo sapiens

<400> SEQUENCE: 83
```

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe
                165

<210> SEQ ID NO 84
<211> LENGTH: 740
<212> TYPE: PRT
<213> ORGANISM: Artificial Sequence
<220> FEATURE:
<223> OTHER INFORMATION: Chimera 5 fused to GFP tag

<400> SEQUENCE: 84

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
                20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
        50                  55                  60

Ser Val Ala Ala Asp Val Ile Ser Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe Gln Phe Glu Val Leu Cys Pro
                165                 170                 175

Ala Pro Arg Pro Gly Ala Ala Ser Asn Leu Ser Tyr Arg Ala Pro Phe
            180                 185                 190

Gln Leu His Ser Ala Ala Leu Asp Phe Ser Pro Pro Gly Thr Glu Val
            195                 200                 205

Ser Ala Leu Cys Arg Gly Gln Leu Pro Ile Ser Val Thr Cys Ile Ala
        210                 215                 220

Asp Glu Ile Gly Ala Arg Trp Asp Lys Leu Ser Gly Asp Val Leu Cys
225                 230                 235                 240

Pro Cys Pro Gly Arg Tyr Leu Arg Ala Gly Lys Cys Ala Glu Leu Pro
                245                 250                 255

Asn Cys Leu Asp Asp Leu Gly Gly Phe Ala Cys Glu Cys Ala Thr Gly
            260                 265                 270

Phe Glu Leu Gly Lys Asp Gly Arg Ser Cys Val Thr Ser Gly Glu Gly
            275                 280                 285

Gln Pro Thr Leu Gly Gly Thr Gly Val Pro Thr Arg Arg Pro Pro Ala
290                 295                 300

Thr Ala Thr Ser Pro Val Pro Gln Arg Thr Trp Pro Ile Arg Val Asp
305                 310                 315                 320

Glu Lys Leu Gly Glu Thr Pro Leu Val Pro Glu Gln Asp Asn Ser Val
                325                 330                 335

```
Thr Ser Ile Pro Glu Ile Pro Arg Trp Gly Ser Gln Ser Thr Met Ser
            340             345                 350

Thr Leu Gln Met Ser Leu Gln Ala Glu Ser Lys Ala Thr Ile Thr Pro
        355                 360                 365

Ser Gly Ser Val Ile Ser Lys Phe Asn Ser Thr Thr Ser Ser Ala Thr
    370                 375                 380

Pro Gln Ala Phe Asp Ser Ser Ala Val Val Phe Ile Phe Val Ser
385                 390                 395                 400

Thr Ala Val Val Val Leu Val Ile Leu Thr Met Thr Val Leu Gly Leu
                405                 410                 415

Val Lys Leu Cys Phe His Glu Ser Pro Ser Ser Gln Pro Arg Lys Glu
            420                 425                 430

Ser Met Gly Pro Pro Gly Leu Glu Ser Asp Pro Glu Pro Ala Ala Leu
            435                 440                 445

Gly Ser Ser Ser Ala His Cys Thr Asn Asn Gly Val Lys Val Gly Asp
            450                 455                 460

Cys Asp Leu Arg Asp Arg Ala Glu Gly Ala Leu Leu Ala Glu Ser Pro
465                 470                 475                 480

Leu Gly Ser Ser Asp Ala Leu Gln Ser Thr Val Pro Arg Ala Arg Asp
                485                 490                 495

Pro Pro Val Ala Thr Met Val Ser Lys Gly Glu Glu Leu Phe Thr Gly
            500                 505                 510

Val Val Pro Ile Leu Val Glu Leu Asp Gly Asp Val Asn Gly His Lys
            515                 520                 525

Phe Ser Val Ser Gly Glu Gly Glu Gly Asp Ala Thr Tyr Gly Lys Leu
            530                 535                 540

Thr Leu Lys Phe Ile Cys Thr Thr Gly Lys Leu Pro Val Pro Trp Pro
545                 550                 555                 560

Thr Leu Val Thr Thr Leu Thr Tyr Gly Val Gln Cys Phe Ser Arg Tyr
                565                 570                 575

Pro Asp His Met Lys Gln His Asp Phe Phe Lys Ser Ala Met Pro Glu
            580                 585                 590

Gly Tyr Val Gln Glu Arg Thr Ile Phe Phe Lys Asp Asp Gly Asn Tyr
            595                 600                 605

Lys Thr Arg Ala Glu Val Lys Phe Glu Gly Asp Thr Leu Val Asn Arg
            610                 615                 620

Ile Glu Leu Lys Gly Ile Asp Phe Lys Glu Asp Gly Asn Ile Leu Gly
625                 630                 635                 640

His Lys Leu Glu Tyr Asn Tyr Asn Ser His Asn Val Tyr Ile Met Ala
                645                 650                 655

Asp Lys Gln Lys Asn Gly Ile Lys Val Asn Phe Lys Ile Arg His Asn
            660                 665                 670

Ile Glu Asp Gly Ser Val Gln Leu Ala Asp His Tyr Gln Gln Asn Thr
            675                 680                 685

Pro Ile Gly Asp Gly Pro Val Leu Leu Pro Asp Asn His Tyr Leu Ser
            690                 695                 700

Thr Gln Ser Ala Leu Ser Lys Asp Pro Asn Glu Lys Arg Asp His Met
705                 710                 715                 720

Val Leu Leu Glu Phe Val Thr Ala Ala Gly Ile Thr Leu Gly Met Asp
                725                 730                 735

Glu Leu Tyr Lys
            740
```

-continued

```
<210> SEQ ID NO 85
<211> LENGTH: 745
<212> TYPE: PRT
<213> ORGANISM: Artificial Sequence
<220> FEATURE:
<223> OTHER INFORMATION: Chimera 6 fused to GFP tag

<400> SEQUENCE: 85

Met Arg Pro Ala Phe Ala Leu Cys Leu Leu Trp Gln Ala Leu Trp Pro
1               5                   10                  15

Gly Pro Gly Gly Gly Glu His Pro Thr Ala Asp Arg Ala Gly Cys Ser
            20                  25                  30

Ala Ser Gly Ala Cys Tyr Ser Leu His His Ala Thr Met Lys Arg Gln
        35                  40                  45

Ala Ala Glu Glu Ala Cys Ile Leu Arg Gly Gly Ala Leu Ser Thr Val
    50                  55                  60

Arg Ala Gly Ala Glu Leu Arg Ala Val Leu Ala Leu Leu Arg Ala Gly
65                  70                  75                  80

Pro Gly Pro Gly Gly Gly Ser Lys Asp Leu Leu Phe Trp Val Ala Leu
                85                  90                  95

Glu Arg Arg Arg Ser His Cys Thr Leu Glu Asn Glu Pro Leu Arg Gly
            100                 105                 110

Phe Ser Trp Leu Ser Ser Asp Pro Gly Gly Leu Glu Ser Asp Thr Leu
        115                 120                 125

Gln Trp Val Glu Glu Pro Gln Arg Ser Cys Thr Ala Arg Arg Cys Ala
130                 135                 140

Val Leu Gln Ala Thr Gly Gly Val Glu Pro Ala Gly Trp Lys Glu Met
145                 150                 155                 160

Arg Cys His Leu Arg Ala Asn Gly Tyr Leu Cys Lys Tyr His Phe Pro
                165                 170                 175

Ala Thr Cys Arg Pro Leu Ala Val Glu Pro Gly Ala Ala Ala Ala Ala
            180                 185                 190

Val Ser Ile Thr Tyr Gly Thr Pro Phe Ala Ala Arg Gly Ala Asp Phe
        195                 200                 205

Gln Ala Leu Pro Val Gly Ser Ser Ala Ala Val Ala Pro Leu Gly Leu
    210                 215                 220

Gln Leu Met Cys Thr Ala Pro Pro Gly Ala Val Gln Gly His Trp Ala
225                 230                 235                 240

Arg Glu Ala Pro Gly Ala Cys Pro Gly Arg Tyr Leu Arg Ala Gly Lys
                245                 250                 255

Cys Ala Glu Leu Pro Asn Cys Leu Asp Asp Leu Gly Gly Phe Ala Cys
            260                 265                 270

Glu Cys Ala Thr Gly Phe Glu Leu Gly Lys Asp Gly Arg Ser Cys Val
        275                 280                 285

Thr Ser Gly Glu Gly Gln Pro Thr Leu Gly Gly Thr Gly Val Pro Thr
    290                 295                 300

Arg Arg Pro Pro Ala Thr Ala Thr Ser Pro Val Pro Gln Arg Thr Trp
305                 310                 315                 320

Pro Ile Arg Val Asp Glu Lys Leu Gly Glu Thr Pro Leu Val Pro Glu
                325                 330                 335

Gln Asp Asn Ser Val Thr Ser Ile Pro Glu Ile Pro Arg Trp Gly Ser
            340                 345                 350

Gln Ser Thr Met Ser Thr Leu Gln Met Ser Leu Gln Ala Glu Ser Lys
        355                 360                 365

Ala Thr Ile Thr Pro Ser Gly Ser Val Ile Ser Lys Phe Asn Ser Thr
```

```
              370                 375                 380
Thr Ser Ser Ala Thr Pro Gln Ala Phe Asp Ser Ser Ala Val Val
385                 390                 395                 400

Phe Ile Phe Val Ser Thr Ala Val Val Leu Val Ile Leu Thr Met
                405                 410                 415

Thr Val Leu Gly Leu Val Lys Leu Cys Phe His Glu Ser Pro Ser Ser
            420                 425                 430

Gln Pro Arg Lys Glu Ser Met Gly Pro Pro Gly Leu Glu Ser Asp Pro
            435                 440                 445

Glu Pro Ala Ala Leu Gly Ser Ser Ala His Cys Thr Asn Asn Gly
450                 455                 460

Val Lys Val Gly Asp Cys Asp Leu Arg Asp Arg Ala Glu Gly Ala Leu
465                 470                 475                 480

Leu Ala Glu Ser Pro Leu Gly Ser Asp Ala Leu Gln Ser Thr Val
                485                 490                 495

Pro Arg Ala Arg Asp Pro Pro Val Ala Thr Met Val Ser Lys Gly Glu
                500                 505                 510

Glu Leu Phe Thr Gly Val Val Pro Ile Leu Val Glu Leu Asp Gly Asp
            515                 520                 525

Val Asn Gly His Lys Phe Ser Val Ser Gly Glu Gly Glu Gly Asp Ala
530                 535                 540

Thr Tyr Gly Lys Leu Thr Leu Lys Phe Ile Cys Thr Thr Gly Lys Leu
545                 550                 555                 560

Pro Val Pro Trp Pro Thr Leu Val Thr Thr Leu Thr Tyr Gly Val Gln
                565                 570                 575

Cys Phe Ser Arg Tyr Pro Asp His Met Lys Gln His Asp Phe Phe Lys
                580                 585                 590

Ser Ala Met Pro Glu Gly Tyr Val Gln Glu Arg Thr Ile Phe Phe Lys
            595                 600                 605

Asp Asp Gly Asn Tyr Lys Thr Arg Ala Glu Val Lys Phe Glu Gly Asp
610                 615                 620

Thr Leu Val Asn Arg Ile Glu Leu Lys Gly Ile Asp Phe Lys Glu Asp
625                 630                 635                 640

Gly Asn Ile Leu Gly His Lys Leu Glu Tyr Asn Tyr Asn Ser His Asn
                645                 650                 655

Val Tyr Ile Met Ala Asp Lys Gln Lys Asn Gly Ile Lys Val Asn Phe
                660                 665                 670

Lys Ile Arg His Asn Ile Glu Asp Gly Ser Val Gln Leu Ala Asp His
            675                 680                 685

Tyr Gln Gln Asn Thr Pro Ile Gly Asp Gly Pro Val Leu Leu Pro Asp
690                 695                 700

Asn His Tyr Leu Ser Thr Gln Ser Ala Leu Ser Lys Asp Pro Asn Glu
705                 710                 715                 720

Lys Arg Asp His Met Val Leu Leu Glu Phe Val Thr Ala Ala Gly Ile
                725                 730                 735

Thr Leu Gly Met Asp Glu Leu Tyr Lys
                740                 745

<210> SEQ ID NO 86
<211> LENGTH: 173
<212> TYPE: PRT
<213> ORGANISM: Homo sapiens

<400> SEQUENCE: 86
```

```
Met Arg Pro Ala Phe Ala Leu Cys Leu Leu Trp Gln Ala Leu Trp Pro
1               5                   10                  15

Gly Pro Gly Gly Gly Glu His Pro Thr Ala Asp Arg Ala Gly Cys Ser
            20                  25                  30

Ala Ser Gly Ala Cys Tyr Ser Leu His His Ala Thr Met Lys Arg Gln
            35                  40                  45

Ala Ala Glu Glu Ala Cys Ile Leu Arg Gly Gly Ala Leu Ser Thr Val
50                      55                  60

Arg Ala Gly Ala Glu Leu Arg Ala Val Leu Ala Leu Leu Arg Ala Gly
65                  70                  75                  80

Pro Gly Pro Gly Gly Gly Ser Lys Asp Leu Leu Phe Trp Val Ala Leu
                85                  90                  95

Glu Arg Arg Ser His Cys Thr Leu Glu Asn Glu Pro Leu Arg Gly
                100                 105                 110

Phe Ser Trp Leu Ser Ser Asp Pro Gly Gly Leu Glu Ser Asp Thr Leu
            115                 120                 125

Gln Trp Val Glu Glu Pro Gln Arg Ser Cys Thr Ala Arg Arg Cys Ala
        130                 135                 140

Val Leu Gln Ala Thr Gly Gly Val Glu Pro Ala Gly Trp Lys Glu Met
145                 150                 155                 160

Arg Cys His Leu Arg Ala Asn Gly Tyr Leu Cys Lys Tyr
                165                 170

<210> SEQ ID NO 87
<211> LENGTH: 27
<212> TYPE: DNA
<213> ORGANISM: Mus <mouse, genus>
<220> FEATURE:
<221> NAME/KEY: source
<222> LOCATION: 1..27
<223> OTHER INFORMATION: /mol_type="unassigned DNA"
      /organism="Mus <mouse, genus>"

<400> SEQUENCE: 87
cagcagtgga gtagttaccc gctcacg                                   27
```

INHIBITORS OF THE INTERACTION BETWEEN CLEC14A AND MULTIMERIN-2 FOR INHIBITION OF ANGIOGENESIS

This application is a continuation of U.S. application Ser. No. 15/544,323, filed Jul. 18, 2017, which is a national phase entry pursuant to 35 U.S.C. § 371 of International Application No. PCT/GB2016/050134, filed Jan. 21, 2016, which claims the benefit of priority of GB Application No. 1501004.4, filed Jan. 21, 2015, the contents of each of which are incorporated herein by reference in their entirety.

The Instant application contains a Sequence Listing submitted as an ASCII text file via EFS-Web and hereby incorporated by reference in its entirety. Said ASCII copy, created on Aug. 3, 2020, is named P59790PC_sequence_listing_03_Aug_2020.txt and is 72,198 bytes in size.

The present invention relates generally to endothelium specific genes and polypeptides, inhibitors of these endothelium specific genes/polypeptides for inhibiting angiogenesis and combating other diseases, and the use of antibodies that bind these polypeptides for imaging and targeting neovasculature. In particular, the present invention relates to CLEC14A, antibodies against CLEC14A, and the use of agents that inhibit the interaction between CLEC14A and MMRN2, including antibodies.

The endothelium plays a central role in many physiological and pathological processes and it is known to be an exceptionally active transcriptional site. Approximately 1,000 distinct genes are expressed in an endothelial cell, although many of them are not endothelial cell specific. In contrast red blood cells were found to express 8, platelets 22 and smooth muscle 127 separate genes (Adams et al (1995) *Nature* 377 (6547 Suppl): 3-174). Known endothelial specific genes attract much attention from both basic research and the clinical community. For example, the endothelial-specific tyrosine kinases Tie, TIE2/TEK, KDR, and flt1 are crucial players in the regulation of vascular integrity, endothelium-mediated inflammatory processes and angiogenesis.

Endothelial cells form a single cell layer that lines all blood vessels and regulates exchanges between the blood stream and the surrounding tissues. New blood vessels develop from the walls of existing small vessels by the outgrowth of endothelial cells in the process called angiogenesis. Endothelial cells even have the capacity to form hollow capillary tubes when isolated in culture. Once the vascular system is fully developed, endothelial cells of blood vessels normally remain quiescent with no new vessel formation, with the exception of the formation of new blood vessels in natural wound healing. However, some tumours attract a new blood supply by secreting factors that stimulate nearby endothelial cells to construct new capillary sprouts. Angiogenesis plays a major role in the progression of solid tumours and is widely recognised as a rate-limiting process in the growth of solid tumours. Tumours that fail to attract a blood supply are severely limited in their growth. Thus the ability to inhibit inappropriate or undesirable angiogenesis may be useful in the treatment of solid tumours.

The development of new blood vessels is essential for both local tumour progression and the development of distant metastases. Indeed, the growth and survival of tumours is dependent on their ability to obtain a blood supply and damage inflicted on the tumour endothelium has been shown to effectively eradicate tumours (Burrows et al (1993) "Eradication of large solid tumors in mice with an immunotoxin directed against tumor vasculature." *Proc Natl Aced Sci USA*, 90(19): 8996-9000). Tumour angiogenesis involves the degradation of the basement membrane by activated tissue or circulating endothelial precursors, proliferation and migration of endothelial cells, interaction with the extracellular matrix, morphological differentiation, cell adherence and vascular tube formation. Inhibition of tumour angiogenesis is thus a target for anti-tumour therapies, employing either angiogenesis inhibitors alone or in combination with standard cancer treatments. However, targeting anti-tumour agents to the site of angiogenesis depends upon the identification of specific markers of tumour angiogenesis. It is now accepted that the growth of solid tumours is dependent on their capacity to acquire a blood supply, and much effort has been directed towards the development of anti-angiogenic agents that disrupt this process. It has also become apparent that targeted destruction of the established tumour vasculature is another avenue for exciting therapeutic opportunities, and the discovery of widely expressed tumour endothelial markers promises much clinical benefit (Neri & Bicknell (2005) "Tumour vascular targeting." *Nat Rev Cancer* 5(6): 436-446).

The inventors have previously identified CLEC14A as a tumour endothelial marker (WO 2011/027132). CLEC14A is a single-pass transmembrane glycoprotein that belongs to the vascular restricted C-type lectin family 14, whose other members include CD248/TEM1/Endosialin, Thrombomodulin and CD93. Available data on CLEC14A suggests that manipulation of CLEC14A levels or function blocking antibodies will regulate endothelial migration (9-12 and WO2011/027132).

The inventors have now found that the interaction between CLEC14A and multimerin 2 (MMRN2) plays an important role in angiogenesis. MMRN2 is an endothelial specific marker of the emilin family and a component of the extracellular matrix (14, 15). MMRN2 was recently identified as an extracellular interacting protein for CLEC14A and was found to be co-expressed with CLEC14A in the tumour vasculature (11). However, to the best of our knowledge, the function of this interaction, and particularly its role in angiogenesis, was previously unknown.

WO2013/187724 discloses CLEC14A antibodies, and in particular ones that bind to the C-type lectin domain. However, it does not mention or suggest antibodies that inhibit the interaction between CLEC14A and MMRN2, and as shown by the present inventors, not all antibodies that target the C-type lectin domain block this interaction and have an inhibitory effect on angiogenesis.

Given the present observations, therefore, the inventors consider that agents that inhibit the interaction between CLEC14A and MMRN2 will be therapeutically useful in the inhibition of angiogenesis and in combating diseases such as cancer.

Accordingly, a first aspect of the invention provides a method of inhibiting angiogenesis in an individual, the method comprising administering to the individual an agent that inhibits the interaction between CLEC14A and MMRN2.

This aspect also includes an agent that inhibits the interaction between CLEC14A and MMRN2, for use in inhibiting angiogenesis in an individual. The aspect further includes the use of an agent that inhibits the interaction between CLEC14A and MMRN2, in the preparation of a medicament for inhibiting angiogenesis in an individual.

For the avoidance of doubt, it will also be appreciated that the invention also includes an in vitro or ex vivo method of inhibiting angiogenesis (eg tumour angiogenesis) comprising administering an agent that inhibits the interaction between CLEC14A and MMRN2 to tissue or cells in vitro or ex vivo. The cells may be established cell lines, or cells that have been removed from an individual. The tissue or cells are preferably mammalian tissue or cells (eg endothelial tissue or cells), and most preferably are human tissue or cells. When the method is an ex vivo method, the agent may be administered to an angiogenesis model ex vivo. Suitable angiogenesis assays include assays for endothelial cell proliferation, migration and invasion, sponge assays and aortic ring assays. Further angiogenesis assays are described below and in the Examples.

By "inhibiting angiogenesis" we include the meaning of reducing the rate or level of angiogenesis. The reduction can be a low level reduction of about 10%, or about 20%, or about 30%, or about 40% of the rate or level of angiogenesis. Preferably, the reduction is a medium level reduction of about 50%, or about 60%, or about 70%, or about 80% reduction of the rate or level of angiogenesis. More preferably, the reduction is a high level reduction of about 90%, or about 95%, or about 99%, or about 99.9% of the rate or level of angiogenesis. Most preferably, inhibition can also include the elimination of angiogenesis or its reduction to an undetectable level. Methods and assays for determining the rate or level of angiogenesis, and hence for determining whether and to what extent an antibody inhibits angiogenesis, are known in the art and are described in further detail herein, including in the Examples.

Typically, the angiogenesis that is inhibited is tumour angiogenesis. Thus, the individual may have a solid tumour, which can be treated by inhibiting tumour angiogenesis, ie the solid tumour is associated with new blood vessel production. The term "tumour" is to be understood as referring to all forms of neoplastic cell growth including, but not limited to, tumours of the breast, ovary, liver, bladder, prostate, kidney, pancreas, stomach, oesophagus, lung and thyroid. Particularly, angiogenesis of a pancreatic tumour may be inhibited.

Typically, the tumour is associated with undesirable neovasculature formation and the inhibitor of the interaction between CLEC14A and MMRN2 reduces this to a useful extent. The reduction of undesirable neovasculature formation may halt the progression of the tumour and can lead to a clinically useful reduction of tumour size and growth, e.g. a reduction in tumour size or growth rate of at least 5, 10, 15, 20, 25, 30, 40, 50, 60, 70, 80 or 90%. Thus, the inhibition of tumour angiogenesis can be used to treat the tumour, for example, to prevent the (further) growth of the tumour, to prevent the spread of the tumour (metastasis), or to reduce the size of the tumour. The size of a tumour can be measured by imaging the tumour e.g. using an appropriate antibody specific for the tumour being targeted. Methods of tumour imaging are well known in the art. The growth rate of a tumour can be determined by measuring tumour size over a time period (e.g. before and after treatment, to determine whether treatment results in a reduction in the growth rate).

Preferably, the methods and medicaments of the invention are used to treat humans, in which case the agent is an inhibitor of the interaction between human CLEC14A and human MMRN2. It is appreciated, however, that when the methods and medicaments of the invention are for treatment of non-human mammals, it is preferred if the agent is one that inhibits the interaction between CLEC14A and MMRN2 from the other species.

CLEC14A

The gene CLEC14A (C-type lectin domain family 14, member A), which is located at 14q21.1, was previously known as C14orf27, CEG1 and EGFR5. CLEC14A encodes a 490 amino acid residue polypeptide with a predicted MW of 51 kDa. By the CLEC14A polypeptide we include the meaning of a gene product of human CLEC14A, including naturally occurring variants thereof. Human CLEC14A polypeptide includes the amino acid sequence found in Genbank Accession No NP_778230 and naturally occurring variants thereof. The CLEC14A polypeptide sequence from NP_778230 is shown in FIG. 9 (SEQ ID NO: 17). Also included are CLEC14A orthologous found in other species, such as in horse, dog, pig, cow, sheep, rat, mouse, guinea pig or a primate.

A cDNA sequence corresponding to a human CLEC14A mRNA is found in Genbank Accession No NM_175060 and shown in FIG. 9 (SEQ ID NO: 18). The coding region of this cDNA from NM_175060 is from nucleotide 348 to nucleotide 1820, and this is also shown in FIG. 9 (SEQ ID NO: 19).

CLEC14A is a type I transmembrane protein with a signal peptide at residues 1-21. The mature human polypeptide is 469 amino acids in length (amino acid residues 22-490), and contains a 375 residue extracellular region (residues 22-396), a transmembrane region (residues 397-425), and a cytoplasmic region (residues 426-490). The extracellular region contains a C-type lectin like domain (residues 32-173) and an EGF-like region (residues 245-287).

MMRN2

The gene MMRN2 is located at 10q23.2 and encodes a 888 amino acid residue polypeptide. By the MMRN2 polypeptide we include the meaning of a gene product of human MMRN2, including naturally occurring variants thereof. Human MMRN2 polypeptide includes the amino acid sequence found in Genbank Accession No XP_006718033 and naturally occurring variants thereof. The MMRN2 polypeptide sequence from XP_006718033 is shown in FIG. 10 (SEQ ID NO: 20). Also included are MMRN2 orthologous found in other species, such as in horse, dog, pig, cow, sheep, rat, mouse, guinea pig or a primate.

A cDNA sequence corresponding to a human MMRN2 mRNA is found in Genbank Accession No NM_024756.2, and the coding region is also shown in FIG. 10 (SEQ ID NO: 21).

Agents that Inhibit the Interaction Between CLEC14A and MMRN2

By an agent that inhibits the interaction between CLEC14A and MMRN2, we include the meaning of an agent that reduces the level of binding between CLEC14A and MMRN2, as compared to the level of binding between CLEC14A and MMRN2 in the absence of the agent. Preferably, the agent is one that reduces the level of binding between CLEC14A and MMRN2 by at least 10%, 20%, 30%, 40% or 50%, and more preferably the agent is one that reduces the level of binding between CLEC14A and MMRN2 by at least 70%, 80%, 90%, 95% or 99%. Most preferably, the agent is one that reduces the level of binding between CLEC14A and MMRN2 to an undetectable level, or eliminates binding between CLEC14A and MMRN2.

Suitable methods for detecting and/or measuring (quantifying) the binding of CLEC14A to MMRN2 are well known to those skilled in the art. Examples of appropriate methods include pull-down assays, enzyme linked immunosorbent assays (ELISA), surface plasmon resonance assays, chip-based assays, immunocytofluorescence, yeast two-hybrid technology and phage display, which are common practice in the art and are described, for example, in Plant et al (1995) *Analyt Biochem*, 226(2), 342-348. and Sambrook et al (2001) Molecular Cloning A Laboratory Manual. Third Edition. Cold Spring Harbor Laboratory Press, Cold Spring Harbor, New York Other methods of detecting binding between CLEC14A and MMRN2 include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities (i.e. CLEC14A and MMRN2 or portions or variants thereof) may be measured by measuring the interaction of the fluorescent labels when in close proximity to each other.

The agent may be any of an antibody, a polypeptide, a peptide, a polynucleotide, a peptidomimetic, a natural product, a carbohydrate, an aptamer or a small molecule. Particular examples of what the agent may be are described below, and methods for identifying suitable agents feature in a subsequent aspect of the invention.

It is appreciated that the agent itself may inhibit the interaction between CLEC14 and MMRN2 directly (eg by binding to CLEC14A or MMRN2).

It will be appreciated that polypeptide agents that inhibit the interaction between CLEC14A and MMRN2 may be administered directly, or may be administered in the form of a polynucleotide that encodes the agent. Thus, as used herein, unless the context demands otherwise, by administering to the individual an agent that inhibits the interaction between CLEC14A and MMRN2 which agent is a polypeptide, we include the meanings of administering the inhibitor directly, or administering a polynucleotide that encodes the inhibitor, typically in the form of a vector. Similarly, as used herein, unless the context demands otherwise, by a medicament or a composition comprising an agent that inhibits the interaction between CLEC14A and MMRN2 which is a polypeptide, we include the meanings that the medicament or composition comprises the agent itself, or comprises a polynucleotide that encodes the agent.

For the avoidance of doubt, by an agent that inhibits the interaction between CLEC14A and MMRN2, we also include the meaning of prodrugs thereof. For example, the agent may be administered as a prodrug which is metabolised or otherwise converted into its active form once inside the body of a subject. The term "prodrug" as used in this application refers to a precursor or derivative form of a pharmaceutically active substance that is less active compared to the parent drug and is capable of being enzymatically activated or converted into the more active parent form (see, for example, D. E. V. Wilman "Prodrugs in Cancer Chemotherapy" Biochemical Society Transactions 14, 375-382 (615th Meeting, Belfast 1986) and V. J. Stella et al. "Prodrugs: A Chemical Approach to Targeted Drug Delivery" Directed Drug Delivery R. Borchardt et al (ed.) pages 247-267 (Humana Press 1985)).

Antibodies

In a preferred embodiment, the agent is an antibody that inhibits the interaction between CLEC14A and MMRN2.

The antibody may be one that binds specifically to regions of CLEC14A and/or MMRN2 that are involved either directly or indirectly in the interaction between CLEC14 and MMRN2. For example, the antibody may bind to the MMRN2 binding site in CLEC14A and so directly block binding of MMRN2, or the antibody may bind to a region of CLEC14A outside the MMRN2 binding site that is nevertheless required for a stable interaction and so indirectly affects binding to MMRN2. Similarly, the antibody may bind to the CLEC14A binding site in MMRN2 and so directly block binding of CLEC14A, or the antibody may bind to a region of MMRN2 outside the CLEC14A binding site that is nevertheless required for a stable interaction and so indirectly affects binding to CLEC14A.

Antibodies that are especially active at inhibiting tumour angiogenesis are preferred for anti-cancer therapeutic agents, and they can be selected for this activity using methods well known in the art and as described below.

Suitable antibodies which bind to CLEC14A or MMRN2, or to specified portions thereof, can be made by the skilled person using technology long-established in the art. Methods of preparation of monoclonal antibodies and antibody fragments are well known in the art and include hybridoma technology (Kohler & Milstein (1975) "Continuous cultures of fused cells secreting antibody of predefined specificity. *Nature* 256: 495-497); antibody phage display (Winter et al (1994) "Making antibodies by phage display technology." *Annu. Rev. Immunol.* 12: 433-455); ribosome display (Schaffitzel et al (1999) "Ribosome display: an in vitro method for selection and evolution of antibodies from libraries." *J. Immunol. Methods* 231: 119-135); and iterative colony filter screening (Giovannoni et al (2001) "Isolation of anti-angiogenesis antibodies from a large combinatorial repertoire by colony filter screening." *Nucleic Acids Res.* 29: E27). Further, antibodies and antibody fragments suitable for use in the present invention are described, for example, in the following publications: "*Monoclonal Hybridoma Antibodies: Techniques and Application*", Hurrell (CRC Press, 1982); "*Monoclonal Antibodies: A Manual of Techniques*", H. Zola, CRC Press, 1987, ISBN: 0-84936-476-0; "*Antibodies: A Laboratory Manual*" $1^{st}$ Edition, Harlow & Lane, Eds, Cold Spring Harbor Laboratory Press, New York, 1988. ISBN 0-87969-314-2; "*Using Antibodies: A Laboratory Manual*" $2^{nd}$ Edition, Harlow & Lane, Eds, Cold Spring Harbor Laboratory Press, New York, 1999. ISBN 0-87969-543-9; and "*Handbook of Therapeutic Antibodies*" Stefan Dübel, Ed., $1^{st}$ Edition—Wiley-VCH, Weinheim, 2007. ISBN: 3-527-31453-9.

By an antibody that selectively binds to CLEC14A or MMRN2, we include the meaning that the antibody molecule binds CLEC14A or MMRN2 with a greater affinity than for an irrelevant polypeptide, such as human serum albumin (HSA). Preferably, the antibody binds the CLEC14A or MMRN2 with at least 5, or at least 10 or at least 50 times greater affinity than for the irrelevant polypeptide. More preferably, the antibody molecule binds the CLEC14A or MMRN2 with at least 100, or at least 1,000, or at least 10,000 times greater affinity than for the irrelevant polypeptide. Such binding may be determined by methods well known in the art, such as one of the Biacore® systems.

It is preferred that the antibody that selectively binds CLEC14A or MMRN2 does not bind a related polypeptide, such as thrombomodulin in the case of CLEC14A or multimerin 1 in the case of MMRN2, or that the antibody molecule binds CLEC14A or MMRN2 with a greater affinity than for the related polypeptide, such as thrombomodulin in the case of CLEC14A or multimerin 1 in the case of MMRN2. Preferably, the antibody binds the CLEC14A or MMRN2 with at least 5, or at least 10 or at least 50 times greater affinity than for the related polypeptide. More preferably, the antibody molecule binds the CLEC14A or MMRN2 with at least 100, or at least 1,000, or at least 10,000 times greater affinity than for the related polypeptide. Such binding may be determined by methods well known in the art, such as one of the Biacore® systems.

It is preferred if the antibodies have an affinity for CLEC14A or MMRN2 of at least $10^{-5}$ M, $10^{-6}$ M, or $10^{-7}$ M and more preferably $10^{-8}$ M, although antibodies with higher affinities, e.g. $10^{-9}$ M, or higher, may be even more preferred.

In a particularly preferred embodiment, the antibody is one that selectively binds to the CLEC14A polypeptide.

Typically, the antibody that selectively binds to CLEC14A binds to the mature peptide (residues 22-490) and not to the signal peptide (residues 1-21). Preferably, the antibody that selectively binds CLEC14A binds to the extracellular region of CLEC14A (residues 22-396). The antibody may bind to the EGF-like region (residues 245-287), but it is preferred if the antibody binds to the C-type lectin domain (residues 32-173). More preferably, the antibody binds to the region spanning amino acid residues 97-108 of CLEC14A which is within the C-type lectin domain, namely ERRRSCHTLENE (SEQ ID NO: 39).

It is especially preferred if the antibody that selectively binds to the CLEC14A polypeptide, selectively binds to the MMRN2 binding region of the CLEC14A polypeptide within the C-type lectin domain. Thus, the antibody may be one that competes with MMRN2 for specific binding to the CLEC14A polypeptide. Whether or not a given antibody selectively binds to the MMRN2 binding region or competes with MMRN2 for specific binding to the CLEC14A polypeptide can be determined using routine methods in the art such as epitope mapping, competition binding studies and other methods described in Example 1. For example, binding of CLEC14A to the given antibody can be assessed following pre-incubation with varying concentrations of MMRN2.

In an embodiment, the antibody that selectively binds to the CLEC14A polypeptide does not bind to the region spanning amino acid residues 31-72 of CLEC14A, and/or the region spanning amino acid residues 31-92 of CLEC14A, and/or the region spanning amino acid residues 92-172 of CLECA, and/or the region spanning amino acid residues 112-172 of CLEC14A, and/or the region spanning amino acid residues 152-172 of CLEC14A. Whether or not the antibody binds to any of these regions can be assessed using standard techniques in the art, including the binding assays described herein such as ELISA.

In another embodiment, the antibody is one that selectively binds to the MMRN2 polypeptide. Thus, the antibody may be one that competes with CLEC14A for specific binding to the MMRN2 polypeptide. In this embodiment, it is preferred if the antibody selectively binds to the CLEC14A binding region of the MMRN2 polypeptide. Again, whether or not a given antibody binds to the CLEC14A binding region of the MMRN2 polypeptide or competes with CLEC14A for specific binding to the MMRN2 polypeptide can be determined using routine methods in the art such as epitope mapping, competition binding studies and other methods described in Example 1.

By an antibody that selectively binds a specific portion of CLEC14A or MMRN2 we include the meaning that not only does the antibody selectively bind to the target as described above, the antibody molecule also binds the specified portion of the CLEC14A or MMRN2 with a greater affinity than for any other portion of it. Preferably, the antibody binds the specified portion with at least 2, or at least 5, or at least 10 or at least 50 times greater affinity than for any other epitope on CLEC14A or MMRN2. More preferably, the antibody molecule binds the specified portion with at least 100, or at least 1,000, or at least 10,000 times greater affinity than for than for any other epitope on the CLEC14A or MMRN2. Such binding may be determined by methods well known in the art, such as one of the Biacore® systems. It is preferred if the antibodies have an affinity for their target epitope on the CLEC14A or MMRN2 of at least $10^{-7}$ M and more preferably $10^{-8}$ M, although antibodies with higher affinities, e.g. $10^{-9}$ M, or higher, may be even more preferred. Preferably, the antibody selectively binds the particular specified epitope within the CLEC14A or MMRN2 and does not bind any other epitopes within it.

Preferably, when the antibody is administered to an individual, the antibody binds to the target CLEC14A or MMRN2 or to the specified portion thereof with a greater affinity than for any other molecule in the individual. Preferably, the antibody binds to (a specified portion of) the CLEC14A or MMRN2 with at least 2, or at least 5, or at least 10 or at least 50 times greater affinity than for any other molecule in the individual. More preferably, the agent binds the CLEC14A or MMRN2 (at the specific domain) with at least 100, or at least 1,000, or at least 10,000 times greater affinity than any other molecule in the individual. Preferably, the antibody molecule selectively binds the CLEC14A or MMRN2 without significantly binding other polypeptides in the body.

As described in Example 1, the inventors have identified an antibody that specifically binds to CLEC14A and which inhibits binding of CLEC14A to MMRN2. The amino acid sequences of the variable heavy and light chains of this antibody, and the nucleotide sequences encoding them, are provided in FIG. 11, where the sequences of the CDRs are highlighted in bold text. CDR regions may be predicted with any suitable algorithm. The CDR regions disclosed herein were predicted with the Abysis algorithm (www.bioinf.org.uk/abysis/sequence_input/key_annotation/key_annotation.cgi) or the IMGT algorithm (ImMunoGeneTics) which can be found at www.IMGT.org, see for example Lefranc et al 2009 NAR 37: D1006-D1012 and Lefranc 2003 Leukemia 17: 260-266. CDR regions identified by either algorithm are considered to be equally suitable for use in the invention.

Accordingly, in one embodiment of the first aspect of the invention, the agent is an antibody that comprises:
(a) a heavy chain CDR1 comprising the amino acid sequence SSYWIE (SEQ ID No: 1) or GYTFSSYW (SEQ ID NO: 40);
(b) a heavy chain CDR2 comprising the amino acid sequence WIGEILPGSGST (SEQ ID No: 2) or WIGEILPGSGSTN (SEQ ID NO: 78) or ILPGSGST (SEQ ID NO: 41); and/or
(c) a heavy chain CDR3 comprising the amino acid sequence ARGGDYDEEYYLMD (SEQ ID No: 3) or ARGGDYDEEYYLMDY (SEQ ID NO: 42);
or a variant of any of these sequences comprising 1, 2 or 3 amino acid substitutions.

In a further embodiment of the first aspect of the invention, the agent is an antibody that comprises:
(a) a light chain CDR1 comprising the amino acid sequence SYMYWY (SEQ ID No: 4) or SSVSY (SEQ ID NO: 43);
(b) a light chain CDR2 comprising the amino acid sequence LLIYDTSNLA (SEQ ID No: 5) or DTS; and/or
(c) a light chain CDR3 comprising the amino acid sequence QQWSSYPL (SEQ ID No: 6) or QQWSSYPLT (SEQ ID NO: 44);
or a variant of any of these sequences comprising 1, 2 or 3 amino acid substitutions.

In yet a further embodiment of the first aspect of the invention, the agent may be an antibody that comprises both light and heavy chain CDRs as described above. For instance, the antibody may comprise: a heavy chain CDR1 comprising the amino acid sequence SSYWIE (SEQ ID No: 1); a heavy chain CDR2 comprising the amino acid sequence WIGEILPGSGST (SEQ ID No: 2) or a heavy chain CDR2 comprising the amino acid sequence WIGEILPGSGSTN (SEQ ID NO: 78); a heavy chain CDR3 comprising the amino acid sequence ARGGDYDEEYYLMD (SEQ ID No: 3); a light chain CDR1 comprising the amino acid sequence SYMYWY (SEQ ID No: 4); a light chain CDR2 comprising the amino acid sequence LLIYDTSNLA (SEQ ID No: 5); and a light chain CDR3 comprising the amino acid sequence QQWSSYPL (SEQ ID No: 6), or a variant of any of said sequences comprising 1, 2, or 3 amino acid substitutions; or the antibody may comprise: a heavy chain CDR1 comprising the amino acid sequence GYTFSSYW (SEQ ID No: 40); a heavy chain CDR2 comprising the amino acid sequence ILPGSGST (SEQ ID No: 41); a heavy chain CDR3 comprising the amino acid sequence ARGGDYDEEYYLMDY (SEQ ID No: 42); a light chain CDR1 comprising the amino acid sequence SSVSY (SEQ ID No: 43); a light chain CDR2 comprising the amino acid sequence DTS; and a light chain CDR3 comprising the amino acid sequence QQWSSYPLT (SEQ ID No: 44), or a variant of any of said sequences comprising 1, 2, or 3 amino acid substitutions In a further embodiment of the first aspect of the invention, the agent is an antibody that comprises:
(a) a heavy chain CDR1 comprising the amino acid sequence SSYWIE (SEQ ID No: 1) or GYTFSSYW (SEQ ID NO: 40);
(b) a heavy chain CDR2 comprising the amino acid sequence WIGEILPGSGSTN (SEQ ID No: 78) or ILPGSGST (SEQ ID NO: 41); and/or
(c) a heavy chain CDR3 comprising the amino acid sequence ARGGDYDEEYYVMD (SEQ ID No: 77) or ARGGDYDEEYYVMDY (SEQ ID NO: 45);
or a variant of any of these sequences comprising 1, 2 or 3 amino acid substitutions.

In yet a further embodiment of the first aspect of the invention, the agent may be an antibody that comprises both light and heavy chain CDRs as described above. For instance, the antibody may comprise: a heavy chain CDR1 comprising the amino acid sequence (SEQ ID No: 1); a heavy chain CDR2 comprising the amino acid sequence (SEQ ID No: 78); a heavy chain CDR3 comprising the amino acid sequence (SEQ ID No: 77); a light chain CDR1 comprising the amino acid sequence (SEQ ID No: 4); a light chain CDR2 comprising the amino acid sequence (SEQ ID No: 5); and a light chain CDR3 comprising the amino acid sequence (SEQ ID No: 6), or a variant of any of said sequences comprising 1, 2, or 3 amino acid substitutions; or the antibody may comprise: a heavy chain CDR1 comprising the amino acid sequence (SEQ ID No: 40); a heavy chain CDR2 comprising the amino acid sequence (SEQ ID No: 41); a heavy chain CDR3 comprising the amino acid sequence (SEQ ID No: 45); a light chain CDR1 comprising the amino acid sequence (SEQ ID No: 43); a light chain CDR2 comprising the amino acid sequence DTS; and a light chain CDR3 comprising the amino acid sequence (SEQ ID No: 44), or a variant of any of said sequences comprising 1, 2, or 3 amino acid substitutions.

In yet a further embodiment of the first aspect of the invention, the agent is an antibody that comprises:
(a) a heavy chain CDR1 comprising the amino acid sequence SSYWIE (SEQ ID No: 1) or GYTFSSYW (SEQ ID NO: 40);
(b) a heavy chain CDR2 comprising the amino acid sequence WIGEILPGSGSTN (SEQ ID No: 78) or ILPGSGST (SEQ ID NO: 41); and/or
(c) a heavy chain CDR3 comprising the amino acid sequence ARGGDYDEEYYAMD (SEQ ID No: 46) or ARGGDYDEEYYAMDY (SEQ ID NO: 47);
or a variant of any of these sequences comprising 1, 2 or 3 amino acid substitutions.

In a further embodiment of the first aspect of the invention, the agent is an antibody that comprises:
(a) a light chain CDR1 comprising the amino acid sequence SYMYWY (SEQ ID No: 4) or SSVSY (SEQ ID NO: 43);
(b) a light chain CDR2 comprising the amino acid sequence LLIYDTSNLA (SEQ ID No: 5) or DTS; and/or
(c) a light chain CDR3 comprising the amino acid sequence QQWSSYPL (SEQ ID No: 6) or QQWSSYPLTF (SEQ ID NO: 48);
or a variant of any of these sequences comprising 1, 2 or 3 amino acid substitutions.

In yet a further embodiment of the first aspect of the invention, the agent may be an antibody that comprises both light and heavy chain CDRs as described above. For instance, the antibody may comprise: a heavy chain CDR1 comprising the amino acid sequence (SEQ ID No: 1); a heavy chain CDR2 comprising the amino acid sequence (SEQ ID No: 78); a heavy chain CDR3 comprising the amino acid sequence (SEQ ID No: 46); a light chain CDR1 comprising the amino acid sequence (SEQ ID No: 4); a light chain CDR2 comprising the amino acid sequence (SEQ ID No: 5); and a light chain CDR3 comprising the amino acid sequence (SEQ ID No: 6), or a variant of any of said sequences comprising 1, 2, or 3 amino acid substitutions; or the antibody may comprise: a heavy chain CDR1 comprising the amino acid sequence (SEQ ID No: 40); a heavy chain CDR2 comprising the amino acid sequence (SEQ ID No: 41); a heavy chain CDR3 comprising the amino acid sequence (SEQ ID No: 47); a light chain CDR1 comprising the amino acid sequence (SEQ ID No: 43); a light chain CDR2 comprising the amino acid sequence DTS; and a light chain CDR3 comprising the amino acid sequence (SEQ ID No: 48), or a variant of any of said sequences comprising 1, 2, or 3 amino acid substitutions.

For the avoidance of doubt, where variants of particular CDR sequences of an antibody are mentioned, it will be appreciated that one or more of the CDRs in the antibody as defined may be varied. Thus, where the antibody is defined as comprising light chain or heavy chain CDRs (eg CDRs 1-3), each having a particular sequence, up to one, two, or three of those particular sequences may be varied and so on. Similarly, where the antibody is defined as comprising light chain and heavy chains CDRs (ie six CDRs), each having a particular sequence, up to one, two, three, four, five, or all six of those particular sequences may be varied.

It will be appreciated that any of the variants of the specific sequences described herein should not affect the desired activity of the antibody, namely its selective binding to CLEC14A and/or its ability to inhibit the interaction between CLEC14A and MMRN2.

By not affecting selective binding to CLEC14A we include the meaning that the variants should have substantially the same or greater binding affinity for CLEC14A as the binding affinity of the antibodies having the particular sequences described herein. For example, the variants may have at least 80%, 85%, 90%, 95%, 96%, 97%, 98%, 99%, 100%, 105%, 110%, 115%, 120%, or more of the binding affinity of an antibody having a particular amino acid sequence described herein.

By not affecting the ability to inhibit the interaction between CLEC14A and MMRN2 we include the meaning that the variants should have substantially the same or greater ability to inhibit the interaction between CLEC14A and MMRN2, as the ability to inhibit the interaction between CLEC14A and MMRN2 of the antibodies having the particular sequences described herein. For example, the variants may have at least 80%, 85%, 90%, 95%, 96%, 97%, 98%, 99%, 100%, 105%, 110%, 115%, 120%, or more of the ability to inhibit the interaction between CLEC14A and MMRN2 of an antibody having a particular amino acid sequence described herein.

Typically, it is preferred that the amino acid substitutions of the variants disclosed herein are conservative amino acid substitutions, for example where an amino acid residue is replaced with an amino acid residue having a similar side chain. Conservative amino acid substitutions are well known in the art and include (original residue↔Substitution) Ala (A)↔Val, Gly or Pro; Arg (R)↔Lys or His; Asn (N)↔Gln; Asp (D)↔Glu; Cys (C)↔Ser; Gln (Q)↔Asn; Glu (G)↔Asp; Gly (G)↔Ala; His (H)↔Arg; Ile (I)↔Leu; Leu (L)↔Ile, Val or Met; Lys (K)↔Arg; Met (M)↔Leu; Phe (F)↔Tyr; Pro (P)↔Ala; Ser (S)↔Thr or Cys; Thr (T)↔Ser; Trp (W)↔Tyr; Tyr (Y)↔Phe or Trp; and Val (V)↔Leu or Ala.

It is appreciated that molecules containing three or fewer CDR regions (in some cases, even just a single CDR or a part thereof) are capable of retaining the antigen-binding activity of the antibody from which the CDR(s) are derived. For example, Gao et al (1994, *J. Biol. Chem.*, 269: 32389-93) describe a whole $V_L$ chain (including all three CDRs) having high affinity for its substrate.

Molecules containing two CDR regions are described, for example, by Vaughan & Sollazzo (2001, *Combinatorial Chemistry & High Throughput Screening*, 4: 417-430). On page 418 (right column—3 Our Strategy for Design) a minibody including only the H1 and H2 CDR hypervariable regions interspersed within framework regions is described. The minibody is described as being capable of binding to a target. Pessi et al (1993, Nature, 362: 367-9) and Bianchi et al (1994, *J. Mol. Biol.*, 236: 649-59) are referenced by Vaughan & Sollazzo and describe the H1 and H2 minibody and its properties in more detail. Qiu et al (2007, *Nature Biotechnology*, 25:921-9) demonstrate that a molecule consisting of two linked CDRs are capable of binding antigen (abstract and page 926, right-hand column). Quiocho (1993, Nature, 362: 293-4) provides a summary of the Pessi et al. "minibody" technology. Ladner (2007, *Nature Biotechnology*, 25:875-7) reviews the Qiu et al. article and comments that molecules containing two CDRs are capable of retaining antigen-binding activity (page 875, right-hand column).

Molecules containing a single CDR region are described, for example, by Laune et al (1997, *JBC*, 272: 30937-44) who demonstrate that a range of hexapeptides derived from a CDR display antigen-binding activity (abstract) and note that synthetic peptides of a complete, single, CDR display strong binding activity (page 30942, right-hand column). Monnet et al (1999, *JBC*, 274: 3789-96) show that a range of 12-mer peptides and associated framework regions have antigen-binding activity (abstract) and comment that a CDR3-like peptide alone is capable of binding antigen (page 3785, left-hand column). Heap et al (2005, *J. Gen. Virol.*, 86: 1791-1800) report that a "micro-antibody" (a molecule containing a single CDR) is capable of binding antigen (abstract and page 1791, left-hand column) and shows that a cyclic peptide from an anti-HIV antibody has antigen-binding activity and function. Nicaise et al (2004, *Protein Science*, 13:1882-91) show that a single CDR can confer antigen-binding activity and affinity for its lysozyme antigen.

In a more specific embodiment of the first aspect of the invention, the antibody comprises a heavy chain variable region comprising the amino acid sequence (SEQ ID No: 7)
MAQVQLQQSGAELMKPGASVKISCKATGYTFSSYWIEWVNRRPGHGLEWI

GEILPGSGSTNYNEKFKGKATFTADTSSNTAYMQLSSLTSEDSAVYYCAR

GGDYDEEYYLMDYWGQGTTLTVSS;

or (SEQ ID NO: 49)
MAQVQLQQSGAELMKPGASVKISCKATGYTFSSYWIEWVNRRPGHGLEWI

GEILPGSGSTNYNEKFKGKATFTADTSSNTAYMQLSSLTSEDSAVYYCAR

GGDYDEEYYLMDYWGQGTTLTV;

or a variant of this sequence comprising 1, 2, 3, 4, or 5 amino acid substitutions.

Additionally or alternatively (ie optionally in combination with the heavy chain amino acid sequence described above), the antibody may comprise a light chain variable region comprising the amino acid sequence (SEQ ID No: 8)
QIVLTQSPAIMSASPGEKVTMTCSASSSVSYMYWYQQKPGSSPRLLIYDT

SNLASGVPVRFSGSGSGTSYSLTISRMEAEDAATYYCQQWSSYPLTFGAG

TKLEIKRAA;

or (SEQ ID NO: 50)
QIVLTQSPAIMSASPGEKVTMTCSASSSVSYMYWYQQKPGSSPRLLIYDT

SNLASGVPVRFSGSGSGTSYSLTISRMEAEDAATYYCQQWSSYPLTFGAG

TKLEIKRAAA;

or a variant of this sequence comprising 1, 2, 3, 4, or 5 amino acid substitutions.

Thus, in a particularly preferred embodiment, the agent is an antibody that comprises a heavy chain variable region comprising the amino acid sequence MAQVQLQQSGAELMKPGASVKISCKATGYTFSSYWIEWVNRRPGHGLEWIGEILPGSG STNYNEKFKGKATFTADTSSNTAYMQLSSLTSEDSAVYYCARGGDYDEEYYLMDYWG QGTTLTVSS (SEQ ID No: 7) or MAQVQLQQSGAELMKPGASVKISCKATGYTFSSYWIEWVNRRPGHGLEWIGEILPGSG STNYNEKFKGKATFTADTSSNTAYMQLSSLTSEDSAVYYCARGGDYDEEYYLMDYWG QGTTLTV (SEQ ID NO: 49) or a variant of any of these sequences comprising 1, 2, 3, 4, or 5 amino acid substitutions.

and a light chain variable region comprising the amino acid sequence QIVLTQSPAIMSASPGEKVTMTCSASSSVSYMYWYQQKPGSSPRLLIYDTSNLASGVPV RFSGSGSGTSYSLTISRMEAEDAATYYCQQWSSYPLTFGAGTKLEIKRAA (SEQ ID No: 8) or QIVLTQSPAIMSASPGEKVTMTCSASSSVSYMYWYQQKPGSSPRLLIYDTSNLASGVPVRFSGSGSGTSYSLTISRMEAEDAATYYCQQWSSYPLTFGAGTKLEIKRAAA (SEQ ID NO: 50) or a variant of any of these sequences comprising 1, 2, 3, 4, or 5 amino acid substitutions.

In a further more specific embodiment of the first aspect of the invention, the antibody comprises a heavy chain variable region comprising the amino acid sequence MAEVQLQQSGAELMKPGASVKISCKATGYTFSSY-WIEWVKQRPGHGLEWIGEILPGSG STNYNEKFK-GKATFTADTSSNTAYMQLSSLTSEDSAVYYCARGG-DYDEEYYVMDYWG QGTSVTV (SEQ ID NO:51); or a variant of this sequence comprising 1, 2, 3, 4, or 5 amino acid substitutions.

Additionally or alternatively (ie optionally in combination with the heavy chain amino acid sequence described above), the antibody may comprise a light chain variable region comprising the amino acid sequence (SEQ ID NO: 52)
QIVLTQSPAIMSASPGEKVTMTCSASSSVSYMYWYQQKPGSSPRLLIYDT

SNLASGVPVRFSGSGSGTSYSLTISRMEAEDAATYYCQQWSSYPLTFGAG

TKLELKR;

or a variant of this sequence comprising 1, 2, 3, 4, or 5 amino acid substitutions.

Thus, in a particularly preferred embodiment, the agent is an antibody that comprises a heavy chain variable region comprising the amino acid sequence (SEQ ID No: 51) or a variant of this sequence comprising 1, 2, 3, 4, or 5 amino acid substitutions, and a light chain variable region comprising the amino acid sequence (SEQ ID No: 52) or a variant of this sequence comprising 1, 2, 3, 4, or 5 amino acid substitutions.

In yet a further more specific embodiment of the first aspect of the invention, the antibody comprises a heavy chain variable region comprising the amino acid sequence (SEQ ID NO: 53)
MAEVQLQQSGAELMKPGASVKISCKATGYTFSSYWIEWVNQRPGHGLEWI

GEILPGSGSTNYNEKFKGKATFTADTSSNTAYMQLSSLTSEDSAVYYCAR

GGDYDEEYYAMDYWGQGTSVTL;

or a variant of this sequence comprising 1, 2, 3, 4, or 5 amino acid substitutions.

Additionally or alternatively (ie optionally in combination with the heavy chain amino acid sequence described above), the antibody may comprise a light chain variable region comprising the amino acid sequence (SEQ ID NO: 54)
QIVLTQSPAIMSASPGEKVTMTCSASSSVSYMYWYQQKPGSSPRLLIYDT

SNLASGVPVRFSGSGSGTSYSLTISRMEAEDGATYYCQQWSSYPLTFGAG

TKLELKR;

or a variant of this sequence comprising 1, 2, 3, 4, or 5 amino acid substitutions.

Thus, in a particularly preferred embodiment, the agent is an antibody that comprises a heavy chain variable region comprising the amino acid sequence (SEQ ID No: 53) or a variant of this sequence comprising 1, 2, 3, 4, or 5 amino acid substitutions, and a light chain variable region comprising the amino acid sequence (SEQ ID No: 54) or a variant of this sequence comprising 1, 2, 3, 4, or 5 amino acid substitutions.

When the antibody is defined as having a light chain variable region comprising a particular amino acid sequence and a heavy chain variable region having a particular amino acid sequence, it will be appreciated that up to one or two of those sequences may be varied as defined herein. The variation may be within the non-CDR regions of the sequences or the variation may be within the CDR regions. Typically a single CDR region in a given heavy chain variable region or a given light chain variable region may have 1, 2, or 3 amino acid substitutions. It will be appreciated therefore that each of the three CDR regions in a given heavy chain variable region or a given light chain variable region may have up to 3 amino acid substitutions. Each given heavy chain variable region or given light chain region may additionally comprise a number of amino acid substitutions in non-CDR regions, for example 1, 2, 3, 4, or 5 amino acid substitutions.

Preferences for the type of amino acid substitution are detailed above in relation to the first aspect of the invention. Preferably the substitutions are conservative amino acid substitutions.

In a further specific embodiment of the first aspect of the invention, the antibody comprises the sequence MAQVQLQQSGAELMKPGASVKISCKATGYTFSSY-WIEWVNRRPGHGLEWIGEILPGSG STNYNEKFKGK-ATFTADTSSNTAYMQLSSLTSEDSVVYYCARGGD-YDEEYYLMDYWG QGTTLTVSSGGGGSGGGGS-GGGGSQIVLTQSPAIMSASPGEKVTMTCSASSS-VSYMY WYQQKPGSSPRLLIYDTSNLASGVPVRF-SGSGSGTSYSLTISRMEAEDAATYYCQQWS SYPLT-FGAGTKLEIKRAAA (SEQ ID NO: 55) or a variant of this sequence comprising 1, 2, 3, 4, or 5 amino acid substitutions.

In another specific embodiment of the first aspect of the invention, the antibody comprises the sequence MAEVQLQQSGAELMKPGASVKISCKATGYTFSSY-WIEWVKQRPGHGLEWIGEILPGSG STNYNEKFKG-KATFTADTSSNTAYMQLSSLTSEDSAVYYCARGGDY-DEEYYVMDYWG QGTSVTVSSGGGGSGGGGSG-GGGSQIVLTQSPAIMSASPGEKVTMTCSASSSVSYMY WYQQKPGSSPRLLIYDTSNLASGVPVRFSGSGSGT-SYSLTISRMEAEDAATYYCQQWS SYPLTFGAG-TKLELKR (SEQ ID NO:56) or a variant of this sequence comprising 1, 2, 3, 4, or 5 amino acid substitutions.

In another specific embodiment of the first aspect of the invention, the antibody comprises the sequence MAEVQLQQSGAELMKPGASVKISCKATGYTFSSY-WIEWVNQRPGHGLEWIGEILPGSG STNYNEKFK-GKATFTADTSSNTAYMQLSSLTSEDSAVYYCARGG-DYDEEYYAMDYWG QGTSVTLSSGGGGSGGGGSG-GGGSQIVLTQSPAIMSASPGEKVTMTCSASSSVSYMY WYQQKPGSSPRLLIYDTSNLASGVPVRFSGSGSGT-SYSLTISRMEAEDAATYYCQQWS SYPLTFGAGT-KLELKR (SEQ ID NO:57) or a variant of this sequence comprising 1, 2, 3, 4, or 5 amino acid substitutions.

It will be appreciated that the agent may also be an antibody that competes with any of the antibodies whose sequences are defined herein for specific binding to CLEC14A, such as specific binding to the MMRN2 binding region.

As mentioned above, the agent that inhibits the interaction between CLEC14A and MMRN2 may be a polynucleotide that encodes the agent.

Thus, the agent may be a polynucleotide that encodes any of the antibodies described herein that are defined by reference to particular sequences. The polynucleotide sequences of the variable light and heavy chains of these antibodies are provided in FIG. 11.

Thus, the agent may be a polynucleotide comprising one or more of the following nucleotide sequences:

(i)
(SEQ ID No: 9)
AGTAGCTACTGGATAGAG;

(ii)
(SEQ ID No: 10)
TGGATTGGAGAGATTTTACCTGGAAGTGGTAGTACTAAT;

(iii)
(SEQ ID No: 11)
GCGAGAGGGGGGATTACGACGAAGAATACTATCTCATGGAC;

(iv)
(SEQ ID No: 12)
AGTTACATGTACTGGTAC;

(v)
(SEQ ID No: 13)
CTCCTGATTTATGACACATCCAACCTGGCT;
and (vi)
(SEQ ID No: 14)
CAGCAGTGGAGTAGTTACCCGCTC;

(vii)
(SEQ ID NO: 60)
GGCTACACATTCAGTAGCTACTGG (viii)
(SEQ ID NO: 61)
ATTTTACCTGGAGTGGTAGTACT (ix)
(SEQ ID NO: 62)
GCGAGAGGGGGGATTACGACGAAGAATACTATCTCATGGACTAC (x)
(SEQ ID NO: 63)
TCAAGTGTAAGTTAC (xi)
GACACATCC (xii)
(SEQ ID NO: 64)
CAGCAGTGGAGTAGTTACCCGCTCACG (xiii)
(SEQ ID NO: 58)
GCAAGAGGGGGGATTACGACGAAGAATACTATGTCATGGAC (xiv)
(SEQ ID NO: 66)
ATTTTACCTGGAAGTGGTAGTACT (xv)
(SEQ ID NO: 65)
GCAAGAGGGGGGATTACGACGAAGAATACTATGCTATGGACTAC (xvi)
(SEQ ID NO: 59)
GCAAGAGGGGGGATTACGACGAAGAATACTATGCTATGGAC (xvii)
(SEQ ID NO: 66)
ATTTTACCTGGAAGTGGTAGTACT (xviii)
(SEQ ID NO: 67)
GCAAGAGGGGGGATTACGACGAAGAATACTATGTCATGGACTAC (xix)
(SEQ ID NO: 46)
CAGCAGTGGAGTAGTTACCCGCTCACG (xx)
(SEQ ID NO: 79)
TGGATTGGAGAGATTTTACCTGGAAGTGGTAGTACT Polynucleotide sequence (i) (SEQ ID No: 9) encodes heavy chain CDR SSYWIE (SEQ ID No: 1); polynucleotide sequence (ii) (SEQ ID No: 10) encodes heavy chain CDR WIGEILPGSGSTN (SEQ ID No: 78); polynucleotide sequence (xx) (SEQ ID NO: 79) encodes heavy chain CDR WIGEILPGSGST (SEQ ID NO: 2); polynucleotide sequence (iii) (SEQ ID No: 11) encodes heavy chain CDR ARGGDYDEEYYLMD (SEQ ID No: 3); polynucleotide sequence (iv) (SEQ ID No: 12) encodes light chain CDR SYMYWY (SEQ ID No: 4); polynucleotide sequence (v) (SEQ ID No: 13) encodes light chain CDR LLIYDTSNLA (SEQ ID No: 5); and polynucleotide sequence (vi) (SEQ ID No: 14) encodes light chain CDR QQWSSYPL (SEQ ID No: 6). Thus, the polynucleotide encoding the antibody may comprise any 1, 2 or 3 of polynucleotide sequences (i); (ii) or (xx); and (iii) and/or any 1, 2 or 3 of polynucleotide sequences (iv)-(vi). Preferably, the polynucleotide comprises all six of polynucleotide sequences (i); (ii) or (xx); (iii); (iv); (v) and (vi).

Polynucleotide sequence (vii) (SEQ ID No: 60) encodes heavy chain CDR GYTFSSYW (SEQ ID No: 40); polynucleotide sequence (viii) (SEQ ID No: 61) encodes heavy chain CDR ILPGSGST (SEQ ID No: 41); polynucleotide sequence (ix) (SEQ ID No: 62) encodes heavy chain CDR ARGGDYDEEYYLMDY (SEQ ID No: 42); polynucleotide sequence (x) (SEQ ID No: 63) encodes light chain CDR SSVSY (SEQ ID No: 43); polynucleotide sequence (xi) encodes light chain CDR DTS; and polynucleotide sequence (xii) (SEQ ID No: 64) encodes light chain CDR QQWSSY-PLT (SEQ ID No: 44). Thus, the polynucleotide encoding the antibody may comprise any 1, 2 or 3 of polynucleotide sequences (vii)-(ix) and/or any 1, 2 or 3 of polynucleotide sequences (x)-(xii). Preferably, the polynucleotide comprises all six of polynucleotide sequences (vii)-(xii).

It will be appreciated that any of the polynucleotide sequences encoding the heavy chain CDR sequences (i); (ii) or (xx); and (iii); may be substituted for any of the corresponding heavy chain CDR sequences of (vii)-(ix) and vice versa; and any of the polynucleotide sequences encoding the light chain CDR sequences (iv)-(vi) may be substituted for any of the corresponding light chain CDR sequences (x)-(xii) and vice versa.

Polynucleotide sequence (i) (SEQ ID NO: 9) encodes heavy chain CDR SSYWIE (SEQ ID No: 1); polynucleotide sequence (ii) (SEQ ID No: 10) encodes heavy chain CDR WIGEILPGSGSTN (SEQ ID No: 78); polynucleotide sequence (xiii) (SEQ ID No: 58) encodes heavy chain CDR ARGGDYDEEYYVMD (SEQ ID No: 77); polynucleotide sequence (iv) (SEQ ID No: 12) encodes light chain CDR SYMYWY (SEQ ID No: 4); polynucleotide sequence (v) (SEQ ID No: 13) encodes light chain CDR LLIYDTSNLA (SEQ ID No: 5); and polynucleotide sequence (vi) (SEQ ID No: 14) encodes light chain CDR QQWSSYPL (SEQ ID No: 6). Thus, the polynucleotide encoding the antibody may comprise any 1, 2 or 3 of polynucleotide sequences (i), (ii) and (xiii) and/or any 1, 2 or 3 of polynucleotide sequences (iv), (v) and (vi). Preferably, the polynucleotide comprises all six of polynucleotide sequences (i), (ii), (xiii) (iv), (v) and (vi).

Polynucleotide sequence (vii) (SEQ ID NO: 60) encodes heavy chain CDR GYTFSSYW (SEQ ID No: 40); polynucleotide sequence (xvii) (SEQ ID No: 66) encodes heavy chain CDR ILPGSGST (SEQ ID No: 41); polynucleotide sequence (xv) (SEQ ID No: 65) encodes heavy chain CDR ARGGDYDEEYYVMDY (SEQ ID No: 45); polynucleotide sequence (x) (SEQ ID No: 63) encodes light chain CDR SSVSY (SEQ ID No: 43); polynucleotide sequence (xi) encodes light chain CDR DTS; and polynucleotide sequence (xii) (SEQ ID No:64) encodes light chain CDR QQWSSYPLT (SEQ ID No: 44). Thus, the polynucleotide encoding the antibody may comprise any 1, 2 or 3 of polynucleotide sequences (vii), (xvii) and (xv) and/or any 1, 2 or 3 of polynucleotide sequences (x), (xi) and (xii). Preferably, the polynucleotide comprises all six of polynucleotide sequences (vii), (xvii), (xv), (x), (xi) and (xii).

It will be appreciated that any of the polynucleotide sequences encoding the heavy chain CDR sequences (i), (ii) and (xiii) may be substituted for any of the corresponding heavy chain CDR sequences of (vii), (xvii) and (xv) and vice versa; and any of the polypeptide sequences encoding the light chain CDR sequences (iv), (v) and (vi) may be substituted for any of the corresponding light chain CDR sequences (x), (xi) and (xii) and vice versa.

Polynucleotide sequence (i) (SEQ ID NO: 9) encodes heavy chain CDR SSYWIE (SEQ ID No: 1); polynucleotide sequence (ii) (SEQ ID No: 10) encodes heavy chain CDR WIGEILPGSGSTN (SEQ ID No: 78); polynucleotide sequence (xvi) (SEQ ID No: 59) encodes heavy chain CDR ARGGDYDEEYYAMD (SEQ ID No: 46); polynucleotide sequence (iv) (SEQ ID No: 12) encodes light chain CDR SYMYWY (SEQ ID No: 4); polynucleotide sequence (v) (SEQ ID No: 13) encodes light chain CDR LLIYDTSNLA (SEQ ID No: 5); and polynucleotide sequence (vi) (SEQ ID No: 14) encodes light chain CDR QQWSSYPL (SEQ ID No: 6). Thus, the polynucleotide encoding the antibody may comprise any 1, 2 or 3 of polynucleotide sequences (i), (ii) and (xvi) and/or any 1, 2 or 3 of polynucleotide sequences (iv), (v), and (vi). Preferably, the polynucleotide comprises all six of polynucleotide sequences (i), (ii), (xvi), (iv), (v), and (vi).

Polynucleotide sequence (vii) (SEQ ID NO: 60) encodes heavy chain CDR GYTFSSYW (SEQ ID No: 40); polynucleotide sequence (xiv) (SEQ ID No: 66) encodes heavy chain CDR ILPGSGST (SEQ ID No: 41); polynucleotide sequence (xviii) (SEQ ID No: 67) encodes heavy chain CDR ARGGDYDEEYYAMDY (SEQ ID No: 47); polynucleotide sequence (x) (SEQ ID No: 63) encodes light chain CDR SSVSY (SEQ ID No:43); polynucleotide sequence (xi) encodes light chain CDR DTS; and polynucleotide sequence (xix) (SEQ ID No: 46) encodes light chain CDR QQWSSY-PLTF (SEQ ID No: 48). Thus, the polynucleotide encoding the antibody may comprise any 1, 2 or 3 of polynucleotide sequences (vii), (xiv) and (xviii) and/or any 1, 2 or 3 of polynucleotide sequences (x), (xi), (xix). Preferably, the polynucleotide comprises all six of polynucleotide sequences (vii), (xiv) and (xviii), (x), (xi), (xix).

It will be appreciated that any of the polynucleotide sequences encoding the heavy chain CDR sequences (i), (ii) and (xvi) may be substituted for any of the corresponding heavy chain CDR sequences of (vii), (xiv) and (xviii) and vice versa; and any of the polypeptide sequences encoding the light chain CDR sequences (iv), (v), and (vi) may be substituted for any of the corresponding light chain CDR sequences (x), (xi), (xix) and vice versa.

In a more specific embodiment, the agent is a polynucleotide comprising the nucleotide sequence ATGGCCCAGGTTCAGCTGCAGCAGTCTGGAGCT-GAGCTGATGAAGCCTGGGGCCT CAGTGAAGA-TATCCTGCAAGGCTACTGGCTACACATTCAGTAGC-TACTGGATAGAG TGGGTAAACCGGAGGCCTGGAC-ATGGCCTTGAGTGGATTGGAGAGATTTTACCTGG AAGTGGTAGTACTAATTACAATGAGAAGTTCAA-GGGCAAGGCCACATTCACTGCAG ATACATCCTC-CAATACAGCCTACATGCAACTCAGCAGCCTCACA-TCTGAGGACTCTG CCGTCTATTACTGTGCGA-GAGGGGGGGATTACGACGAAGAATACTATCTCAT-GGAC TACTGGGGTCAAGGCACCACTCTCACAGT-CTCCTCA (SEQ ID No: 15), which encodes the variable heavy chain of SEQ ID No: 7.

In a further more specific embodiment, the agent is a polynucleotide comprising the nucleotide sequence CAAATTGTTCTCACCCAGTCTCCAGCAATCATGTC-TGCATCTCCAGGGGAGAAGGT CACCATGACCTGC-AGTGCCAGCTCAAGTGTAAGTTACATGTACTGGT-ACCAGCAGA AGCCAGGATCCTCCCCCAGACTCCT-GATTTATGACACATCCAACCTGGCTTCTGGA GTC-CCTGTTCGCTTCAGTGGCAGTGGGTCTGGGACCT-CTTACTCTCTCACAATCAG CCGAATGGAGGCT-GAAGATGCTGCCACTTATTACTGCCAGCAGTG-GAGTAGTTACC CGCTCACGTTCGGTGCTGGGAC-CAAGCTGGAAATCAAACGTGCGGCCGC (SEQ ID No: 16), which encodes the variable light chain of SEQ ID No: 8.

Preferably, the agent is a polynucleotide comprising the nucleotide sequence of SEQ ID No: 15 and the nucleotide sequence of SEQ ID No: 16.

In another specific embodiment, the agent is a polynucleotide comprising the nucleotide sequence ATGGCCCAGGTTCAGCTGCAGCAGTCTGGAGCT-GAGCTGATGAAGCCTGGGGCCT CAGTGAAGA-TATCCTGCAAGGCTACTGGCTACACATTCAGTAGC-TACTGGATAGAG TGGGTAAACCGGAGGCCTG-GACATGGCCTTGAGTGGATTGGAGAGATTTTACC-TGG AAGTGGTAGTACTAATTACAATGAGAAGTT-CAAGGGCAAGGCCACATTCACTGCAG ATACATC-CTCCAATACAGCCTACATGCAACTCAGCAGCCTCA-CATCTGAGGACTCTG TCGTCTATTACTGTGCGA-GAGGGGGGGATTACGACGAAGAATACTATCTCATG-GAC TACTGGGGTCAAGGCACCACTCTCACAGTC (SEQ ID No: 68), which encodes the variable heavy chain of SEQ ID No: 49.

In a further more specific embodiment, the agent is a polynucleotide comprising the nucleotide sequence CAAATTGTTCTCACCCAGTCTCCAGCAATCATG-TCTGCATCTCCAGGGGAGAAGGT CACCATGAC-CTGCAGTGCCAGCTCAAGTGTAAGTTACATGTA-CTGGTACCAGCAGA AGCCAGGATCCTCCCCCA-GACTCCTGATTTATGACACATCCAACCTGGCTT-CTGGA GTCCCTGTTCGCTTCAGTGGCAGTGGGT-CTGGGACCTCTTACTCTCTCACAATCAG CCGAATG-GAGGCTGAAGATGCTGCCACTTATTACTGCCA-GCAGTGGAGTAGTTACC CGCTCACGTTCGGT-GCTGGGACCAAGCTGGAAATCAAACGT (SEQ ID No: 69), which encodes the variable light chain of SEQ ID No: 50.

Preferably, the agent is a polynucleotide comprising the nucleotide sequence of SEQ ID No: 68 and the nucleotide sequence of SEQ ID No: 69.

In a further specific embodiment, the agent is a polynucleotide comprising the nucleotide sequence ATGGCCGAGGTTCAGCTTCAGCAGTCTGGAGCT-GAGCTGATGAAGCCTGGGGCCT CAGTGAAGA-TATCCTGCAAGGCTACTGGCTACACATTCAGTAGC-TACTGGATAGAG TGGGTAAAGCAGAGGCCT-GGACATGGCCTTGAGTGGATTGGAGAGATTT-TACCTGG AAGTGGTAGTACTAATTACAATGAGAA- GTTCAAGGGCAAGGCCACATTCACTGCAG ATA-
CATCCTCCAACACAGCCTACATGCAACTCAGCAG-
CCTGACATCTGAGGACTCT GCCGTCTATTACTGT-
GCAAGAGGGGGGGATTACGACGAAGAATACTATG-
TCATGGA CTACTGGGGTCAAGGAACCTCAGT-
CACTGTC (SEQ ID No: 70), which encodes the variable heavy chain of SEQ ID No: 51.

In a further more specific embodiment, the agent is a polynucleotide comprising the nucleotide sequence CAAATTGTTCTCACCCAGTCTCCAGCAATCATGT-
CTGCATCTCCAGGGGAGAAGGT CACCATGACC-
TGCAGTGCCAGCTCAAGTGTAAGTTACATGTACT-
GGTACCAGCAGA AGCCAGGATCCTCCCCCA-
GACTCCTGATTTATGACACATCCAACCTGGCTT-
CTGGA GTCCCTGTTCGCTTCAGTGGCAGTGG-
GTCTGGGACCTCTTACTCTCTCACAATCAG CCGA-
ATGGAGGCTGAAGATGCTGCCACTTATTACTGC-
CAGCAGTGGAGTAGTTACC CGCTCACGTTCGGTG-
CTGGGACCAAGCTGGAGCTGAAACGT (SEQ ID No: 71), which encodes the variable light chain of SEQ ID No: 52.

Preferably, the agent is a polynucleotide comprising the nucleotide sequence of SEQ ID No: 70 and the nucleotide sequence of SEQ ID No: 71.

In a further more specific embodiment, the agent is a polynucleotide comprising the nucleotide sequence ATGGCCGAGGTTCAGCTTCAGCAGTCTGGAGCT-
GAGCTGATGAAGCCTGGGGCCT CAGTGAAGA-
TATCCTGCAAGGCTACTGGCTACACATTCAGTAGC-
TACTGGATAGAG TGGGTAAATCAGAGGCCT-
GGACATGGCCTTGAGTGGATTGGAGAGATTTTAC-
CTGG AAGTGGTAGTACTAATTACAATGAGAAGTT-
CAAGGGCAAGGCCACATTCACTGCAG ATACATCC-
TCCAACACAGCCTACATGCAACTCAGCAGCCTGA-
CATCTGAGGACTCT GCCGTCTATTACTGTGCA-
AGAGGGGGGGATTACGACGAAGAATACTATGC-
TATGGA CTACTGGGGTCAAGGAACCTCAGT-
CACCCTC (SEQ ID No: 72), which encodes the variable heavy chain of SEQ ID No: 53.

In a further more specific embodiment, the agent is a polynucleotide comprising the nucleotide sequence CAAATTGTTCTCACCCAGTCTCCAGCAATCATGT-
CTGCATCTCCAGGGGAGAAGGT CACCATGA-
CCTGCAGTGCCAGCTCAAGTGTAAGTTACATGTA-
CTGGTACCAGCAGA AGCCAGGATCCTCCCCCA-
GACTCCTGATTTATGACACATCCAACCTGGCT-
TCTGGA GTCCCTGTTCGCTTCAGTGGCAGTGGGT-
CTGGGACCTCTTACTCTCTCACAATCAG CCGAATG-
GAGGCTGAAGATGCTGCCACTTATTACTGCC-
AGCAGTGGAGTAGTTACC CGCTCACGTTCGG-
TGCTGGGACCAAGCTGGAGCTGAAACGT (SEQ ID No: 73), which encodes the variable light chain of SEQ ID No: 54.

Preferably, the agent is a polynucleotide comprising the nucleotide sequence of SEQ ID No: 72 and the nucleotide sequence of SEQ ID No: 73.

The agent may further be a variant of the polynucleotide sequences as defined herein, e.g. a variant with at least 85, 90, 95, 96, 97, 98 or 99% sequence identity to a polynucleotide sequence as defined herein. Sequence identity can be determined using programs well known in the art, (e.g. Align Query or Blast 2). It will be appreciated that any such variants will encode variants of the antibodies defined above by reference to particular sequences, for example variants of those antibodies that do not affect the desired activity of the antibody (eg functional antibodies). A skilled person will appreciate that polynucleotide sequences which are degenerate to the above described sequences are encompassed by the invention, as are RNA sequences which encode the same product.

It is appreciated that CLEC14A and MMRN2 may be glycoproteins. Thus, the antibody that binds to CLEC14A or MMRN2 may bind to any combination of the protein or carbohydrate components of CLEC14A or MMRN2.

The term "antibody" or "antibody molecule" as used herein includes but is not limited to polyclonal, monoclonal, chimeric, single chain, Fab fragments and fragments produced by a Fab expression library. Such fragments include fragments of whole antibodies which retain their binding activity for a target substance, Fv, F(ab') and F(ab')2 fragments, as well as single chain antibodies (scFv), fusion proteins and other synthetic proteins which comprise the antigen-binding site of the antibody. The term also includes antibody-like molecules which may be produced using phage-display techniques or other random selection techniques for molecules which bind to the specified polypeptide or to particular regions of it. Thus, the term antibody includes all molecules which contain a structure, preferably a peptide structure, which is part of the recognition site (i.e. the part of the antibody that binds or combines with the epitope or antigen) of a natural antibody. Furthermore, the antibodies and fragments thereof may be humanised antibodies, which are now well known in the art.

By "ScFv molecules" we mean molecules wherein the $V_H$ and $V_L$ partner domains are linked via a flexible oligopeptide. Engineered antibodies, such as ScFv antibodies, can be made using the techniques and approaches long known in the art. The advantages of using antibody fragments, rather than whole antibodies, are several-fold. The smaller size of the fragments may lead to improved pharmacological properties, such as better penetration to the target site. Effector functions of whole antibodies, such as complement binding, are removed. Fab, Fv, ScFv and dAb antibody fragments can all be expressed in and secreted from E. coli, thus allowing the facile production of large amounts of the fragments. Whole antibodies, and F(ab')$_2$ fragments are "bivalent". By "bivalent" we mean that the antibodies and F(ab')$_2$ fragments have two antigen combining sites. In contrast, Fab, Fv, ScFv and dAb fragments are usually monovalent, having only one antigen combining site.

It is possible however that the ScFv may be monovalent, divalent, trivalent or tetravalent. The ScFv may be a diabody, tribody, or a tetrabody. The two or more $V_H$ and $V_L$ partner domains in a divalent, trivalent or tetravalent or diabody, tribody, or a tetrabody may be different. For example, in one embodiment, the ScFv agent comprises a $V_H$ and $V_L$ from one antibody disclosed herein, and also comprises a $V_H$ and $V_L$ domain from a different antibody disclosed herein. In such a situation, an ScFv agent may comprise more than 2 or more than 3, for example 4 different $V_H$ and $V_L$ domains. In an additional embodiment, the ScFv agent disclosed herein may comprise $V_H$ and $V_L$ domains from additional antibodies to those disclosed herein, for example other antibodies considered to be useful in the inhibition of angiogenesis, or the treatment of cancer.

Furthermore, the $V_H$ and/or $V_L$ domains disclosed herein that make up a particular ScFv agent may be shorter than the sequences disclosed herein. For example, the $V_H$ and/or $V_L$ domains may be 1 residue shorter, or may be 2, 3, 4, 5, 6, 7, 8, 9, 10, 11, 12, 13, 14, 15, 16, 17, 18, 19 or 20 residues or more shorter than the sequences disclosed herein.

Thus, in a further embodiment, the agent is a polynucleotide comprising the nucleotide sequence ATGGCCCAGGTTCAGCTGCAGCAGTCTGGAGCT- GAGCTGATGAAGCCTGGGGCCT CAGTGAAGATATCCTGCAAGGCTACTGGCTACACATTCAGTAGCTACTGGATAGAG TGGGTAAACCGGAGGCCTGGACATGGCCTTGAGTGGATTGGAGAGATTTTACCTGG AAGTGGTAGTACTAATTACAATGAGAAGTTCAAGGGCAAGGCCACATTCACTGCAG ATACATCCTCCAATACAGCCTACATGCAACTCAGCAGCCTCACATCTGAGGACTCTG TCGTCTATTACTGTGCGAGAGGGGGGGATTACGACGAAGAATACTATCTCATGGAC TACTGGGGTCAAGGCACCACTCTCACAGTCTCCTCAGGTGGAGGCGGTTCAGGCG GAGGTGGCTCTGGCGGTGGCGGATCGCAAATTGTTCTCACCCAGTCTCCAGCAATC ATGTCTGCATCTCAGGGGAGAAGGTCACCATGACCTGCAGTGCCAGCTCAAGTGT AAGTTACATGTACTGGTACCAGCAGAAGCCAGGATCCTCCCCAGACTCCTGATTT ATGACACATCCAACCTGGCTTCTGGAGTCCCTGTTCGCTTCAGTGGCAGTGGGTCT GGGACCTCTTACTCTCTCACAATCAGCCGAATGGAGGCTGAAGATGCTGCACTTA TTACTGCCAGCAGTGGAGTAGTTACCCGCTCACGTTCGGTGCTGGGACCAAGCTG GAAATCAAACGTGCGGCCGCA (SEQ ID No: 74), which encodes the ScFv region of SEQ ID No: 55.

Thus, in a further embodiment, the agent is a polynucleotide comprising the nucleotide sequence ATGGCCGAGGTTCAGCTTCAGCAGTCTGGAGCTGAGCTGATGAAGCCTGGGGCCT CAGTGAAGATATCCTGCAAGGCTACTGGCTACACATTCAGTAGCTACTGGATAGAG TGGGTAAAGCAGAGGCCTGGACATGGCCTTGAGTGGATTGGAGAGATTTTACCTGG AAGTGGTAGTACTAATTACAATGAGAAGTTCAAGGGCAAGGCCACATTCACTGCAG ATACATCCTCCAACACAGCCTACATGCAACTCAGCAGCCTGACATCTGAGGACTCT GCCGTCTATTACTGTGCAAGAGGGGGGATTACGACGAAGAATACTATGTCATGGA CTACTGGGGTCAAGGAACCTCAGTCACTGTCTCCTCAGGTGGAGGCGGTTCAGGC GGAGGTGGCTCTGGCGGTGGCGGATCGCAAATTGTTCTCACCCAGTCTCCAGCAA TCATGTCTGCATCTCCAGGGGAGAAGGTCACCATGACCTGCAGTGCCAGCTCAAGT GTAAGTTACATGTACTGGTACCAGCAGAAGCCAGGATCCTCCCCAGACTCCTGAT TTATGACACATCCAACCTGGCTTCTGGAGTCCCTGTTCGCTTCAGTGGCAGTGGGT CTGGGACCTCTTACTCTCTCACAATCAGCCGAATGGAGGCTGAAGATGCTGCCACT TATTACTGCCAGCAGTGGAGTAGTTACCCGCTCACGTTCGGTGCTGGGACCAAGCTG GAGCTGAAACGT (SEQ ID No: 75), which encodes the ScFv region of SEQ ID No: 56.

In a further specific embodiment the agent is a polynucleotide comprising the nucleotide sequence ATGGCCGAGGTTCAGCTTCAGCAGTCTGGAGCTGAGCTGATGAAGCCTGGGGCCT CAGTGAAGATATCCTGCAAGGCTACTGGCTACACATTCAGTAGCTACTGGATAGAG TGGGTAAATCAGAGGCCTGGACATGGCCTTGAGTGGATTGGAGAGATTTTACCTGG AAGTGGTAGTACTAATTACAATGAGAAGTTCAAGGGCAAGGCCACATTCACTGCAG ATACATCCTCCAACACAGCCTACATGCAACTCAGCAGCCTGACATCTGAGGACTCT GCCGTCTATTACTGTGCAAGAGGGGGGATTACGACGAAGAATACTATGCTATGGA CTACTGGGGTCAAGGAACCTCAGTCACCCTCTCCTCAGGTGGAGGCGGTTCAGGC GGAGGTGGCTCTGGCGGTGGCGGATCGCAAATTGTTCTCACCCAGTCTCCAGCAA TCATGTCTGCATCTCCAGGGGAGAAGGTCACCATGACCTGCAGTGCCAGCTCAAGT GTAAGTTACATGTACTGGTACCAGCAGAAGCCAGGATCCTCCCCAGACTCCTGAT TTATGACACATCCAACCTGGCTTCTGGAGTCCCTGTTCGCTTCAGTGGCAGTGGGT CTGGGACCTCTTACTCTCTCACAATCAGCCGAATGGAGGCTGAAGATGCTGCCACT TATTACTGCCAGCAGTGGAGTAGTTACCCGCTCACGTTCGGTGCTGGGACCAAGCT GGAGCTGAAACGT (SEQ ID No: 76), which encodes the ScFv region of SEQ ID No: 57.

Antibodies may be produced by standard techniques, for example by immunisation with the appropriate (glyco)polypeptide or portion(s) thereof, or by using a phage display library.

If polyclonal antibodies are desired, a selected mammal (e.g., mouse, rabbit, goat, horse, etc) is immunised with an immunogenic polypeptide bearing a desired epitope(s), optionally haptenised to another polypeptide. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. Serum from the immunised animal is collected and treated according to known procedures. If serum containing polyclonal antibodies to the desired epitope contains antibodies to other antigens, the polyclonal antibodies can be purified by immunoaffinity chromatography. Techniques for producing and processing polyclonal antisera are well known in the art.

Monoclonal antibodies directed against entire polypeptides or particular epitopes thereof can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against the polypeptides listed above can be screened for various properties; i.e., for isotype and epitope affinity. Monoclonal antibodies may be prepared using any of the well known techniques which provides for the production of antibody molecules by continuous cell lines in culture.

It is preferred if the antibody is a monoclonal antibody. In some circumstances, particularly if the antibody is to be administered repeatedly to a human patient, it is preferred if the monoclonal antibody is a human monoclonal antibody or a humanised monoclonal antibody, which are suitable for administration to humans without engendering an immune response by the human against the administered immunoglobulin. Suitably prepared non-human antibodies can be "humanised" in known ways, for example by inserting the CDR regions of mouse antibodies into the framework of human antibodies. Humanised antibodies can be made using the techniques and approaches described in Verhoeyen et al (1988) *Science,* 239, 1534-1536, and in Kettleborough et al, (1991) *Protein Engineering,* 14(7), 773-783. In some instances, Fv framework residues of the human immunoglobulin are replaced by corresponding non-human residues. In general, the humanised antibody will contain variable domains in which all or most of the CDR regions correspond to those of a non-human immunoglobulin, and framework regions which are substantially or completely those of a human immunoglobulin consensus sequence.

Completely human antibodies may be produced using recombinant technologies. Typically large libraries comprising billions of different antibodies are used. In contrast to the previous technologies employing chimerisation or humanisation of e.g. murine antibodies this technology does not rely on immunisation of animals to generate the specific antibody. Instead the recombinant libraries comprise a huge number of pre-made antibody variants wherein it is likely that the library will have at least one antibody specific for any antigen. Thus, using such libraries, an existing antibody having the desired binding characteristics can be identified. In order to find the good binder in a library in an efficient manner, various systems where phenotype i.e. the antibody or antibody fragment is linked to its genotype i.e. the encoding gene have been devised. The most commonly used such system is the so called phage display system where antibody fragments are expressed, displayed, as fusions with phage coat proteins on the surface of filamentous phage particles, while simultaneously carrying the genetic information encoding the displayed molecule (McCafferty et al, 1990, *Nature* 348: 552-554). Phage displaying antibody fragments specific for a particular antigen may be selected through binding to the antigen in question. Isolated phage may then be amplified and the gene encoding the selected antibody variable domains may optionally be transferred to other antibody formats, such as e.g. full-length immunoglobulin, and expressed in high amounts using appropriate vectors and host cells well known in the art. Alternatively, the "human" antibodies can be made by immunising transgenic mice which contain, in essence, human immunoglobulin genes (Vaughan et al (1998) *Nature Biotechnol.* 16, 535-539).

It is appreciated that when the antibody is for administration to a non-human individual, the antibody may have been specifically designed/produced for the intended recipient species.

The format of displayed antibody specificities on phage particles may differ. The most commonly used formats are Fab (Griffiths et al, 1994. *EMBO J.* 13: 3245-3260) and single chain (scFv) (Hoogenboom et al, 1992, *J Mol Biol.* 227: 381-388) both comprising the variable antigen binding domains of antibodies. The single chain format is composed of a variable heavy domain ($V_H$) linked to a variable light domain ($V_L$) via a flexible linker (U.S. Pat. No. 4,946,778). Before use as a therapeutic agent, the antibody may be transferred to a soluble format e.g. Fab or scFv and analysed as such. In later steps the antibody fragment identified to have desirable characteristics may be transferred into yet other formats such as full-length antibodies.

WO 98/32845 and Soderlind et al (2000) *Nature BioTechnol.* 18: 852-856 describe technology for the generation of variability in antibody libraries. Antibody fragments derived from this library all have the same framework regions and only differ in their CDRs. Since the framework regions are of germline sequence the immunogenicity of antibodies derived from the library, or similar libraries produced using the same technology, are expected to be particularly low (Soderlind et al, 2000). This property is of great value for therapeutic antibodies, reducing the risk that the patient forms antibodies to the administered antibody, thereby reducing risks for allergic reactions, the occurrence of blocking antibodies, and allowing a long plasma half-life of the antibody. Thus, when developing therapeutic antibodies to be used in humans, modern recombinant library technology (Soderlind et al, 2001, *Comb. Chem. & High Throughput Screen.* 4: 409-416) is now used in preference to the earlier hybridoma technology.

By antibodies we also include heavy-chain antibodies structurally derived from camelidae antibodies, such as Nanobodies® (Ablynx). These are antibody-derived therapeutic proteins that contain the structural and functional properties of naturally-occurring heavy-chain antibodies. The Nanobody® technology was developed following the discovery that camelidae (camels and llamas) possess fully functional antibodies that lack light chains. These heavy-chain antibodies contain a single variable domain (VHH) and two constant domains ($C_H2$ and $C_H3$). The cloned and isolated VHH domain is a perfectly stable polypeptide harbouring the full antigen-binding capacity of the original heavy-chain antibody. These VHH domains with their unique structural and functional properties form the basis of Nanobodies®. They combine the advantages of conventional antibodies (high target specificity, high target affinity and low inherent toxicity) with important features of small molecule drugs (the ability to inhibit enzymes and access receptor clefts). Furthermore, they are stable, have the potential to be administered by means other than injection, are easier to manufacture, and can be humanised. (See, for example U.S. Pat. Nos. 5,840,526; 5,874,541; 6,005,079, 6,765,087; EP 1 589 107; WO 96/34103; WO97/49805; U.S. Pat. Nos. 5,800,988; 5,874,541 and 6,015,695).

A second aspect of the invention provides an antibody that competes with MMRN2 for specific binding to the CLEC14A polypeptide.

For the avoidance of doubt, the antibody of this aspect of the invention includes any of those described above in relation to the first aspect of the invention, and it will be appreciated that any antibody described in this aspect of the invention may also be used in the methods and uses of the first aspect of the invention.

It is preferred if the antibody that competes with MMRN2 for specific binding reduces the level of binding between CLEC14A and MMRN2 by at least 10%, 20%, 30%, 40% or 50% compared to the level of binding between CLEC14A and MMRN2 in the absence of the antibody, and more preferably reduces the level of binding by at least 70%, 80%, 90%, 95% or 99%. Most preferably, the antibody that competes with MMRN2 for specific binding is one that reduces the level of binding between CLEC14A and MMRN2 to an undetectable level, or eliminates binding between CLEC14A and MMRN2.

Methods for assessing whether an antibody competes with MMRN2 for specific binding to the CLEC14A polypeptide are well known in the art, and are described, for example, in relation to the first aspect of the invention and in Example 1. Generally, the method involves assessing the level of binding between CLEC14A and MMRN2 in the presence of varying concentrations of the given antibody, or assessing the level of binding between CLEC14A and the given antibody in the presence of varying concentrations of MMRN2. If the given antibody and MMRN2 compete for specific binding to the CLEC14A polypeptide, the level of binding that is measured is expected to change when the concentration of either the given antibody or MMRN2 is varied. For example, if the given antibody and MMRN2 compete for specific binding, the level of binding between CLEC14A and the given antibody in the presence of MMRN2 is expected to be less than the level of binding between CLEC14A and the given antibody in the absence of MMRN2. If the given antibody and MMRN2 did not compete for specific binding (eg they bound to discrete regions of the CLEC14A polypeptide), no change in the level of binding would be expected. Suitable techniques for measuring binding are described elsewhere herein, for example in relation to the first aspect of the invention, and include immunoprecipitation techniques, ELISA and western blotting.

Preferably, the antibody is one that binds specifically to regions of CLEC14A that are involved directly in the interaction between CLEC14 and MMRN2. For example, the antibody may bind to the MMRN2 binding site in CLEC14A and so directly block binding of MMRN2. The MMRN2 binding site is within the C-type lectin domain of CLEC14A, and so it will be appreciated that the antibody is typically one that specifically binds to MMRN2 binding site within the C-type lectin domain of the CLEC14A polypeptide (residues 32-173).

In an embodiment, the antibody that selectively binds to the CLEC14A polypeptide does not bind to the region spanning amino acid residues 31-72 of CLEC14A, and/or the region spanning amino acid residues 31-92 of CLEC14A, and/or the region spanning amino acid residues 92-172 of CLECA, and/or the region spanning amino acid residues 112-172 of CLEC14A, and/or the region spanning amino acid residues 152-172 of CLEC14A. Whether or not the antibody binds to any of these regions can be assessed using standard techniques in the art, including the binding assays described herein such as ELISA.

As described in Example 1, the inventors have shown that antibodies that inhibit the interaction between CLEC14A and MMRN2 have anti-angiogenic properties as well as anti-cancer properties. In particular, a CLEC14A-MMRN2 blocking antibody was to inhibit tube formation and sprouting angiogenesis in vitro and in vivo, and inhibited tumour growth in mice with Lewis lung carcinoma. Thus, in one embodiment of this aspect of the invention, the antibody is one that inhibits angiogenesis, for example as demonstrated in an angiogenesis assay, and/or is one that inhibits tumour growth, for example as demonstrated in an animal model of cancer (eg a mouse with Lewis lung carcinoma). Suitable angiogenesis assays are well known in the art and include an aortic ring assay, a sponge angiogenesis assay, an assay of endothelial cell proliferation, an assay of endothelial cell migration and/or an assay of endothelial cell invasion. Likewise, suitable animal models of cancer are well known in the art.

Hence, in a particularly preferred embodiment, the antibody of the second aspect of the invention is an antibody that competes with MMRN2 for specific binding to the CLEC14A polypeptide, and which antibody inhibits angiogenesis, for example as demonstrated in an angiogenesis assay (eg an aortic ring assay or a sponge angiogenesis assay), and/or which antibody inhibits tumour growth, for example as demonstrated in an animal model of cancer (eg a mouse with Lewis lung carcinoma).

The amino acid and polynucleotide sequences of the antibody exemplified in Example 1 are provided in FIG. 11.

In an embodiment, the antibody comprises
(a) a heavy chain CDR1 comprising the amino acid sequence SSYWIE (SEQ ID No: 1) or GYTFSSYW (SEQ ID NO: 40);
(b) a heavy chain CDR2 comprising the amino acid sequence WIGEILPGSGST (SEQ ID No: 2), or WIGEILPGSGSTN (SEQ ID NO: 78) or ILPGSGST (SEQ ID NO: 41); and/or
(c) a heavy chain CDR3 comprising the amino acid sequence ARGGDYDEEYYLMD (SEQ ID No: 3) or ARGGDYDEEYYLMDY (SEQ ID NO: 42);
or a variant of any of these sequences comprising 1, 2 or 3 amino acid substitutions.

In another embodiment, the antibody comprises
(a) a light chain CDR1 comprising the amino acid sequence SYMYWY (SEQ ID No: 4) or SSVSY (SEQ ID NO: 43);
(b) a light chain CDR2 comprising the amino acid sequence LLIYDTSNLA (SEQ ID No: 5) or DTS; and/or
(c) a light chain CDR3 comprising the amino acid sequence QQWSSYPL (SEQ ID No: 6) or QQWSSYPLT (SEQ ID NO: 44);
or a variant of any of these sequences comprising 1, 2 or 3 amino acid substitutions.

In a further embodiment, the antibody comprises one or more of, or all of,
(a) a heavy chain CDR1 comprising the amino acid sequence SSYWIE (SEQ ID No: 1); (b) a heavy chain CDR2 comprising the amino acid sequence WIGEILPGSGST (SEQ ID No: 2) or WIGEILPGSGSTN (SEQ ID NO 78); (c) a heavy chain CDR3 comprising the amino acid sequence ARGGDYDEEYYLMD (SEQ ID No: 3); (d) a light chain CDR4 comprising the amino acid sequence SYMYWY (SEQ ID No: 4); (e) a light chain CDR5 comprising the amino acid sequence LLIYDTSNLA (SEQ ID No: 5); and/or (e) a light chain CDR6 comprising the amino acid sequence QQWSSYPL (SEQ ID No: 6); or a variant of any of these sequences comprising 1, 2 or 3 amino acid substitutions;
or the antibody may comprise any one or more or all of:
a heavy chain CDR1 comprising the amino acid sequence GYTFSSYW (SEQ ID No: 40);
a heavy chain CDR2 comprising the amino acid sequence ILPGSGST (SEQ ID No: 41);
a heavy chain CDR3 comprising the amino acid sequence ARGGDYDEEYYLMDY (SEQ ID No: 42); a light chain CDR1 comprising the amino acid sequence SSVSY (SEQ ID No: 43); a light chain CDR2 comprising the amino acid sequence DTS; and a light chain CDR3 comprising the amino acid sequence QQWSSYPLT (SEQ ID No: 44), or a variant of any of said sequences comprising 1, 2, or 3 amino acid substitutions.

In a further embodiment of the second aspect of the invention, the antibody comprises:
(a) a heavy chain CDR1 comprising the amino acid sequence SSYWIE (SEQ ID No: 1) or GYTFSSYW (SEQ ID NO: 40);
(b) a heavy chain CDR2 comprising the amino acid sequence WIGEILPGSGSTN (SEQ ID No: 78) or ILPGSGST (SEQ ID NO: 41); and/or
(c) a heavy chain CDR3 comprising the amino acid sequence ARGGDYDEEYYVMD (SEQ ID No: 77) or ARGGDYDEEYYVMDY (SEQ ID NO: 45);
or a variant of any of these sequences comprising 1, 2 or 3 amino acid substitutions.

In yet a further embodiment of the second aspect of the invention, the antibody may comprise both light and heavy chain CDRs as described above. For instance, the antibody may comprise: a heavy chain CDR1 comprising the amino acid sequence (SEQ ID No: 1); a heavy chain CDR2 comprising the amino acid sequence (SEQ ID No: 78); a heavy chain CDR3 comprising the amino acid sequence (SEQ ID No: 77); a light chain CDR1 comprising the amino acid sequence (SEQ ID No: 4); a light chain CDR2 comprising the amino acid sequence (SEQ ID No: 5); and a light chain CDR3 comprising the amino acid sequence (SEQ ID No: 6), or a variant of any of said sequences comprising 1, 2, or 3 amino acid substitutions; or the antibody may comprise: a heavy chain CDR1 comprising the amino acid sequence (SEQ ID No: 40); a heavy chain CDR2 comprising the amino acid sequence (SEQ ID No: 41); a heavy chain CDR3 comprising the amino acid sequence (SEQ ID No:

45); a light chain CDR1 comprising the amino acid sequence (SEQ ID No: 43); a light chain CDR2 comprising the amino acid sequence DTS; and a light chain CDR3 comprising the amino acid sequence (SEQ ID No: 44), or a variant of any of said sequences comprising 1, 2, or 3 amino acid substitutions.

In yet a further embodiment of the second aspect of the invention, the antibody comprises:
(a) a heavy chain CDR1 comprising the amino acid sequence SSYWIE (SEQ ID No: 1) or GYTFSSYW (SEQ ID NO: 40); (b) a heavy chain CDR2 comprising the amino acid sequence WIGEILPGSGSTN (SEQ ID No: 78) or ILPGSGST (SEQ ID NO: 41); and/or (c) a heavy chain CDR3 comprising the amino acid sequence ARGGDYDEEYYAMD (SEQ ID No: 46) or ARGGDYDEEYYAMDY (SEQ ID NO: 47);
or a variant of any of these sequences comprising 1, 2 or 3 amino acid substitutions.

In a further embodiment of the second aspect of the invention, the antibody comprises:
(a) a light chain CDR1 comprising the amino acid sequence SYMYWY (SEQ ID No: 4) or SSVSY (SEQ ID NO: 43);
(b) a light chain CDR2 comprising the amino acid sequence LLIYDTSNLA (SEQ D No: 5) or DTS; and/or
(c) a light chain CDR3 comprising the amino acid sequence QQWSSYPL (SEQ ID No: 6) or QQWSSYPLTF (SEQ ID NO: 48); or a variant of any of these sequences comprising 1, 2 or 3 amino acid substitutions.

In yet a further embodiment of the second aspect of the invention, the antibody may comprise both light and heavy chain CDRs as described above.

For instance, the antibody may comprise: a heavy chain CDR1 comprising the amino acid sequence (SEQ ID No: 1); a heavy chain CDR2 comprising the amino acid sequence (SEQ ID No: 78); a heavy chain CDR3 comprising the amino acid sequence (SEQ ID No: 46); a light chain CDR1 comprising the amino acid sequence (SEQ ID No: 4); a light chain CDR2 comprising the amino acid sequence (SEQ ID No: 5); and a light chain CDR3 comprising the amino acid sequence (SEQ ID No: 6), or a variant of any of said sequences comprising 1, 2, or 3 amino acid substitutions; or the antibody may comprise: a heavy chain CDR1 comprising the amino acid sequence (SEQ ID No: 40); a heavy chain CDR2 comprising the amino acid sequence (SEQ ID No: 41); a heavy chain CDR3 comprising the amino acid sequence (SEQ ID No: 47); a light chain CDR1 comprising the amino acid sequence (SEQ ID No: 43); a light chain CDR2 comprising the amino acid sequence DTS; and a light chain CDR3 comprising the amino acid sequence (SEQ ID No: 48), or a variant of any of said sequences comprising 1, 2, or 3 amino acid substitutions.

In a more specific embodiment of the second aspect of the invention, the antibody comprises a heavy chain variable region comprising the amino acid sequence (SEQ ID No: 7)
MAQVQLQQSGAELMKPGASVKISCKATGYTFSSYWIEWVNRRPGHGLEWIG

EILPGSGSTNYNEKFKGKATFTADTSSNTAYMQLSSLTSEDSAVYYCARGG

DYDEEYYLMDYWGQGTTLTVSS;
or (SEQ ID NO: 49)
MAQVQLQQSGAELMKPGASVKISCKATGYTFSSYWIEWVNRRPGHGLEWIG

EILPGSGSTNYNEKFKGKATFTADTSSNTAYMQLSSLTSEDSAVYYCARGG

DYDEEYYLMDYWGQGTTLTV;

or a variant of this sequence comprising 1, 2, 3, 4, or 5 amino acid substitutions.

Additionally or alternatively (ie optionally in combination with the heavy chain amino acid sequence described above), the antibody may comprise a light chain variable region comprising the amino acid sequence (SEQ ID No: 8)
QIVLTQSPAIMSASPGEKVTMTCSASSSVSYMYWYQQKPGSSPRLLIYDTS

NLASGVPVRFSGSGSGTSYSLTISRMEAEDAATYYCQQWSSYPLTFGAGTK

LEIKRAA;
or (SEQ ID NO: 50)
QIVLTQSPAIMSASPGEKVTMTCSASSSVSYMYWYQQKPGSSPRLLIYDTS

NLASGVPVRFSGSGSGTSYSLTISRMEAEDAATYYCQQWSSYPLTFGAGTK

LEIKRAAA;

or a variant of this sequence comprising 1, 2, 3, 4, or 5 amino acid substitutions.

Thus, in a particularly preferred embodiment, the antibody may comprise a heavy chain variable region comprising the amino acid sequence MAQVQLQQSGAELMKPGASVKISCKATGYTFSSYWIEWVNRRPGHGLEWIG EILPGSG STNYNEKFKGKATFTADTSSNTAYMQLSSLTSEDSAVYYCARGGDYDEEYYLMDYWG QGTTLTVSS (SEQ ID No: 7) or MAQVQLQQSGAELMKPGASVKISCKATGYTFSSYWIEWVNRRPGHGLEWIGEILPGSG STNYNEKFKGKATFTADTSSNTAYMQLSSLTSEDSAVYYCARGGDYDEEYYLMDYWG QGTTLTV (SEQ ID NO: 49) or a variant of this sequence comprising 1, 2, 3, 4, or 5 amino acid substitutions;

and a light chain variable region comprising the amino acid sequence QIVLTQSPAIMSASPGEKVTMTCSASSSVSYMYWYQQKPGSSPRLLIYDTSNLASGVPV RFSGSGSGTSYSLTISRMEAEDAATYYCQQWSSYPLTFGAGTKLEIKRAA (SEQ ID No: 8) or QIVLTQSPAIMSASPGEKVTMTCSASSSVSYMYWYQQKPGSSPRLLIYDTSNLASGVPV RFSGSGSGTSYSLTISRMEAEDAATYYCQQWSSYPLTFGAGTKLEIKRAAA (SEQ ID NO: 50) or a variant of this sequence comprising 1, 2, 3, 4, or 5 amino acid substitutions.

In a further more specific embodiment of the second aspect of the invention, the antibody comprises a heavy chain variable region comprising the amino acid sequence MAEVQLQQSGAELMKPGASVKISCKATGYTFSSYWIEWVKQRPGHGLEWIGEILPGSG STNYNEKFKGKATFTADTSSNTAYMQLSSLTSEDSAVYYCARGGDYDEEYYVMDYWG QGTSVTV (SEQ ID NO:51); or a variant of this sequence comprising 1, 2, 3, 4, or 5 amino acid substitutions.

Additionally or alternatively (ie optionally in combination with the heavy chain amino acid sequence described above), the antibody may comprise a light chain variable region comprising the amino acid sequence (SEQ ID NO: 52)
QIVLTQSPAIMASPGEKVTMTCSASSSVSYMYWYQQKPGSSPRLLIYDTSN

LASGVPVRFSGSGSGTSYSLTISRMEAEDAATYYCQQWSSYPLTFGAGTKL

ELKR;

or a variant of this sequence comprising 1, 2, 3, 4, or 5 amino acid substitutions.

Thus, in a particularly preferred embodiment, the antibody may comprise a heavy chain variable region comprising the amino acid sequence (SEQ ID No: 51), and a light chain variable region comprising the amino acid sequence (SEQ ID No: 52) or a variant of these sequences comprising 1, 2, 3, 4, or 5 amino acid substitutions.

In yet a further more specific embodiment of the second aspect of the invention, the antibody comprises a heavy chain variable region comprising the amino acid sequence (SEQ ID NO: 53)
MAEVQLQQSGAELMKPGASVKISCKATGYTFSSYWIEWVNQRPGHGLEWIG

EILPGSGSTNYNEKFKGKATFTADTSSNTAYMQLSSLTSEDSAVYYCARGG

DYDEEYYAMDYWGQGTSVTV;

or a variant of this sequence comprising 1, 2, 3, 4, or 5 amino acid substitutions.

Additionally or alternatively (ie optionally in combination with the heavy chain amino acid sequence described above), the antibody may comprise a light chain variable region comprising the amino acid sequence (SEQ ID NO: 54)
QIVLTQSPAIMSASPGEKVTMTCSASSSVSYMYWYQQKPGSSPRLLIYDTS

NLASGVPVRFSGSGSGTSYSLTISRMEAEDGATYYCQQWSSYPLTFGAGTK

LELKR;

or a variant of this sequence comprising 1, 2, 3, 4, or 5 amino acid substitutions.

Thus, in a particularly preferred embodiment, the antibody may comprise a heavy chain variable region comprising the amino acid sequence (SEQ ID No: 53), and a light chain variable region comprising the amino acid sequence (SEQ ID No: 54) or a variant of this sequence comprising 1, 2, 3, 4, or 5 amino acid substitutions.

As explained above, when the antibody is defined as having a light chain variable region comprising a particular amino acid sequence and a heavy chain variable region having a particular amino acid sequence, it will be appreciated that up to one or two of those sequences may be varied as defined. The variation may be within the non-CDR regions of the sequences. Preferences for such variants include those described above in relation to the first aspect of the invention.

In a further specific embodiment of the second aspect of the invention, the antibody comprises the sequence MAQVQLQQSGAELMKPGASVKISCKATGYTFSSY-WIEWVNRRPGHGLEWIGEILPGSG STNYNEKFK-GKATFTADTSSNTAYMQLSSLTSEDSVVYYCARGG-DYDEEYYLMDYWG QGTTLTVSSGGGGSGGGGS-GGGGSQIVLTQSPAIMSASPGEKVTMTCSASSS-VSYMY WYQQKPGSSPRLLIYDTSNLASGVPVRFS-GSGSGTSYSLTISRMEAEDAATYYCQQWS SYPLT-FGAGTKLEIKRAAA (SEQ ID NO: 55) or a variant of this sequence comprising 1, 2, 3, 4, or 5 amino acid substitutions.

In another specific embodiment of the second aspect of the invention, the antibody comprises the sequence MAEVQLQQSGAELMKPGASVKISCKATGYTFSSY-WIEWVKQRPGHGLEWIGEILPGSG STNYNEKF-KGKATFTADTSSNTAYMQLSSLTSEDSAVYY-CARGGDYDEEYYVMDYWG QGTSVTVSSGG-GGSGGGGSGGGGSQIVLTQSPAIMSASPGEKV-TMTCSASSSVSYMY WYQQKPGSSPRLLIYDTSN-LASGVPVRFSGSGSGTSYSLTISRMEAEDAATYY-CQQWS SYPLTFGAGTKLELKR
(SEQ ID NO:56) or a variant of this sequence comprising 1, 2, 3, 4, or 5 amino acid substitutions.

In another specific embodiment of the second aspect of the invention, the antibody comprises the sequence MAEVQLQQSGAELMKPGASVKISCKATGYTFSSY-WIEWVNQRPGHGLEWIGEILPGSG STNYNEKFK-GKATFTADTSSNTAYMQLSSLTSEDSAVYYCARGG-DYDEEYYAMDYWG QGTSVTLSSGGGGSGGGGSG-GGGSQIVLTQSPAIMSASPGEKVTMTCSASSSVSYMY WYQQKPGSSPRLLIYDTSNLASGVPVRFSGSGSGT-SYSLTISRMEAEDAATYYCQQWS SYPLTFGAGTKLELKR (SEQ ID NO:57) or a variant of this sequence comprising 1, 2, 3, 4, or 5 amino acid substitutions.

This aspect of the invention also includes an antibody that competes with any of the antibodies described herein, for example by reference to particular amino acid sequences, for specific binding to the CLEC14A polypeptide. Thus, the invention provides an antibody that selectively binds to the epitope in CLEC14A that is selectively bound by any of the antibodies described herein. In a particularly preferred embodiment, the invention provides an antibody that binds to the epitope in CLECA14A that is selectively bound by an antibody comprising a heavy chain variable region having SEQ ID No: 7 and a light chain variable region having SEQ ID No: 8; or comprising a heavy chain variable region having SEQ ID NO: 49 and a light chain variable region having SEQ ID NO: 50; or comprising a heavy chain variable region having SEQ ID NO: 51 and a light chain variable region having SEQ ID NO: 52; or comprising a heavy chain variable region having SEQ ID NO: 53 and a light chain variable region having SEQ ID NO: 54.

A third aspect of the invention provides a polynucleotide encoding an antibody of the second aspect of the invention. It will be appreciated that the third aspect of the invention provides a nucleic acid molecule comprising a polynucleotide encoding an antibody of the second aspect of the invention. The polynucleotide may be a DNA or RNA molecule.

In an embodiment, the polynucleotide comprises one or more of the following nucleotide sequences:

(i)
(SEQ ID No: 9)
AGTAGCTACTGGATAGAG;

(ii)
(SEQ ID No: 10)
TGGATTGGAGAGATTTTACCTGGAAGTGGTAGTACTAAT;

(iii)
(SEQ ID No: 11)
GCGAGAGGGGGGATTACGACGAAGAATACTATCTCATGGAC;

(iv)
(SEQ ID No: 12)
AGTTACATGTACTGGTAC;

(v)
CTCCTGATTTATGACACATCCAACCTGGCT;  (SEQ ID No: 13)
and (vi)
CAGCAGTGGAGTAGTTACCCGCTC;  (SEQ ID No: 14)

(vii)
GGCTACACATTCAGTAGCTACTGG  (SEQ ID NO: 60)

(viii)
ATTTTACCTGGAGTGGTAGTACT  (SEQ ID NO: 61)

(ix)
GCGAGAGGGGGGATTACGACGAAGAATACTATCTCATGGACTAC  (SEQ ID NO: 62)

(x)
TCAAGTGTAAGTTAC  (SEQ ID NO: 63)

(xi)
GACACATCC (xii)
CAGCAGTGGAGTAGTTACCCGCTCACG  (SEQ ID NO: 64)

(xiii)
GCAAGAGGGGGGATTACGACGAAGAATACTATGTCATGGAC  (SEQ ID NO: 58)

(xiv)
ATTTTACCTGGAAGTGGTAGTACT  (SEQ ID NO: 66)

(xv)
GCAAGAGGGGGGATTACGACGAAGAATACTATGCTATGGACTAC  (SEQ ID NO: 65)

(xvi)
GCAAGAGGGGGGATTACGACGAAGAATACTATGCTATGGAC  (SEQ ID NO: 59)

(xvii)
ATTTTACCTGGAAGTGGTAGTACT  (SEQ ID NO: 66)

(xviii)
GCAAGAGGGGGGATTACGACGAAGAATACTATGTCATGGACTAC  (SEQ ID NO: 67)

(xix)
CAGCAGTGGAGTAGTTACCCGCTCACG  (SEQ ID NO: 46)

(xx)
TGGATTGGAGAGATTTTACCTGGAAGTGGTAGTACT  (SEQ ID NO: 79)

Polynucleotide sequence (i) (SEQ ID No: 9) encodes heavy chain CDR SSYWIE (SEQ ID No: 1); polynucleotide sequence (ii) (SEQ ID No: 10) encodes heavy chain CDR WIGEILPGSGSTN (SEQ ID No: 78); polynucleotide sequence (xx) (SEQ ID NO: 79) encodes heavy chain CDR WIGEILPGSGST (SEQ ID NO: 2); polynucleotide sequence (iii) (SEQ ID No: 11) encodes heavy chain CDR ARGGDYDEEYYLMD (SEQ ID No: 3); polynucleotide sequence (iv) (SEQ ID No: 12) encodes light chain CDR SYMYWY (SEQ ID No: 4); polynucleotide sequence (v) (SEQ ID No: 13) encodes light chain CDR LLIYDTSNLA (SEQ ID No: 5); and polynucleotide sequence (vi) (SEQ ID No: 14) encodes light chain CDR QQWSSYPL (SEQ ID No: 6). Thus, the polynucleotide encoding the antibody may comprise any 1, 2 or 3 of polynucleotide sequences (i); (ii) or (xx); and (iii) and/or any 1, 2 or 3 of polynucleotide sequences (iv)-(vi). Preferably, the polynucleotide comprises all six of polynucleotide sequences (i); (ii) or (xx); (iii); (iv); (v); and (vi).

Polynucleotide sequence (vii) (SEQ ID No: 60) encodes heavy chain CDR GYTFSSYW (SEQ ID No: 40); polynucleotide sequence (viii) (SEQ ID No: 61) encodes heavy chain CDR ILPGSGST (SEQ ID No: 41); polynucleotide sequence (ix) (SEQ ID No: 62) encodes heavy chain CDR ARGGDYDEEYYLMDY (SEQ ID No: 42); polynucleotide sequence (x) (SEQ ID No: 63) encodes light chain CDR SSVSY (SEQ ID No: 43); polynucleotide sequence (xi) encodes light chain CDR DTS; and polynucleotide sequence (xii) (SEQ ID No: 64) encodes light chain CDR QQWSSYPLT (SEQ ID No: 44). Thus, the polynucleotide encoding the antibody may comprise any 1, 2 or 3 of polynucleotide sequences (vii)-(ix) and/or any 1, 2 or 3 of polynucleotide sequences (x)-(xii). Preferably, the polynucleotide comprises all six of polynucleotide sequences (vii)-(xii).

It will be appreciated that any of the polynucleotide sequences encoding the heavy chain CDR sequences (i)-(iii) may be substituted for any of the corresponding heavy chain CDR sequences of (vii)-(ix) and vice versa; and any of the polynucleotide sequences encoding the light chain CDR sequences (iv)-(vi) may be substituted for any of the corresponding light chain CDR sequences (x)-(xii) and vice versa.

Polynucleotide sequence (i) (SEQ ID NO: 9) encodes heavy chain CDR SSYWIE (SEQ ID No: 1); polynucleotide sequence (ii) (SEQ ID No: 10) encodes heavy chain CDR WIGEILPGSGST (SEQ ID No: 78); polynucleotide sequence (xiii) (SEQ ID No: 58) encodes heavy chain CDR ARGGDYDEEYYVMDN (SEQ ID No: 77); polynucleotide sequence (iv) (SEQ ID No: 12) encodes light chain CDR SYMYWY (SEQ ID No: 4); polynucleotide sequence (v) (SEQ ID No: 13) encodes light chain CDR LLIYDTSNLA (SEQ ID No: 5); and polynucleotide sequence (vi) (SEQ ID No: 14) encodes light chain CDR QQWSSYPL (SEQ ID No: 6). Thus, the polynucleotide encoding the antibody may comprise any 1, 2 or 3 of polynucleotide sequences (i), (ii) and (xiii) and/or any 1, 2 or 3 of polynucleotide sequences (iv), (v) and (vi). Preferably, the polynucleotide comprises all six of polynucleotide sequences (i), (ii), (xiii) (iv), (v) and (vi).

Polynucleotide sequence (vii) (SEQ ID NO: 60) encodes heavy chain CDR GYTFSSYW (SEQ ID No: 40); polynucleotide sequence (xvii) (SEQ ID No: 66) encodes heavy chain CDR ILPGSGST (SEQ ID No: 41); polynucleotide sequence (xv) (SEQ ID No: 65) encodes heavy chain CDR ARGGDYDEEYYVMDY (SEQ ID No: 45); polynucleotide sequence (x) (SEQ ID No: 63) encodes light chain CDR SSVSY (SEQ ID No: 43); polynucleotide sequence (xi) encodes light chain CDR DTS; and polynucleotide sequence (xii) (SEQ ID No:64) encodes light chain CDR QQWSSYPLT (SEQ ID No: 44). Thus, the polynucleotide encoding the antibody may comprise any 1, 2 or 3 of polynucleotide sequences (vii), (xvii) and (xv) and/or any 1, 2 or 3 of polynucleotide sequences (x), (xi) and (xii). Preferably, the polynucleotide comprises all six of polynucleotide sequences (vii), (xvii), (xv), (x), (xi) and (xii).

It will be appreciated that any of the polynucleotide sequences encoding the heavy chain CDR sequences (i), (ii) and (xiii) may be substituted for any of the corresponding heavy chain CDR sequences of (vii), (xvii) and (xv) and vice versa; and any of the polypeptide sequences encoding the light chain CDR sequences (iv), (v) and (vi) may be substituted for any of the corresponding light chain CDR sequences (x), (xi) and (xii) and vice versa.

Polynucleotide sequence (i) (SEQ ID NO: 9) encodes heavy chain CDR SSYWIE (SEQ ID No: 1); polynucleotide sequence (ii) (SEQ ID No: 10) encodes heavy chain CDR WIGEILPGSGSTN (SEQ ID No: 78); polynucleotide sequence (xvi) (SEQ ID No: 59) encodes heavy chain CDR ARGGDYDEEYYAMD (SEQ ID No: 46); polynucleotide sequence (iv) (SEQ ID No: 12) encodes light chain CDR SYMYWY (SEQ ID No: 4); polynucleotide sequence (v) (SEQ ID No: 13) encodes light chain CDR LLIYDTSNLA (SEQ ID No: 5); and polynucleotide sequence (vi) (SEQ ID No: 14) encodes light chain CDR QQWSSYPL (SEQ ID No: 6). Thus, the polynucleotide encoding the antibody may comprise any 1, 2 or 3 of polynucleotide sequences (i), (ii) and (xvi) and/or any 1, 2 or 3 of polynucleotide sequences (iv), (v), and (vi). Preferably, the polynucleotide comprises all six of polynucleotide sequences (i), (ii), (xvi), (iv), (v), and (vi).

Polynucleotide sequence (vii) (SEQ ID NO: 60) encodes heavy chain CDR GYTFSSYW (SEQ ID No: 40); polynucleotide sequence (xiv) (SEQ ID No: 66) encodes heavy chain CDR ILPGSGST (SEQ ID No: 41); polynucleotide sequence (xviii) (SEQ ID No: 67) encodes heavy chain CDR ARGGDYDEEYYAMDY (SEQ ID No: 47); polynucleotide sequence (x) (SEQ ID No: 63) encodes light chain CDR SSVSY (SEQ ID No:43); polynucleotide sequence (xi) encodes light chain CDR DTS; and polynucleotide sequence (xix) (SEQ ID No: 46) encodes light chain CDR QQWSSY-PLTF (SEQ ID No: 48). Thus, the polynucleotide encoding the antibody may comprise any 1, 2 or 3 of polynucleotide sequences (vii), (xiv) and (xviii) and/or any 1, 2 or 3 of polynucleotide sequences (x), (xi), (xix). Preferably, the polynucleotide comprises all six of polynucleotide sequences (vii), (xiv) and (xviii), (x), (xi), (xix).

It will be appreciated that any of the polynucleotide sequences encoding the heavy chain CDR sequences (i), (ii) and (xvi) may be substituted for any of the corresponding heavy chain CDR sequences of (vii), (xv) and (xviii) and vice versa; and any of the polypeptide sequences encoding the light chain CDR sequences (iv), (v), and (vi) may be substituted for any of the corresponding light chain CDR sequences (x), (xi), (xix) and vice versa.

In a specific embodiment, the polynucleotide comprises the nucleotide sequence ATGGCCCAGGTTCAGCTGCAGCAGTCTGGAGCTGAGCTGATGAAGCCTGGGGCCT CAGTGAAGATATCCTGCAAGGCTACTGGCTACACATTCAGTAGCTACTGGATAGAG TGGGTAAACCGGAGGCCTGGACATGGCCTTGAGTGGATTGGAGAGATTTTACCTGG AAGTGGTAGTACTAATTACAATGAGAAGTTCAAGGGCAAGGCCACATTCACTGCAG ATACATCCTCCAATACAGCCTACATGCAACTCAGCAGCCTCACATCTGAGGACTCTG CCGTCTATTACTGTGCGAGAGGGGGGGATTACGACGAAGAATACTATCTCATGGAC TACTGGGGTCAAGGCACCACTCTCACAGTCTCCTCA (SEQ ID No: 15) and/or the nucleotide sequence CAAATTGTTCTCACCCAGTCTCCAGCAATCATGTCTGCATCTCCAGGGGAGAAGGT CACCATGACCTGCAGTGCCAGCTCAAGTGTAAGTTACATGTACTGGTACCAGCAGA AGCCAGGATCCTCCCCCAGACTCCTGATTTATGACACATCCAACCTGGCTTCTGGA GTCCCTGTTCGCTTCAGTGGCAGTGGGTCTGGGACCTCTTACTCTCTCACAATCAG CCGAATGGAGGCTGAAGATGCTGCCACTTATTACTGCCAGCAGTGGAGTAGTTACC CGCTCACGTTCGGTGCTGGGACCAAGCTGGAAATCAAACGTGCGGCCGC (SEQ ID No: 16). Preferably, the polynucleotide comprises the nucleotide sequence of SEQ ID No: 15 and the nucleotide sequence of SEQ ID No: 16. In this case, it will be appreciated that the two coding regions may be on the same polynucleotide, for example on a polynucleotide for expression of a single chain antibody such as a ScFv antibody.

In another specific embodiment, the polynucleotide comprises the nucleotide sequence ATGGCCCAGGTTCAGCTGCAGCAGTCTGGAGCTGAGCTGATGAAGCCTGGGGCCT CAGTGAAGATATCCTGCAAGGCTACTGGCTACACATTCAGTAGCTACTGGATAGAG TGGGTAAACCGGAGGCCTGGACATGGCCTTGAGTGGATTGGAGAGATTTTACCTGG AAGTGGTAGTACTAATTACAATGAGAAGTTCAAGGGCAAGGCCACATTCACTGCAG ATACATCCTCCAATACAGCCTACATGCAACTCAGCAGCCTCACATCTGAGGACTCTG TCGTCTATTACTGTGCGAGAGGGGGGGATTACGACGAAGAATACTATCTCATGGAC TACTGGGGTCAAGGCACCACTCTCACAGTC (SEQ ID No: 68), which encodes the variable heavy chain of SEQ ID No: 49.

In a further more specific embodiment, the polynucleotide comprises the nucleotide sequence CAAATTGTTCTCACCCAGTCTCCAGCAATCATGTCTGCATCTCCAGGGGAGAAGGT CACCATGACCTGCAGTGCCAGCTCAAGTGTAAGTTACATGTACTGGTACCAGCAGA AGCCAGGATCCTCCCCCAGACTCCTGATTTATGACACATCCAACCTGGCTTCTGGA GTCCCTGTTCGCTTCAGTGGCAGTGGGTCTGGGACCTCTTACTCTCTCACAATCAG CCGAATGGAGGCTGAAGATGCTGCCACTTATTACTGCCAGCAGTGGAGTAGTTACC CGCTCACGTTCGGTGCTGGGACCAAGCTGGAAATCAAACGT (SEQ ID No: 69), which encodes the variable light chain of SEQ ID No: 50.

Preferably, the polynucleotide comprises the nucleotide sequence of SEQ ID No: 68 and the nucleotide sequence of SEQ ID No: 69. Such a polynucleotide may express a single chain antibody such as a ScFv antibody.

In a further specific embodiment, the polynucleotide comprises the nucleotide sequence ATGGCCGAGGTTCAGCTTCAGCAGTCTGGAGCTGAGCTGATGAAGCCTGGGGCCT CAGTGAAGATATCCTGCAAGGCTACTGGCTACACATTCAGTAGCTACTGGATAGAG TGGGTAAAGCAGAGGCCTGGACATGGCCTTGAGTGGATTGGAGAGATTTTACCTGG AAGTGGTAGTACTAATTACAATGAGAAGTTCAAGGGCAAGGCCACATTCACTGCAG ATACATCCTCCAACACAGCCTACATGCAACTCAGCAGCCTGACATCTGAGGACTCT GCCGTCTATTACTGTGCAAGAGGGGGGGATTACGACGAAGAATACTATGTCATGGA CTACTGGGGTCAAGGAACCTCAGTCACTGTC (SEQ ID No: 70), which encodes the variable heavy chain of SEQ ID No: 51.

In a further more specific embodiment, the polynucleotide comprises the nucleotide sequence CAAATTGTTCTCACCCAGTCTCCAGCAATCATGTCTGCATCTCCAGGGGAGAAGGT CACCATGACCTGCAGTGCCAGCTCAAGTGTAAGTTACATGTACTGGTACCAGCAGA AGCCAGGATCCTCCCCCAGACTCCTGATTTATGACACATCCAACCTGGCTTCTGGA GTCCCTGTTCGCTTCAGTGGCAGTGGGTCTGGGACCTCTTACTCTCTCACAATCAG CCGAATGGAGGCTGAAGATGCTGCCACTTATTACTGCCAGCAGTGGAGTAGTTACC CGCTCACGTTCGGTGCTGGGACCAAGCTGGAGCTGAAACGT (SEQ ID No: 71), which encodes the variable light chain of SEQ ID No: 52.

Preferably, the polynucleotide comprises the nucleotide sequence of SEQ ID No: 70 and the nucleotide sequence of SEQ ID No: 71. Such a polynucleotide may express a single chain antibody such as a ScFv antibody.

In a further more specific embodiment, the polynucleotide comprises the nucleotide sequence ATGGCCGAGGTTCAGCTTCAGCAGTCTGGAGCT-GAGCTGATGAAGCCTGGGGCCT CAGTGAAGA-TATCCTGCAAGGCTACTGGCTACACATTCAGTAGC-TACTGGATAGAG TGGGTAAATCAGAGGCCTGG-ACATGGCCTTGAGTGGATTGGAGAGATTTTACCT-GG AAGTGGTAGTACTAATTACAATGAGAAGTT-CAAGGGCAAGGCCACATTCACTGCAG ATA-CATCCTCCAACACAGCCTACATGCAACTCAGC-AGCCTGACATCTGAGGACTCT GCCGTCTAT-TACTGTGCAAGAGGGGGGGATTACGACGAAGA-ATACTATGCTATGGA CTACTGGGGTCAAGG-AACCTCAGTCACCCTC (SEQ ID No: 72), which encodes the variable heavy chain of SEQ ID No: 53.

In a further more specific embodiment, the polynucleotide comprises the nucleotide sequence CAAATTGTTCT-CACCCAGTCTCCAGCAATCATGTCTGCATCTCC-AGGGGAGAAGGT CACCATGACCTGCAGTGCC-AGCTCAAGTGTAAGTTACATGTACTGGTACCAG-CAGA AGCCAGGATCCTCCCCCAGACTCCTGATT-TATGACACATCCAACCTGGCTTCTGGA GTCCCT-GTTCGCTTCAGTGGCAGTGGGTCTGGGACCTCT-TACTCTCTCACAATCAG CCGAATGGAGGCTGAA-GATGCTGCCACTTATTACTGCCAGCAGTG-GAGTAGTTACC CGCTCACGTTCGGTGCTGGGAC-CAAGCTGGAGCTGAAACGT (SEQ ID No: 73), which encodes the variable light chain of SEQ ID No: 54.

Preferably, the polynucleotide comprises the nucleotide sequence of SEQ ID No: 72 and the nucleotide sequence of SEQ ID No: 73. Such a polynucleotide may express a single chain antibody such as a ScFv antibody.

As discussed previously, the invention further encompasses RNA sequences corresponding to or complementary to the DNA sequences provided above. Particularly, RNA sequences which encode an antibody of the invention are encompassed (e.g. which encode a scFv of the invention).

Combination Therapy

According to a National Cancer Institute Press Release dated 14 Apr. 2005, updated 16 Jun. 2005, ("Bevacizumab Combined With Chemotherapy Improves Progression-Free Survival for Patients With Advanced Breast Cancer"), the angiogenesis inhibitor anti-VEGF monoclonal antibody bevacizumab improves the clinical outcome for a number of solid tumours when administered in combination with standard chemotherapy. Combinations that have been used include bevacizumab in combination with irinotecan, fluorouracil, and leucovorin; bevacizumab in combination with FOLFOX4 (a regimen of oxaliplatin, 5-fluorouracil and leucovorin); bevacizumab in combination with paclitaxel; and bevacizumab in combination with paclitaxel and carboplatin.

It is therefore appreciated that although the agents that inhibit the interaction between CLEC14A and MMRN2 described above may be clinically effective in the absence of any other therapeutic agent (eg anti-cancer compound and/or anti-angiogenesis compound), it may be advantageous to administer these inhibitors in conjunction with a further therapeutic agent (eg anticancer agent and/or anti-angiogenesis compound).

Accordingly, in an embodiment, the method may also comprise administering to the individual at least one further therapeutic agent (eg anticancer agent and/or anti-angiogenesis compound). The method may comprise administering to the individual a pharmaceutical composition containing the agent that inhibits the interaction between CLEC14A and MMRN2 (eg antibody), and the further therapeutic agent (eg anticancer agent and/or anti-angiogenesis compound). However, it is appreciated that the agent that inhibits the interaction between CLEC14A and MMRN2 (eg antibody, polynucleotide or cells) and further therapeutic agent (eg anticancer agent and/or anti-angiogenesis compound) may be administered separately, for instance by separate routes of administration. Thus it is appreciated that the agent that inhibits the interaction between CLEC14A and MMRN2 (eg antibody) and the at least one further therapeutic agent (eg anticancer agent and/or anti-angiogenesis compound) can be administered sequentially or (substantially) simultaneously. They may be administered within the same pharmaceutical formulation or medicament or they may be formulated and administered separately.

In an embodiment of the medical uses of the invention, the medicament containing the agent that inhibits the interaction between CLEC14A and MMRN2 may also comprise at least one further therapeutic agent (eg anticancer agent and/or anti-angiogenesis compound).

In another embodiment of the medical uses, the individual to be treated may be one who is administered at least one further therapeutic agent (eg anticancer agent and/or anti-angiogenesis compound). It is appreciated that the individual may be administered the further therapeutic agent (eg anticancer agent and/or anti-angiogenesis compound) at the same time as the medicament containing the agent that inhibits the interaction between CLEC14A and MMRN2 (eg antibody), although the individual may have been (or will be) administered the further therapeutic agent (eg anticancer agent and/or anti-angiogenesis compound) before (or after) receiving the medicament containing the agent that inhibits the interaction between CLEC14A and MMRN2.

It will also be appreciated that the invention also provides a method of treatment, wherein a further therapeutic agent (eg anticancer agent and/or anti-angiogenesis compound) is administered to an individual in need thereof, wherein the individual is one who is administered an agent that inhibits the interaction between CLEC14A and MMRN2 (eg antibody), although the individual may have been (or will be) administered the agent that inhibits the interaction between CLEC14A and MMRN2 (eg antibody) before (or after) receiving the medicament containing the further therapeutic agent (eg anticancer agent and/or anti-angiogenesis compound).

Preferably, the further therapeutic agent is an anti-cancer agent. The further anticancer agent may be selected from alkylating agents including nitrogen mustards such as mechlorethamine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulphan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin); natural products including vinca alkaloids such as vinblastine (VLB) and vincristine; epipodophyllotoxins such as etoposide and teniposide; antibiotics such as dactinomycin (actinomycin D), daunorubicin (daunomycin;

rubidomycin), doxorubicin, bleomycin, plicamycin (mithramycin) and mitomycin (mitomycin C); enzymes such as L-asparaginase; and biological response modifiers such as interferon alphenomes; miscellaneous agents including platinum coordination complexes such as cisplatin (cisDDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p'-DDD) and aminoglutethimide; taxol and analogues/derivatives; cell cycle inhibitors; proteosome inhibitors such as Bortezomib (Velcade®); signal transductase (e.g. tyrosine kinase) inhibitors such as Imatinib (Glivec®), COX-2 inhibitors, and hormone agonists/antagonists such as flutamide and tamoxifen. Particularly, tirapazamine may be utilised.

The clinically used anticancer agents are typically grouped by mechanism of action: Alkylating agents, Topoisomerase I inhibitors, Topoisomerase II inhibitors, RNA/DNA antimetabolites, DNA antimetabolites and Antimitotic agents. The US NIH/National Cancer Institute website lists 122 compounds (http://dtp.nci.nih.gov/docs/cancer/searches/standard_mechanism.html), all of which may be used in conjunction with an inhibitor of CLEC14A. They include Alkylating agents including Asaley, AZQ, BCNU, Busulfan, carboxyphthalatoplatinum, CBDCA, CCNU, CHIP, chlorambucil, chlorozotocin, cis-platinum, clomesone, cyanomorpholino-doxorubicin, cyclodisone, dianhydrogalactitol, fluorodopan, hepsulfam, hycanthone, melphalan, methyl CCNU, mitomycin C, mitozolamide, nitrogen mustard, PCNU, piperazine, piperazinedione, pipobroman, porfiromycin, spirohydantoin mustard, teroxirone, tetraplatin, picoplatin (SP-4-3) (cis-aminedichloro(2-methylpyridine)Pt(II)), thio-tepa, triethylenemelamine, uracil nitrogen mustard, Yoshi-864; anitmitotic agents including allocolchicine, Halichondrin B, colchicine, colchicine derivative, dolastatin 10, maytansine, rhizoxin, taxol, taxol derivative, thiocolchicine, trityl cysteine, vinblastine sulphate, vincristine sulphate; Topoisomerase I Inhibitors including camptothecin, camptothecin, Na salt, aminocamptothecin, 20 camptothecin derivatives, morpholinodoxorubicin; Topoisomerase II Inhibitors including doxorubicin, amonafide, m-AMSA, anthrapyrazole derivative, pyrazoloacridine, bisantrene HCL, daunorubicin, deoxydoxorubicin, mitoxantrone, menogaril, N, N-dibenzyl daunomycin, oxanthrazole, rubidazone, VM-26, VP-16; RNA/DNA antimetabolites including L-alanosine, 5-azacytidine, 5-fluorouracil, acivicin, 3 aminopterin derivatives, an antifol, Baker's soluble antifol, dichlorallyl lawsone, brequinar, ftorafur (pro-drug), 5,6-dihydro-5-azacytidine, methotrexate, methotrexate derivative, N-(phosphonoacetyl)-L-aspartate (PALA), pyrazofurin, trimetrexate; DNA antimetabolites including, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole, hydroxyurea, inosine glycodialdehyde, macbecin II, pyrazoloimidazole, thioguanine and thiopurine.

It is, however, preferred that the at least one further anticancer agent is selected from cisplatin; carboplatin; picoplatin; 5-flurouracil; paclitaxel; mitomycin C; doxorubicin; gemcitabine; tomudex; pemetrexed; methotrexate; irinotecan, fluorouracil and leucovorin; oxaliplatin, 5-fluorouracil and leucovorin; and paclitaxel and carboplatin.

When the further anticancer agent has been shown to be particularly effective for a specific tumour type, it may be preferred that the agent that inhibits the interaction between CLEC14A and MMRN2 is used in combination with that further anticancer agent to treat that specific tumour type.

Preferred anti-angiogenesis compounds include bevacizumab (Avastin®); itraconazole; carboxyamidotriazole; TNP-470 (an analog of fumagillin); CM 101; IFN-α; IL-12; platelet factor-4; suramin; SU5416; thrombospondin; VEGFR antagonists; angiostatic steroids+heparin; Cartilage-Derived Angiogenesis Inhibitory Factor; matrix metalloproteinase inhibitors; angiostatin; endostatin; 2-methoxyestradiol; tecogalan; tetrathiomolybdate; thalidomide; prolactin; $\alpha v \beta_3$ inhibitors; linomide; tasquinimod; ranibizumab; sorafenib; (Nexavar®); sunitinib (Sutent®); pazopanib (Votrient®); and everolimus (Afinitor®).

Compounds Comprising a Cytotoxic Moiety

A fourth aspect of the invention provides a compound comprising an antibody according to the second aspect of the invention, and a cytotoxic moiety.

The cytotoxic moiety may be directly or indirectly toxic to cells in neovasculature or cells which are in close proximity to and associated with neovasculature. By "directly cytotoxic" we include the meaning that the moiety is one which on its own is cytotoxic. By "indirectly cytotoxic" we include the meaning that the moiety is one which, although is not itself cytotoxic, can induce cytotoxicity, for example by its action on a further molecule or by further action on it. For example, an indirect cytotoxic moiety may act to recruit an immune cell (eg a cytotoxic immune cell such as a cytotoxic T cell), and thereby indirectly induce a cytotoxic effect.

Typically, the cytotoxic moiety is selected from a directly cytotoxic chemotherapeutic agent, a directly cytotoxic polypeptide, a moiety which is able to convert a prodrug into a cytotoxic drug, a radiosensitizer, a directly cytotoxic nucleic acid, a nucleic acid molecule that encodes a directly or indirectly cytotoxic polypeptide or a radioactive atom. Examples of such cytotoxic moieties, as well as methods of making the conjugates comprising the antibody and the cytotoxic moiety, are provided in our earlier publications WO 02/36771, WO 2004/046191, and WO 2011/027132 incorporated herein by reference.

In one embodiment the cytotoxic moiety is a cytotoxic chemotherapeutic agent. Cytotoxic chemotherapeutic agents, such as anticancer agents, are well known in the art, and include those described above.

Antibody-drug conjugates, such as for cancer therapy are reviewed by Carter & Senter (2008), *Cancer J.* 14(3): 154-69, and Chari et al (2014) Angewandte Chemie International Edition 53: 3751, incorporated herein by reference, and it will be appreciated that the compounds of this aspect of the invention may considered such antibody drug conjugates (see also U.S. Pat. Nos. 5,773,001; 5,767,285; 5,739,116; 5,693,762; 5,585,089; US 2006/0088522; US 2011/0008840; U.S. Pat. No. 7,659,241; Hughes (2010) *Nat Drug Discov* 9: 665, Lash (2010); *In vivo: The Business & Medicine Report* 32-38; Mahato et al (2011) *Adv Drug Deliv Rev* 63: 659; Jeffrey et al (2006) *BMCL* 16: 358; Drugs R D 11(1): 85-95). ADCs generally comprise a monoclonal antibody against a target present on a tumour cell, a cytotoxic drug, and a linker that attaches the antibody to the drug.

Various of the cytotoxic moieties mentioned above, such as cytotoxic chemotherapeutic agents, have previously been attached to antibodies and other targeting agents, and so compounds of the invention comprising these agents may readily be made by the person skilled in the art. For example, carbodiimide conjugation (Bauminger & Wilchek (1980) *Methods Enzymol.* 70, 151-159) may be used to conjugate a variety of agents, including doxorubicin, to antibodies.

Other methods for conjugating a cytotoxic moiety to an antibody can also be used. For example, sodium periodate oxidation followed by reductive alkylation of appropriate reactants can be used, as can glutaraldehyde cross-linking. Methods of cross-linking polypeptides are known in the art and described in WO 2004/046191. However, it is recognised that, regardless of which method of producing a compound of the invention is selected, a determination must be made that the antibody maintains its targeting ability and that the attached moiety maintains its relevant function.

In a further embodiment of the invention, the cytotoxic moiety may be a cytotoxic peptide or polypeptide moiety by which we include any moiety which leads to cell death. Cytotoxic peptide and polypeptide moieties are well known in the art and include, for example, ricin, abrin, *Pseudomonas* exotoxin, tissue factor and the like. Methods for linking them to targeting moieties such as antibodies are also known in the art, and include, for example, conventional ways of crosslinking polypeptides and production of the compound as a fusion polypeptide using recombinant DNA techniques. The use of ricin as a cytotoxic agent is described in Burrows & Thorpe (1993) *Proc. Natl. Acad. Sci. USA* 90, 8996-9000, and the use of tissue factor, which leads to localised blood clotting and infarction of a tumour, has been described by Ran et al (1998) *Cancer Res.* 58, 4646-4653 and Huang et al (1997) *Science* 275, 547-550. Tsai et al (1995) *Dis. Colon Rectum* 38, 1067-1074 describes the abrin A chain conjugated to a monoclonal antibody. Other ribosome inactivating proteins are described as cytotoxic agents in WO 96/06641. *Pseudomonas* exotoxin may also be used as the cytotoxic polypeptide moiety (Aiello et al (1995) *Proc. Natl. Acad. Sci. USA* 92, 10457-10461).

Certain cytokines, such as TNFα, INFγ and IL-2, may also be useful as cytotoxic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the compound of the invention are such that a dose of more than 4000 cGy (preferably at least 6000, 8000 or 10000 cGy) is delivered to the target site and, preferably, to the cells at the target site and their organelles, particularly the nucleus.

The radioactive atom may be attached to the antibody in known ways. For example EDTA or another chelating agent may be attached to the antibody and used to attach $^{111}$In or $^{90}$Y. Tyrosine residues may be labelled with $^{125}$I or $^{131}$I.

The cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole (see, for example, McGinn et al (1996) *J. Natl. Cancer Inst.* 88, 1193-11203; Shewach & Lawrence (1996) *Invest. New Drugs* 14, 257-263; Horsman (1995) *Acta Oncol.* 34, 571-587; Shenoy & Singh (1992) *Clin. Invest.* 10, 533-551; Mitchell et al (1989) *Int. J. Radiat. Biol.* 56, 827-836; Iliakis & Kurtzman (1989) *Int. J. Radiat. Oncol. Biol. Phys.* 16, 1235-1241; Brown (1989) *Int. J. Radiat. Oncol. Biol. Phys.* 16, 987-993; Brown (1985) *Cancer* 55, 2222-2228).

The cytotoxic moiety may be a procoagulant factor, such as the extracellular domain of tissue factor (Rippmann et al (2000) "Fusion of the tissue factor extracellular domain to a tumour stroma specific single-chain fragment variable antibody results in an antigen-specific coagulation-promoting molecule." *Biochem J.* 349: 805-12; Huang et al (1997) "Tumor infarction in mice by antibody-directed targeting of tissue factor to tumor vasculature." *Science.* 275(5299): 547-550.

The cytotoxic moiety may be an indirectly cytotoxic polypeptide. In a particularly preferred embodiment, the indirectly cytotoxic polypeptide is a polypeptide which has enzymatic activity and can convert a relatively non-toxic prodrug into a cytotoxic drug. When the targeting moiety is an antibody, this type of system is often referred to as ADEPT (Antibody-Directed Enzyme Prodrug Therapy). The system requires that the targeting moiety locates the enzymatic portion to the desired site in the body of the patient (e.g. the site of new vascular tissue associated with a tumour) and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues (Senter et al (1988) "Anti-tumor effects of antibody-alkaline phosphatase conjugates in combination with etoposide phosphate" *Proc. Natl. Acad. Sci. USA* 85, 4842-4846; Bagshawe (1987) *Br. J. Cancer* 56, 531-2; and Bagshawe, et al (1988) "A cytotoxic agent can be generated selectively at cancer sites" *Br. J. Cancer.* 58, 700-703); Bagshawe (1995) *Drug Dev. Res.* 34, 220-230 and WO 2004/046191, describe various enzyme/prodrug combinations which may be suitable in the context of this invention.

Typically, the prodrug is relatively non-toxic compared to the cytotoxic drug. Typically, it has less than 10% of the toxicity, preferably less than 1% of the toxicity as measured in a suitable in vitro cytotoxicity test.

It is likely that the moiety which is able to convert a prodrug to a cytotoxic drug will be active in isolation from the rest of the compound but it is necessary only for it to be active when (a) it is in combination with the rest of the compound and (b) the compound is attached to, adjacent to or internalised in target cells.

The cytotoxic moiety may be one which becomes cytotoxic, or releases a cytotoxic moiety, upon irradiation. For example, the boron-10 isotope, when appropriately irradiated, releases a particles which are cytotoxic (U.S. Pat. No. 4,348,376; Primus et al (1996) *Bioconjug. Chem.* 7: 532-535).

Similarly, the cytotoxic moiety may be one which is useful in photodynamic therapy such as photofrin (see, for example, Dougherty et al (1998) *J. Natl. Cancer Inst.* 90, 889-905).

In a particular embodiment, the cytotoxic moiety is an antibody, such as one that specifically binds to an immune cell, such as a cytotoxic immune cell (eg T cell). Thus, in this case, the compound of the invention may be an asymmetric IgG-like antibody (eg triomab/quadroma, Trion Pharma/Fresenius Biotech; knobs-into-holes, Genentech; Cross MAbs, Roche; electrostatically matched antibodies, AMGEN; LUZ-Y, Genentech; strand exchange engineered domain (SEED) body, EMD Serono; biolonic, erus; and Fab-exchanged antibodies, Genmab), symmetric IgG-like antibodies (eg dual targeting (DT)-Ig, GSK/Domantis; two-in-one antibody, Genentech; crosslinked MAbs, karmanos cancer center; mAb <2>, F-star; and Coy X-body, Coy X/Pfizer), IgG fusions (eg dual variable domain (DVD)-Ig, Abbott; IgG-like bispecific antibodies, Eli Lilly; Ts2Ab, Medimmune/AZ; BsAb, ZymoGenetics; HERCULES, Biogen Idee; TvAb, Roche) Fc fusions (eg ScFv/Fc fusions, Academic Institution; SCORPION, Emergent BioSolutions/Trubion, ZymoGenetics/BMS; dual affinity retargeting technology (Fc-DART), MacroGenics; dual (ScFv) 2-Fab, National Research Center for Antibody Medicine) Fab fusions (eg F(ab) 2, Medarex/AMGEN; dual-action or Bis-Fab, Genentech; Dock-and-Lock (DNL), ImmunoMedics; bivalent bispecific, Biotechnol; and Fab-Fv, UCB-Celltech), ScFv- and diabody-based antibodies (eg bispecific T cell engagers (BiTEs), Micromet; tandem diabodies (Tandab), Affimed; DARTs, MacroGenics; Single-chain diabody, Academic; TCR-like antibodies, AIT, Receptor Logics; human serum albumin ScFv fusion, Merrimack; and COMBODIES, Epigen Biotech), IgG/non-IgG fusions (eg immunocytokins, EMDSerono, Philogen, ImmunGene, ImmunoMedics; superantigen fusion protein, Active Biotech; and immune mobilising mTCR Against Cancer, ImmTAC) and oligoclonal antibodies (eg Symphogen and Merus).

In another embodiment, the cytotoxic moiety is a pyrrolobenzodiazepine dimer (PBD). PBDs are potent anticancer agents which have been shown to have broad spectrum anti-tumour activity in vivo. These drugs exert their activity by binding the minor groove of DNA and linking the two DNA strands together in a way that cells find difficult to recognise and repair. Thus the compound of the invention may be an ADC comprising a PBD. Further information on PBDs can be found in Hartley et al, 2012 (*Invest New Drugs* 30: 950-958).

A fifth aspect of the invention provides a polynucleotide encoding a compound as defined above in the fourth aspect of the invention, wherein the antibody and the cytotoxic moiety are polypeptides which are fused.

Compounds Comprising a Detectable Moiety

A sixth aspect of the invention provides a compound comprising an antibody according to the second aspect of the invention and a detectable moiety. Such a compound can be used, in combination with an appropriate detection method, to detect the location of the compound in the individual, and hence to identify the sites and extent of angiogenesis (eg tumour angiogenesis) in the individual, as well as inhibition of angiogenesis (eg tumour angiogenesis) in the individual.

By a "detectable moiety" we include the meaning that the moiety is one which, when located at the target site following administration of the compound of the invention into a patient, may be detected, typically non-invasively from outside the body, and the site of the target located. Thus, the compounds of this aspect of the invention are useful in imaging and diagnosis, especially in the imaging and diagnosis of neovasculature of solid tumours, as is described further below.

Typically, the detectable moiety is or comprises a magnetic nano-particle, a radionuclide or a fluorophore.

Thus, in an embodiment, the detectable moiety may be a radioactive atom which is useful in imaging. Suitable radioactive atoms include technetium-99m or iodine-123 for scintigraphic studies. Others may be selected from the group consisting of: iodine-124; iodine-125; iodine-126; iodine-131; iodine-133; indium-111; indium-113m, fluorine-18; fluorine-19; carbon-11; carbon-13; copper-64; nitrogen-13; nitrogen-15; oxygen-15; oxygen-17; arsenic-72; gadolinium; manganese; iron; deuterium; tritium; yttrium-86; zirconium-89; bromine-77, gallium-67; gallium-68, ruthenium-95, ruthenium-97, ruthenium-103, ruthenium-105, mercury-107, rhenium-99m, rhenium-101, rhenium-105, scandium-47. Suitable methods for coupling such radioisotopes to the antibodies—either directly or via a chelating agent such as EDTA or DTPA—can be employed, as is known in the art.

Other readily detectable moieties include, for example, spin labels for magnetic resonance imaging (MRI) such as iodine-123 again, iodine-131, indium-111, fluorine-19, carbon-13, nitrogen-15, oxygen-17, gadolinium, manganese or iron. Clearly, the compound of the invention must have sufficient of the appropriate atomic isotopes in order for the molecule to be detectable.

The radio- or other label may be incorporated in the compound in known ways. For example, if the antibody may be biosynthesised or synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the antibody. Yttrium-90 can be attached via a lysine residue. The IODOGEN method (Fraker et al (1978) *Biochem. Biophys. Res. Comm.* 80, 49-57) can be used to incorporate iodine-123. The reference ("Monoclonal Antibodies in Immunoscintigraphy", J. F. Chatal, CRC Press, 1989) describes other methods in detail.

Many suitable fluorophores and detection methods are well known in the art and are described, for example by Stefan Andersson-Engels et al (1997) "In vivo fluorescence imaging for tissue diagnostics. *Phys. Med. Biol.* 42: 815-824; Altinoğlu et al (2008) "Near-Infrared Emitting Fluorophore-Doped Calcium Phosphate Nanoparticles for In Vivo Imaging of Human Breast Cancer" *ACS Nano* 2(10): 2075-84; and Chin et al (2009) "In-vivo optical detection of cancer using chlorin e6—polyvinylpyrrolidone induced fluorescence imaging and spectroscopy" *BMC Medical Imaging* 9:1 (doi:10.1186/1471-2342-9-1). Examples include fluorescein and its derivatives, fluorochrome, rhodamine and its derivatives, Green Fluorescent Protein (GFP), dansyl, umbelliferone etc. In such conjugates, the antibodies of the invention or their functional fragments can be prepared by methods known to the person skilled in the art.

The detectable moiety may comprise a detectable enzyme such as peroxidase, alkaline phosphatase, beta-D-galactosidase, glucose oxidase, glucose amylase, carbonic anhydrase, acetylcholinesterase, lysozyme, malate dehydrogenase or glucose 6-phosphate dehydrogenase.

The detectable moiety may comprise a molecule such as biotin, digoxygenin or 5-bromodeoxyuridine.

The detectable moiety may comprise a chemiluminescent label such as luminol and the dioxetanes, or a bioluminescent label such as luciferase and luciferin.

A seventh aspect of the invention provides a polynucleotide encoding a compound as defined above in the sixth aspect of the invention, wherein the antibody and the detectable moiety are polypeptides which are fused. It will be appreciated that the seventh aspect of the invention also provides a nucleic acid comprising a polynucleotide encoding a compound as defined above in the sixth aspect of the invention, wherein the antibody and the detectable moiety are polypeptides which are fused.

Polynucleotides, Vectors and Expression

The nucleic acid molecule of any of the third, fifth and seventh aspects of the invention may be DNA or RNA, and is preferably DNA, in particular circumstances. In other circumstances, e.g. when employing cell therapy, RNA encoding an antibody of the invention may be preferred. It may comprise deoxyribonucleotides, ribonucleotides, modified nucleotides or bases, and/or their analogues, or any substrate that can be incorporated into a polymer by DNA or RNA polymerase, or by a synthetic reaction. A polynucleotide may comprise modified nucleotides, such as methylated nucleotides and their analogues. If present, modification to the nucleotide structure may be imparted before or after assembly of the polymer. The sequence of nucleotides may be interrupted by non-nucleotide components. Some specific examples of nucleic acid molecules encoding antibodies of the invention are described herein. Other suitable sequences can readily be determined based upon the knowledge of antibody structure and the genetic code.

An eighth aspect of the invention provides a vector comprising the polynucleotide of any of the third, fifth and seventh aspects of the invention.

A ninth aspect of the invention provides a host cell comprising a polynucleotide according to any of the third, fifth, or seventh aspect of the invention, and/or an antibody according to the second aspect of the invention or a vector according to the eighth aspect of the invention.

The vector can be of any type, for example a recombinant vector such as an expression vector. The expression vectors contain elements (e.g., promoter, signals of initiation and termination of translation, as well as appropriate regions of regulation of transcription) which allow the expression and/or the secretion of the antibodies in a host cell. Particularly, the vector may be a viral vector, e.g. a retrovirus, lentivirus or adenovirus. Most particularly, the vector may be a gamma retrovirus. Any of a variety of host cells can be used, such as a prokaryotic cell, for example, *E. coli*, or a eukaryotic cell, for example a mammalian cell such as Chinese Hamster Ovary (CHO) cell, or a yeast, insect or plant cell. Many suitable vectors and host cells are very well known in the art. Preferably, the host cell is a stable cell line. Alternatively, the host cell may be a cell obtained from a patient, e.g. a T cell or other immune cell, as discussed further below.

It is appreciated that in certain embodiments the nucleic acid molecule and the expression vector may be used in the treatment aspects of the invention via a gene therapy approach using formulations and methods described below and known in the art.

The invention also includes methods for making an antibody of the invention. For example, the invention comprises expressing in a suitable host cell a recombinant vector encoding the antibody (e.g. an antibody fragment), and recovering the antibody. Methods for expressing and purifying antibodies are very well known in the art.

The invention also provides a method of producing a cell comprising introducing a polynucleotide molecule according to the third, fifth, seventh aspects of the invention, or a vector according to the eighth aspect of the invention. Suitable methods of introducing polynucleotide molecules and/or vectors include those described above, and are generally known in the art. Particularly, electroporation may be used.

Any of a variety of host cells can be used, such as a prokaryotic cell, for example, *E. coli*, or a eukaryotic cell, for example a mammalian cell such as Chinese Hamster Ovary (CHO) cell, or a yeast, insect or plant cell.

In addition to a host cell being used in a method to produce an antibody of the invention, the host cell itself may be used directly in therapy, for example in cell mediated therapy. Thus, the invention provides a method of treatment, comprising administering a host cell according to the invention to the subject, for example for use in medicine or for the treatment of cancer and/or for inhibiting angiogenesis. Accordingly, the invention also provides a host cell comprising a polynucleotide molecule according to the third, fifth or seventh aspect of the invention, e.g. an RNA molecule, or a vector according to the eighth aspect of the invention, e.g. a gamma retrovirus, for use in medicine, for example for use in the treatment of cancer. The invention also provides for the use of said host cell in the manufacture of a medicament for use in medicine, for example for use in the treatment of cancer. Preferences for the antibody produced by the host cell and polynucleotides expressing it are as outlined above.

In a preferred embodiment, the host cell is a mammalian cell (eg a human cell).

In a further preferred embodiment, the host cell is an immune cell, preferably a mammalian immune cell such as a human immune cell. Immune cells include T cells and natural killer (NK) cells. The T cell may be any of an alpha-beta T cell, a gamma-delta T cell, a memory T cell (eg a memory T cell with stem cell-like properties). The NK cell may be an invariant NK cell.

In a particularly preferred embodiment, the immune cell is a memory T cell with stem cell like properties.

The cell may be "autologous" or "allogeneic", as described further below.

Immune cells such as T cells can be obtained from a number of sources peripheral blood mononuclear cells, bone marrow, lymph node tissue, cord blood, thymus tissue, tissue from a site of infection, ascites, pleural effusion, spleen tissue, and tumors. Any number of cell lines (eg immune cell lines such as T cell lines) available in the art, may also be used.

In an embodiment, immune cells (eg T cells) are obtained from a unit of blood collected from a subject using any suitable techniques known in the art such as Ficoll™ separation. In another embodiment, cells from the circulating blood of a subject are obtained by apheresis. The apheresis product typically contains lymphocytes, including T cells, monocytes, granulocytes, B cells, other nucleated white blood cells, red blood cells, and platelets. It will be appreciated that the cells collected by apheresis may be washed to remove the plasma fraction and to place the cells in an appropriate buffer or media for subsequent processing steps. For example, the cells may be washed with phosphate buffered saline (PBS). Alternatively, the wash solution lacks calcium and may lack magnesium or may lack many if not all divalent cations. Initial activation steps in the absence of calcium can lead to magnified activation. A washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In an embodiment, T cells are isolated from peripheral blood lymphocytes by lysing the red blood cells and depleting the monocytes, for example, by centrifugation through a PERCOLL™ gradient or by counter-flow centrifugal elutriation. Specific subpopulations of T cells, such as CD3+, CD28+, CD4+, CD8+, CD45RA+, and CD45RO+ T cells, may be further isolated by positive or negative selection techniques known in the art. For example, T cells may be isolated by incubation with anti-CD3/anti-CD28 (e.g., 3×28)-conjugated beads, such as DYNABEADS® M-450 CD3/CD28 T, for a time period sufficient for positive selection of the desired T cells. Additionally or alternatively, a population of T cells may be enriched by negative selection, for instance by a combination of antibodies directed to surface markers unique to the negatively selected cells. Cell sorting and/or selection via negative magnetic immunoadherence or flow cytometry may be used It will be understood that cells derived from subjects that are to be modified to express the antibody of the invention may be stored for a period of time prior to their use (see, for example, therapeutic methods below). For example, the cells may be frozen, optionally after they have been washed, or they may be incubated under suitable conditions for them to remain viable until needed (eg on a rotator at 2-10° C. or at room temperature). In this way, the cells can be stored until such time as they might be needed. They may be stored in an unmodified state (ie wherein they do not express the antibody of the invention) or in a modified state (ie wherein they have been modified to express the antibody of the invention).

Prior to use in the therapeutic applications described further below, the cells may be activated and expanded generally using methods known in the art. For example, T cells may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9): 13191328, 1999; Garland et al., J. Immunol Meth. 227(1-2):53-63, 1999).

T cells that have been exposed to varied stimulation times may exhibit different characteristics. For example, typical blood or apherised peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Particularly, T cells may be expanded prior to transduction with a polynucleotide or vector of the invention.

In an embodiment, the cell that expresses an antibody of the invention is further modified to comprise or express one or more other agents that enhance the activity of the antibody expressing cell (eg T cell).

For example, the other agent may be an agent that inhibits an inhibitory molecule that is known to decrease the ability of the antibody-expressing cell to mount an effective immune response. Examples of inhibitory molecules include PD1, PD-L1, CTLA4, TIM3, LAG3, VISTA, BTLA, TIGIT, LAIR1, CD160, 2B4 and TGFR beta. The agent that inhibits the inhibitory molecule may comprise a first polypeptide, eg an inhibitory molecule, associated with a second polypeptide that provides a positive signal to the cell, eg an intracellular signalling domain described herein.

Additionally or alternatively, the other agent may be a pro-inflammatory or pro-proliferative cytokine. The purpose of such cytokines may be to provide autocrine support to enhance the function, proliferation and/or persistence of antibody-expressing cells, and/or favourably alter the tumour microenvironment and recruit endogenous innate and cognate immune effects.

Formulations and Routes of Administration

A tenth aspect of the invention provides a pharmaceutical composition comprising an antibody according to the second aspect of the invention, or a polynucleotide according to any of the third, fifth, or seventh aspects of the invention, a vector according to the eighth aspect of the invention, a cell according to the ninth aspect of the invention, or a compound according to any of the fourth or sixth aspects of the invention, and a pharmaceutically acceptable diluent, carrier or excipient.

It is appreciated that the agent, antibody or compound inhibitor of CLEC14A will typically be formulated for administration to an individual as a pharmaceutical composition, i.e. together with a pharmaceutically acceptable carrier, diluent or excipient.

By "pharmaceutically acceptable" is included that the formulation is sterile and pyrogen free. Suitable pharmaceutical carriers, diluents and excipients are well known in the art of pharmacy. The carrier(s) must be "acceptable" in the sense of being compatible with the inhibitor and not deleterious to the recipients thereof. Typically, the carriers will be water or saline which will be sterile and pyrogen free; however, other acceptable carriers may be used. In an embodiment, the pharmaceutical compositions or formulations of the invention are for parenteral administration, more particularly for intravenous administration. In a preferred embodiment, the pharmaceutical composition is suitable for intravenous administration to a patient, for example by injection.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

In an alternative preferred embodiment, the pharmaceutical composition is suitable for topical administration to a patient.

Preferably, the formulation is a unit dosage containing a daily dose or unit, daily sub-dose or an appropriate fraction thereof, of the active ingredient.

The agent, antibody or compound may be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the agent, antibody or compound will generally be administered in admixture with a suitable pharmaceutical excipient, diluent or carrier selected with regard to the intended route of administration and standard pharmaceutical practice.

For example, the agent, antibody or compound may be administered orally, buccally or sublingually in the form of tablets, capsules, ovules, elixirs, solutions or suspensions, which may contain flavouring or colouring agents, for immediate-, delayed- or controlled-release applications. The agent, antibody or compound may also be administered via intracavernosal injection.

Suitable tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The agent, antibody or compound can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of an agent, antibody or compound will usually be from 1 to 1,000 mg per adult (i.e. from about 0.015 to 15 mg/kg), administered in single or divided doses.

Thus, for example, the tablets or capsules of the agent, antibody or compound may contain from 1 mg to 1,000 mg of active agent for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The agent, antibody or compound can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichloro-tetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a antibody and a suitable powder base such as lactose or starch. Such formulations may be particularly useful for treating solid tumours of the lung, such as, for example, small cell lung carcinoma, non-small cell lung carcinoma, pleuropulmonary blastoma or carcinoid tumour.

Aerosol or dry powder formulations are preferably arranged so that each metered dose or "puff" contains at least 1 mg of the inhibitor for delivery to the patient. It will be appreciated that the overall daily dose with an aerosol will vary from patient to patient, and may be administered in a single dose or, more usually, in divided doses throughout the day.

Alternatively, the agent, antibody or compound can be administered in the form of a suppository or pessary, particularly for treating or targeting colon, rectal or prostate tumours.

The agent, antibody or compound may also be administered by the ocular route. For ophthalmic use, the inhibitor can be formulated as, e.g., micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum. Such formulations may be particularly useful for treating solid tumours of the eye, such as retinoblastoma, medulloepithelioma, uveal melanoma, rhabdomyosarcoma, intraocular lymphoma, or orbital lymphoma.

The agent, antibody or compound may be applied topically in the form of a lotion, solution, cream, ointment or dusting powder, or may be transdermally administered, for example, by the use of a skin patch. For application topically to the skin, the agent, antibody or compound can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water. Such formulations may be particularly useful for treating solid tumours of the skin, such as, for example, basal cell cancer, squamous cell cancer or melanoma.

For skin cancers, the agent, antibody or compound can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with inhibitor or can simply act as "bullets" that generate pores in the skin through which the agent, antibody or compound can enter.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier. Such formulations may be particularly useful for treating solid tumours of the mouth and throat.

In an embodiment, when the agent, antibody or compound is a polypeptide, such as an anti-CLEC14A antibody, it may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The agent, antibody or compound can be administered by a surgically implanted device that releases the drug directly to the required site, for example, into the eye to treat ocular tumours. Such direct application to the site of disease achieves effective therapy without significant systemic side-effects.

An alternative method for delivery of polypeptide agents, antibody or compound, such as antibodies, is the ReGel injectable system that is thermo-sensitive. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Polypeptide pharmaceuticals such as antibodies can also be delivered orally. The process employs a natural process for oral uptake of vitamin $B_{12}$ in the body to co-deliver proteins and peptides. By riding the vitamin $B_{12}$ uptake system, the protein or peptide can move through the intestinal wall. Complexes are synthesised between vitamin $B_{12}$ analogues and the drug that retain both significant affinity for intrinsic factor (IF) in the vitamin $B_{12}$ portion of the complex and significant bioactivity of the drug portion of the complex.

The polynucleotide may be administered as a suitable genetic construct as described below and delivered to the patient where it is expressed. Typically, the polynucleotide in the genetic construct is operatively linked to a promoter which can express the compound in the cell. The genetic constructs of the invention can be prepared using methods well known in the art, for example in Sambrook et al (2001).

Although genetic constructs for delivery of polynucleotides can be DNA or RNA, it is preferred if they are DNA.

Preferably, the genetic construct is adapted for delivery to a human cell. Means and methods of introducing a genetic construct into a cell are known in the art, and include the use of immunoliposomes, liposomes, viral vectors (including vaccinia, modified vaccinia, lentivurus, parvovirus, retroviruses, adenovirus and adeno-associated viral (AAV) vectors), and by direct delivery of DNA, e.g. using a gene-gun and electroporation. Furthermore, methods of delivering polynucleotides to a target tissue of a patient for treatment are also well known in the art. In an alternative method, a high-efficiency nucleic acid delivery system that uses receptor-mediated endocytosis to carry DNA macromolecules into cells is employed. This is accomplished by conjugating the iron-transport protein transferrin to polycations that bind nucleic acids. High-efficiency receptor-mediated delivery of the DNA constructs or other genetic constructs of the invention using the endosome-disruption activity of defective or chemically inactivated adenovirus particles produced by the methods of Cotten et al (1992) Proc. Natl. Acad. Sci. USA 89, 6094-6098 may also be used. It will be appreciated that "naked DNA" and DNA complexed with cationic and neutral lipids may also be useful in introducing the DNA of the invention into cells of the individual to be treated. Non-viral approaches to gene therapy are described in Ledley (1995, Human Gene Therapy 6, 1129-1144).

Although for cancer/tumours of specific tissues it may be useful to use tissue-specific promoters in the vectors encoding a polynucleotide inhibitor, this is not essential, as the risk of expression of the agent or antibody in the body at locations other than the cancer/tumour would be expected to be tolerable in compared to the therapeutic benefit to a patient suffering from a cancer/tumour. It may be desirable to be able to temporally regulate expression of the polynucleotide inhibitor in the cell, although this is also not essential.

The antibodies, agents, and compounds of the invention may be lyophilised for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. In one embodiment, the lyophilised (freeze dried) antibody loses no more than about 20%, or no more than about 25%, or no more than about 30%, or no more than about 35%, or no more than about 40%, or no more than about 45%, or no more than about 50% of its activity (prior to lyophilisation) when re-hydrated.

An eleventh aspect of the invention provides an antibody according to the second aspect of the invention, or a polynucleotide according to any of the third, fifth, or seventh aspects of the invention, a vector according to the eighth aspect of the invention, a cell according to the ninth aspect of the invention, or a compound according to any of the fourth or sixth aspects of the invention, for use in medicine. The antibodies of the invention have all shown utility in the treatment of cancer. Accordingly, in one embodiment, the antibody according to the second aspect of the invention, or a polynucleotide according to any of the third, fifth or seventh aspects of the invention, a vector according to the eighth aspect of the invention, a cell according to the ninth aspect of the invention, or a compound according to any of the fourth or sixth aspects of the invention is for use in the treatment of cancer.

In a further embodiment, the antibody according to the second aspect of the invention, or a polynucleotide according to any of the third, fifth or seventh aspects of the invention, a vector according to the eighth aspect of the invention, a cell according to the ninth aspect of the invention, or a compound according to any of the fourth or sixth aspects of the invention is for use in inhibiting angiogenesis. Methods of manufacturing a medicament using an active agent, such as the antibody, nucleic acid molecule/expression vector or compound of the invention, are well known to persons skilled in the art of medicine and pharmacy.

Targeted Delivery of Cytotoxic Agents

A twelfth aspect of the invention provides a method of targeting a cytotoxic agent to neovasculature in the body of an individual, the method comprising:

administering to the individual a compound according to the fourth aspect of the invention (ie a compound comprising an antibody according to the second aspect of the invention and a cytotoxic agent). Preferably, the neovasculature is tumour neovasculature.

This aspect of the invention includes a compound according to the fourth aspect of the invention for use in targeting a cytotoxic agent to vasculature in the body of an individual. This aspect of the invention further includes the use of a compound according to the fourth aspect of the invention in the preparation of a medicament for targeting a cytotoxic agent to vasculature in the body of an individual.

It is appreciated that targeting a cytotoxic agent to neovasculature will act to inhibit angiogenesis. Hence, a thirteenth aspect of the invention provides a method of inhibiting angiogenesis in an individual, the method comprising:

administering to the individual a compound according to the fourth aspect of the invention. Preferably, the neovasculature is tumour neovasculature and the angiogenesis is tumour angiogenesis.

This aspect of the invention includes a compound according to the fourth aspect of the invention for use in inhibiting angiogenesis in an individual. This aspect of the invention further includes the use of a compound according to the fourth aspect of the invention in the preparation of a medicament for inhibiting angiogenesis in an individual.

Typically, the individual in the twelfth and thirteenth aspects of the invention has a solid tumour, preferably such as those described above with respect to the first aspect of the invention.

It is appreciated that targeting a cytotoxic moiety to tumour neovasculature to inhibit tumour neoangiogenesis as described in the twelfth and thirteenth aspects of the invention may be clinically effective in the absence of any other anti-cancer compound, it may nevertheless be advantageous to administer the compounds in conjunction with a further antiocancer agent. Accordingly, in an embodiment of the twelfth and thirteenth aspects of the invention, the method may comprise administering to the individual a further anticancer agent.

Preferences for the further anticancer agent to be administered include any of the cytotoxic agents described above. For example, the anticancer agent may be any one or more of of cisplatin; carboplatin; 5-flurouracil; paclitaxel; mitomycin C; doxorubicin; gemcitabine; tomudex; pemetrexed; methotrexate; irinotecan, fluorouracil and leucovorin; oxaliplatin, 5-fluorouracil and leucovorin; and paclitaxel and carboplatin.

The compound according to the fourth aspect of the invention and the further anticancer agent may be administered in the form of a pharmaceutical composition containing both of these components. However, it is appreciated that the compound and the further anticancer agent, may be administered separately, for instance by separate routes of administration. Thus it is appreciated that the compound and the at least one further anticancer agent can be administered sequentially or (substantially) simultaneously. They may be administered within the same pharmaceutical formulation or medicament or they may be formulated and administered separately.

Thus, the method may comprise administering the compound according to the fourth aspect of the invention to the individual wherein the individual is one who is administered a further anticancer agent. Similarly, the method may comprise administering a further anticancer to an individual wherein the individual is one who is administered the compound according to the fourth aspect of the invention.

Imaging, Detection and Diagnosis

A fourteenth aspect of the invention provides a method of imaging neovasculature in the body of an individual the method comprising:

administering to the individual a compound according to the sixth aspect of the invention, and imaging the detectable moiety in the body. Preferably, the neovasculature is tumour neovasculature.

Typically, the individual has a solid tumour, preferably such as those described above with respect to the first aspect of the invention, and the neovasculature of the tumour is imaged. Thus, the localisation of the antibody at a particular organ in the body indicates that the individual may have or may be developing a solid tumour at that organ. This method may be useful, for example, in determining the size of a previously diagnosed solid tumour, determining the effectiveness of a therapy against the solid tumour, or determining the extent of metastasis of the tumour. Methods for imaging the detectable moiety in the body are well known in the art, and include PET (positron emission tomography).

Accordingly, this aspect of the invention provides a method of detecting, diagnosing and prognosing a solid tumour in an individual, the method comprising: administering to the individual a compound according to the sixth aspect of the invention, and detecting the presence and/or location of the detectable moiety in the body.

Further Medical Uses

Inhibition of angiogenesis may be useful in combating any disease or condition involving unwanted, undesirable or inappropriate angiogenesis. Such conditions include tumours/cancer, psoriasis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation.

Accordingly, a fifteenth aspect of the invention provides a method of combating a disease or condition selected from the group consisting of cancer, psoriasis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation, the method comprising administering an agent that inhibits the interaction between CLEC14A and MMRN2 to an individual in need thereof.

This aspect of the invention includes an agent that inhibits the interaction between CLEC14A and MMRN2 for use in combating a disease or condition selected from the group consisting of cancer, psoriasis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation. This aspect of the invention further includes the use of an agent that inhibits the interaction between CLEC14A and MMRN2 in the preparation of a medicament for combating a disease or condition selected from the group consisting of cancer, psoriasis, menorrhagia, endometriosis, arthritis (both inflammatory and rheumatoid), macular degeneration, Paget's disease, retinopathy and its vascular complications (including proliferative and of prematurity, and diabetic retinopathy), benign vascular proliferations, fibroses, obesity and inflammation.

Preferences for the agent that inhibits the interaction between CLEC14A and MMRN2 include those described above in relation to the first aspect of the invention. It is particularly preferred if the agent is an antibody, for example an antibody according to the second aspect of the invention, and most preferably a CLEC14A antibody, for example one that is defined by reference to amino acid sequences mentioned herein.

By "combating" we include the meaning that the method can be used to alleviate symptoms of the disorder (ie the method is used palliatively), or to treat the disorder, or to prevent the disorder (ie the method is used prophylactically).

Thus, the invention provides a method of treating an individual who has a disease in which angiogenesis contributes to pathology, the method comprising the step of administering to the individual an agent that inhibits the interaction between CLEC14A and MMRN2 (eg an antibody according to the second aspect of the invention).

In any of the methods or uses of the invention described herein, the individual is preferably a human. However, it will also be understood that the individual can be non-human, such as any non-human mammal, for example a horse, dog, pig, cow, sheep, rat, mouse, guinea pig or a primate.

Typically, in any of the methods or uses of the invention described herein, the individual has a solid tumour, such as a tumour of the colon, rectum, ovary, liver, bladder, prostate, breast, kidney, pancreas, stomach, oesophagus, lung or thyroid.

Screening

That the inventors have identified new control pathways for angiogenesis and tumour growth involving CLEC14A and MMRN2 opens new possibilities for screening for agents that may be useful in modulating angiogenesis and/or in combating cancer. Hence, a sixteenth aspect of the invention provides a method of identifying an agent that may be useful in modulating angiogenesis or in combating cancer, or a lead compound for the identification of an agent that may be useful in modulating angiogenesis or in combating cancer, the method comprising:

providing CLEC14A or a portion or variant thereof, said portion or variant being capable of binding to MMRN2;
providing a candidate agent; and
determining whether the candidate agent modulates binding of CLEC14A or the portion or variant thereof, to MMRN2, or a portion or variant of MMRN2, said portion or variant being capable of binding to CLEC14A.

By "modulating angiogenesis" we include the meaning of inhibiting or enhancing angiogenesis.

By CLEC14A polypeptide we include a polypeptide having the sequence listed in FIG. 9 (SEQ ID NO: 17), and naturally-occurring variants thereof.

By portion or variant of CLEC14A being capable of binding to MMRN2, we include any portion or variant of CLEC14A that is capable of binding to MMRN2. Assessing protein-protein interactions is standard practice in the art and is described in more detail below.

Typically, the portion of CLEC14A that is capable of binding to MMRN2 is at least 20 amino acid residues in length, and may be between 20 and 50 residues or between 50 and 100 residues or between 100 and 150 residues or between 150 and 200 residues in length, or more. In a particular embodiment, the portion of CLEC14A that is capable of binding to MMRN2 is less than 400, 350, 300, 250, 150, 140, 130, 110, 100, 95, 90 or 85 amino acid residues in length. It is preferred that the portion of CLEC14A that is capable of binding to MMRN2 is a portion of, or that the portion contains, the extracellular region of CLEC14A (residues 22-396), or that the portion is a portion of, or that the portion contains the C-type lectin like domain (residues 32-173), or that the portion contains residues 97-108 of the C-type lectin like domain.

By a variant of CLEC14A that is capable of binding to MMRN2, we include variants of CLEC14A that have at least 60% sequence identity to human CLEC14A, the sequence of which is provided in FIG. 9 (SEQ ID No: 17), for example variants with at least 65%, 70%, 75%, 80%, 85%, 90%, 95%, 96%, 97%, 98% or 99% sequence identity to human CLEC14A. It is preferred if the variant polypeptide has a consecutive region of at least 20 amino acid residues, more preferably at least 50 residues, of the sequence of the CLEC14A polypeptide listed in FIG. 9. Such variants may be made, for example, using the methods of recombinant DNA technology, protein engineering and site-directed mutagenesis which are well known in the art.

It will be appreciated that the portions of CLEC14A described above may also be portions of CLEC14A variants. Generally, the portions of CLEC14A have at least 60% sequence identity to human CLEC14A, the sequence of which is provided in FIG. 9 (SEQ ID No: 17), for example at least 65%, 70%, 75%, 80%, 85%, 90%, 95%, 96%, 97%, 98%, or 99% sequence identity over the length of the portion.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., (1994) *Nucleic Acids Res* 22, 4673-80). The parameters used may be as follows: Fast pairwise alignment parameters: K-tuple(word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

By MMRN2 polypeptide we include a polypeptide having the sequence listed in FIG. 10 (SEQ ID NO: 20), and naturally-occurring variants thereof.

By portion or variant of MMRN2 being capable of binding to CLEC14A, we include any portion or variant of MMRN2 that is capable of binding to CLEC14A. Assessing protein-protein interactions is standard practice in the art and is described in more detail below.

Typically, the portion of MMRN2 that is capable of binding to CLEC14A is at least 20 amino acid residues in length, and may be between 20 and 50 residues or between 50 and 100 residues or between 100 and 150 residues or between 150 and 200 residues in length, or more. In a particular embodiment, the portion of MMRN2 that is capable of binding to CLEC14A is less than 800, 700, 600, 500, 400, 350, 300, 250, 150, 140, 130, 110, 100, 95, 90 or 85 amino acid residues in length.

By a variant of MMRN2 that is capable of binding to CLEC14A, we include variants of MMRN2 that have at least 60% sequence identity to human MMRN2, the sequence of which is provided in FIG. 10 (SEQ ID No: 20), for example variants with at least 65%, 70%, 75%, 80%, 85%, 90%, 95%, 96%, 97%, 98% or 99% sequence identity to human MMRN2. It is preferred if the variant polypeptide has a consecutive region of at least 20 amino acid residues, more preferably at least 50 residues, of the sequence of the MMRN2 polypeptide listed in FIG. 10. Such variants may be made, for example, using the methods of recombinant DNA technology, protein engineering and site-directed mutagenesis which are well known in the art.

It will be appreciated that the portions of MMRN2 described above may also be portions of MMRN2 variants. Generally, the portions of MMRN2 have at least 60% sequence identity to human MMRN2, the sequence of which is provided in FIG. 10 (SEQ ID No: 20), for example at least 65%, 70%, 75%, 80%, 85%, 90%, 95%, 96%, 97%, 98%, or 99% sequence identity over the length of the portion.

The candidate agent may be any of an antibody, a peptide, a peptidomimetic, a natural product, a carbohydrate, an aptamer or a small organic molecule.

In an embodiment, the candidate agent is an antibody that selectively binds the CLEC14A polypeptide, or a fragment thereof, or an antibody that selectively binds the MMRN2 polypeptide, or a fragment thereof. Suitable antibodies are described above.

In another embodiment, the candidate agent may be a peptide. Suitable peptides that bind to the CLEC14A polypeptide or the MMRN2 polypeptide, or a fragment thereof, may be identified by methods such as phage display of peptide libraries (Scott & Smith (1990) "Searching for peptide ligands with an epitope library." *Science* 249: 386-390; Felici et al (1995) "Peptide and protein display on the surface of filamentous bacteriophage." *Biotechnol. Annu. Rev.* 1: 149-183); and Collins et al (2001) "Cosmix-plexing: a novel recombinatorial approach for evolutionary selection from combinatorial libraries." *J. Biotechnol.* 74: 317-338); including in vivo panning (Pasqualini et al (1997) "αv integrins as receptors for tumor targeting by circulating ligands. *Nature Biotechnol.* 15: 542-546), and solid-phase parallel synthesis (Frank (2002) "The SPOT-synthesis technique. Synthetic peptide arrays on membrane supports—principles and applications." *J. Immunol. Methods* 267: 13-26; and Pinilla et al (2003) "Advances in the use of synthetic combinatorial chemistry: mixture-based libraries." *Nature Med.* 9: 118-122). The dissociation constants of peptides are typically in the micromolar range, although avidity can be improved by multimerization (Terskikh et al (1997) "Peptabody": a new type of high avidity binding protein. *Proc. Natl Acad. Sci. USA* 94, 1663-1668; and Wrighton et al (1997) "Increased potency of an erythropoietin peptide mimetic through covalent dimerization. *Nature Biotechnol.* 15, 1261-1265).

The primary ligands of C-type lectins are carbohydrates, even though binding of other proteins, lipids or inorganic compounds has been shown. Thus, in another embodiment, the candidate agent may be a carbohydrate, or a molecule containing carbohydrate moieties such as a glycoprotein or gycolipid. It is appreciated that carbohydrate recognition and binding by C-type lectins is calcium dependent. Thus, in this embodiment, the method is carried out in the presence of calcium ions.

In still another embodiment, the candidate agent may be an aptamer, i.e. a single-stranded DNA molecule that folds into a specific ligand-binding structure. Suitable aptamers that bind to the CLEC14A polypeptide, or to the MMRN2 polypeptide, or a fragment thereof, may be identified by methods such as in vitro selection and amplification (Ellington & Szostak (1992) "Selection in vitro of single stranded DNA molecules that fold into specific ligand binding structures." *Nature* 355: 850-852; and Daniels et al (2003) "A tenascin-C aptamer identified by tumor cell SELEX: systematic evolution of ligands by exponential enrichment." *Proc. Natl Acad. Sci. USA* 100, 15416-15421). The aptamer may be a nuclease-stable 'Spiegelmer' (Helmling et al (2004) "Inhibition of ghrelin action in vitro and in vivo by an RNA-Spiegelmer." *Proc. Natl Acad. Sci. USA* 101: 13174-13179). Aptamers typically have dissociation constants in the micromolar to the subnanomolar range.

In yet another embodiment, the candidate agent may be a small organic molecule. Suitable small molecule that bind to the CLEC14A polypeptide or MMRN2 polypeptide, or a fragment thereof, may be identified by methods such as screening large libraries of compounds (Beck-Sickinger & Weber (2001) Combinational Strategies in Biology and Chemistry (John Wiley & Sons, Chichester, Sussex); by structure—activity relationship by nuclear magnetic resonance (Shuker et al (1996) "Discovering high-affinity ligands for proteins: SAR by NMR. *Science* 274: 1531-1534); encoded self-assembling chemical libraries Melkko et al (2004) "Encoded self-assembling chemical libraries." *Nature Biotechnol.* 22: 568-574); DNA-templated chemistry (Gartner et al (2004) "DNA-templated organic synthesis and selection of a library of macrocycles. *Science* 305: 1601-1605); dynamic combinatorial chemistry (Ramstrom & Lehn (2002) "Drug discovery by dynamic combinatorial libraries." *Nature Rev. Drug Discov.* 1: 26-36); tethering (Arkin & Wells (2004) "Small-molecule inhibitors of protein-protein interactions: progressing towards the dream. *Nature Rev. Drug Discov.* 3: 301-317); and speed screen (Muckenschnabel et al (2004) "SpeedScreen: label-free liquid chromatography-mass spectrometry-based high-throughput screening for the discovery of orphan protein ligands." *Anal. Biochem.* 324: 241-249). Typically, small organic molecules will have a dissociation constant for the polypeptide in the nanomolar range, particularly for antigens with cavities. The benefits of most small organic molecule binders include their ease of manufacture, lack of immunogenicity, tissue distribution properties, chemical modification strategies and oral bioavailability. Small molecules with molecular weights of less than 5000 daltons are preferred, for example less than 400, 3000, 2000, or 1000 daltons, or less than 500 daltons.

The capability of a candidate agent to modulate binding of CLEC14A or the portion or variant thereof, to MMRN2, or the portion or variant thereof, may be assessed by any method of detecting/measuring a protein/protein interaction or other compound/protein interaction, as discussed further below. Suitable methods include methods such as, for example, yeast two-hybrid interactions, co-purification, ELISA, co-immunoprecipitation and surface plasmon resonance methods. Thus, the candidate agent may be considered capable of modulating binding between CLEC14A and MMRN2 (or portions or fragments thereof) if the interaction between CLEC14A and MMRN2 (or portions or variants thereof) as determined by ELISA, co-immunoprecipitation or surface plasmon resonance methods or by a yeast two-hybrid interaction or a copurification method, is changed (eg increased or decreased) compared to the interaction between CLEC14A and MMRN2 measured in the absence of the candidate agent. It is preferred that the interaction can be detected using a surface plasmon resonance method. Surface plasmon resonance methods are well known to those skilled in the art. Techniques are described in, for example, O'Shannessy D J (1994) "Determination of kinetic rate and equilibrium binding constants for macromolecular interactions: a critique of the surface plasmon resonance literature" *Curr Opin Biotechnol.* 5(1):65-71; Fivash et al (1998) "BIAcore for macromolecular interaction." *Curr Opin Bio-* technol. 9(1):97-101; Malmqvist (1999) "BIACORE: an affinity biosensor system for characterization of biomolecular interactions." *Biochem Soc Trans.* 27(2):335-40.

It is appreciated that screening assays which are capable of high throughput operation are particularly preferred. Examples may include cell based assays and protein-protein binding assays. An SPA-based (Scintillation Proximity Assay; Amersham International) system may be used.

Other methods of detecting polypeptide/polypeptide interactions include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities may be measured by measuring the interaction of the fluorescent labels when in close proximity to each other.

It will be appreciated that the candidate agent may be added to either the CLEC14A polypeptide (or portion or variant thereof) before addition to the MMRN2 polypeptide, or it may be added to the MMRN2 polypeptide (or portion or variant thereof) before addition to the CLEC14A polypeptide (or portion or variant thereof), and its effect on binding assessed.

Conveniently, at least one or other of CLEC14A and MMRN2 (or portions or variants thereof) are detectably labelled so as to facilitate detection of their binding and consequently the effect of the candidate agent. Examples of suitable labels include a peptide label, a nucleic acid label (Kerr et al (1993) JACS vol. 115, p. 2529-2531; and Brenner & Lerner (1992) *Proc. Natl. Acad. Sci. USA* vol. 89, p. 5381-5383), a chemical label (Ohlmeyer et al (1993) *Proc. Natl. Acad. Sci. USA* vol. 90, p. 109222-10926; and Maclean et al (1997) *Proc. Natl. Acad. Sci. USA* vol. 94, p. 2805-2810); a fluorescent label (Yamashita & Weinstock (SmithKline Beecham Corporation), WO95/32425 (1995); and Sebestyen et al (1993) *Pept. Proc. Eur. Pept. Symp. 22nd* 1992, p. 63-64), or a radio frequency tag (Nicolaou et al (1995) *Angew. Chem. Int. Ed. Engl.* vol. 34, p. 2289-2291; and Moran et al (1995) JACS vol. 117, p. 10787-10788).

In one embodiment, the candidate agent is one that reduces the level of binding between CLEC14A, or the portion or variant thereof, to MMRN2, or the portion or variant thereof, in which case it may be an agent that is useful in combating any disease or condition involving unwanted, undesirable or inappropriate angiogenesis, or may be a lead compound to the identification of an agent that is so useful Preferably, the candidate agent reduces the level of binding between CLEC14A and MMRN2 (or portion(s) or variant(s) thereof) by at least 10%, 20%, 30%, 40% or 50%, and more preferably the candidate agent is one that reduces the level of binding between CLEC14A and MMRN2 (or portion(s) or variant(s) thereof) by at least 70%, 80%, 90%, 95% or 99%, compared to the level of binding in the absence of the candidate agent. Most preferably, the agent is one that reduces the level of binding between CLEC14A and MMRN2 (or portion(s) or variant(s) thereof) to an undetectable level, or eliminates binding between CLEC14A and MMRN2 (or portion(s) or variant(s) thereof).

It is appreciated that the identification of a candidate agent that modulates binding of CLEC14A, or the portion or variant thereof, to MMRN2, or the portion or variant thereof, may be an initial step in a drug screening pathway, and the identified agents may be further selected e.g. for the ability to inhibit angiogenesis and/or for the ability to inhibit tumour growth. Thus, the method may further comprise the step of testing the candidate agent in an angiogenesis assay and/or testing the candidate agent for efficacy in an animal model of a solid tumour.

Methods and assays for determining the rate or level of angiogenesis, and hence for determining whether and to what extent a candidate agent inhibits angiogenesis, are known in the art. For example, U.S. Pat. No. 6,225,118, incorporated herein by reference, describes a multicellular ex vivo assay for modelling the combined stages of angiogenesis namely the proliferation, migration and differentiation stages of cell development. The AngioKit, Catalogue No. ZHA-1000, by TCS CellWorks Ltd, Buckingham MK18 2LR, UK, is a suitable model of human angiogenesis for analysing the anti-angiogenic properties of compounds. The rate or level of angiogenesis can also be determined using the aortic ring assay and the sponge angiogenesis assay that are well known in the art, and described in Example 1.

Assays for endothelial cell proliferation, migration and invasion are also useful as angiogenesis assays. Suitable assays for endothelial cell proliferation and migration are known to a person of skill in the art. Suitable assays for endothelial cell invasion are also known to a person of skill in the art and include the BD BioCoat™ Angiogenesis System for Endothelial Cell Invasion which is available as Catalogue Nos. 354141 and 354142 from BD Biosciences, Bedford, MA, USA, and the QCM™ Endothelial Cell Invasion Assay (EMD Millipore).

It is appreciated that these methods may be a drug screening methods, a term well known to those skilled in the art, and the candidate agent may be a drug-like compound or lead compound for the development of a drug-like compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 Daltons and which may be water-soluble. A drug-like compound may additionally exhibit features of selective interaction with a particular protein or proteins and be bioavailable and/or able to penetrate target cellular membranes or the blood:brain barrier, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

In an embodiment, the identified agent is modified, and the modified agent is tested for the ability to modulate binding between CLEC14A and MMRN2 (or portion(s) or variant(s) thereof).

It is appreciated that the screening methods can be used to identify agents that may be useful in combating any disease or condition involving unwanted, undesirable or inappropriate angiogenesis, such as solid tumours. Thus, the screening methods preferably also comprise the further step of testing the identified agent or the modified agent for efficacy in an animal model of cancer, particularly a solid tumour. Suitable models are known in the art and include Lewis lung carcinoma subcutaneous implants in mice (homograft in Black 57 mice) or HT29 xenografts subcutaneous implants in nude mice.

The invention may comprise the further step of synthesising and/or purifying the identified agent or the modified agent. The invention may further comprise the step of formulating the agent into a pharmaceutically acceptable composition.

Agents may also be subjected to other tests, for example toxicology or metabolism tests, as is well known to those skilled in the art.

The invention includes a method for preparing an anti-angiogenic compound that may be useful in the treatment of any disease or condition involving unwanted, undesirable or inappropriate angiogenesis, the method comprising identifying an agent using the screening methods described above and synthesising, purifying and/or formulating the identified agent.

The invention includes a method for preparing an anti-cancer compound that may be useful in the treatment of a solid tumour, the method comprising identifying an agent using the screening methods described above and synthesising, purifying and/or formulating the identified agent.

The invention also includes a method of making a pharmaceutical composition comprising the step of mixing the agent identified using the methods described above with a pharmaceutically acceptable carrier.

All of the documents referred to herein are incorporated herein, in their entirety, by reference.

The listing or discussion of an apparently prior-published document in this specification should not necessarily be taken as an acknowledgement that the document is part of the state of the art or is common general knowledge The invention will now be described in more detail by reference to the following Examples and Figures.

FIG. 1—SiRNA knockdown of CLEC14A reveals a role for CLEC14A in endothelial sprouting. [A] SiRNA duplex targeting CLEC14A can efficiently knockdown CLEC14A mRNA expression in HUVEC, as determined by qPCR. Relative expression was determined by normalising expression to flotilin2. [B] Knockdown of CLEC14A at the protein level was determined by Western blot analysis. Tubulin was used as a loading control. [C] Representative images of sprout outgrowth after 16 hours for control or clec14a targeted siRNA treated HUVEC. [D] Quantitation of sprouts for 27 spheroids (9 spheroids from 3 cords) for control and CLEC14A knockdown HUVEC; Mann-Whitney statistical test p<0.001. [E] Representative images of sprout outgrowth after 24 hours for mixed control (green) and clec14a targeted siRNA treated HUVEC (red). [F] Quantitation of the percentage of tip and stalk cells derived from control (CON) and CLEC14A knockdown (KD) HUVEC; two-way ANOVA statistical test with Bonferroni post-tests ***=p<0.001, ns=not significant.

FIG. 2—Loss of CLEC14A inhibits sprouting in vitro and in vivo. [A] Schematic diagram of clec14a gene in C57BL/6 (clec14a +/+) or C57BL/6$^{(Clec14atm1(KOMP)Vlcg)}$ (clec14a −/−) mice. [B] Quantitative PCR analysis of cDNA generated from three clec14a +/+ mice (white bars) and three clec14a −/− mice (black bars) for the 5' untranslated region (UTR), coding sequence (CDS) and 3' UTR of clec14a. Relative expression was determined by normalising expression to flotilin2. [C] Western blot analysis of CLEC14A protein expression in lung lysates from clec14a +/+ and clec14a −/− mice using polyclonal antisera against murine CLEC14A. Tubulin was used as a loading control. [D] Representative images of the aortic ring sprouting assay from clec14a +/+ and clec14a −/− mice. Quantitation of tubes formed per ring [E], and quantitation of the maximal distance migrated by an endothelial tube from the aortic ring [F], data from 48 rings per genotype, 6 mice for each genotype; Mann-Whitney statistical test p<0.001. [G] Representative images of haematoxylin and eosin stained sections of sponge implant from clec14a +/+ and clec14a −/− mice, sections at the centre of the sponge were analysed. [H] Quantitation of cellular invasion into the sponge implants shown in G; Mann-Whitney statistical test p<0.05. [I] Quantitation of vessel density; Mann-Whitney statistical test p<0.001. [J] Sections of liver and sponge tissue stained with x-gal from clec14a −/− mice, counterstained with haematoxylin and eosin.

Figure 3:
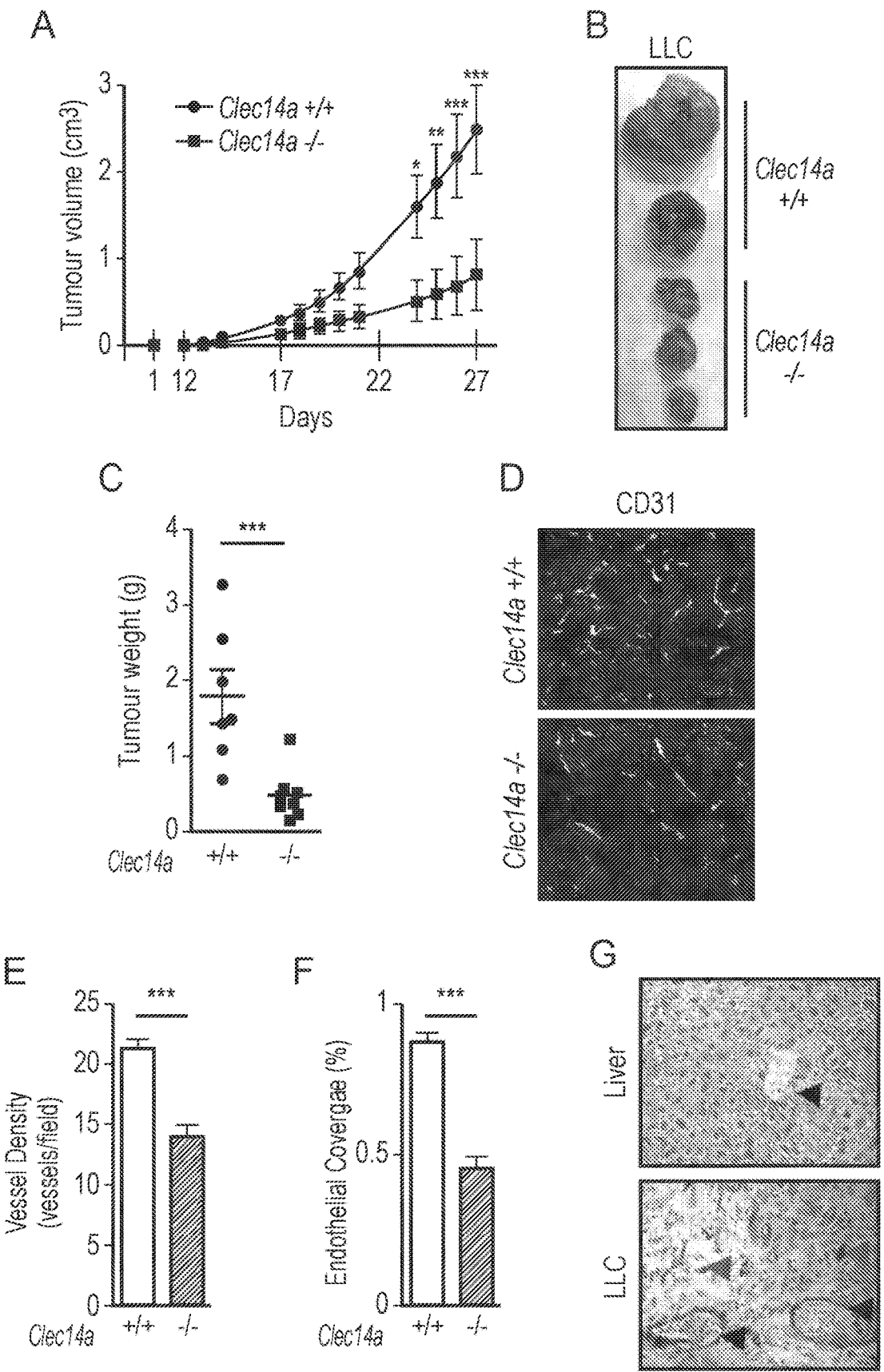

FIG. 3—Loss of CLEC14A inhibits tumour growth. [A] Lewis lung carcinoma (LLC) tumour growth in clec14a +/+(black line with dots) and clec14a −/− (black line with squares) mice; two-way ANOVA statistical analysis, *=p<0.05, =p<0.01, *=p<0.001. [B] Representative images of LLC tumours. [C] Endpoint tumour weight for 7 clec14a +/+(dots) and 7 clec14a −/− (squares) mice; Mann-Whitney statistical test p<0.001. [D] Representative images of immunofluorescent staining of LLC tumour sections stained for murine CD31. Quantitation of vessel density [E] and percentage endothelial coverage [F] from clec14a +/+ and clec14a −/− mice; Mann-Whitney statistical test p<0.0001. [G] Sections of liver and LLC tumour tissue from clec14a −/− mice stained with x-gal, counterstained with haematoxylin and eosin.

Figure 4:
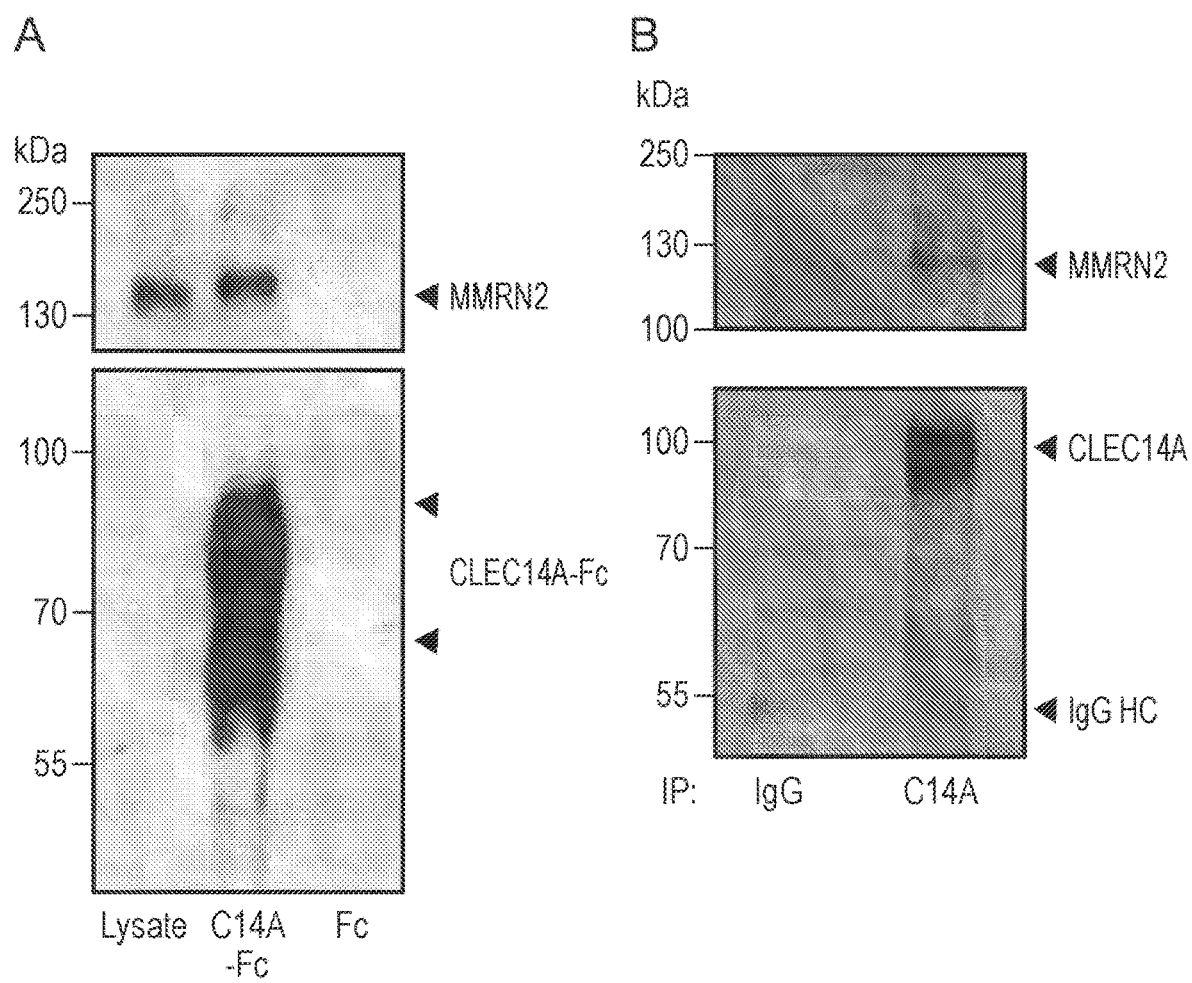

FIG. 4—MMRN2 binds to CLEC14A. [A] 20 µg CLEC14A-ECD-Fc or Fc was used to precipitate interacting partners. Precipitates and HUVEC lysates were separated on an SDS-PAG and blotted for MMRN2 (top panel) or CLEC14A-ECD-Fc (bottom panel). [B] CLEC14A was immunoprecipitated from HUVEC lysates using polyclonal antisera against CLEC14A. Immunoprecipitates were analysed by Western blot for MMRN2 (top panel) and CLEC14A (bottom panel).

Figure 5:
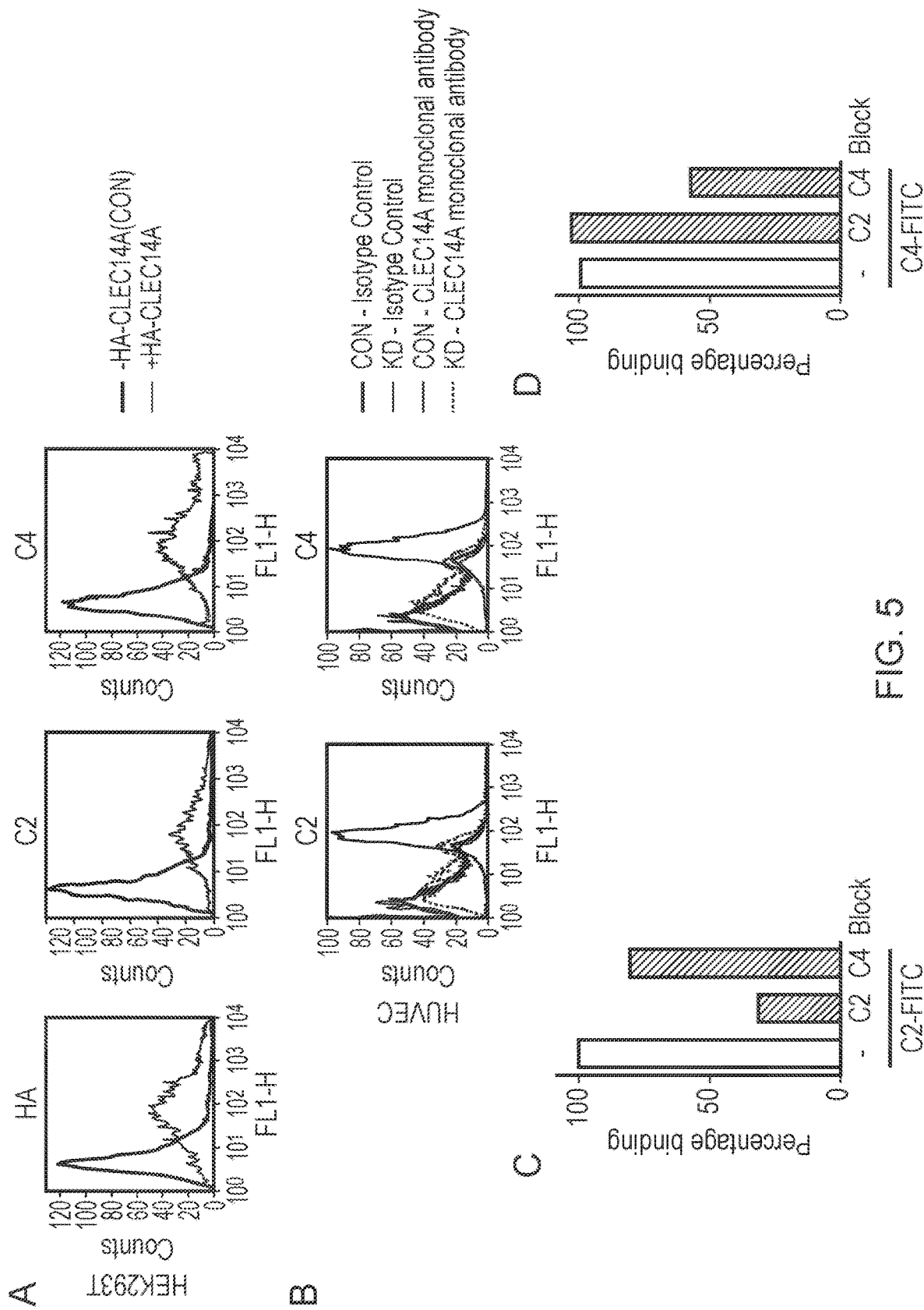
Figure 5:
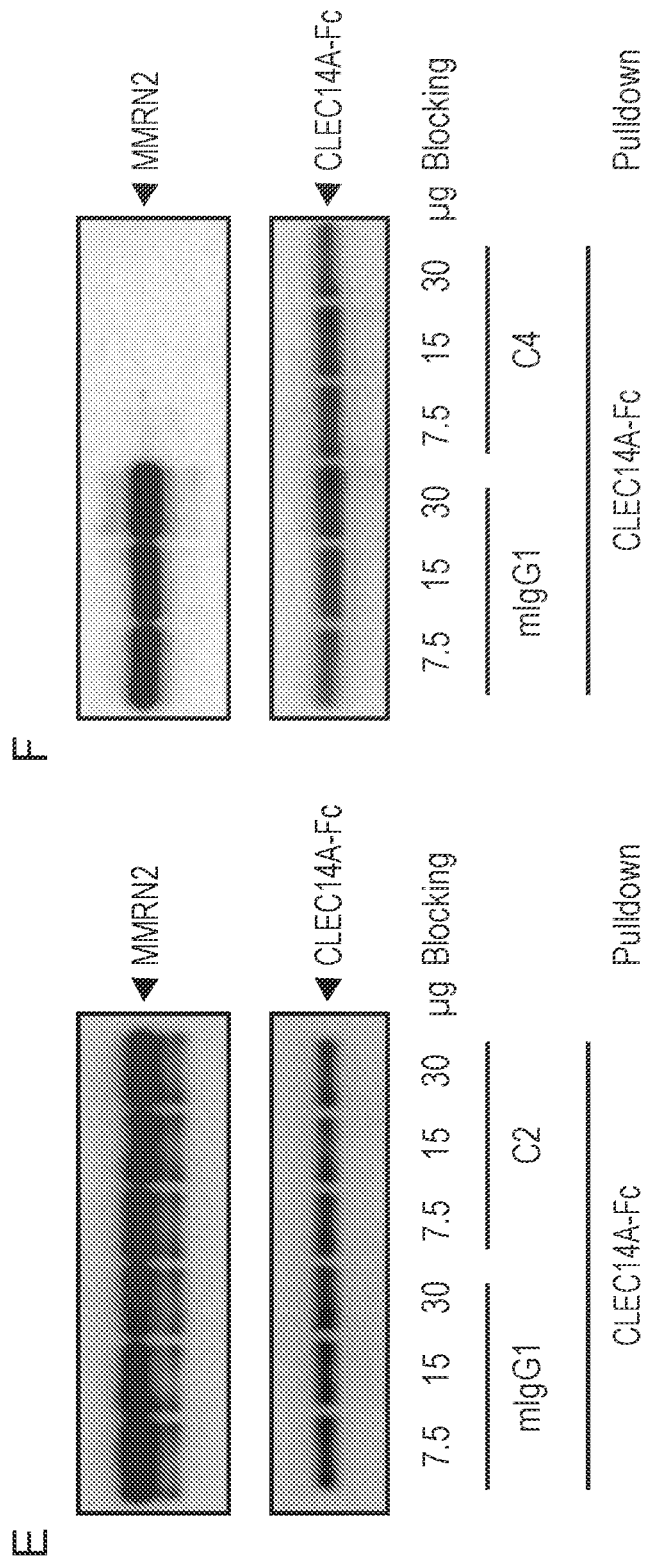

FIG. 5—CLEC14A monoclonal antibodies block MMRN2-CLEC14A interaction. [A] HEK293T cells expressing HA-CLEC14A or an empty vector (CON) were stained with an HA tag antibody (column 1), or monoclonal antibodies against CLEC14A C2 (column 2) or C4 (column 3). Cells were analysed by flow cytometry and displayed as histograms of increasing fluorescence (x-axis) versus counts (y-axis). [B] HUVECstransfected with negative control siRNA duplexes or siRNA duplexes targeting CLEC14A were probed with C2 or C4 antibodies and analysed as in A. [C] HUVECs were pre-treated with blocking buffer (−), 100 µg C2 antibody or 100 µg C4 antibody, prior to C2-FITC staining. Cells were analysed by flow cytometry. Geometric means were normalised to staining for the cells pre-treated with blocking buffer. [D] as for C, except stained with C4-FITC. [E] CLEC14A-Fc (5 µg) protein G agarose bead complexes were blocked with 7.5, 15, 30, µg mIgG or C2, prior to MMRN2 pulldown from HEK293T lysates. Precipitates were separated by SDS-PAGE and blotted for MMRN2 (upper panel) and CLEC14A-Fc (lower panel). [F] as in E, except C4 was used to block instead of C2.

Figure 6:
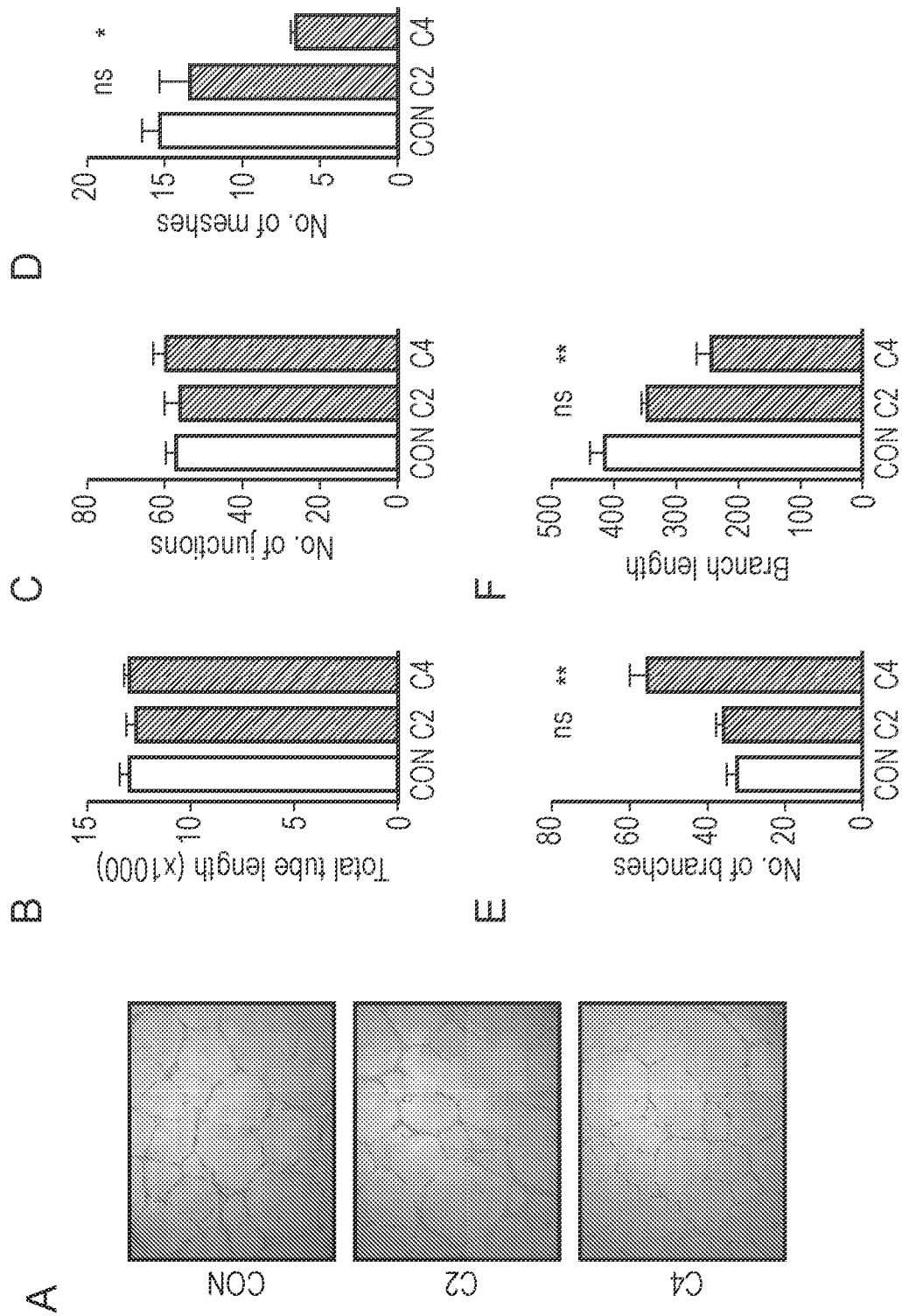
Figure 6:
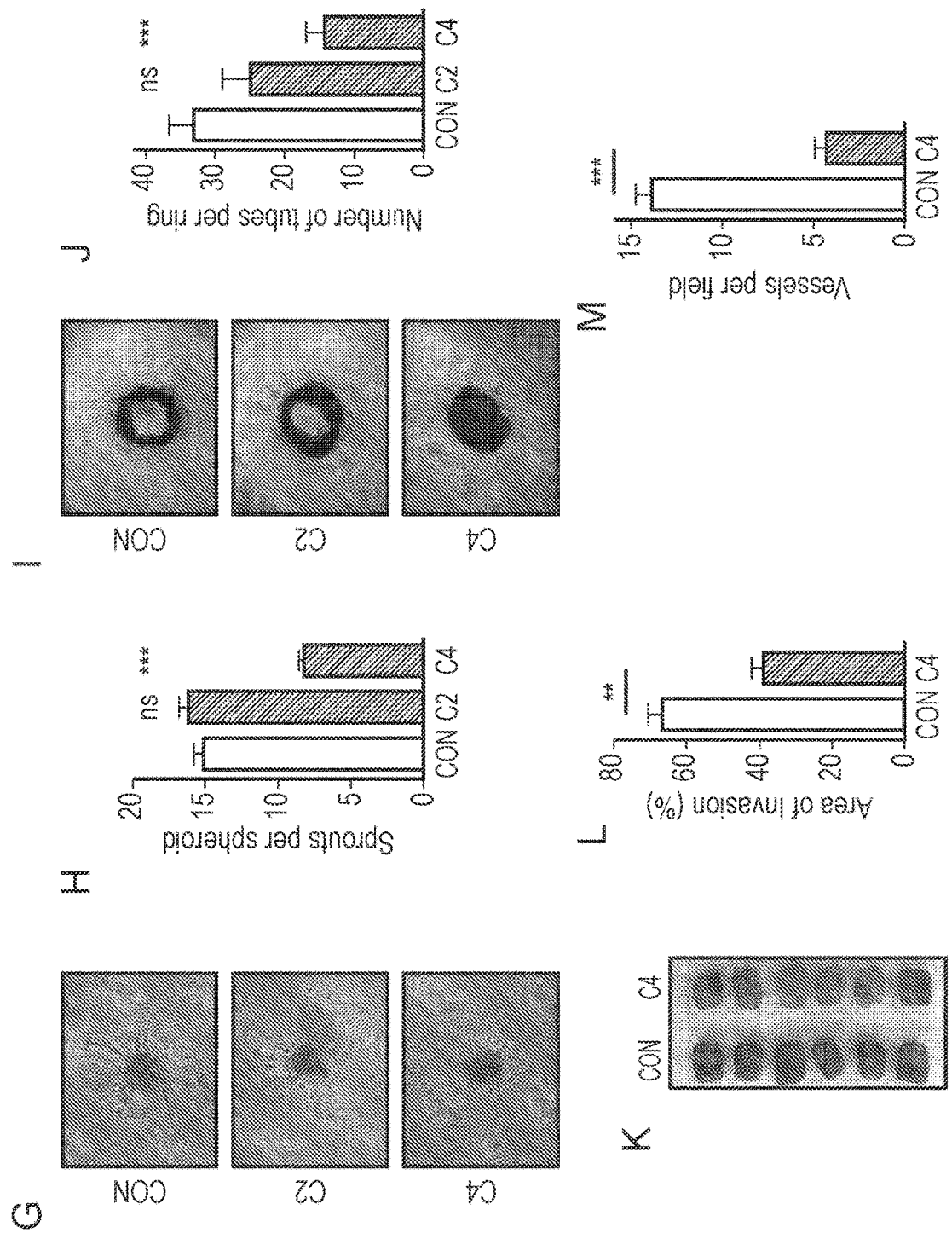

FIG. 6—MMRN2-CLEC14A interaction blocking antibody inhibits endothelial tube formation and sprouting in vitro and in vivo. HUVECs were plated onto Matrigel and grown in the presence of 20 µg/ml mIgG1 (CON), C2, or C4 antibodies for 16 hours. [A] Representative images. Tube formation was analysed for tube length [B], number of junctions per field [C], number of meshes [D], number of branches [E] and the branch length [F]. Representative data from 1 of 3 independent experiments; Kruskal-Wallis statistical test, *=p<0.05, =p<0.01, ns=not significant. HUVEC spheroids embedded in a collagen gel were stimulated to sprout with VEGF supplemented with 20 μg/ml mIgG1 (CON), C2 or C4. [G] Representative images. [H] Quantitation of sprouts per spheroid for 27 spheroids from 3 independent experiments; Kruskal-Wallis statistical test *=p<0.001, ns=not significant. Aortic rings from C57BL/6 mice were cultured in the presence of 20 μg/ml mIgG1 (CON), C2 or C4. [I] Representative images. [J] Quantitation of tubes formed per ring, data from 30 rings, at least 6 mice were used for each condition; Kruskal-Wallis statistical test ***=p<0.001, ns=not significant. [K] Representative images of sponge implants injected with bFGF and mIgG1 (CON) or C4 antibody. [L] Quantitation of cellular invasion into these sponge implants by analysis of haematoxylin and eosin stained sections; Mann-Whitney statistical test p<0.01. [M] Quantitation of vessel density from K; Mann-Whitney statistical test p<0.001.

Figure 7:
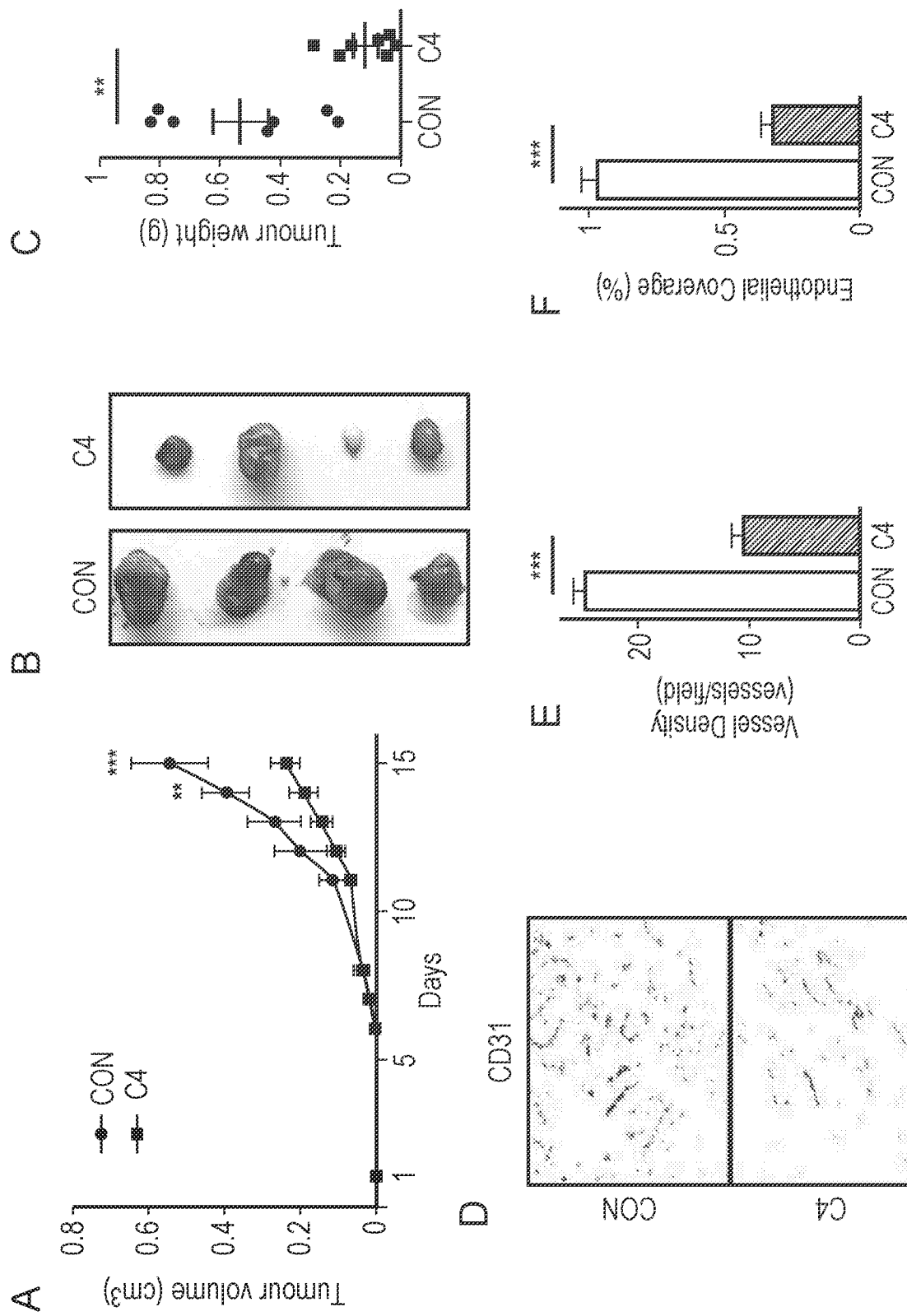

FIG. 7—MMRN2-CLEC14A interaction blocking antibody inhibits tumour growth. [A] Mice injected with LLC were treated with 100 μg injections of mIgG1 (black line with dots; n=7) or C4 antibody (black line with squares; n=7); two-way ANOVA statistical analysis, =p<0.01, *=p<0.001. [B] Representative images of LLC tumours. [C] Endpoint tumour weight for 7 mIgG1 treated mice (dots) and 7 C4 antibody treated mice (squares); Mann-Whitney statistical test p<0.001. [D] Representative images of immunofluorescent staining of LLC tumour sections stained for murine CD31. Quantitation of vessel density [E] and percentage endothelial coverage [F] from mice treated with mIgG1 or C4 antibody; Mann-Whitney statistical test p<0.001.

Figure 8:
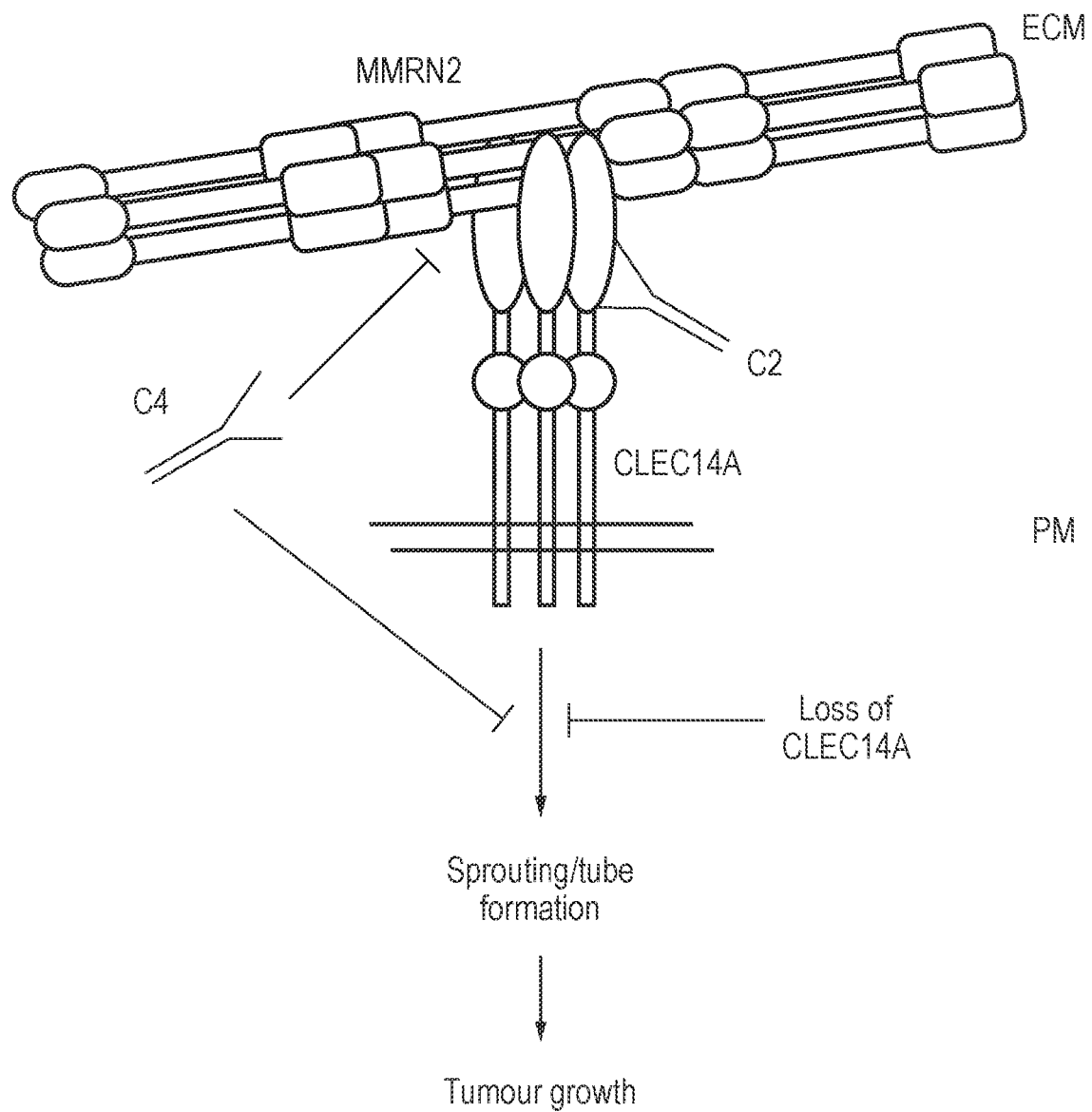

FIG. 8—CLEC14A-MMRN2 binding is an important component of endothelial sprout formation and a regulator of tumour growth. ECM=extracellular matrix, PM=plasma membrane.

FIG. 9—A: Polypeptide sequence of human CLEC14A from Genbank Accession No. NP_778230 (SEQ ID NO: 17). B: cDNA of human CLEC14A from Genbank Accession No. NM_175060 (SEQ ID NO: 18). C: Coding region of human CLEC14A cDNA from positions 348-1820 of NM_175060 (SEQ ID NO: 19).

FIG. 10—Polypeptide sequence of human MMRN2 (SEQ ID NO: 20) and coding polynucleotide sequence of human MMRN2 (SEQ ID NO: 21).

FIG. 11—Polypeptide and polynucleotide sequences of variable light chain and variable heavy chain of CLEC14A antibody, C4.

Figure 12:
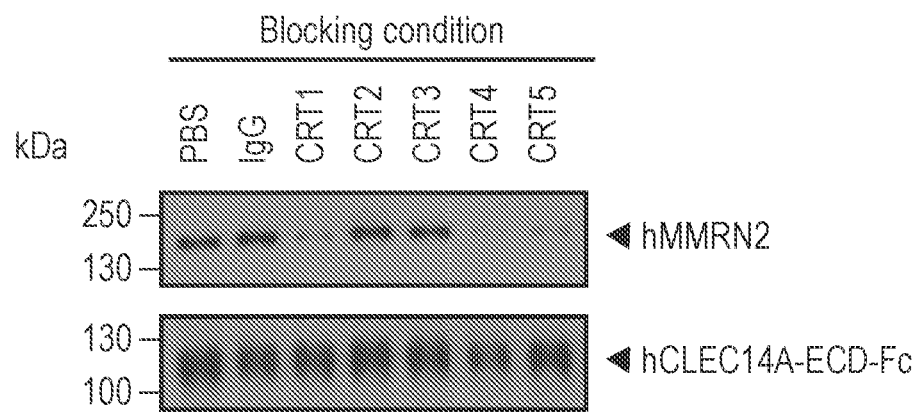

FIG. 12—CLEC14A monoclonal antibodies C1, C4 and C5 block CLEC14A-MMRN2 interaction. Human CLEC14A-ECD-Fc was bound to protein A beads, blocked in 20% FCS and then incubated with each blocking condition. This was then added to lysates of HEK293T cells overexpressing full-length human MMRN2 with a His tag. Pre-incubating with CRT1, CRT4 and CRT5 decreased the levels of MMRN2 pulled down by CLEC14A-ECD-Fc.

Figure 13:
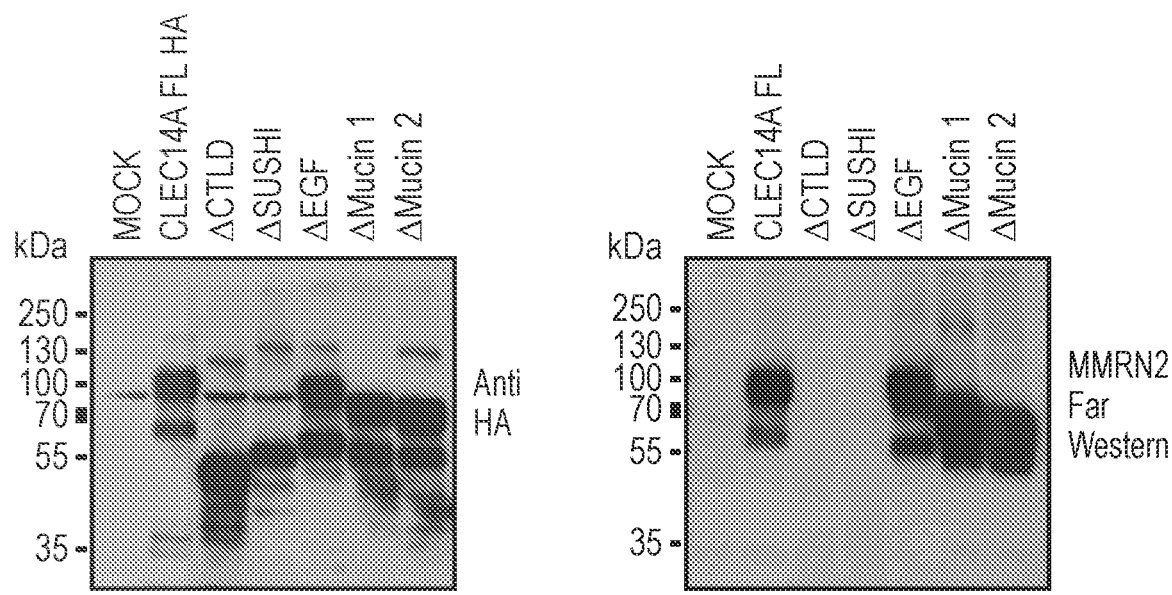

FIG. 13—MMRN2 directly binds to either the C-type lectin or sushi domain of CLEC14A under non-reduced conditions. HEK293T cells were mock transfected or transfected with pCS2 vectors containing CLEC14A wild type (WT) or constructs with each major domain deleted (Δ) with an N-terminal HA tag. Upon far western blotting with MMRN2 protein lysate, binding can be seen in all mutants except those missing the C-type lectin domain (CTLD) or the sushi domain. An anti-HA blot was included to show all mutant proteins were expressed.

FIG. 14—Protein sequences of the CD141 CTLD (SEQ ID NO: 83), chimeric proteins Chimera 5 (SEQ ID NO: 84) and Chimera 6 (SEQ ID NO: 85).

Figure 15:
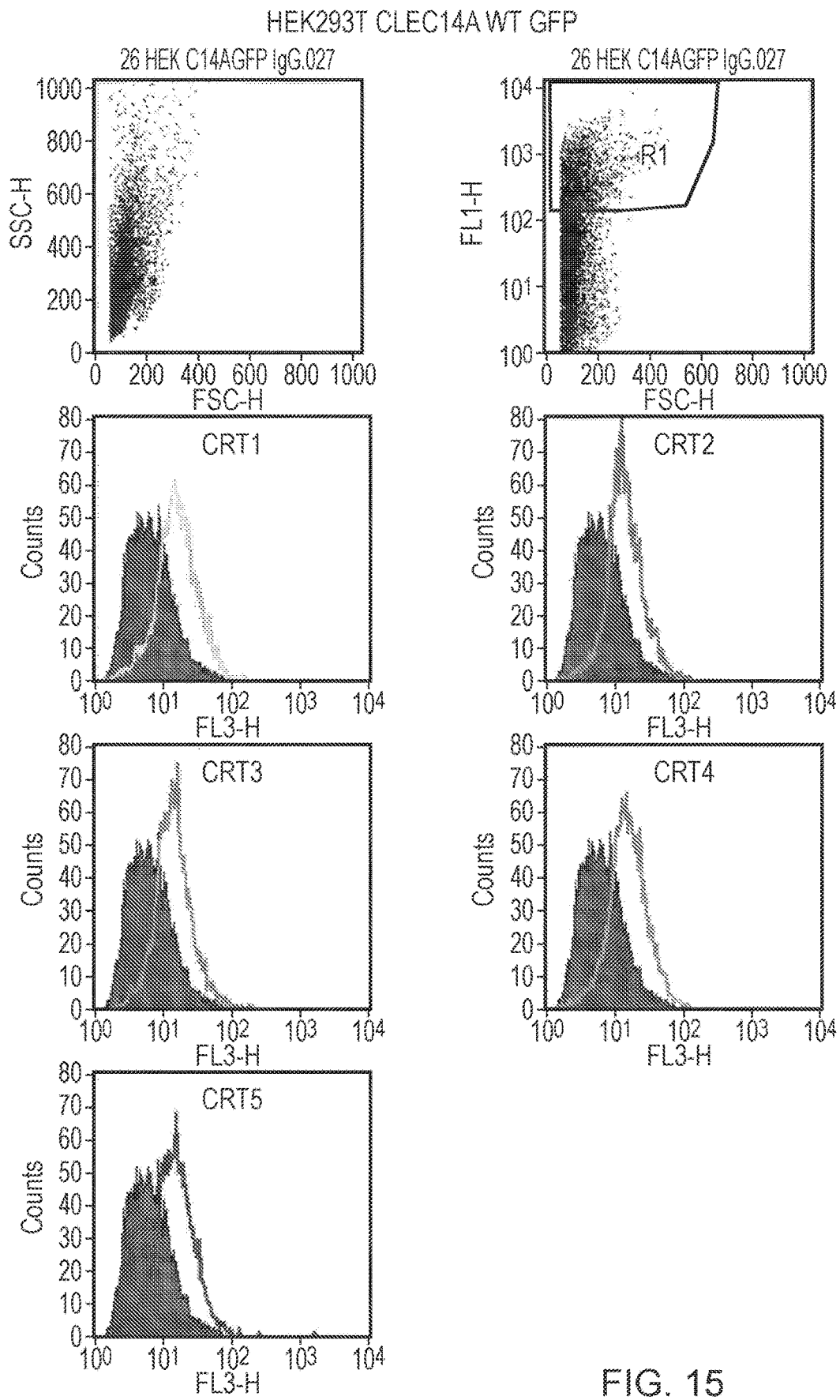
Figure 15:
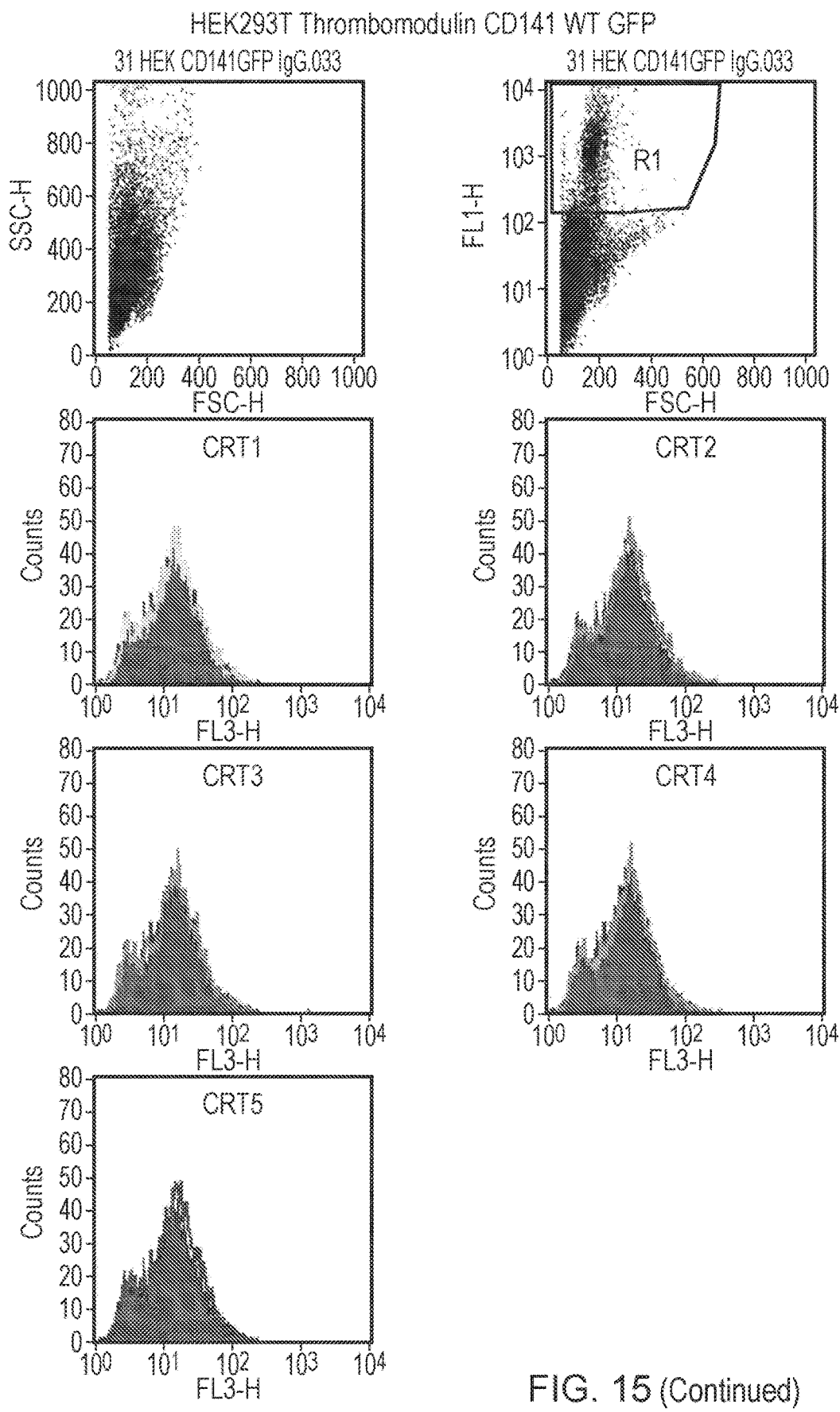

FIG. 15—Binding of CRT antibodies was analysed using flow cytometry. All constructs have a C-terminus GFP tag so green cells were gated and stained red. All CRT antibodies bind to CLEC14A wild type with a C terminal GFP tag expressed in HEK293T cells. None of the CRT antibodies bind to wild type thrombomodulin with GFP tag expressed in HEK293T cells.

FIG. 16—Alignment of CLEC14A regions 1-42 of CD141; CLEC14A regions 97-108 of CD141; and CLEC14A regions 122-142 of CD141. CLEC14A CTLD SEQ ID NO: 86; CD141 CTLD SEQ ID NO: 83.

Figure 17:
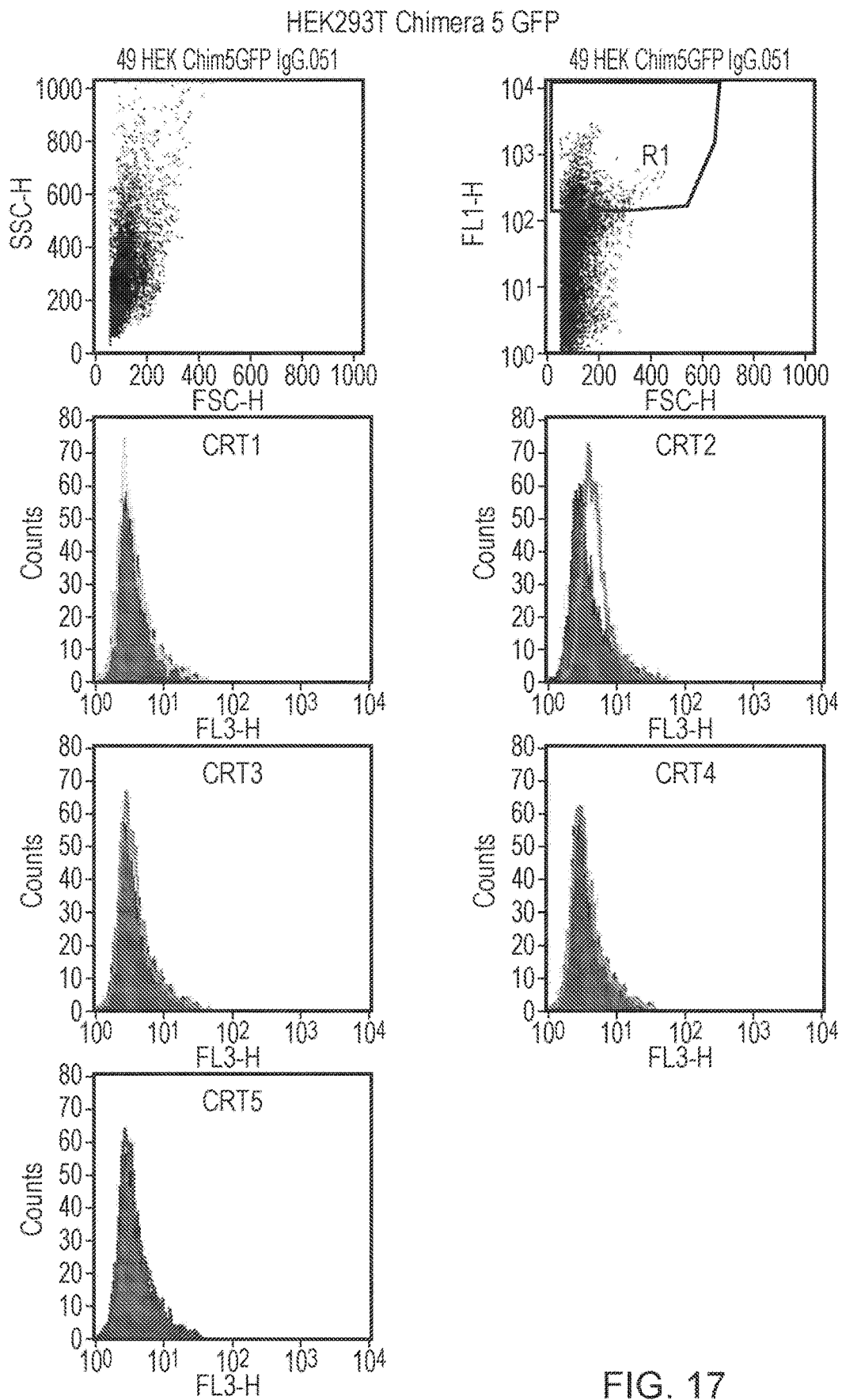
Figure 17:
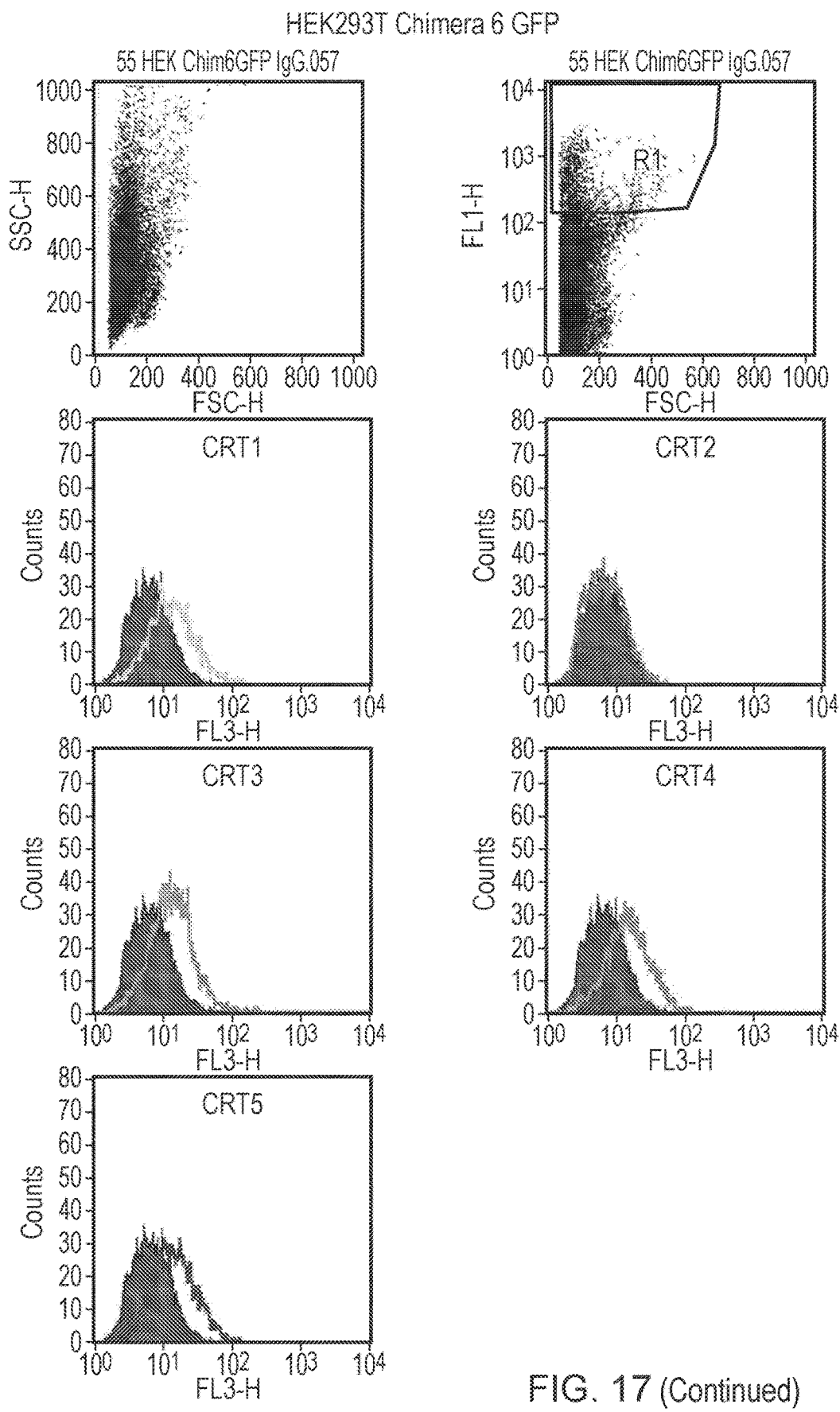

FIG. 17—Chimera 5 (CTLD of thrombomodulin, rest CLEC14A) is not recognised by any of the CRT antibodies except a slight shift in fluorescence with CRT2. Chimera 6 (Sushi of thrombomodulin to ensure correct folding of CTLD of CLEC14A) results in binding of all CRT antibodies except CRT2.

Figure 18:
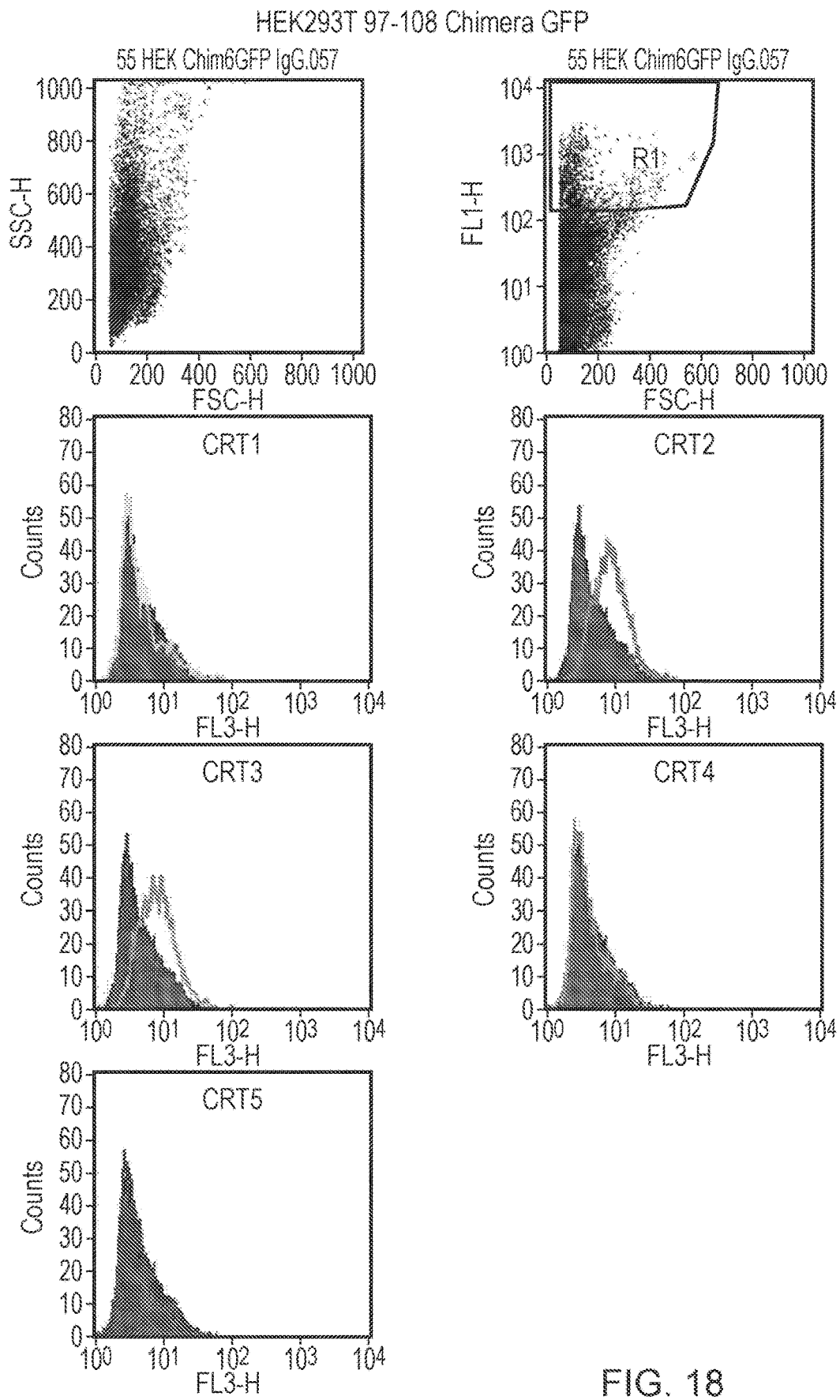

FIG. 18—Residues 97-108 were swapped with corresponding regions from thrombomodulin. This resulted in correct folding as CRT2 and CRT3 can still bind. However CRT1, CRT4 and CRT5 cannot recognise this mutant suggesting this to be the binding region.

Figure 19:
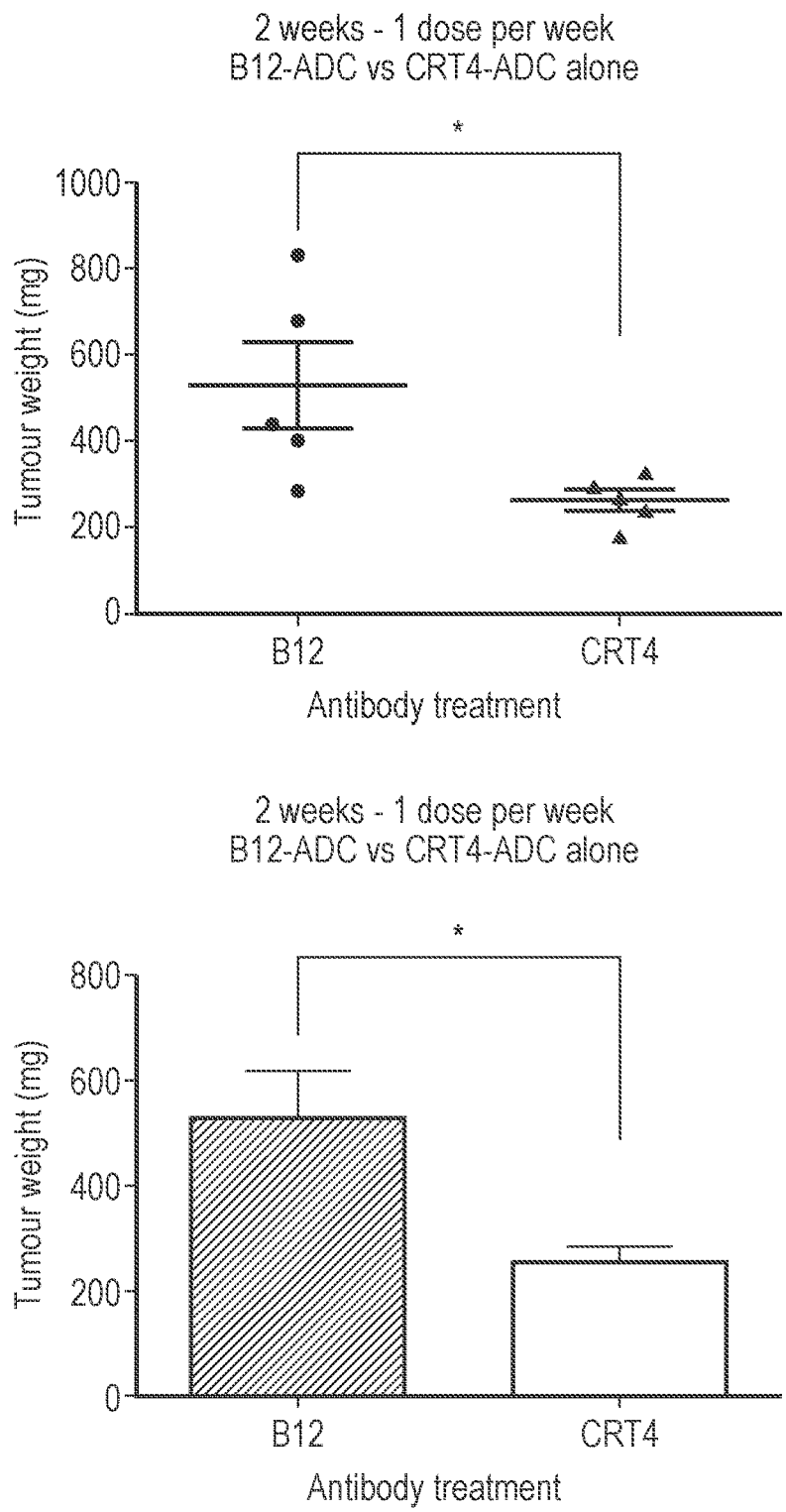

FIG. 19—1 million Lewis lung carcinoma cells were injected subcutaneously into the right flank of mice and allowed to grow to a visible size. End point tumour weights of antibody drug conjugate treatments at two weeks. There was a significant difference between the wet weights of CRT4-ADC treatment group when compared with B12-ADC treatment group. Mann Whitney test p=0.0317. Error bars SEM, n=5. Data pooled from two separate experiments of the same method.

Peptide and nucleotide sequences disclosed herein are summarised in the table below. CDR regions were predicted with the Abysis algorithm (www.bioinf.org.uk/abysis/sequence_input/key_annotation/key_annotation.cgi) or the IMGT algorithm (ImMunoGeneTics) located at www.IMGT.org see for example Lefranc et al 2009 NAR 37: D1006-D1012 and Lefranc 2003 Leukemia 17: 260-266.

V1 in the table below refers to the CDRs as predicted by the Abysis algorithm, whilst V2 refers to the CDRs as predicted by the IMGT algorithm.

| | SEQ ID NO: | SEQUENCE |
|---|---|---|
| C4 V1 | | |
| C4 HC CDR1 (protein) | 1 | SSYWIE |
| C4 HC CDR2 (protein) | 2 | WIGEILPGSGST |
| C4 HC CDR2 (protein) | 78 | WIGEILPGSGSTN |

-continued

| | SEQ ID NO: | SEQUENCE |
|---|---|---|
| C4 HC CDR3 (protein) | 3 | ARGGDYDEEYYLMD |
| C4 LC CDR1 (protein) | 4 | SYMYWY |
| C4 LC CDR2 (protein) | 5 | LLIYDTSNLA |
| C4 LC CDR3 (protein) | 6 | QQWSSYPL |
| C4 HC (protein) | 7 | MAQVQLQQSGAELMKPGASVKISCKATGYTFSS YWIEWVNRRPGHGLEWIGEILPGSGSTNYNEKFK GKATFTADTSSNTAYMQLSSLTSEDSAVYYCARG GDYDEEYYLMDYWGQGTTLTVSS |
| C4 LC (protein) | 8 | QIVLTQSPAIMSASPGEKVTMTCSASSSVSYMYW YQQKPGSSPRLLIYDTSNLASGVPVRFSGSGSGT SYSLTISRMEAEDAATYYCQQWSSYPLTFGAGTK LEIKRAA |
| C4 HC CDR1 (nucleotide) | 9 | AGTAGCTACTGGATAGAG |
| C4 HC CDR2 (nucleotide) | 79 | TGGATTGGAGAGATTTTACCTGGAAGTGGTAGT ACT |
| C4 HC CDR2 (nucleotide) | 10 | TGGATTGGAGAGATTTTACCTGGAAGTGGTAGT ACTAAT |
| C4 HC CDR3 (nucleotide) | 11 | GCGAGAGGGGGGATTACGACGAAGAATACTA TCTCATGGAC |
| C4 LC CDR1 (nucleotide) | 12 | AGTTACATGTACTGGTAC |
| C4 LC CDR2 (nucleotide) | 13 | CTCCTGATTTATGACACATCCAACCTGGCT |
| C4 LC CDR3 (nucleotide) | 14 | CAGCAGTGGAGTAGTTACCCGCTC |
| C4 HC (nucleotide) | 15 | ATGGCCCAGGTTCAGCTGCAGCAGTCTGGAGC TGAGCTGATGAAGCCTGGGGCCTCAGTGAAGA TATCCTGCAAGGCTACTGGCTACACATTCAGTA GCTACTGGATAGAGTGGGTAAACCGGAGGCCT GGACATGGCCTTGAGTGGATTGGAGAGATTTTA CCTGGAAGTGGTAGTACTAATTACAATGAGAAG TTCAAGGGCAAGGCCACATTCACTGCAGATACA TCCTCCAATACAGCCTACATGCAACTCAGCAGC CTCACATCTGAGGACTCTGCCGTCTATTACTGT GCGAGAGGGGGGATTACGACGAAGAATACTA TCTCATGGACTACTGGGGTCAAGGCACCACTCT CACAGTCTCCTCA |
| C4 LC (nucleotide) | 16 | CAAATTGTTCTCACCCAGTCTCCAGCAATCATG TCTGCATCTCCAGGGGAGAAGGTCACCATGAC CTGCAGTGCCAGCTCAAGTGTAAGTTACATGTA CTGGTACCAGCAGAAGCCAGGATCCTCCCCCA GACTCCTGATTTATGACACATCCAACCTGGCTT CTGGAGTCCCTGTTCGCTTCAGTGGCAGTGGG TCTGGGACCTCTTACTCTCTCACAATCAGCCGA ATGGAGGCTGAAGATGCTGCCACTTATTACTGC CAGCAGTGGAGTAGTTACCCGCTCACGTTCGG TGCTGGGACCAAGCTGGAAATCAAACGTGCGG CCGC |

C4 V2

| | SEQ ID NO: | SEQUENCE |
|---|---|---|
| C4 HC CDR1 (protein) | 40 | GYTFSSYW |
| C4 HC CDR2 (protein) | 41 | ILPGSGST |
| C4 HC CDR3 (protein) | 42 | ARGGDYDEEYYLMDY |
| C4 LC CDR1 (protein) | 43 | SSVSY |
| C4 LC CDR2 (protein) | | DTS |
| C4 LC CDR3 (protein) | 44 | QQWSSYPLT |

-continued

| | SEQ ID NO: | SEQUENCE |
|---|---|---|
| C4 HC (protein) | 49 | MAQVQLQQSGAELMKPGASVKISCKATGYTFSS YWIEWVNRRPGHGLEWIGEILPGSGSTNYNEKFK GKATFTADTSSNTAYMQLSSLTSEDSAVYYCARG GDYDEEYYLMDYWGQGTTLTV |
| C4 LC (protein) | 50 | QIVLTQSPAIMSASPGEKVTMTCSASSSVSYMYW YQQKPGSSPRLLIYDTSNLASGVPVRFSGSGSGT SYSLTISRMEAEDAATYYCQQWSSYPLTFGAGTK LEIKRAAA |
| C4 ScFv (protein) | 55 | MAQVQLQQSGAELMKPGASVKISCKATGYTFSS YWIEWVNRRPGHGLEWIGEILPGSGSTNYNEKFK GKATFTADTSSNTAYMQLSSLTSEDSVVYYCARG GDYDEEYYLMDYWGQGTTLTVSSGGGGSGGGG SGGGGSQIVLTQSPAIMSASPGEKVTMTCSASSS VSYMWYQQKPGSSPRLLIYDTSNLASGVPVRFS GSGSGTSYSLTISRMEAEDAATYYCQQWSSYPLT FGAGTKLEIKRAAA |
| C4 HC CDR1 (nucleotide) | 60 | GGCTACACATTCAGTAGCTACTGG |
| C4 HC CDR2 (nucleotide) | 61 | ATTTTACCTGGAGTGGTAGTACT |
| C4 HC CDR3 (nucleotide) | 62 | GCGAGAGGGGGGATTACGACGAAGAATACTA TCTCATGGACTAC |
| C4 LC CDR1 (nucleotide) | 63 | TCAAGTGTAAGTTAC |
| C4 LC CDR2 (nucleotide) | | GACACATCC |
| C4 LC CDR3 (nucleotide) | 64 | CAGCAGTGGAGTAGTTACCCGCTCACG |
| C4 HC (nucleotide) | 68 | ATGGCCCAGGTTCAGCTGCAGCAGTCTGGAGC TGAGCTGATGAAGCCTGGGGCCTCAGTGAAGA TATCCTGCAAGGCTACTGGCTACACATTCAGTA GCTACTGGATAGAGTGGGTAAACCGGAGGCCT GGACATGGCCTTGAGTGGATTGGAGAGATTTTA CCTGGAAGTGGTAGTACTAATTACAATGAGAAG TTCAAGGGCAAGGCCACATTCACTGCAGATACA TCCTCCAATACAGCCTACATGCAACTCAGCAGC CTCACATCTGAGGACTCTGTCGTCTATTACTGT GCGAGAGGGGGGATTACGACGAAGAATACTA TCTCATGGACTACTGGGGTCAAGGCACCACTCT CACAGTC |
| C4 LC (nucleotide) | 69 | CAAATTGTTCTCACCCAGTCTCCAGCAATCATG TCTGCATCTCCAGGGGAGAAGGTCACCATGAC CTGCAGTGCCAGCTCAAGTGTAAGTTACATGTA CTGGTACCAGCAGAAGCCAGGATCCTCCCCCA GACTCCTGATTTATGACACATCCAACCTGGCTT CTGGAGTCCCTGTTCGCTTCAGTGGCAGTGGG TCTGGGACCTCTTACTCTCTCACAATCAGCCGA ATGGAGGCTGAAGATGCTGCCACTTATTACTGC CAGCAGTGGAGTAGTTACCCGCTCACGTTCGG TGCTGGGACCAAGCTGGAAATCAAACGT |
| C4 ScFv (nucleotide) | 74 | ATGGCCCAGGTTCAGCTGCAGCAGTCTGGAGC TGAGCTGATGAAGCCTGGGGCCTCAGTGAAGA TATCCTGCAAGGCTACTGGCTACACATTCAGTA GCTACTGGATAGAGTGGGTAAACCGGAGGCCT GGACATGGCCTTGAGTGGATTGGAGAGATTTTA VCCTGGAAGTGGTAGTACTAATTACAATGAGAAG TTCAAGGGCAAGGCCACATTCACTGCAGATACA TCCTCCAATACAGCCTACATGCAACTCAGCAGC CTCACATCTGAGGACTCTGTCGTCTATTACTGT GCGAGAGGGGGGATTACGACGAAGAATACTA TCTCATGGACTACTGGGGTCAAGGCACCACTCT CACAGTCTCCTCAGGTGGAGGCGGTTCAGGCG GAGGTGGCTCTGGCGGTGGCGGATCGCAAATT GTTCTCACCCAGTCTCCAGCAATCATGTCTGCA TCTCCAGGGGAGAAGGTCACCATGACCTGCAG TGCCAGCTCAAGTGTAAGTTACATGTACTGGTA CCAGCAGAAGCCAGGATCCTCCCCCAGACTCC TGATTTATGACACATCCAACCTGGCTTCTGGAG TCCCTGTTCGCTTCAGTGGCAGTGGGTCTGGG |

-continued

| SEQ ID NO: | SEQUENCE |
|---|---|
| | ACCTCTTACTCTCTCACAATCAGCCGAATGGAG GCTGAAGATGCTGCCACTTATTACTGCCAGCAG TGGAGTAGTTACCCGCTCACGTTCGGTGCTGG GACCAAGCTGGAAATCAAACGTGCGGCCGCA |

C1 v1

| | SEQ ID NO: | SEQUENCE |
|---|---|---|
| C1 HC CDR1 (protein) | 1 | SSYWIE |
| C1 HC CDR2 (protein) | 78 | WIGEILPGSGSTN |
| C1 HC CDR3 (protein) | 77 | ARGGDYDEEYYVMD |
| C1 LC CDR1 (protein) | 4 | SYMYWY |
| C1 LC CDR2 (protein) | 5 | LLIYDTSNLA |
| C1 LC CDR3 (protein) | 6 | QQWSSYPL |
| C1 HC CDR1 (nucleotide) | 9 | AGTAGCTACTGGATAGAG |
| C1 HC CDR2 (nucleotide) | 10 | TGGATTGGAGAGATTTTACCTGGAAGTGGTAGT ACTAAT |
| C1 HC CDR3 (nucleotide) | 58 | GCAAGAGGGGGGGATTACGACGAAGAATACTA TGTCATGGAC |
| C1 LC CDR1 (nucleotide) | 12 | AGTTACATGTACTGGTAC |
| C1 LC CDR2 (nucleotide) | 13 | CTCCTGATTTATGACACATCCAACCTGGCT |
| C1 LC CDR3 (nucleotide) | 14 | CAGCAGTGGAGTAGTTACCCGCTC |

C1 v2

| | SEQ ID NO: | SEQUENCE |
|---|---|---|
| C1 HC CDR1 (protein) | 40 | GYTFSSYW |
| C1 HC CDR2 (protein) | 41 | ILPGSGST |
| C1 HC CDR3 (protein) | 45 | ARGGDYDEEYYVMDY |
| C1 LC CDR1 (protein) | 43 | SSVSY |
| C1 LC CDR2 (protein) | | DTS |
| C1 LC CDR3 (protein) | 44 | QQWSSYPLT |
| C1 HC CDR1 (nucleotide) | 60 | GGCTACACATTCAGTAGCTACTGG |
| C1 HC CDR2 (nucleotide) | 66 | ATTTTACCTGGAAGTGGTAGTACT |
| C1 HC CDR3 (nucleotide) | 65 | GCAAGAGGGGGGGATTACGACGAAGAATACTA TGTCATGGACTAC |
| C1 LC CDR1 (nucleotide) | 63 | TCAAGTGTAAGTTAC |
| C1 LC CDR2 (nucleotide) | | GACACATCC |
| C1 LC CDR3 (nucleotide) | 64 | CAGCAGTGGAGTAGTTACCCGCTCACG |
| C1 HC (protein) | 51 | MAEVQLQQSGAELMKPGASVKISCKATGYTFSSY WIEWVKQRPGHGLEWIGEILPGSGST NYNEKFKGKATFTADTSSNTAYMQLSSLTSEDSA VYYCARGGDYDEEYYVMDYWGQGTSV TV |
| C1 LC (protein) | 52 | QIVLTQSPAIMSASPGEKVTMTCSASSSVSYMYW YQQKPGSSPRLLIYDTSNLASGVP VRFSGSGSGTSYSLTISRMEAEDAATYYCQQWS SYPLTFGAGTKLELKR |
| C1 ScFv (protein) | 56 | MAEVQLQQSGAELMKPGASVKISCKATGYTFSSY WIEWVKQRPGHGLEWIGEILPGSGSTNYNEKFKG KATFTADTSSNTAYMQLSSLTSEDSAVYYCARGG DYDEEYYVMDYWGQGTSVTVSSGGGGSGGGG SGGGGSQIVLTQSPAIMSASPGEKVTMTCSASSS |

| | SEQ ID NO: | SEQUENCE |
|---|---|---|
| | | VSYMYWYQQKPGSSPRLLIYDTSNLASGVPVRFSGSGSGTSYSLTISRMEAEDAATYYCQQWSSYPLTFGAGTKLELKR |
| C1 HC (nucleotide) | 70 | ATGGCCGAGGTTCAGCTTCAGCAGTCTGGAGCTGAGCTGATGAAGCCTGGGGCCTCAGTGAAGATATCCTGCAAGGCTACTGGCTACACATTCAGTAGCTACTGGATAGAGTGGGTAAAGCAGAGGCCTGGACATGGCCTTGAGTGGATTGGAGAGATTTTACCTGGAAGTGGTAGTACTAATTACAATGAGAAGTTCAAGGGCAAGGCCACATTCACTGCAGATACATCCTCCAACACAGCCTACATGCAACTCAGCAGCCTGACATCTGAGGACTCTGCCGTCTATTACTGTGCAAGAGGGGGGGATTACGACGAAGAATACTATGTCATGGACTACTGGGGTCAAGGAACCTCAGTCACTGTC |
| C1 LC (nucleotide) | 71 | CAAATTGTTCTCACCCAGTCTCCAGCAATCATGTCTGCATCTCCAGGGGAGAAGGTCACCATGACCTGCAGTGCCAGCTCAAGTGTAAGTTACATGTACTGGTACCAGCAGAAGCCAGGATCCTCCCCCAGACTCCTGATTTATGACACATCCAACCTGGCTTCTGGAGTCCCTGTTCGCTTCAGTGGCAGTGGGTCTGGGACCTCTTACTCTCTCACAATCAGCCGAATGGAGGCTGAAGATGCTGCCACTTATTACTGCCAGCAGTGGAGTAGTTACCCGCTCACGTTCGGTGCTGGGACCAAGCTGGAGCTGAAACGT |
| C1 Sc Fv (nucleotide) | 75 | ATGGCCGAGGTTCAGCTTCAGCAGTCTGGAGCTGAGCTGATGAAGCCTGGGGCCTCAGTGAAGATATCCTGCAAGGCTACTGGCTACACATTCAGTAGCTACTGGATAGAGTGGGTAAAGCAGAGGCCTGGACATGGCCTTGAGTGGATTGGAGAGATTTTACCTGGAAGTGGTAGTACTAATTACAATGAGAAGTTCAAGGGCAAGGCCACATTCACTGCAGATACATCCTCCAACACAGCCTACATGCAACTCAGCAGCCTGACATCTGAGGACTCTGCCGTCTATTACTGTGCAAGAGGGGGGGATTACGACGAAGAATACTATGTCATGGACTACTGGGGTCAAGGAACCTCAGTCACTGTCTCCTCAGGTGGAGGCGGTTCAGGCGGAGGTGGCTCTGGCGGTGGCGGATCGCAAATTGTTCTCACCCAGTCTCCAGCAATCATGTCTGCATCTCCAGGGGAGAAGGTCACCATGACCTGCAGTGCCAGCTCAAGTGTAAGTTACATGTACTGGTACCAGCAGAAGCCAGGATCCTCCCCCAGACTCCTGATTTATGACACATCCAACCTGGCTTCTGGAGTCCCTGTTCGCTTCAGTGGCAGTGGGTCTGGGACCTCTTACTCTCTCACAATCAGCCGAATGGAGGCTGAAGATGCTGCCACTTATTACTGCCAGCAGTGGAGTAGTTACCCGCTCACGTTCGGTGCTGGGACCAAGCTGGAGCTGAAACGT |
| | | C5 V1 |
| C5 HC CDR1 (protein) | 1 | SSYWIE |
| C5 HC CDR2 (protein) | 78 | WIGEILPGSGSTN |
| C5 HC CDR3 (protein) | 46 | ARGGDYDEEYYAMD |
| C5 LC CDR1 (protein) | 4 | SYMYWY |
| C5 LC CDR2 (protein) | 5 | LLIYDTSNLA |
| C5 LC CDR3 (protein) | 6 | QQWSSYPL |
| C5 HC CDR1 (nucleotide) | 9 | AGTAGCTACTGGATAGAG |
| C5 HC CDR2 (nucleotide) | 10 | TGGATTGGAGAGATTTTACCTGGAAGTGGTAGTACTAAT |
| C5 HC CDR3 (nucleotide) | 59 | GCAAGAGGGGGGGATTACGACGAAGAATACTATGCTATGGAC |
| C5 LC CDR1 (nucleotide) | 12 | AGTTACATGTACTGGTAC |

-continued

| | SEQ ID NO: | SEQUENCE |
|---|---|---|
| C5 LC CDR2 (nucleotide) | 13 | CTCCTGATTTATGACACATCCAACCTGGCT |
| C5 LC CDR3 (nucleotide) | 14 | CAGCAGTGGAGTAGTTACCCGCTC |
| C5 v2 | | |
| C5 HC CDR1 (protein) | 40 | GYTFSSYW |
| C5 HC CDR2 (protein) | 41 | ILPGSGST |
| C5 HC CDR3 (protein) | 47 | ARGGDYDEEYYAMDY |
| C5 LC CDR1 (protein) | 43 | SSVSY |
| C5 LC CDR2 (protein) | | DTS |
| C5 LC CDR3 (protein) | 48 | QQWSSYPLTF |
| C5 HC CDR1 (nucleotide) | 60 | GGCTACACATTCAGTAGCTACTGG |
| C5 HC CDR2 (nucleotide) | 66 | ATTTTACCTGGAAGTGGTAGTACT |
| C5 HC CDR3 (nucleotide) | 67 | GCAAGAGGGGGGATTACGACGAAGAATACTA TGCTATGGACTAC |
| C5 LC CDR1 (nucleotide) | 63 | TCAAGTGTAAGTTAC |
| C5 LC CDR2 (nucleotide) | | GACACATCC |
| C5 LC CDR3 (nucleotide) | 46 | CAGCAGTGGAGTAGTTACCCGCTCACG |
| C5 HC (protein) | 53 | MAEVQLQQSGAELMKPGASVKISCKATGYTFSSY WIEWVNQRPGHGLEWIGEILPGSGST NYNEKFKGKATFTADTSSNTAYMQLSSLTSEDSA VYYCARGGDYDEEYYAMDYWGQGTSVTL |
| C5 LC (protein) | 54 | QIVLTQSPAIMSASPGEKVTMTCSASSSVSYMYW YQQKPGSSPRLLIYDTSNLASGVP VRFSGSGSGTSYSLTISRMEAEDGATYYCQQWS SYPLTFGAGTKLELKR |
| C5 ScFv (protein) | 57 | MAEVQLQQSGAELMKPGASVKISCKATGYTFSSY WIEWVNQRPGHGLEWIGEILPGSGSTNYNEKFK GKATFTADTSSNTAYMQLSSLTSEDSAVYYCARG GDYDEEYYAMDYWGQGTSVTLSSGGGGSGGG GSGGGGSQIVLTQSPAIMSASPGEKVTMTCSASS SVSYMYWYQQKPGSSPRLLIYDTSNLASGVPVRF SGSGSGTSYSLTISRMEAEDAATYYCQQWSSYP LTFGAGTKLELKR |
| C5 HC (nucleotide) | 72 | ATGGCCGAGGTTCAGCTTCAGCAGTCTGGAGC TGAGCTGATGAAGCCTGGGGCCTCAGTGAAGA TATCCTGCAAGGCTACTGGCTACACATTCAGTA GCTACTGGATAGAGTGGGTAAATCAGAGGCCT GGACATGGCCTTGAGTGGATTGGAGAGATTTTA CCTGGAAGTGGTAGTACTAATTACAATGAGAAG TTCAAGGGCAAGGCCACATTCACTGCAGATACA TCCTCCAACACAGCCTACATGCAACTCAGCAGC CTGACATCTGAGGACTCTGCCGTCTATTACTGT GCAAGAGGGGGGATTACGACGAAGAATACTA TGCTATGGACTACTGGGGTCAAGGAACCTCAG TCACCCTC |
| C5 LC (nucleotide) | 73 | CAAATTGTTCTCACCCAGTCTCCAGCAATCATG TCTGCATCTCCAGGGGAGAAGGTCACCATGAC CTGCAGTGCCAGCTCAAGTGTAAGTTACATGTA CTGGTACCAGCAGAAGCCAGGATCCTCCCCCA GACTCCTGATTTATGACACATCCAACCTGGCTT CTGGAGTCCCTGTTCGCTTCAGTGGCAGTGGG TCTGGGACCTCTTACTCTCTCACAATCAGCCGA ATGGAGGCTGAAGATGCTGCCACTTATTACTGC CAGCAGTGGAGTAGTTACCCGCTCACGTTCGG TGCTGGGACCAAGCTGGAGCTGAAACGT |

| SEQ ID NO: | SEQUENCE |
|---|---|
| C5 ScFv (nucleotide) | 76 | ATGGCCGAGGTTCAGCTTCAGCAGTCTGGAGC
TGAGCTGATGAAGCCTGGGGCCTCAGTGAAGA
TATCCTGCAAGGCTACTGGCTACACATTCAGTA
GCTACTGGATAGAGTGGGTAAATCAGAGGCCT
GGACATGGCCTTGAGTGGATTGGAGAGATTTTA
CCTGGAAGTGGTAGTACTAATTACAATGAGAAG
TTCAAGGGCAAGGCCACATTCACTGCAGATACA
TCCTCCAACACAGCCTACATGCAACTCAGCAGC
CTGACATCTGAGGACTCTGCCGTCTATTACTGT
GCAAGAGGGGGGGATTACGACGAAGAATACTA
TGCTATGGACTACTGGGGTCAAGGAACCTCAG
TCACCCTCTCCTCAGGTGGAGGCGGTTCAGGC
GGAGGTGGCTCTGGCGGTGGCGGATCGCAAAT
TGTTCTCACCCAGTCTCCAGCAATCATGTCTGC
ATCTCCAGGGGAGAAGGTCACCATGACCTGCA
GTGCCAGCTCAAGTGTAAGTTACATGTACTGGT
ACCAGCAGAAGCCAGGATCCTCCCCCAGACTC
CTGATTTATGACACATCCAACCTGGCTTCTGGA
GTCCCTGTTCGCTTCAGTGGCAGTGGGTCTGG
GACCTCTTACTCTCTCACAATCAGCCGAATGGA
GGCTGAAGATGCTGCCACTTATTACTGCCAGCA
GTGGAGTAGTTACCCGCTCACGTTCGGTGCTG
GGACCAAGCTGGAGCTGAAACGT |

OTHER SEQUENCES

| CLEC14A (protein) | 17 | MRPAFALCLLWQALWPGPGGGEHPTADRAGCS
ASGACYSLHHATMKRQAAEEACILRGGALSTVRA
GAELRAVLALLRAGPGPGGGSKDLLFWVALERR
RSHCTLENEPLRGFSWLSSDPGGLESDTLQWVE
EPQRSCTARRCAVLQATGGVEPAGWKEMRCHL
RANGYLCKYQFEVLCPAPRPGAASNLSYRAPFQL
HSAALDFSPPGTEVSALCRGQLPISVTCIADEIGA
RWDKLSGDVLCPCPGRYLRAGKCAELPNCLDDL
GGFACECATGFELGKDGRSCVTSGEGQPTLGGT
GVPTRRPPATATSPVPQRTWPIRVDEKLGETPLV
PEQDNSVTSIPEIPRWGSQSTMSTLQMSLQAESK
ATITPSGSVISKFNSTTSSATPQAFDSSSAVVFIFV
STAVVVLVILTMTVLGLVKLCFHESPSSQPRKESM
GPPGLESDPEPAALGSSSAHCTNNGVKVGDCDL
RDRAEGALLAESPLGSSDA |
| CLEC14A (nucleotide) | 18 | CTCCTCTTGCTCTAAGCAGGGTGTTTGACCTTC
TAGTCGACTGCGTCCCTGTACCCGGCGCCAG
CTGTGTTCCTGACCCCAGAATAACTCAGGGCTG
CACCGGGCCTGGCAGCGCTCCGCACACATTTC
CTGTCGCGGCCTAAGGGAAACTGTTGGCCGCT
GGGCCCGCGGGGGGATTCTTGGCAGTTGGGG
GGTCCGTCGGGAGCGAGGGCGGAGGGGAAGG
GAGGGGGAACCGGGTTGGGGAAGCCAGCTGT
AGAGGGCGGTGACCGCGCTCCAGACACAGCTC
TGCGTCCTCGAGCGGGACAGATCCAAGTTGGG
AGCAGCTCTGCGTGCGGGGCCTCAGAGAATGA
GGCCGGCGTTCGCCCTGTGCCTCCTCTGGCAG
GCGCTCTGGCCCGGGCCGGGCGGCGGCGAAC
ACCCCACTGCCGACCGTGCTGGCTGCTCGGCC
TCGGGGGCCTGCTACAGCCTGCACCACGCTAC
CATGAAGCGGCAGGCGGCCGAGGAGGCCTGC
ATCCTGCGAGGTGGGCGCTCAGCACCGTGC
GTGCGGGCGCCGAGCTGCGCGCTGTGCTCGC
GCTCCTGCGGGCAGGCCCAGGGCCCGGAGGG
GGCTCCAAAGACCTGCTGTTCTGGGTCGCACT
GGAGCGCAGGCGTTCCCACTGCACCCTGGAGA
ACGAGCCTTTGCGGGGTTTCTCCTGGCTGTCC
TCCGACCCCGGCGGTCTCGAAAGCGACACGCT
GCAGTGGGTGGAGGAGCCCCAACGCTCCTGCA
CCGCGCGGAGATGCGCGGTACTCCAGGCCAC
CGGTGGGGTCGAGCCCGCAGGCTGGAAGGAG
ATGCGATGCCACCTGCGCGCCAACGGCTACCT
GTGCAAGTACCAGTTTGAGGTCTTGTGTCCTGC
GCCGCGCCCCGGGGCCGCCTCTAACTTGAGCT
ATCGCGCGCCCTTCCAGCTGCACAGCGCCGCT
CTGGACTTCAGTCCACCTGGGACCGAGGTGAG
TGCGCTCTGCCGGGGACAGCTCCCGATCTCAG
TTACTTGCATCGCGGACGAAATCGGCGCTCGC |

| SEQ ID NO: | SEQUENCE |
|---|---|
|  | TGGGACAAACTCTCGGGCGATGTGTTGTGTCC<br>CTGCCCCGGGAGGTACCTCCGTGCTGGCAAAT<br>GCGCAGAGCTCCCTAACTGCCTAGACGACTTG<br>GGAGGCTTTGCCTGCGAATGTGCTACGGGCTT<br>CGAGCTGGGGAAGGACGGCCGCTCTTGTGTGA<br>CCAGTGGGAAGGACAGCCGACCCTTGGGGG<br>GACCGGGGTGCCCACCAGGCGCCCGCCGGCC<br>ACTGCAACCAGCCCCGTGCCGCAGAGAACATG<br>GCCAATCAGGGTCGACGAGAAGCTGGGAGAGA<br>CACCACTTGTCCCTGAACAAGACAATTCAGTAA<br>CATCTATTCCTGAGATTCCTCGATGGGGATCAC<br>AGAGCACGATGTCTACCCTTCAAATGTCCCTTC<br>AAGCCGAGTCAAAGGCCACTATCACCCCATCA<br>GGGAGCGTGATTTCCAAGTTTAATTCTACGACT<br>TCCTCTGCCACTCCTCAGGCTTTCGACTCCTCC<br>TCTGCCGTGGTCTTCATATTTGTGAGCACAGCA<br>GTAGTAGTGTTGGTGATCTTGACCATGACAGTA<br>CTGGGGCTTGTCAAGCTCTGCTTTCACGAAAGC<br>CCCTCTTCCCAGCCAAGGAAGGAGTCTATGGG<br>CCCGCCGGGCCTGGAGAGTGATCCTGAGCCC<br>GCTGCTTTGGGCTCCAGTTCTGCACATTGCACA<br>AACAATGGGGTGAAAGTCGGGGACTGTGATCT<br>GCGGGACAGAGCAGAGGGTGCCTTGCTGGCG<br>GAGTCCCCTCTTGGCTCTAGTGATGCATAGGG<br>AAACAGGGGACATGGGCACTCCTGTGAACAGT<br>TTTTCACTTTTGATGAAACGGGGAACCAAGAGG<br>AACTTACTTGTGTAACTGACAATTTCTGCAGAAA<br>TCCCCCTTCCTCTAAATTCCCTTTACTCCACTGA<br>GGAGCTAAATCAGAACTGCACACTCCTTCCCTG<br>ATGATAGAGGAAGTGGAAGTGCCTTTAGGATG<br>GTGATACTGGGGGACCGGGTAGTGCTGGGGA<br>GAGATATTTTCTTATGTTTATTCGGAGAATTTGG<br>AGAAGTGATTGAACTTTTCAAGACATTGGAAAC<br>AAATAGAACACAATATAATTTACATTAAAAAATA<br>ATTTCTACCAAAATGGAAAGGAAATGTTCTATGT<br>TGTTCAGGCTAGGAGTATATTGGTTCGAAATCC<br>CAGGGAAAAAAATAAAAATAAAAAATTAAAGGAT<br>TGT |
| 19 | ATGAGGCCGGCGTTCGCCCTGTGCCTCCTCTG<br>GCAGGCGCTCTGGCCCGGGCCGGGCGGCGGC<br>GAACACCCCACTGCCGACCGTGCTGGCTGCTC<br>GGCCTCGGGGGCCTGCTACAGCCTGCACCAC<br>GCTACCATGAAGCGGCAGGCGGCCGAGGAGG<br>CCTGCATCCTGCGAGGTGGGGCGCTCAGCACC<br>GTGCGTGCGGGCGCCGAGCTGCGCGCTGTGC<br>TCGCGCTCCTGCGGGCAGGCCCAGGGCCCGG<br>AGGGGGCTCCAAAGACCTGCTGTTCTGGGTCG<br>CACTGGAGCGCAGGCGTTCCCACTGCACCCTG<br>GAGAACGAGCCTTTGCGGGGTTTCTCCTGGCT<br>GTCCTCCGACCCCGGCGGTCTCGAAAGCGACA<br>CGCTGCAGTGGGTGGAGGAGCCCCAACGCTC<br>CTGCACCGCGCGGAGATGCGCGGTACTCCAG<br>GCCACCGGTGGGGTCGAGCCCGCAGGCTGGA<br>AGGAGATGCGATGCCACCTGCGCGCCAACGGC<br>TACCTGTGCAAGTACCAGTTTGAGGTCTTGTGT<br>CCTGCGCCGCGCCCCGGGGCCGCCTCTAACTT<br>GAGCTATCGCGCGCCCTTCCAGCTGCACAGCG<br>CCGCTCTGGACTTCAGTCCACCTGGGACCGAG<br>GTGAGTGCGCTCTGCCGGGGACAGCTCCCGAT<br>CTCAGTTACTTGCATCGCGGACGAAATCGGCG<br>CTCGCTGGGACAAACTCTCGGGCGATGTGTTG<br>TGTCCCTGCCCCGGGAGGTACCTCCGTGCTGG<br>CAAATGCGCAGAGCTCCCTAACTGCCTAGACG<br>ACTTGGGAGGCTTTGCCTGCGAATGTGCTACG<br>GGCTTCGAGCTGGGGAAGGACGGCCGCTCTTG<br>TGTGACCAGTGGGGAAGGACAGCCGACCCTTG<br>GGGGGACCGGGTGCCCACCAGGCGCCCGCC<br>GGCCACTGCAACCAGCCCCGTGCCGCAGAGAA<br>CATGGCCAATCAGGGTCGACGAGAAGCTGGGA<br>GAGACACCACTTGTCCCTGAACAAGACAATTCA<br>GTAACATCTATTCCTGAGATTCCTCGATGGGGA<br>TCACAGAGCACGATGTCTACCCTTCAAATGTCC<br>CTTCAAGCCGAGTCAAAGGCCACTATCACCCCA<br>TCAGGGAGCGTGATTTCCAAGTTTAATTCTACG<br>ACTTCCTCTGCCACTCCTCAGGCTTTCGACTCC |

| SEQ ID NO: | SEQUENCE |
|---|---|
| | TCCTCTGCCGTGGTCTTCATATTTGTGAGCACA GCAGTAGTAGTGTTGGTGATCTTGACCATGACA GTACTGGGGCTTGTCAAGCTCTGCTTTCACGAA AGCCCCTCTTCCCAGCCAAGGAAGGAGTCTAT GGGCCCGCCGGGCCTGGAGAGTGATCCTGAG CCCGCTGCTTTGGGCTCCAGTTCTGCACATTGC ACAAACAATGGGGTGAAAGTCGGGGACTGTGA TCTGCGGGACAGAGCAGAGGGTGCCTTGCTGG CGGAGTCCCCTCTTGGCTCTAGTGATGCATAG |

| | SEQ ID NO: | SEQUENCE |
|---|---|---|
| MMRN2 (protein) | 20 | MILSLLFSLGGPLGWGLLGAWAQASSTSLSDLQS SRTPGVWKAEAEDTGKDPVGRNWCPYPMSKLV TLLALCKTEKFLIHSQQPCPQGAPDCQKVKVMYR MAHKPVYQVKQKVLTSLAWRCCPGYTGPNCEHH DSMAIPEPADPGDSHQEPQDGPVSFKPGHLAAVI NEVEVQQEQQEHLLGDLQNDVHRVADSLPGLWK ALPGNLTAAVMEANQTGHEFPDRSLEQVLLPHVD TFLQVHFSPIWRSFNQSLHSLTQAIRNLSLDVEAN RQAISRVQDSAVARADFQELGAKFEAKVQENTQ RVGQLRQDVEDRLHAQHFTLHRSISELQADVDTK LKRLHKAQEAPGTNGSLVLATPGAGARPEPDSLQ ARLGQLQRNLSELHMTTARREEELQYTLEDMRAT LTRHVDEIKELYSESDETFDQISKVERQVEELQVN HTALRELRVILMEKSLIMEENKEEVERQLLELNLTL QHLQGGHADLIKYVKDCNCQKLYLDLDVIREGQR DATRALEETQVSLDERRQLDGSSLQALQNAVDAV SLAVDAHKAEGERARAATSRLRSQVQALDDEVG ALKAAAAEARHEVRQLHSAFAALLEDALRHEAVL AALFGEEVLEEMSEQTPGPLPLSYEQIRVALQDA ASGLQEQALGWDELAARVTALEQASEPPRPAEH LEPSHDAGREEAATTALAGLARELQSLSNDVKNV GRCCEAEAGAGAASLNASLDGLHNALFATQRSLE QHQRLFHSLFGNFQGLMEANVSLDLGKLQTMLS RKGKKQQKDLEAPRKRDKKEAEPLVDIRVTGPVP GALGAALWEAGSPVAFYASFSEGTAALQTVKFNT TYINIGSSYFPEHGYFRAPERGVYLFAVSVEFGPG PGTGQLVFGGHHRTPVCTTGQGSGSTATVFAMA ELQKGERVWFELTQGSITKRSLSGTAFGGFLMFK T |
| MMRN2 (nucleotide) | 21 | ATGATCCTGAGCTTGCTGTTCAGCCTTGGGGG CCCCCTGGGCTGGGGGCTGCTGGGGGCATGG GCCCAGGCTTCCAGTACTAGCCTCTCTGATCTG CAGAGCTCCAGGACACCTGGGGTCTGGAAGGC AGAGGCTGAGGACACCGGCAAGGACCCCGTTG GACGTAACTGGTGCCCCTACCCAATGTCCAAG CTGGTCACCTTACTAGCTCTTTGCAAAACAGAG AAATTCCTCATCCACTCGCAGCAGCCGTGTCCG CAGGGAGCTCCAGACTGCCAGAAAGTCAAAGT CATGTACCGCATGGCCCACAAGCCAGTGTACC AGGTCAAGCAGAAGGTGCTGACCTCTTTGGCC TGGAGGTGCTGCCCTGGCTACACGGGCCCCAA CTGCGAGCACCACGATTCCATGGCAATCCCTG AGCCTGCAGATCCTGGTGACAGCCACCAGGAA CCTCAGGATGGACCAGTCAGCTTCAAACCTGG CCACCTTGCTGCAGTGATCAATGAGGTTGAGGT GCAACAGGAACAGCAGGAACATCTGCTGGGAG ATCTCCAGAATGATGTGCACCGGGTGGCAGAC AGCCTGCCAGGCCTGTGGAAAGCCCTGCCTGG TAACCTCACAGCTGCAGTGATGGAAGCAAATCA AACAGGGCACGAGTTCCCTGATAGATCCTTGG AGCAGGTGCTGCTACCCCACGTGGACACCTTC CTACAAGTGCATTTCAGCCCCATCTGGAGGAG CTTTAACCAAAGCCTGCACAGCCTTACCCAGGC CATAAGAAACCTGTCTCTTGACGTGGAGGCCAA CCGCCAGGCCATCTCCAGAGTCCAGGACAGTG CCGTGGCCAGGGCTGACTTCCAGGAGCTTGGT GCCAAATTTGAGGCCAAGGTCCAGGAGAACAC TCAGAGAGTGGGTCAGCTGCGACAGGACGTGG AGGACCGCCTGCACGCCCAGCACTTTACCCTG CACCGCTCGATCTCAGAGCTCCAAGCCGATGT GGACACCAAATTGAAGAGGCTGCACAAGGCTC AGGAGGCCCCAGGGACCAATGGCAGTCTGGTG TTGGCAACGCCTGGGGCTGGGCAAGGCCTG AGCCGGACAGCCTGCAGGCCAGGCTGGGCCA GCTGCAGAGGAACCTCTCAGAGCTGCACATGA |

| SEQ ID NO: | SEQUENCE |
|---|---|
| | CCACGGCCCGCAGGGAGGAGGAGTTGCAGTA CACCCTGGAGGACATGAGGGCCACCCTGACCC GGCACGTGGATGAGATCAAGGAACTGTACTCC GAATCGGACGAGACTTTCGATCAGATTAGCAAG GTGGAGCGGCAGGTGGAGGAGCTGCAGGTGA ACCACACGGCGCTCCGTGAGCTGCGCGTGATC CTGATGGAGAAGTCTCTGATCATGGAGGAGAA CAAGGAGGAGGTGGAGCGGCAGCTCCTGGAG CTCAACCTCACGCTGCAGCACCTGCAGGGTGG CCATGCCGACCTCATCAAGTACGTGAAGGACT GCAATTGCCAGAAGCTCTATTTAGACCTGGACG TCATCCGGGAGGGCCAGAGGGACGCCACGCG TGCCCTGGAGGAGACCCAGGTGAGCCTGGAC GAGCGGCGGCAGCTGGACGGCTCCTCCCTGC AGGCCCTGCAGAACGCCGTGGACGCCGTGTC GCTGGCCGTGGACGCGCACAAAGCGGAGGGC GAGCGGGCGCGGGCGGCCACGTCGCGGCTCC GGAGCCAAGTGCAGGCGCTGGATGACGAGGT GGGCGCGCTGAAGGCGGCCGCGGCCGAGGCC CGCCACGAGGTGCGCCAGCTGCACAGCGCCTT CGCCGCCCTGCTGGAGGACGCGCTGCGGCAC GAGGCGGTGCTGGCCGCGCTCTTCGGGGAGG AGGTGCTGGAGGAGATGTCTGAGCAGACGCCG GGACCGCTGCCCCTGAGCTACGAGCAGATCCG CGTGGCCCTGCAGGACGCCGCTAGCGGGCTG CAGGAGCAGGCGCTCGGCTGGGACGAGCTGG CCGCCCGAGTGACGGCCCTGGAGCAGGCCTC GGAGCCCCGCGGCCGGCAGAGCACCTGGAG CCCAGCCACGACGCGGGCCGCGAGGAGGCCG CCACCACCGCCCTGGCCGGGCTGGCGCGGGA GCTCCAGAGCCTGAGCAACGACGTCAAGAATG TCGGGCGGTGCTGCGAGGCTGAGGCCGGGGC CGGGGCCGCCTCCCTCAACGCCTCCCTTGACG GCCTCCACAACGCACTCTTCGCCACTCAGCGC AGCTTGGAGCAGCACCAGCGGCTCTTCCACAG CCTCTTTGGGAACTTCCAAGGGCTCATGGAAG CCAACGTCAGCCTGGACCTGGGGAAGCTGCAG ACCATGCTGAGCAGGAAAGGGAAGAAGCAGCA GAAAGACCTGGAAGCTCCCCGGAAGAGGGACA AGAAGGAAGCGGAGCCTTTGGTGGACATACGG GTCACAGGGCCTGTGCCAGGTGCCTTGGGCGC GGCGCTCTGGGAGGCAGGATCCCCTGTGGCCT TCTATGCCAGCTTTTCAGAAGGGACGGCTGCC CTGCAGACAGTGAAGTTCAACACCACATACATC AACATTGGCAGCAGCTACTTCCCTGAACATGGC TACTTCCGAGCCCCTGAGCGTGGTGTCTACCT GTTTGCAGTGAGCGTTGAATTTGGCCCAGGGC CAGGCACCGGGCAGCTGGTGTTTGGAGGTCAC CATCGGACTCCAGTCTGTACCACTGGGCAGGG GAGTGGAAGCACAGCAACGGTCTTTGCCATGG CTGAGCTGCAGAAGGGTGAGCGAGTATGGTTT GAGTTAACCCAGGGATCAATAACAAAGAGAAGC CTGTCGGGCACTGCATTTGGGGGCTTCCTGAT GTTTAAGACCTGA |
| CLEC14A fwd (nucleotide) | 22 | 5'TAGTAGGAATTCGAGAGAATGAGGCCGGCGT TCGCCCTG |
| CLEC14A rev (nucleotide) | 23 | AGAACCGCGGCCGCTGGAGGAGTCGAAAGCCT GAGGAGT |
| murine CLEC14A fwd (nucleotide) | 24 | TAGTAGGAATTCGAGAGAATGAGGCCAGCGCT TGCCCTG |
| murine CLEC14A rev (nucleotide) | 25 | CTACTAGCGGCCGCTCGTGGAAGAGGTGTCGA AAGT |
| human CLEC14A fwd (nucleotide) | 26 | TAGTAGTTAATTAAGAGAGAATGAGGCCGGCGT TC |
| murine CLEC14A fwd (nucleotide) | 27 | TAGTAGTTAATTAAGAGAGAATGAGGCCAGCG CTT |
| human Fc rev (nucleotide) | 28 | CTACTAGTTTAAACTCATTTACCCGGAGACAGG GA |

-continued

| SEQ ID NO: | SEQUENCE |
|---|---|---|
| MMRN2 fwd (nucleotide) | 29 | CCGGACCGGTCAGGCTTCCAGTACTAGCC( |
| MMRN2 rev (nucleotide) | 30 | CGGGGTACCGGTCTTAAACATCAGGAAGC |
| 5'UTR fwd (nucleotide) | 31 | TTCCTTTTCCAGGGTTTGTG |
| 5' UTR rev (nucleotide) | 32 | GCCTACAAGGTGGCTTGAAT |
| CDS fwd (nucleotide) | 33 | AAGCTGTGCTCCTGCTCTTG |
| CDS rev (nucleotide) | 34 | TCCTGAGTGCACTGTGAGATG |
| 3' UTR fwd (nucleotide) | 35 | CTGTAGAGGGCGGTGACTTT |
| 3' UTR rev (nucleotide) | 36 | AGCTGCTCCCAAGTCCTCT |
| mACTB fwd (nucleotide) | 37 | CTAAGGCCAACCGTGAAAAG |
| mACTB rev (nucleotide) | 38 | ACCAGAGGCATACAGGGACA |
| Residues 97-108 of CLEC14A C-type lectin domain | 39 | ERRRSCHTLENE |
| regions 1-42 of CD141 | 80 | MLGVLVLGALALAGLGFPAPAEPQPGGSQC VEHDCFALY |
| regions 97-108 of CD141 | 81 | QLPPGCGDPKRL |
| regions 122-142 of CD141 | 82 | TSYSRWARLDLNGAPLCGPL |
| CD141 CTLD | 83 | See FIG. 14 |
| amino acid sequence of whole chimera 5 fused to GFP tag | 84 | See FIG. 14 |
| amino acid sequence of whole chimera 6 fused to GFP tag | 85 | See FIG. 14 |
| CLEC14A CTLD | 86 | See FIG. 16 |

EXAMPLE 1: BLOCKING CLEC14A-MMRN2 BINDING INHIBITS SPROUTING ANGIOGENESIS AND TUMOUR GROWTH

Summary

CLEC14A is a tumour endothelial marker. Here we show CLEC14A is a regulator of sprouting angiogenesis in vitro and in vivo. Using a HUVEC spheroid sprouting assay we found CLEC14A to be a regulator of sprout initiation. Analysis of endothelial sprouting in aortic ring and in vivo subcutaneous sponge assays from clec14a +/+ and clec14a -/- mice revealed defects in sprouting angiogenesis in CLEC14A deficient animals. Tumour growth was retarded and vascularity reduced in clec14a -/- mice. Pull-down and co-immunoprecipitation experiments confirmed MMRN2 binds to the extracellular region of CLEC14A. The CLEC14A-MMRN2 interaction was interrogated using mouse monoclonal antibodies. Monoclonal antibodies were screened for their ability to block this interaction. Clone C4 but not C2 blocked CLEC14A-MMRN2 binding. C4 antibody perturbed tube formation and endothelial sprouting in vitro and in vivo, with a similar phenotype to loss of CLEC14A. Significantly, tumour growth was impaired in C4 treated animals and vascular density was also reduced in the C4 treated group. We conclude that CLEC14A-MMRN2 binding has a role in inducing sprouting angiogenesis during tumour growth, that has the potential to be manipulated in future anti-angiogenic therapy design.

Introduction

It is well established that solid tumour growth relies on the recruitment of endothelial cells and ultimately blood vessels from the surrounding healthy tissue. These recruited blood vessels deliver oxygen and nutrients, through blood flow, to the tumour. A primary mechanism of this recruitment is through sprouting angiogenesis of vessels adjacent to the tumour arising from tumour-derived release of VEGF. Sprouting angiogenesis is a tightly regulated process, where the main regulatory components are VEGFR2, Notch and Angpoietin/Tie2 signalling pathways with cross-talk been these systems essential for direction, growth and cell specification.[1,2] However, recent studies have highlighted the role of multiple other pathways as regulators of this process, including factors involved in glycolysis,[3] PKA signalling,[4] as well as new regulators of extracellular matrix composition.[5,6] Manipulation of these factors has also been shown to suppress angiogenic sprouting in vitro and in vivo.

Targeting angiogenesis in cancer has many therapeutic advantages, including efficient delivery to target tissue type, stable genetic profile, and lower potential for side effects than conventional chemotherapy. Current anti-angiogenic therapies in the clinic primarily target the VEGF signalling pathway, but with limited success.[7] More recent efforts to develop effective anti-angiogenic therapies have focussed on understanding and targeting the endothelial tip and stalk cells during sprouting angiogenesis.[2] For this to be effective, greater knowledge is required to understand the pathways involved in tip cell formation and behaviour.

CLEC14A is a single-pass transmembrane glycoprotein that belongs to the vascular restricted C-type lectin family 14, whose other members include CD248/TEM1/Endosialin, Thrombomodulin and CD93.[8] CLEC14A was originally identified to be an endothelial specific gene that is highly upregulated on vessels associated with multiple solid tumours.[9] More recent work has shown CLEC14A as part of a "common angiogenesis signature" in a meta-analysis of 121 head and neck squamous cell carcinomas, 959 breast cancers and 170 clear cell renal cell carcinomas.[13] MMRN2, an endothelial specific member of the emilin family and component of the extracellular matrix,[14, 15] is an extracellular interacting protein for CLEC14A and co-expression of MMRN2 and CLEC14A has been seen on tumour vasculature.[11] In this study we have investigated CLEC14A in sprouting angiogenesis and for the first time examined its role in vivo.

Results

CLEC14A Regulates Sprouting Angiogenesis In Vitro

We previously described a role for CLEC14A in endothelial migration and tube formation in vitro.[9] To investigate the role of CLEC14A in sprouting angiogenesis in vitro, HUVEC spheroids were generated from HUVECs treated with siRNA targeting clec14a or a non-complementary siRNA duplex. Knockdown of clec14a expression was confirmed at the mRNA level by qPCR with an average reduction of 74% across three experiments (FIG. 1A) and at the protein level by Western blot analysis of protein extracts probed with an anti-CLEC14A polyclonal antisera (FIG. 1B). VEGF induced sprouting from CLEC14A knockdown spheroids was impaired, knockdown spheroids produced on average 6.9 sprouts per spheroid, compared to 13.2 for control cells (FIGS. 1C and 1D). To determine the role of CLEC14A in tip/stalk cell formation, control HUVECs and knockdown HUVECs were stained either red or green and mixed, prior to spheroid formation and induced sprouting (FIG. 1E). Knockdown of CLEC14A reduced the percentage of cells at the tip position (33%) compared to control cells (67%), however, there was no effect on the percentage of stalk cells that were derived from CLEC14A knockdown HUVECs (FIG. 1F). These data suggest CLEC14A has a role in sprout initiation and migration.

CLEC14A Regulates Sprouting Angiogenesis In Vivo

Previously published data for CLEC14A has demonstrated its role in endothelial biology in vitro, however its in vivo role has not been reported. To investigate the role of CLEC14A in vivo and ex vivo, mice were generated to replace the clec14a coding sequence with a lacZ reporter (FIG. 2A). Breeding of heterozygotes (clec14a −/+) produced equal proportions of male and female mice (49.5%/50.5% respectively) and a Mendelian ratio of wildtype:heterozygote:homozygote mice (26.4%:47.2%:26.4% respectively). As clec14a is an endothelial-restricted gene, aortas were isolated from clec14a +/+ and clec14a −/− mice. Extracted cDNA was analysed by qPCR and confirmed loss of the clec14a coding region but expression of the 5' and 3' untranslated regions were retained (FIG. 2B). Loss of CLEC14A at the protein level was also confirmed by Western blot analysis of lung tissue lysates (FIG. 10).

To confirm the role of CLEC14A in sprouting angiogenesis in multicellular three dimensional co-culture, aortas were isolated, cut into rings and embedded in collagen. Cellular outgrowth was stimulated by VEGF and monitored over 7 days before end-point quantitation of endothelial sprouting. Again, loss of CLEC14A impaired endothelial sprout outgrowth and migration (FIG. 2D). Aortic rings from wildtype mice produced over double the number of tubes compared to that observed for CLEC14A knockout mice (30.6 tubes compared to 13.4 tubes respectively) (FIG. 2E). In addition, the maximum migration, which is defined by the furthest distance migrated away from each aortic ring, was also reduced in knockout cultures (FIG. 2F). To assess whether CLEC14A has a similar function in vivo, sponge barrels were implanted subcutaneously into CLEC14A knockout mice. Cellular infiltration and neo-angiogenesis were stimulated using bFGF injections into the sponge every two days for two weeks. Macroscopic analysis of sponge sections stained with haematoxylin and eosin revealed impaired infiltration of cells into the sponge in clec14a −/− animals (FIGS. 2G and 2H). In addition, vascularity was significantly reduced (p<0.01) for clec14a −/− animals (FIG. 2I). To confirm the endothelial cells lining the neoangiogenic vessels express clec14a in this model, sponges and livers from CLEC14A KO mice were stained with x-gal. Strong x-gal staining was observed on blood vessels within the sponge compared to matched liver sections (FIG. 2J). From these data we can conclude that mouse CLEC14A expression regulates endothelial migration and angiogenic sprouting in vivo, as well as in vitro, and CLEC14A is upregulated on sprouting endothelium.

CLEC14A Promotes Tumour Growth

CLEC14A expression is found highly up-regulated on human tumour vessels compared to vessels from healthy tissue, suggesting that cancer therapies could be targeted against CLEC14A.[9] Therefore, to investigate whether loss of CLEC14A effects tumour growth we used the syngeneic Lewis lung carcinoma (LLC) model. For this $1 \times 10^6$ LLC cells were injected subcutaneously into the right flank of either clec14a +/+ or clec14a −/− mice. Tumour growth was impaired in the clec14a −/− mice compared to clec14a +/+ littermates (FIG. 3A). This was confirmed by three independent experiments. Excised tumours taken from clec14a −/− mice were smaller in size (FIG. 3B) and smaller in weight (FIG. 3C) than clec14a +/+ littermates. To determine whether the vascular density within these tumours was also effected, tissue sections were stained with an anti-CD31 antibody. Analysis shows a reduced density of discrete vessels (FIGS. 3D and 3E) and reduced percentage endothelial coverage (FIG. 3F). Furthermore, x-gal staining of tumour and liver sections taken from clec14a −/− mice reveals high expression of clec14a on both mature vessels, with erythrocyte filled lumens (FIG. 3G, black arrows), and immature microvessels within the tumour (FIG. 3G, red arrows), confirming clec14a is upregulated on tumour vessels.

Identification and Confirmation of CLEC14A-MMRN2 Interaction

To identify potential binding partners for the extracellular domain for CLEC14A, we first purified CLEC14A extracellular domain protein tagged with human Fc. This protein or Fc alone was incubated with HUVEC whole cell lysates and precipitated using protein A agarose beads. The precipitated proteins were then washed and separated on a SDS-PAG. Seven gel regions were excised, digested and analysed by mass spectrometry. The most abundant protein identified was MMRN2 with 12 peptides (11 unique), and no peptides in the corresponding control pulldown fraction. Western blot analysis of the precipitates confirmed the presence of MMRN2 in the CLEC14A-ECD-Fc pull-down and was not detected in the Fc alone pull-down (FIG. 4A). To further confirm this interaction, endogenous CLEC14A was immunoprecipitated from HUVEC whole cell lysates. Western blot analysis confirmed MMRN2 co-precipitation in the CLEC14A precipitate but was not detected in the IgG control (FIG. 4B).

Development and Validation of CLEC14A Monoclonal Antibodies

To further our understanding of CLEC14A, we next produced cross-species reactive antibodies. To enable this, murine CLEC14A protein with a human Fc tag was expressed in HEK293T cells and purified on a protein A column. Mice were then immunised with 50 μg mCLEC14A with complete Freund's adjuvant to break tolerance. Clones were screened for activity against human CLEC14A or human Fc. To confirm the clones could recognise cell bound CLEC14A, HEK293T cells overexpressing HA-CLEC14A were stained with clone C2 or C4 or a monoclonal HA tag antibody. FACs analysis shows increased fluorescence for each of the antibodies in the HA-CLEC14A overexpressing cells compared to control transfected cells (FIG. 5A). To confirm that antibodies recognise the endogenous form of CLEC14A, these clones were used to stain HUVEC treated with control or clec14a targeted siRNAs. Control HUVEC were stained strongly by clone C2 and C4 and this staining was reduced to isotype control levels by knockdown of CLEC14A (FIG. 5B). These results confirmed the specificity of the CLEC14A monoclonal antibodies.

To determine whether the C2 and C4 clones bind to the same region of CLEC14A, HUVECs were pre-treated with BSA, C2 or C4 antibody prior to C2-FITC staining. C2 incubation blocked C2-FITC staining effectively, but C4 had little effect (FIG. 5C). The same pre-treatment was repeated prior to C4-FITC staining. C2 antibody did not effect C4-FITC staining however, HUVECs pre-treated with C4 showed reduced binding of C4-FITC (FIG. 5D). From these results we can conclude that C2 and C4 bind to discrete regions of CLEC14A.

A CLEC14A Monoclonal Antibody Blocks CLEC14A-MMRN2 Binding

To determine whether either of these CLEC14A monoclonal antibodies could inhibit the binding of MMRN2 to CLEC14A, CLEC14A-ECD-Fc was pre-incubated with increasing concentrations of mIgG1, or C2, or C4, prior to incubation with lysates from HEK293T cells overexpressing MMRN2. Precipitates were then separated and probed for MMRN2 or CLEC14A-ECD-Fc. MMRN2 binding was observed for CLEC14A-ECD-Fc precipitates blocked with mIgG1 or C2 (FIG. 5E) but no MMRN2 binding was observed in the C4 blocked precipitates (FIG. 5F). This confirms that the C4 but not the C2 monoclonal antibody blocks MMRN2 binding to CLEC14A.

CLEC14A-MMRN2 Blocking Antibody Inhibits Tube Formation and Sprouting Angiogenesis In Vitro and In Vivo We previously showed that CLEC14A expression regulates endothelial cell migration and tube formation.[9] To assess whether C2 or C4 have a role in modulating endothelial cell migration, wounds were scratched into HUVEC monolayers and treated with 20 μg/ml mIgG1, C2 or C4. Wound closure was assessed at 16-24 hours. However, no difference was observed between any of the treatments (data not shown). To determine whether the CLEC14A monoclonal antibodies have regulatory properties in in vitro tube formation, HUVECs were plated onto Matrigel and treated with either mIgG1, C2 or C4 for 16 hrs. The C2 treatment had no effect on tube formation compared to the mIgG1 control, however, C4 treatment effected branching and meshes (FIG. 6A). Each of the treatments had no effect on the total tube length (FIG. 6B) or the number of junctions (FIG. 6C). In contrast the number of meshes (FIG. 6D) were decreased in the C4 treatment group, with a corresponding increase in the number of branches (FIG. 6E) for this treatment group compared to the control and C2 groups. Furthermore, C4 treated HUVECs have decreased branch length (FIG. 6F). These data suggest that C4 inhibits the sprouting or sensing and delays interconnectivity of the tubes, but the second CLEC14A targeted antibody (C2) was without activity on tube formation.

To investigate how disruption of the MMRN2-CLEC14A interaction effects sprouting in vitro, we treated HUVEC spheroids with 20 μg/ml C4 or C2 or mIgG1 control antibodies. Control, mIgG1 treated, spheroids formed sprouts after 16 hours as expected (FIG. 6G). C2 treatment had no effect on sprouting, but C4 treatment inhibited sprout formation by 50% (FIGS. 6G and 6H). To further investigate, aortic ring cultures were also supplemented with 20 μg/ml C4 or C2 or mIgG1 antibodies. Endothelial outgrowth and tube formation was well established after 7 days culture in the presence of mIgG1 (FIG. 6I). C4 antibody effectively inhibited tube outgrowth, however C2 antibody was inactive in regulating tube/sprout formation from aortic rings (FIGS. 6I and 6J).

To evaluate the role of the MMRN2-CLEC14A interaction in vivo, subcutaneous sponge implants were used. Sponge infiltration was stimulated as previously described with the addition of either 10 μg mIgG1 or C4 antibody. Total cellular sponge infiltration was significantly reduced ($p<0.01$) in the C4 treatment group compared to the mIgG1 controls (FIGS. 6K and 6L). Vascular density of the invaded sponge was also reduced for the C4 antibody group (FIG. 6M). These data demonstrate that the MMRN2-CLEC14A interaction promotes in vivo angiogenesis.

CLEC14A-MMRN2 Blocking Antibody Inhibits Tumour Growth

Mice with LLC tumours were injected intraperitoneally twice per week with 10 μg C4 or mIgG1 (control) for the duration of the experiment. Tumour growth was slowed for mice treated with C4 antibody compared to the control, mIgG1, treatment group (FIG. 7A). Tumours from the C4 treated mice were smaller in size (FIG. 7B) and weight (FIG. 7C) than control animals. Again we examined the vascular density within these tumours. Tissue sections were stained with an anti-CD31 antibody and fluorescent analysis revealed a reduced density of discrete vessels (FIGS. 7D and 7E) and the percentage endothelial coverage (FIG. 7F), suggesting that CLEC14A binding to MMRN2 is an important functional component of tumour induced angiogenesis.

DISCUSSION

CLEC14A is one of a small group of endothelial genes that contribute to tumour angiogenesis in multiple tumour types.[9, 13] Here we demonstrate that through loss of CLEC14A, tumour growth is inhibited in vivo (FIG. 3). A similar phenotype has also been observed for other tumour endothelial markers, such as TEM8,[16] Endoglin,[17] Galectin,[18] ELTD1,[13] and Endosialin,[19] this demonstrates the importance of these tumour endothelial expressed genes in vascularisation and tumour growth. Although many groups have focused on factors involved in physiological sprouting angiogenesis, these tumour endothelial expressed genes could deliver tumour anti-angiogenic therapeutic potential.[20]

Upregulation of CLEC14A has been observed in human tumours[9, 13, 21] and murine models of pancreatic and cervical cancer[11] which supports our findings that clec14a expression is upregulated on tumour vessels in the LLC model (FIG. 3). CLEC14A has been shown to regulate multiple aspects of endothelial biology including adhesion,[10, 12] migration,[9, 10, 12] tube formation,[9-11] and we now demonstrate it is also important for sprouting angiogenesis in vitro and in vivo (FIGS. 1 and 2). We can infer that this role of CLEC14A is through endothelial-endothelial interactions or endothelial-extracellular matrix interactions, because in vitro HUVEC sprouting is perturbed by CLEC14A knockdown, suggesting the presence of other cell types is dispensable. We also observed for the first time upregulation of clec14a expression on neoangiogenic vessels in the subcutaneous sponge assay (FIG. 2). This is expected as newly formed endothelial sprouts have been modelled to experience extremely low shear stress (0.2 Pa) from the 4.2 µm of the bifurcation point to the tip of the sprout,[23] and clec14a expression is known to be upregulated by low shear stress.[9]

Zanivan et al. identified CLEC14A as a component of the extracellular matrix that interacts with MMRN2.[11] We independently verified this interaction through pulldown of proteins from HUVEC lysates using the extracellular domain of CLEC14A, as well as co-immunoprecipitation of the endogenous proteins (FIG. 4). Through the generation and validation of CLEC14A monoclonal antibodies, we identified two antibodies that bind to discrete regions of CLEC14A (FIGS. 5C and 5D) and have shown that the C4 but not the C2 clone blocks the interaction of CLEC14A with MMRN2 (FIG. 5E). To probe the function of the CLEC14A-MMRN2 interaction, we used the C4 antibody in Matrigel tube forming assays and found an increase in branching and decrease in evolved meshes (FIG. 6). Knockdown by siRNA or targeting with polyclonal CLEC14A antisera has a similar effect on branching in this in vitro Matrigel assay.[9] However, another monoclonal antibody that binds CLEC14A but does not block MMRN2 binding had no effect (FIG. 6). In a study using phage display to develop IgGs targeting the c-type lectin domain (CTLD) of CLEC14A, some of the generated IgGs reduced HUVEC cell migration and tube formation, although not all of the clones tested.[12] As our monoclonal antibody has a similar function it is possible that the MMRN2 binding site is within the CTLD region of CLEC14A, although further work is required to confirm this. In vitro and in vivo sprouting assays treated with C4 antibodies also demonstrated the role of the CLEC14A-MMRN2 interaction for endothelial sprouting (FIG. 6). Finally, we found that the CLEC14A-MMRN2 interaction is important for tumour growth (FIG. 7), C4 treatment recapitulated tumour growth and reduced tumour vascularity as seen in clec14a −/− mice (FIG. 3). Antibody inhibition of tumour endothelial marker function has been suggested as a mode of anti-angiogenic therapy for TEM8[24] and our studies corroborate this approach. Although in this example no ligand or mode of activity was identified, this is the first time that CLEC14A and a specific extracellular interaction has been shown to be important for tumour growth, and suggests a hitherto avenue into new anti-angiogenic therapies.

Materials and Methods

Reagents

For Western blotting and immunoprecipitation; primary antibodies: sheep polyclonal anti-human CLEC14A (R&D systems), mouse monoclonal anti-human Tubulin (Sigma), mouse polyclonal anti-human MMRN2 (Abnova); secondary antibodies: goat polyclonal anti-mouse IgG conjugated to horseradish peroxidase (HRP) (Dako), donkey polyclonal anti-sheep IgG conjugated to HRP (R&D systems). For immunofluorescence; primary antibodies: rabbit polyclonal anti-murine PECAM (Santa Cruz); secondary antibodies: donkey polyclonal anti-rabbit conjugated to Alexa Fluor488 (Invitrogen). For flow cytometry; primary antibodies: mouse monoclonal anti-HA tag (CRUK), mouse monoclonal anti-CLEC14A (C2, C4 described below); secondary antibodies: goat polyclonal anti-mouse IgG conjugated to Alexa Fluor488 (Invitrogen).

Plasmids

For protein production; lentiviral plasmids psPAX2 (lentiviral packaging; Addgene), pMD2G (Envelope plasmid; Addgene) and pWPI hCLEC14A-ECD-Fc (lentiviral mammalian expression plasmid containing IRES-EGFP; Addgene) were used. pWPI hCLEC14A-Fc and mCLEC14A-Fc was generated by initial PCR subcloning from c/ec14a IMAGE clone (Origene) into pcDNA3-Fc plasmid. The primers used were as follows: human CLEC14A fwd 5'TAGTAGGAATTCGAGAGAATGAGGCCGGCGTT-CGCCCTG3' (SEQ ID NO: 22); human CLEC14A rev 5'AGAACCGCGGCCGCTGGAGGAGTCGAAAGCCT-GAGGAGT3' (SEQ ID NO: 23); murine CLEC14A fwd-5'TAGTAGGAATTCGAGAGAATGAGGCCAGCGCTT-GCCCTG3' (SEQ ID NO: 24; murine CLEC14A rev 5'CTACTAGCGGCCGCTCGTGGAAGAGGTGTCG-AAAGT3' (SEQ ID NO: 25). EcoR1 and Not1 restriction sites were used to insert CLEC14A. A further round of PCR subcloning was performed to transfer the CLEC14A-Fc fusion into pWPI. The primers used were as follows: human CLEC14A fwd 5'TAGTAGTTAATTAAGAGAGAAT-GAGGCCGGCGTTC3' (SEQ ID NO: 26); murine CLEC14A fwd-5'TAGTAGTTAATTAAGAGAGAAT-GAGGCCAGCGCTT3' (SEQ ID NO: 27); human Fc rev-5'CTACTAGTTTAAACTCATTTACCCGGAGACAG-GGA3' (SEQ ID NO: 28). For this step, Pac1 and Pme1 restriction sites were used. MMRN2 mammalian expression plasmid was constructed by PCR cloning from mmrn2 IMAGE clone (Thermo) into pHL-Avitag3,[25] using the following primers: fwd-CCGGACCGGTCAGGCTTC-CAGTACTAGCC (SEQ ID NO: 29); rev-CGGGGTACCGGTCTTAAACATCAGGAAGC (SEQ ID NO: 30). Age1 and Kpn1 restriction enzymes were used.

Cell Culture

Human Umbilical Vein Endothelial Cells were isolated as described previously.[9] Umbilical cords were obtained from Birmingham Women's Health Care NHS Trust with informed consent. HUVECs were used between passages 1-6 and were cultured in M199 complete medium (cM199) containing 10% fetal calf serum (PAA), 1% bovine brain extract,[26] 90 µg/ml heparin, and 4 mM L-glutamine, 100 U/ml penicillin and 100 µg/ml streptomycin (Invitrogen) and were seeded on plates coated in 0.1% type 1 gelatin from porcine skin. HEK293T cells were cultured in DMEM (Sigma) complete medium (cDMEM) containing 10% fetal calf serum (PAA), 4 mM L-glutamine, 100 U/ml penicillin and 100 µg/ml streptomycin (Invitrogen).

SiRNA transfections in HUVEC were performed as previously described.[9] Lentivirus was produced in HEK293T cells by transient transfection with the lentiviral packaging, envelope and expression plasmids above. Plasmids were incubated in OptiMEM (Invitrogen) with polyethylenimine (36 µg/ml) at a 1:4 ratio for 10 minutes at room temperature prior to adding to HEK293T cells in cDMEM. Media supernatant was used to transduce fresh HEK293T cells. GFP positive HEK293T cells were sorted and used for protein production. Expression of MMRN2 in HEK293T cells was achieved by polyethylenimine transient transfection as above using pHL-Avitag3 hMMRN2.

Quantitative PCR cDNA was prepared using the High-Capacity cDNA Archive kit (Applied Biosystems), from 1 μg of extracted total RNA. qPCR reactions were performed with Express qPCR supermix (Invitrogen) on a RG-3000 (Corbett/Qiagen, Manchester, UK) thermocycler. Primers for human clec14a and flotillin-2 were as previously described.[9] Primers for murine clec14a 5' UTR, CDS and 3' UTR and murine beta-actin, are as follows: 5'UTR fwd-TTCCTTTTCCAGGGTTTGTG (SEQ ID NO: 31); 5' UTR rev-GCCTACAAGGTGGCTTGAAT (SEQ ID NO: 32); CDS fwd AAGCTGTGCTCCTGCTCTTG (SEQ ID NO: 33; CDS rev-TCCTGAGTGCACTGTGAGATG (SEQ ID NO: 34); 3' UTR fwd-CTGTAGAGGGCGGTGACTTT (SEQ ID NO: 35); 3' UTR rev-AGCTGCTCCCAAGTCCTCT (SEQ ID NO: 36); mACTB fwd CTAAGGCCAACCGTGAAAAG (SEQ ID NO: 37); mACTB rev ACCAGAGGCATACAGGGACA (SEQ ID NO: 38). Relative expression ratios were calculated according to the efficiency adjusted mathematical model.[27]

Western Blotting and Immunoprecipitation

Whole cell protein lysates were made and co-immunoprecipitation experiments were performed as previously described,[28] except protein was extracted from 2×10⁷ HUVECs. For initial isolation of CLEC14A interacting proteins 5 μg CLEC14A-Fc or an equimolar amount of hFc was used. For endogenous immunoprecipitation experiments 0.4 μg anti-CLEC14A antibody or sheep IgG was used. For blocking experiments 5 μg CLEC14A-Fc or hFc were bound to protein G beads overnight in PBS. Beads were blocked for 5-6 hours in PBS containing 20% FCS (PAA). Bound CLEC14A-Fc or hFc protein was blocked with increasing concentrations of mIgG, C2 or C4 in binding buffer overnight. Lysates from MMRN2 transfected HEK293T cells were then incubated overnight with the bead complexes before washing and analysing by Western blot. Standard protocols were used for Western blotting and SDS-PAGE. Primary antibodies were used as indicated in the text with corresponding HRP conjugated secondary antibodies.

Flow Cytometry

Cells were detached with cell dissociation buffer (Invitrogen), rinsed in PBS before incubation in blocking buffer (PBS, 3% BSA, 1% NaN$_3$) for 15 minutes. Subsequent staining using 10 μg/ml anti-HA tag (CRUK), 10 μg/ml anti-CLEC14A (C2, C4 described below), as primary antibodies, in blocking buffer for 30 minutes. Cells were rinsed in PBS and stained with goat polyclonal anti-mouse IgG conjugated to Alexa Fluor488 (Invitrogen) in blocking buffer. Data (15,000 events/sample) were collected using a FACSCalibur apparatus (Becton Dickinson, Oxford, UK), and results were analysed with Becton Dickinson Cell Quest software.

HUVEC Spheroid Sprouting Assay and In Vitro Matrigel Tube Forming Assay

Generation of HUVEC spheroids and induction of endothelial sprouting in a collagen gel was performed as previously described,[29] using 1000 HUVECs per spheroid. Quantification was performed 16 hours after embedding. To quantify sprout growth the number of sprouts were counted, the cumulative sprout length and the maximal sprout length was assessed. For two colour sprouting experiments, HUVECs were pre-labelled with orange and green Cell-Tracker dyes (Invitrogen). After 24 hours spheroids were fixed in 4% formaldehyde and mounted with Vectorshield (Vector labs). Slides were imaged with an Axioskop2 microscope and AxioVision SE64 Rel4.8 software (Zeiss, Cambridge, UK).

For the Matrigel tube forming assays 1.4×10⁵ HUVECs were seeded onto 70 μl basement membrane extract (Matrigel, BD Bioscience, Oxford, UK) in a 12 well plate. After 16 hours, images were taken of 5 fields of view per well using a Leica DM IL microscope (Leica, Milton Keynes, UK) with a USB 2.0 2M Xli digital camera (XL Imaging LLC, Carrollton, TX, USA) at 10× magnification. Images were analysed with the Angiogenesis analyser plugin for Image J (Carpentier G. et al., Angiogenesis Analyzer for ImageJ. 4th ImageJ User and Developer Conference proceedings) and available at the NIH website (http://imagej.nih.gov/ij/macros/toolsets/Angiogenesis %20Analyzer.txt).

Protein Production

Culture media (CM) from CLEC14A-Fc expressing HEK293T cells was collected. CM was flowed over a HiTrap protein A HP column (GE healthcare, Amersham, UK) and protein eluted using a 0-100% gradient of 100 mM sodium citrate (pH 3) before neutralising with 1 M Tris base. Fractions were run on a SDS-PAG and assessed for protein purity and specificity by Coomassie staining and Western blotting. Fractions containing similar concentrations of protein were combined and dialysed in PBS prior to functional assays.

Monoclonal Antibody Generation

Mouse monoclonal antibodies were commercially prepared by Serotec Ltd (Oxford, UK) using the following protocol to break tolerance supplied by us. Purified mouse CLEC14A-Fc fusion protein was given at 50 μg in Freunds complete adjuvant subcutaneously. Two weeks later mice were given another 50 μg subcutaneously but this time in Freunds adjuvant. Mice were culled and spleens harvested for fusion two weeks later.

Generation of clec14a −/− Mice

Mice were housed at the Birmingham Biomedical Services Unit (Birmingham, UK). C57BL/6N VGB6 feeder-dependent embryonic stem cells containing the CLEC14A deletion cassette (Clec14atm1(KOMP)Vlcg; project ID VG10554) were procured from the Knockout Mouse Project (University of California, Davis, USA). The Transgenic Mouse Facility at the University of Birmingham generated chimeric mice by injection of embryonic stem cells into albino C57BL/6 mice and were bred to C57BL/6 females to generate mice heterozygous for the cassette. Animal maintenance had appropriate Home Office Approval and Licensing.

Aortic Ring and Murine Subcutaneous Sponge Angiogenesis Assay

Aortas were isolated and processed for aortic ring assays in collagen as previously described.[30] Tube/sprout outgrowth, maximal endothelial migration and total endothelial outgrowth was quantitated. Themurine subcutaneous sponge angiogenesis assay was performed as previously described,[31] with slight modification. Male C57 black mice were implanted with a subcutaneous sterile polyether sponge disc (10×5×5 mm) under the dorsal skin of each flank at day 0. 100 μl bFGF (40 ng/ml; R&D systems) was injected through the skin directly into the sponges every other day for 14 days. Sponges were excised on day 14, fixed in 10% formalin, and paraffin embedded. Sections were stained with haematoxylin and eosin, sponge cross-sections were taken using a Leica MZ 16 microscope (Leica, Milton Keynes, UK) with a USB 2.0 2M Xli digital camera (XL Imaging LLC, Carrollton, TX, USA) at ×1 magnification for cellular invasion analysis. Images captured by Leica DM E microscope (Leica, Milton Keynes, UK) at 40× magnification were analysed for vessel density. Vessel counts were assessed in five fields per section per sponge. All animal experimentation was carried out in accordance with Home Office License number PPL 40/3339 held by RB.

Tumour Implantation Assays $10^6$ Lewis lung carcinoma cells were injected subcutaneously into the flank of male mice at 8-10 weeks of age. Tumour growth was monitored by daily calliper measurements and after two-four weeks growth, tumour mass was determined by weight, fixed in 4% PFA, paraffin embedded and serial sections cut at 6 μm.

Immunofluorescence and X-Gal Staining

Immunofluorescence Staining was Performed as Previously Described.[9]

X-Gal Staining was Performed as Previously Described.[32]

EXAMPLE 2 CLEC14A MONOCLONAL ANTIBODIES C1, C4 AND C5 BLOCK CLEC14A-MMRN2 INTERACTION

To determine which CLEC14A monoclonal antibodies could inhibit the binding of MMRN2 to CLEC14A, CLEC14A-ECD-Fc was pre-incubated with increasing concentrations of mIgG1, or CR1-5, prior to incubation with lysates from HEK293T cells overexpressing MMRN2. Precipitates were then separated and probed for MMRN2 or CLEC14A-ECD-Fc. MMRN2 binding was observed for CLEC14A-ECD-Fc precipitates blocked with mIgG1 or C2 and C3 but no MMRN2 binding was observed in the C1, 4 and 5 blocked precipitates (FIG. 12). This confirms that antibodies C1, 4 and 5 bind CLEC14a on an epitope that is distinct from the one that C2 and 3 monoclonal antibodies bind and thus specifically block the MMRN2 interaction with CLEC14A.

EXAMPLE 3 MAPPING OF MMRN2 BINDING DOMAIN AND CRT ANTIBODIES

1) MMRN2 binds to either the CTLD or SUSHI domain of CLEC14a

The binding of MMRN2 to CLEC14A was narrowed down to the CTLD or SUSHI domain of CLEC14A. It is likely that without the CTLD or SUSHI domain present in the domain deletions, CLEC14A is not properly folded resulting in it no longer binding to MMRN2 (or the CRT antibodies). This was found out using deletion constructs of CLEC14A far Western blotted with MMRN2 as shown in FIG. 13.

2) CRT antibodies bind to CTLD domain of CLEC and not SUSHI

To further determine whether the CTLD or SUSHI was the binding domain, and to ensure correct folding, Chimeric constructs of CLEC14A were made with CTLD or SUSHI domains swapped with those of thrombomodulin (also known as CD141)-a type 14 CTLD family member which does not bind to MMRN2.

The sequences of Chimera 5 (CLEC14A with CTLD of CD141) and Chimera 6 (CLEC14A with SUSHI of CD141) are shown in FIG. 14.

Binding of CRT antibodies was analysed using flow cytometry. All constructs have a C-terminus GFP tag so green cells were gated and stained red. All CRT antibodies bind WT CLEC14A and—as expected—none binds to WT CD141 (FIG. 15). In addition, none of the antibodies bound to Chimera 5 (except slight binding by CRT2) and all of the antibodies bind to Chimera 6 (except CRT2) (FIG. 15). This confirms that the binding site of the antibodies CRT1, 3, 4 and 5 and MMRN2 are within the C type lectin domain. It is possible that CRT2 binds on a region between the CTLD and sushi domain.

3) CRT Antibodies that block MMRN interaction do not bind to the regions specified in WO 2013/187724 but to a region that includes aa 97-108 of CLEC14a CTLD To further determine the binding region of the antibodies and MMRN2, chimeric loop constructs were made. This was based on the structural predictions of CLEC14A CTLD and also the regions that the antibodies identified in WO 2013/187724 bind to.

```
CLEC14A with regions 1-42 of CD141
CD141 sequence-
                                    (SEQ ID NO: 80)
MLGVLVLGALALAGLGFPAPAEPQPGGSQCVEHDCFALY CLEC14A with regions 97-108 of CD141
CD141 sequence-
                                    (SEQ ID NO: 81)
QLPPGCGDPKRL CLEC14A with regions 122-142 of CD141
CD141 sequence-
                                    (SEQ ID NO: 82)
TSYSRWARLDLNGAPLCGPL
```

The alignment is shown in FIG. 16. Unfortunately 1-42 and 122-142 chimeras did not fold correctly. This is thought due to the fact they are present on the cell surface (stain positive for CLEC14A polyclonal antibodies, but they do not stain for any of the C antibodies not even C2.

However the 97-108 chimera does bind C2 and C3 showing that this mutant is correctly folded. This mutant does not bind MMRN2 or C1, 4 or 5 (which are the antibodies thought to block the CLEC14A-MMRN2 interaction) (FIG. 17). Therefore we conclude that the binding domain is dependent upon the loop containing the following residues: ERRRSCHTLENE (SEQ ID NO: 39).

Residues 97-108 were swapped with corresponding regions from thrombomodulin. This resulted in correct folding as C2 and C3 can still bind (FIG. 18). However C1, C4 and C5 cannot recognise this mutant suggesting this to be the binding region.

This experiment has been repeated three times with the same result.

EXAMPLE 4—ANTIBODY DRUG CONJUGATE TUMOUR DATA

Wild type male C57BL6 mice aged between 6-8 weeks were sub-cutaneously injected with 1×10^6 Lewis lung carcinoma (LLC) cells in the right flank. Once tumours reached a palpable size, mice were randomly assigned to each treatment group, B12-ADC, or C4-ADC. Mice received two intravenous injections into the tail vein one week apart of 1 mg/kg. One week after final injection mice were culled, tumours were excised and wet weights were measured. The data is shown in FIG. 19.

REFERENCES

1. Ziyad S, Iruela-Arispe M L. Molecular mechanisms of tumor angiogenesis. *Genes Cancer* 2011; 2: 1085-1096.

2. Welti J, Loges S, Dimmeler S, Carmeliet P. Recent molecular discoveries in angiogenesis and antiangiogenic therapies in cancer. *J Clin Invest* 2013; 123: 3190-3200.
3. De Bock K, Georgiadou M, Schoors S, Kuchnio A, Wong B W, Cantelmo A R et al. Role of PFKFB3-driven glycolysis in vessel sprouting. *Cell* 2013; 154: 651-663.
4. Jin H, Garmy-Susini B, Avraamides C J, Stoletov K, Klemke R L, Varner J A. A PKA Csk-pp60Src signaling pathway regulates the switch between endothelial cell invasion and cell-cell adhesion during vascular sprouting. *Blood* 2010; 116: 5773-5783.
5. Bignon M, Pichol-Thievend C, Hardouin J, Malbouyres M, Bréchot N, Nasciutti L et al. Lysyl oxidase-like protein-2 regulates sprouting angiogenesis and type IV collagen assembly in the endothelial basement membrane. *Blood* 2011; 118: 3979-3989.
6. Welch-Reardon K M, Ehsan S M, Wang K, Wu N, Newman A C, Romero-Lopez M et al. Angiogenic sprouting is regulated by endothelial cell expression of Slug. *J Cell Sci* 2014; 127: 2017-2018.
7. Bergers G, Hanahan D. Modes of resistance to anti-angiogenic therapy. *Nat Rev Cancer* 2008; 8: 592-603.
8. Zelensky A N, Gready J E. The C-type lectin-like domain superfamily. *FEBS J* 2005; 272: 6179-6217.
9. Mura M, Swain R K, Zhuang X, Vorschmitt H, Reynolds G, Durant S et al. Identification and angiogenic role of the novel tumor endothelial marker CLEC14A. *Oncogene* 2012; 31: 293-305.
10. Rho S-S, Choi H-J, Min J-K, Lee H-W, Park H, Park H et al. Clec14a is specifically expressed in endothelial cells and mediates cell to cell adhesion. *Biochem Biophys Res Commun* 2011; 404: 103-108.
11. Zanivan S, Maione F, Hein M Y, Hernandez-Fernaud J R, Ostasiewicz P, Giraudo E et al. SILAC-based proteomics of human primary endothelial cell morphogenesis unveils tumor angiogenic markers. *Mol Cell Proteomics* 2013; 12: 3599-3611.
12. Ki M K, Jeoung M H, Choi J R, Rho S-S, Kwon Y-G, Shim H et al. Human antibodies targeting the C-type lectin-like domain of the tumor endothelial cell marker clec14a regulate angiogenic properties in vitro. *Oncogene* 2013; 32: 5449-5457.
13. Masiero M, Simões F C, Han H D, Snell C, Peterkin T, Bridges E et al. A Core Human Primary Tumor Angiogenesis Signature Identifies the Endothelial Orphan Receptor ELTD1 as a Key Regulator of Angiogenesis. *Cancer Cell* 2013; 24: 229-241.
14. Sanz-Moncasi M P, Garin-Chesa P, Stockert E, Jaffe E A, Old L J, Rettig W J. Identification of a high molecular weight endothelial cell surface glycoprotein, endoGlyx-1, in normal and tumor blood vessels. *Lab Invest* 1994; 71: 366-373.
15. Colombatti A, Spessotto P, Doliana R, Mongiat M, Bressan G M, Esposito G. The EMILIN/Multimerin Family. *Front Immunol* 2011; 2: 93.
16. Cullen M, Seaman S, Chaudhary A, Yang M Y, Hilton M B, Logsdon D et al. Host-derived tumor endothelial marker 8 promotes the growth of melanoma. *Cancer Res* 2009; 69: 6021-6026.
17. Düwel A, Eleno N, Jerkic M, Arevalo M, Bolanôs J P, Bernabeu C et al. Reduced tumor growth and angiogenesis in endoglin haploinsufficient mice. *Tumour Biol* 2007; 28:1-8.
18. Thijssen V L J L, Postel R, Brandwijk R J M G E, Dings R P M, Nesmelova I, Satijn S et al. Galectin-1 is essential in tumor angiogenesis and is a target for antiangiogenesis therapy. *Proc Natl Acad Sci USA* 2006; 103: 15975-15980.
19. Nanda A, Karim B, Peng Z, Liu G, Qiu W, Gan C et al. Tumor endothelial marker 1 (Tem1) functions in the growth and progression of abdominal tumors. *Proc Natl Acad Sci USA* 2006; 103: 3351-3356.
20. Nanda A, St Croix B. Tumor endothelial markers: new targets for cancer therapy. *Curr Opin Oncol* 2004; 16: 44-49.
21. Pircher A, Fiegl M, Untergasser G, Heidegger I, Medinger M, Kern J et al. Favorable prognosis of operable non-small cell lung cancer (NSCLC) patients harboring an increased expression of tumor endothelial markers (TEMs). *Lung Cancer* 2013; 81: 252-258.
22. Zhuang X, Cross D, Heath V L, Bicknell R. Shear stress, tip cells and regulators of endothelial migration. *Biochem Soc Trans* 2011; 39: 1571-1575.
23. Stapor P C, Wang W, Murfee W L, Khismatullin D B. The distribution of fluid shear stresses in capillary sprouts. *Cardiovasc Eng Tech* 2011; 2: 124-136.
24. Chaudhary A, Hilton M B, Seaman S, Haines D C, Stevenson S, Lemotte P K et al. TEM8/ANTXR1 blockade inhibits pathological angiogenesis and potentiates tumoricidal responses against multiple cancer types. *Cancer Cell* 2012; 21: 212-226.
25. Aricescu A R, Lu W, Jones E Y. A time- and cost-efficient system for high-level protein production in mammalian cells. *Acta Crystallogr D Biol Crystallogr* 2006; 62: 1243-1250.
26. Maciag T, Cerundolo J, Ilsley S, Kelley P R, Forand R. An endothelial cell growth factor from bovine hypothalamus: identification and partial characterization. *Proc Natl Acad Sci USA* 1979; 76: 5674-5678.
27. Pfaffl M W. A new mathematical model for relative quantification in real-time RT-PCR. *Nucleic Acids Res* 2001; 29: 2002-2007.
28. Desjobert C, Noy P, Swingler T E, Williams H, Gaston K, Jayaraman P-S. The PRH/Hex repressor protein causes nuclear retention of Groucho/TLE co-repressors. *Biochem J* 2009; 417: 121-132.
29. Korff T, Krauss T, Augustin H G. Three-dimensional spheroidal culture of cytotrophoblast cells mimics the phenotype and differentiation of cytotrophoblasts from normal and preeclamptic pregnancies. *Exp Cell Res* 2004; 297: 415-423.
30. Baker M, Robinson S D, Lechertier T, Barber P R, Tavora B, D'Amico G et al. Use of the mouse aortic ring assay to study angiogenesis. *Nat Protoc* 2011; 7: 89-104.
31. Suchting S, Heal P, Tahtis K, Stewart L M, Bicknell R. Soluble Robo4 receptor inhibits in vivo angiogenesis and endothelial cell migration. *FASEB J* 2005; 19: 121-123.
32. Saunders T L. Reporter molecules in genetically engineered mice. *Methods Mol Biol* 2003; 209: 125-143.

The invention claimed is:

1. A method of inhibiting angiogenesis in an individual, the method comprising administering to the individual an agent that inhibits the interaction between CLEC14A and MMRN2, wherein the agent is an antibody, or an antigen-binding fragment thereof, which selectively binds CLEC14A and comprises:

(i) a heavy chain variable region comprising (a) a heavy-chain variable region CDR1 comprising the sequence of SEQ ID NO: 40; (b) a heavy-chain variable region CDR2 comprising the sequence of SEQ ID NO: 41; and (c) a heavy chain variable region CDR3 comprising the sequence of SEQ ID NO: 47; and a light chain variable region comprising (d) a light-chain variable region CDR1 comprising the sequence of SEQ ID NO: 43; (e) a light-chain variable region CDR2 comprising the sequence DTS; and (f) a light-chain variable region CDR3 comprising the sequence of SEQ ID NO: 48; or (ii) a heavy chain variable region comprising (a) a heavy-chain variable region CDR1 comprising the sequence of SEQ ID NO: 1; (b) a heavy-chain variable region CDR2 comprising the sequence of SEQ ID NO: 2 or SEQ ID NO: 78; and (c) a heavy chain variable region CDR3 comprising the sequence of SEQ ID NO: 3; and a light chain variable region comprising (d) a light-chain variable region CDR1 comprising the sequence of SEQ ID NO: 4; (e) a light-chain variable region CDR2 comprising the sequence of SEQ ID NO: 5; and (f) a light-chain variable region CDR3 comprising the sequence of SEQ ID NO: 6; or (iii) a heavy chain variable region comprising (a) a heavy-chain variable region CDR1 comprising the sequence of SEQ ID NO: 40; (b) a heavy-chain variable region CDR2 comprising the sequence of SEQ ID NO: 41; and (c) a heavy chain variable region CDR3 comprising the sequence of SEQ ID NO: 42; and a light chain variable region comprising (d) a light-chain variable region CDR1 comprising the sequence of SEQ ID NO: 43; (e) a light-chain variable region CDR2 comprising the sequence DTS; and (f) a light-chain variable region CDR3 comprising the sequence of SEQ ID NO: 44; or (iv) a heavy chain variable region comprising (a) a heavy-chain variable region CDR1 comprising the sequence of SEQ ID NO: 1; (b) a heavy-chain variable region CDR2 comprising the sequence of SEQ ID NO: 78; and (c) a heavy chain variable region CDR3 comprising the sequence of SEQ ID NO: 77; and a light chain variable region comprising (d) a light-chain variable region CDR1 comprising the sequence of SEQ ID NO: 4; (e) a light-chain variable region CDR2 comprising the sequence of SEQ ID NO: 5; and (f) a light-chain variable region CDR3 comprising the sequence of SEQ ID NO: 6; or (v) a heavy chain variable region comprising (a) a heavy-chain variable region CDR1 comprising the sequence of SEQ ID NO: 40; (b) a heavy-chain variable region CDR2 comprising the sequence of SEQ ID NO: 41; and (c) a heavy chain variable region CDR3 comprising the sequence of SEQ ID NO: 45; and a light chain variable region comprising (d) a light-chain variable region CDR1 comprising the sequence of SEQ ID NO: 43; (e) a light-chain variable region CDR2 comprising the sequence DTS; and (f) a light-chain variable region CDR3 comprising the sequence of SEQ ID NO: 44; or (vi) a heavy chain variable region comprising (a) a heavy-chain variable region CDR1 comprising the sequence of SEQ ID NO: 1; (b) a heavy-chain variable region CDR2 comprising the sequence of SEQ ID NO: 78; and (c) a heavy chain variable region CDR3 comprising the sequence of SEQ ID NO: 46; and a light chain variable region comprising (d) a light-chain variable region CDR1 comprising the sequence of SEQ ID NO: 4; (e) a light-chain variable region CDR2 comprising the sequence of SEQ ID NO: 5; and (f) a light-chain variable region CDR3 comprising the sequence of SEQ ID NO: 6.

2. A method according to claim 1, wherein the antibody is a monoclonal antibody, a humanised antibody or a single-chain antibody.

3. A method of treating a disease chosen from solid tumor, psoriasis, menorrhagia, endometriosis, arthritis, macular degeneration, Paget's disease, retinopathy and its vascular complications, benign vascular proliferations, fibroses, obesity and inflammation, the method comprising administering an agent that inhibits the interaction between CLEC14A and MMRN2 to an individual in need thereof, wherein the agent is an antibody, or an antigen-binding fragment thereof, which selectively binds CLEC14A and comprises:

(i) a heavy chain variable region comprising (a) a heavy-chain variable region CDR1 comprising the sequence of SEQ ID NO: 40; (b) a heavy-chain variable region CDR2 comprising the sequence of SEQ ID NO: 41; and (c) a heavy chain variable region CDR3 comprising the sequence of SEQ ID NO: 47; and a light chain variable region comprising (d) a light-chain variable region CDR1 comprising the sequence of SEQ ID NO: 43; (e) a light-chain variable region CDR2 comprising the sequence DTS; and (f) a light-chain variable region CDR3 comprising the sequence of SEQ ID NO: 48; or (ii) a heavy chain variable region comprising (a) a heavy-chain variable region CDR1 comprising the sequence of SEQ ID NO: 1; (b) a heavy-chain variable region CDR2 comprising the sequence of SEQ ID NO: 2 or SEQ ID NO: 78; and (c) a heavy chain variable region CDR3 comprising the sequence of SEQ ID NO: 3; and a light chain variable region comprising (d) a light-chain variable region CDR1 comprising the sequence of SEQ ID NO: 4; € a light-chain variable region CDR2 comprising the sequence of SEQ ID NO: 5; and (f) a light-chain variable region CDR3 comprising the sequence of SEQ ID NO: 6; or (iii) a heavy chain variable region comprising (a) a heavy-chain variable region CDR1 comprising the sequence of SEQ ID NO: 40; (b) a heavy-chain variable region CDR2 comprising the sequence of SEQ ID NO: 41; and (c) a heavy chain variable region CDR3 comprising the sequence of SEQ ID NO: 42; and a light chain variable region comprising (d) a light-chain variable region CDR1 comprising the sequence of SEQ ID NO: 43; (e) a light-chain variable region CDR2 comprising the sequence DTS; and (f) a light-chain variable region CDR3 comprising the sequence of SEQ ID NO: 44; or (iv) a heavy chain variable region comprising (a) a heavy-chain variable region CDR1 comprising the sequence of SEQ ID NO: 1; (b) a heavy-chain variable region CDR2 comprising the sequence of SEQ ID NO: 78; and (c) a heavy chain variable region CDR3 comprising the sequence of SEQ ID NO: 77; and a light chain variable region comprising (d) a light-chain variable region CDR1 comprising the sequence of SEQ ID NO: 4; (e) a light-chain variable region CDR2 comprising the sequence of SEQ ID NO: 5; and (f) a light-chain variable region CDR3 comprising the sequence of SEQ ID NO: 6; or (v) a heavy chain variable region comprising (a) a heavy-chain variable region CDR1 comprising the sequence of SEQ ID NO: 40; (b) a heavy-chain variable region CDR2 comprising the sequence of SEQ ID NO: 41; and (c) a heavy chain variable region CDR3 comprising the sequence of SEQ ID NO: 45; and a light chain variable region comprising (d) a light-chain variable region CDR1 comprising the sequence of SEQ ID NO: 43; (e) a light-chain variable region CDR2 comprising the sequence DTS; and (f) a light-chain variable region CDR3 comprising the sequence of SEQ ID NO: 44;

(vi) a heavy chain variable region comprising (a) a heavy-chain variable region CDR1 comprising the sequence of SEQ ID NO: 1; (b) a heavy-chain variable region CDR2 comprising the sequence of SEQ ID NO: 78; and (c) a heavy chain variable region CDR3 comprising the sequence of SEQ ID NO: 46; and a light chain variable region comprising (d) a light-chain variable region CDR1 comprising the sequence of SEQ ID NO: 4; (e) a light-chain variable region CDR2 comprising the sequence of SEQ ID NO: 5; and (f) a light-chain variable region CDR3 comprising the sequence of SEQ ID NO: 6.

4. A method according to claim 1, wherein the agent is a compound comprising (i) an antibody that competes with MMRN2 for specific binding to the CLEC14A polypeptide and wherein the compound further comprises (ii) a cytotoxic moiety.

* * * * *